US006461606B1

(12) United States Patent
Flotte et al.

(10) Patent No.: US 6,461,606 B1
(45) Date of Patent: Oct. 8, 2002

(54) MATERIALS AND METHODS FOR GENE THERAPY

(75) Inventors: Terence R. Flotte, Gainesville, FL (US); Sihong Song, Gainesville, FL (US); Barry J. Byrne, Gainesville, FL (US); Michael Morgan, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 09/299,141

(22) Filed: Apr. 23, 1999

Related U.S. Application Data

(60) Provisional application No. 60/083,025, filed on Apr. 24, 1998.

(51) Int. Cl.[7] ........................ A01N 63/00; A61K 31/70; C12N 5/00; C12N 15/00; C07H 21/04

(52) U.S. Cl. .................. 424/93.2; 424/93.21; 424/93.6; 514/44; 435/320.1; 435/325; 435/69.1; 435/455; 536/23.1; 536/23.5

(58) Field of Search ........................... 514/44; 424/93.2, 424/93.21, 93.6; 435/320.1, 325, 69.1, 455; 530/350; 536/23.1, 23.5

(56) References Cited

U.S. PATENT DOCUMENTS

| | | | | |
|---|---|---|---|---|
| 4,797,368 A | | 1/1989 | Carter et al. | 435/320 |
| 5,139,941 A | | 8/1992 | Muzyczka et al. | 435/172.3 |
| 5,399,346 A | | 3/1995 | Anderson et al. | 424/93.21 |
| 5,439,824 A | * | 8/1995 | Brantly et al. | 435/320.1 |
| 5,587,308 A | | 12/1996 | Carter et al. | 435/240.2 |
| 5,658,776 A | | 8/1997 | Flotte et al. | 435/172.3 |
| 5,658,785 A | | 8/1997 | Johnson | 435/367 |
| 5,846,528 A | | 12/1998 | Podsakoff et al. | 424/93.2 |
| 5,858,351 A | | 1/1999 | Podsakoff et al. | 424/93.2 |
| 5,866,696 A | | 2/1999 | Carter et al. | 536/23.5 |

OTHER PUBLICATIONS

Anderson WF, Nature 392:25–30, 1998.*
Verma et al Nature 389:239–242, 1997.*
Kay et al, PNAS 94:12744–12746, 1997.*
Koeberl et al PNAS 94:1426–1431, 1997.*
Kessler et al PNAS 93(24):14082–7, 1996.*
Doll et al. Gene Ther. 3(5):437–447, 1996.*
Bodine et al Blood 82(7):1975–80, 1993.*
Rosenfeld et al Science 252(5004):374, 1991.*
Afione et al., "In vivo model of adeno–associated virus vector persistence and rescue," *Journal of Virology*, 70:3235–3241, 1996.
Brantly et al., "Use of a highly purified alpha 1–antityrpsin standard to establish ranges for the common normal and deficient alpha 1–antitrypsin phenotypes," *Chest* 100:703–708, 1991.
Fisher et al., "Transduction with recombinant adeno–associated virus for gene therapy is limited by leading strand synthesis," *J. Virol.* 70:520–532, 1996.
Flotte et al., "Gene expression from adeno–associated virus vectors in airway epithelial cells," *Am. J. Respir. Cell Mol. Biol.* 7:349–356, 1992.
Flotte et al., "Expression of the cystic fibrosis transmembrane conductance regulator from a novel adeno–associated virus promoter," *J. Biol. Chem.* 268:3781–3790, 1993.
Flotte et al., "Stable in vivo expression of the cystic fibrosis transmembrane conductance regulator with an adeno–associated virus vector," *Proc. Natl, Acad. Sci. USA*, 90(22):10613–10617, 1993.
Flotte et al., "An improved system for packaging recombinant adeno–associated virus vectors capable of in vivo transduction," *Gene Ther.* 2:29–37, 1995.
Jooss et al., "Transduction of dendritic cells by DNA viral vectors directs the immune response to transgene products in muscle fibers," *J. Virol.* 72:4212–4223, 1998.
Klein et al., "Neuron–specific transduction in the rat septohippocampal or nigrostriatal pathway by recombinant adeno–associated virus vectors," *Exp. Neurol.* 150:183–194, 1998.
Murphy et al., "Long–term correction of obesity and diabetes in genetically obese mice by a single intramuscular injection of recombinant adeno–associated virus encoding mouse leptin," *Proc. Natl. Acad. Sci. USA* 94:13921–13926, 1997.
Muzyczka, "Use of adeno–associated virus as a general transduction vector for mammalian cells," *Curr. Topics Microbiol. Immunol.* 158:97–129, 1992.
Rosenfeld et al., "In vivo transfer of the human cystic fibrosis transmembrane conductance regulator gene to the airway epithelium," *Cell*, 68:143–155, 1992.
Song et al., "Sustained secretion of human alpha 1–antitrypsin from murine muscle transduced with adeno–associated virus vectors," *Proc. Natl, Acad. Sci. USA*, 95:14384–14388, 1998.
Guo et al., "Evaluation of promoter strength for hepatic gene expression in vivo following adenovirus–mediated gene transfer," *Gene Ther.* 3:802–810, 1996.

(List continued on next page.)

*Primary Examiner*—Scott D. Priebe
*Assistant Examiner*—Sumesh Kaushal
(74) *Attorney, Agent, or Firm*—Williams, Morgan & Amerson, P.C.

(57) ABSTRACT

The subject invention concerns materials and methods for gene therapy. One aspect of the invention pertains to vectors which can be used to effect genetic therapy in animals or humans having genetic disorders where expression of high levels of a protein of interest are required to treat or correct the disorder. The subject invention also pertains to methods for treating animals or humans in need of gene therapy to treat or correct a genetic disorder. The materials and methods of the invention can be used to provide therapeutically effective levels of a protein that is non-functional, or that is absent or deficient in the animal or human to be treated. In one embodiment, the materials and methods can be used to treat alpha-1-antitrypsin deficiency.

27 Claims, 58 Drawing Sheets

OTHER PUBLICATIONS

Hofmann et al., "Rapid retroviral delivery of tetracycline–inducible genes in a single autoregulatory cassette," *Proc. Natl, Acad. Sci. USA* 93:5185–5190, 1996.

Hug et al., "Transcriptional repression by methylation: cooperativity between a CpG cluster in the promoter and remote CpG–rich regions," *FEBS Lett*. 379:251–254, 1996.

International Search Report for Application No. PCT/US99/08921, dated Dec. 12, 1999.

Xiao et al., "Adeno–associated virus as a vector for liver–directed gene therapy," *J. Virol*. 72:10222–10226, 1998.

* cited by examiner

Genomic DNA Episomal DNA Control 1 2 3 - 1 2 3 - + -

C-AT (Ligation of pTR and aat) (SEQ ID NO:1)

```
gggggggggg ggggggggtt ggccactccc tctctgcgcg ctcgctcgct cactgaggcc 60
gggcgaccaa aggtcgcccg acgcccgggc tttgcccggg cggcctcagt gagcgagcga 120
gcgcgcagag agggagtggc caactccatc actaggggtt cctagatctg aattcggtac 180
ccgttacata acttacggta aatggcccgc ctggctgacc gcccaacgac ccccgcccat 240
tgacgtcaat aatgacgtat gttcccatag taacgccaat agggactttc cattgacgtc 300
aatgggtgga gtatttacgg taaactgccc acttggcagt acatcaagtg tatcatatgc 360
caagtacgcc ccctattgac gtcaatgacg gtaaatggcc cgcctggcat tatgcccagt 420
acatgacctt atgggacttt cctacttggc agtacatcta cgtattagtc atcgctatta 480
ccatggtgat gcggttttgg cagtacatca atgggcgtgg atagcggttt gactcacggg 540
gatttccaag tctccacccc attgacgtca atgggagttt gttttggcac caaaatcaac 600
gggactttcc aaaatgtcgt aacaactccg ccccattgac gcaaatgggc ggtaggcgtg 660
tacggtggga ggtctatata agcagagctc gtttagtgaa ccgtcagatc gcctggagac 720
gccatccacg ctgttttgac ctccatagaa gacaccggga ccgatccagc ctccggactc 780
tagaactagt ggatcccccg ggctgcagga attcgatatc aagcttgggg attttcaggc 840
accaccactg acctgggaca gtgaatcgac aatgccgtct tctgtctcgt ggggcatcct 900
cctgctggca ggcctgtgct gcctggtccc tgtctccctg gctgaggatc cccagggaga 960
tgctgcccag aagacagata catcccacca tgatcaggat cacccaacct tcaacaagat 1020
cacccccaac ctggctgagt tcgccttcag cctataccgc cagctggcac accagtccaa 1080
cagcaccaat atcttcttct ccccagtgag catcgctaca gcctttgcaa tgctctccct 1140
ggggaccaag gctgacactc acgatgaaat cctggagggc ctgaatttca acctcacgga 1200
gattccggag gctcagatcc atgaaggctt ccaggaactc ctccgtaccc tcaaccagcc 1260
agacagccag ctccagctga ccaccggcaa tggcctgttc ctcagcgagg gcctgaagct 1320
agtggataag tttttggagg atgttaaaaa gttgtaccac tcagaagcct tcactgtcaa 1380
cttcggggac accgaagagg ccaagaaaca gatcaacgat tacgtggaga agggtactca 1440
agggaaaatt gtggatttgg tcaaggagct tgacagagac acagtttttg ctctggtgaa 1500
ttacatcttc tttaaaggca aatggagag  accctttgaa gtcaaggaca ccgaggaaga 1560
ggacttccac gtggaccagg tgaccaccgt gaaggtgcct atgatgaagc gtttaggcat 1620
gtttaacatc cagcactgta agaagctgtc cagctgggtg ctgctgatga aatacctggg 1680
caatgccacc gccatcttct tcctgcctga tgaggggaaa ctacagcacc tggaaaatga 1740
actcacccac gatatcatca ccaagttcct ggaaaatgaa gacagaaggt ctgccagctt 1800
acatttaccc aaactgtcca ttactggaac ctatgatctg aagagcgtcc tgggtcaact 1860
gggcatcact aaggtcttca gcaatggggc tgacctctcc ggggtcacag aggaggcacc 1920
cctgaagctc tccaaggccg tgcataaggc tgtgctgacc atcgacgaga aagggactga 1980
agctgctggg gccatgtttt tagaggccat acccatgtct atcccccccg aggtcaagtt 2040
caacaaaccc tttgtcttct taatgattga acaaaatacc aagtctcccc tcttcatggg 2100
aaaagtggtg aatcccaccc aaaaataact gcctctcgct cctcaacccc tcccctccat 2160
ccctggcccc ctccctggat gacattaaag aagggttgag ctggtaaccc cccccccccc 2220
tgcaggggcc ctcgagcagt gtggttttgc aagaggaagc aaaaagcctc tccacccagg 2280
cctggaatgt ttccacccaa gtcgaaggca gtgtggtttt gcaagaggaa gcaaaaagcc 2340
tctccaccca ggcctggaat gtttccaccc aatgtcgagc aaccccgccc agcgtcttgt 2400
cattggcgaa ttcgaacacg cagatgcagt cggggcggcg cggtcccagg tccacttcgc 2460
atattaaggt gacgcgtgtg gcctcgaaca ccgagcgacc ctgcagccaa tatgggatcg 2520
gccattgaac aagatggatt gcacgcaggt tctccggccg cttgggtgga gaggctattc 2580
ggctatgact gggcacaaca gacaatcggc tgctctgatg ccgccgtgtt ccggctgtca 2640
```

FIG. 15A

C-AT (Ligation of pTR and aat) (cont.)

```
gcgcaggggc gcccggttct ttttgtcaag accgacctgt ccggtgccct gaatgaactg 2700
caggacgagg cagcgcggct atcgtggctg gccacgacgg gcgttccttg cgcagctgtg 2760
ctcgacgttg tcactgaagc gggaagggac tggctgctat tgggcgaagt gccggggcag 2820
gatctcctgt catctcacct tgctcctgcc gagaaagtat ccatcatggc tgatgcaatg 2880
cggcggctgc atacgcttga tccggctacc tgcccattcg accaccaagc gaaacatcgc 2940
atcgagcgag cacgtactcg gatggaagcc ggtcttgtcg atcaggatga tctggacgaa 3000
gagcatcagg ggctcgcgcc agccgaactg ttcgccaggc tcaaggcgcg catgcccgac 3060
ggcgaggatc tcgtcgtgac ccatggcgat gcctgcttgc cgaatatcat ggtggaaaat 3120
ggccgctttt ctggattcat cgactgtggc cggctgggtg tggcggaccg ctatcaggac 3180
atagcgttgg ctacccgtga tattgctgaa gagcttggcg gcgaatgggc tgaccgcttc 3240
ctcgtgcttt acggtatcgc cgctcccgat tcgcagcgca tcgccttcta tcgccttctt 3300
gacgagttct tctgagggga tccgtcgact agagctcgct gatcagcctc gactgtgcct 3360
tctagttgcc agccatctgt tgtttgcccc tcccccgtgc cttccttgac cctggaaggt 3420
gccactccca ctgtcctttc ctaataaaat gaggaaattg catcgcattg tctgagtagg 3480
tgtcattcta ttctgggggg tggggtgggg caggacagca agggggagga ttgggaagac 3540
aatagcaggc atgctgggga gagatctagg aacccctagt gatggagttg gccactccct 3600
ctctgcgcgc tcgctcgctc actgaggccg cccgggcaaa gcccgggcgt cgggcgacct 3660
ttggtcgccc ggcctcagtg agcgagcgag cgcgcagaga gggagtggcc aacccccccc 3720
cccccccccc tgcagccctg cattaatgaa tcggccaacg cgcggggaga ggcggtttgc 3780
gtattgggcg ctcttccgct tcctcgctca ctgactcgct gcgctcggtc gttcggctgc 3840
ggcgagcggt atcagctcac tcaaaggcgg taatacggtt atccacagaa tcaggggata 3900
acgcaggaaa gaacatgtga gcaaaaggcc agcaaaaggc caggaaccgt aaaaaggccg 3960
cgttgctggc gtttttccat aggctccgcc cccctgacga gcatcacaaa aatcgacgct 4020
caagtcagag gtggcgaaac ccgacaggac tataaagata ccaggcgttt ccccctggaa 4080
gctccctcgt gcgctctcct gttccgaccc tgccgcttac cggatacctg tccgcctttc 4140
tcccttcggg aagcgtggcg ctttctcaat gctcacgctg taggtatctc agttcggtgt 4200
aggtcgttcg ctccaagctg ggctgtgtgc acgaaccccc cgttcagccc gaccgctgcg 4260
ccttatccgg taactatcgt cttgagtcca acccggtaag acacgactta tcgccactgg 4320
cagcagccac tggtaacagg attagcagag cgaggtatgt aggcggtgct acagagttct 4380
tgaagtggtg gcctaactac ggctacacta gaaggacagt atttggtatc tgcgctctgc 4440
tgaagccagt taccttcgga aaaagagttg gtagctcttg atccggcaaa caaaccaccg 4500
ctggtagcgg tggttttttt gtttgcaagc agcagattac gcgcagaaaa aaaggatctc 4560
aagaagatcc tttgatcttt tctacggggt ctgacgctca gtggaacgaa aactcacgtt 4620
aagggatttt ggtcatgaga ttatcaaaaa ggatcttcac ctagatcctt ttaaattaaa 4680
aatgaagttt taaatcaatc taaagtatat atgagtaaac ttggtctgac agttaccaat 4740
gcttaatcag tgaggcacct atctcagcga tctgtctatt tcgttcatcc atagttgcct 4800
gactccccgt cgtgtagata actacgatac gggagggctt accatctggc cccagtgctg 4860
caatgatacc gcgagaccca cgctcaccgg ctccagattt atcagcaata aaccagccag 4920
ccggaagggc cgagcgcaga agtggtcctg caactttatc cgcctccatc cagtctatta 4980
attgttgccg ggaagctaga gtaagtagtt cgccagttaa tagtttgcgc aacgttgttg 5040
ccattgctac aggcatcgtg gtgtcacgct cgtcgtttgg tatggcttca ttcagctccg 5100
gttcccaacg atcaaggcga gttacatgat cccccatgtt gtgcaaaaaa gcggttagct 5160
ccttcggtcc tccgatcgtt gtcagaagta agttggccgc agtgttatca ctcatggtta 5220
tggcagcact gcataattct cttactgtca tgccatccgt aagatgcttt tctgtgactg 5280
gtgagtactc aaccaagtca ttctgagaat agtgtatgcg gcgaccgagt tgctcttgcc 5340
```

FIG. 15B

C-AT (Ligation of pTR and aat) (cont.)

```
cggcgtcaat acgggataat accgcgccac atagcagaac tttaaaagtg ctcatcattg 5400
gaaaacgttc ttcggggcga aaactctcaa ggatcttacc gctgttgaga tccagttcga 5460
tgtaacccac tcgtgcaccc aactgatctt cagcatcttt tactttcacc agcgtttctg 5520
ggtgagcaaa aacaggaagg caaaatgccg caaaaaaggg aataagggcg acacggaaat 5580
gttgaatact catactcttc ctttttcaat attattgaag catttatcag ggttattgtc 5640
tcatgagcgg atacatattt gaatgtattt agaaaaataa acaaataggg gttccgcgca 5700
catttccccg aaaagtgcca cctgacgtct aagaaaccat tattatcatg acattaacct 5760
ataaaaatag gcgtatcacg aggccctttc gtctcgcgcg tttcggtgat gacggtgaaa 5820
acctctgaca catgcagctc ccggagacgg tcacagcttg tctgtaagcg gatgccggga 5880
gcagacaagc ccgtcagggc gcgtcagcgg gtgttggcgg gtgtcggggc tggcttaact 5940
atgcggcatc agagcagatt gtactgagag tgcaccatat gcggtgtgaa ataccgcaca 6000
gatgcgtaag gagaaaatac cgcatcagga aattgtaaac gttaatattt tgttaaaatt 6060
cgcgttaaat ttttgttaaa tcagctcatt ttttaaccaa taggccgaaa tcggcaaaat 6120
cccttataaa tcaaaagaat agaccgagat agggttgagt gttgttccag tttggaacaa 6180
gagtccacta ttaaagaacg tggactccaa cgtcaaaggg cgaaaaaccg tctatcaggg 6240
cgatggccca ctacgtgaac catcacccta atcaagtttt ttggggtcga ggtgccgtaa 6300
agcactaaat cggaacccta aagggagccc ccgatttaga gcttgacggg gaaagccggc 6360
gaacgtggcg agaaaggaag ggaagaaagc gaaaggagcg ggcgctaggg cgctggcaag 6420
tgtagcggtc acgctgcgcg taaccaccac acccgccgcg cttaatgcgc cgctacaggg 6480
cgcgtcgcgc cattcgccat tcaggctacg caactgttgg gaagggcgat cggtgcgggc 6540
ctcttcgcta ttacgccagg ctgca                                      6565
```

FIG. 15C

E-AT (Ligation of AAT and elf) (SEQ ID NO:2)

```
gggggggggg ggggggggtt ggccactccc tctctgcgcg ctcgctcgct cactgaggcc 60
gggcgaccaa aggtcgcccg acgcccgggc tttgcccggg cggcctcagt gagcgagcga 120
gcgcgcagag agggagtggc caactccatc actaggggtt cctagatctg aattcggtac 180
cttggagcta agccagcaat ggtagaggga agattctgca cgtcccttcc aggcggcctc 240
cccgtcacca cccccccaa cccgccccga ccggagctga gagtaattca tacaaaagga 300
ctcgcccctg ccttggggaa tcccagggac cgtcgttaaa ctcccactaa cgtagaaccc 360
agagatcgct gcgttcccgc cccctcaccc gcccgctctc gtcatcactg aggtggagaa 420
gagcatgcgt gaggctccgg tgcccgtcag tgggcagagc gcacatcgcc cacagtcccc 480
gagaagttgg ggggaggggt cggcaattga accggtgcct agagaaggtg gcgcggggta 540
aactgggaaa gtgatgtcgt gtactggctc cgcctttttc ccgagggtgg gggagaaccg 600
tatataagtg cagtagtcgc cgtgaacgtt ctttttcgca acgggtttgc cgccagaaca 660
caggtaagtg ccgtgtgtgg ttcccgcggg cctggcctct ttacgggtta tggcccttgc 720
gtgccttgaa ttacttccac gcccctggct gcagtacgtg attcttgatc ccgagcttcg 780
ggttggaagt gggtgggaga gttcgaggcc ttgcgcttaa ggagcccctt cgcctcgtgc 840
ttgagttgag gcctggcctg ggcgctgggg ccgccgcgtg cgaatctggt ggcaccttcg 900
cgcctgtctc gctgctttcg ataagtctct agccatttaa aatttttgat gacctgctgc 960
gacgcttttt ttctggcaag atagtcttgt aaatgcgggc caagatctgc acactggtat 1020
ttcggttttt ggggccgcgg gcggcgacgg ggcccgtgcg tcccagcgca catgttcggc 1080
gaggcggggc ctgcgagcgc ggccaccgag aatcggacgg gggtagtctc aagctggccg 1140
gcctgctctg gtgcctggcc tcgcgccgcc gtgtatcgcc ccgccctggg cggcaaggct 1200
ggcccggtcg gcaccagttg cgtgagcgga aagatggccg cttcccggcc ctgctgcagg 1260
gagctcaaaa tggaggacgc ggcgctcggg agagcgggcg ggtgagtcac ccacacaaag 1320
gaaaagggcc tttccgtcct cagccgtcgc ttcatgtgac tccacggagt accgggcgcc 1380
gtccaggcac ctcgattagt tctcgagctt ttggagtacg tcgtctttag gttgggggga 1440
ggggttttat gcgatggagt ttccccacac tgagtgggtg gagactgaag ttaggccagc 1500
ttggcacttg atgtaattct ccttggaatt tgcccttttt gagtttggat cttggttcat 1560
tctcaagcct cagacagtgg ttcaaagttt ttttcttcca tttcaggtgt cgtgaaaatc 1620
tagaactagt ggatcccccg ggctgcagga attcgatatc aagcttgggg attttcaggc 1680
accaccactg acctgggaca gtgaatcgac aatgccgtct tctgtctcgt ggggcatcct 1740
cctgctggca ggcctgtgct gcctggtccc tgtctccctg gctgaggatc cccagggaga 1800
tgctgcccag aagacagata catcccacca tgatcaggat cacccaacct tcaacaagat 1860
cacccccaac ctggctgagt tcgccttcag cctataccgc cagctggcac accagtccaa 1920
cagcaccaat atcttcttct ccccagtgag catcgctaca gcctttgcaa tgctctccct 1980
ggggaccaag gctgacactc acgatgaaat cctggagggc ctgaatttca acctcacgga 2040
gattccggag gctcagatcc atgaaggctt ccaggaactc ctccgtaccc tcaaccagcc 2100
agacagccag ctccagctga ccaccggcaa tggcctgttc ctcagcgagg gcctgaagct 2160
agtggataag tttttggagg atgttaaaaa gttgtaccac tcagaagcct tcactgtcaa 2220
cttcggggac accgaagagg ccaagaaaca gatcaacgat tacgtggaga agggtactca 2280
agggaaaatt gtggatttgg tcaaggagct tgacagagac acagtttttg ctctggtgaa 2340
ttacatcttc tttaaaggca aatgggagag accctttgaa gtcaaggaca ccgaggaaga 2400
ggacttccac gtggaccagg tgaccaccgt gaaggtgcct atgatgaagc gtttaggcat 2460
gtttaacatc cagcactgta agaagctgtc cagctgggtg ctgctgatga aatacctggg 2520
caatgccacc gccatcttct tcctgcctga tgaggggaaa ctacagcacc tggaaaatga 2580
actcacccac gatatcatca ccaagttcct ggaaaatgaa gacagaaggt ctgccagctt 2640
```

FIG. 16A

E-AT (Ligation of AAT and elf) (cont.)

```
acatttaccc aaactgtcca ttactggaac ctatgatctg aagagcgtcc tgggtcaact 2700
gggcatcact aaggtcttca gcaatggggc tgacctctcc ggggtcacag aggaggcacc 2760
cctgaagctc tccaaggccg tgcataaggc tgtgctgacc atcgacgaga aagggactga 2820
agctgctggg gccatgtttt tagaggccat acccatgtct atcccccccg aggtcaagtt 2880
caacaaaccc tttgtcttct taatgattga acaaaatacc aagtctcccc tcttcatggg 2940
aaaagtggtg aatcccaccc aaaaataact gcctctcgct cctcaacccc tcccctccat 3000
ccctggcccc ctccctggat gacattaaag aagggttgag ctggtaaccc cccccccccc 3060
tgcaggggcc ctcgagcagt gtggttttgc aagaggaagc aaaaagcctc tccacccagg 3120
cctggaatgt ttccacccaa gtcgaaggca gtgtggtttt gcaagaggaa gcaaaaagcc 3180
tctccaccca ggcctggaat gtttccaccc aatgtcgagc aaccccgccc agcgtcttgt 3240
cattggcgaa ttcgaacacg cagatgcagt cggggcggcg cggtcccagg tccacttcgc 3300
atattaaggt gacgcgtgtg gcctcgaaca ccgagcgacc ctgcagccaa tatgggatcg 3360
gccattgaac aagatggatt gcacgcaggt tctccggccg cttgggtgga gaggctattc 3420
ggctatgact gggcacaaca gacaatcggc tgctctgatg ccgccgtgtt ccggctgtca 3480
gcgcaggggc gcccggttct ttttgtcaag accgacctgt ccggtgccct gaatgaactg 3540
caggacgagg cagcgcggct atcgtggctg gccacgacgg gcgttccttg cgcagctgtg 3600
ctcgacgttg tcactgaagc gggaagggac tggctgctat tgggcgaagt gccggggcag 3660
gatctcctgt catctcacct tgctcctgcc gagaaagtat ccatcatggc tgatgcaatg 3720
cggcggctgc atacgcttga tccggctacc tgcccattcg accaccaagc gaaacatcgc 3780
atcgagcgag cacgtactcg gatggaagcc ggtcttgtcg atcaggatga tctggacgaa 3840
gagcatcagg ggctcgcgcc agccgaactg ttcgccaggc tcaaggcgcg catgcccgac 3900
ggcgaggatc tcgtcgtgac ccatggcgat gcctgcttgc cgaatatcat ggtggaaaat 3960
ggccgctttt ctggattcat cgactgtggc cggctgggtg tggcggaccg ctatcaggac 4020
atagcgttgg ctacccgtga tattgctgaa gagcttggcg gcgaatgggc tgaccgcttc 4080
ctcgtgcttt acggtatcgc cgctcccgat tcgcagcgca tcgccttcta tcgccttctt 4140
gacgagttct tctgagggga tccgtcgact agagctcgct gatcagcctc gactgtgcct 4200
tctagttgcc agccatctgt tgtttgcccc tcccccgtgc cttccttgac cctggaaggt 4260
gccactccca ctgtcctttc ctaataaaat gaggaaattg catcgcattg tctgagtagg 4320
tgtcattcta ttctgggggg tggggtgggg caggacagca agggggagga ttgggaagac 4380
aatagcaggc atgctgggga gagatctagg aacccctagt gatggagttg gccactccct 4440
ctctgcgcgc tcgctcgctc actgaggccg cccgggcaaa gcccgggcgt cgggcgacct 4500
ttggtcgccc ggcctcagtg agcgagcgag cgcgcagaga gggagtggcc aacccccccc 4560
cccccccccc tgcagccctg cattaatgaa tcggccaacg cgcggggaga ggcggtttgc 4620
gtattgggcg ctcttccgct tcctcgctca ctgactcgct gcgctcggtc gttcggctgc 4680
ggcgagcggt atcagctcac tcaaaggcgg taatacggtt atccacagaa tcaggggata 4740
acgcaggaaa gaacatgtga gcaaaaggcc agcaaaaggc caggaaccgt aaaaaggccg 4800
cgttgctggc gtttttccat aggctccgcc cccctgacga gcatcacaaa aatcgacgct 4860
caagtcagag gtggcgaaac ccgacaggac tataaagata ccaggcgttt ccccctggaa 4920
gctccctcgt gcgctctcct gttccgaccc tgccgcttac cggatacctg tccgcctttc 4980
tcccttcggg aagcgtggcg ctttctcaat gctcacgctg taggtatctc agttcggtgt 5040
aggtcgttcg ctccaagctg ggctgtgtgc acgaaccccc cgttcagccc gaccgctgcg 5100
ccttatccgg taactatcgt cttgagtcca acccggtaag acacgactta tcgccactgg 5160
cagcagccac tggtaacagg attagcagag cgaggtatgt aggcggtgct acagagttct 5220
tgaagtggtg gcctaactac ggctacacta gaaggacagt atttggtatc tgcgctctgc 5280
tgaagccagt taccttcgga aaaagagttg gtagctcttg atccggcaaa caaaccaccg 5340
ctggtagcgg tggttttttt gtttgcaagc agcagattac gcgcagaaaa aaaggatctc 5400
aagaagatcc tttgatcttt tctacggggt ctgacgctca gtggaacgaa aactcacgtt 5460
```

FIG. 16B

E-AT (Ligation of AAT and elf) (cont.)

```
aagggatttt ggtcatgaga ttatcaaaaa ggatcttcac ctagatcctt ttaaattaaa 5520
aatgaagttt taaatcaatc taaagtatat atgagtaaac ttggtctgac agttaccaat 5580
gcttaatcag tgaggcacct atctcagcga tctgtctatt tcgttcatcc atagttgcct 5640
gactccccgt cgtgtagata actacgatac gggagggctt accatctggc cccagtgctg 5700
caatgatacc gcgagaccca cgctcaccgg ctccagattt atcagcaata aaccagccag 5760
ccggaagggc cgagcgcaga agtggtcctg caactttatc cgcctccatc cagtctatta 5820
attgttgccg ggaagctaga gtaagtagtt cgccagttaa tagtttgcgc aacgttgttg 5880
ccattgctac aggcatcgtg gtgtcacgct cgtcgtttgg tatggcttca ttcagctccg 5940
gttcccaacg atcaaggcga gttacatgat cccccatgtt gtgcaaaaaa gcggttagct 6000
ccttcggtcc tccgatcgtt gtcagaagta agttggccgc agtgttatca ctcatggtta 6060
tggcagcact gcataattct cttactgtca tgccatccgt aagatgcttt tctgtgactg 6120
gtgagtactc aaccaagtca ttctgagaat agtgtatgcg gcgaccgagt tgctcttgcc 6180
cggcgtcaat acgggataat accgcgccac atagcagaac tttaaaagtg ctcatcattg 6240
gaaaacgttc ttcggggcga aaactctcaa ggatcttacc gctgttgaga tccagttcga 6300
tgtaacccac tcgtgcaccc aactgatctt cagcatcttt tactttcacc agcgtttctg 6360
ggtgagcaaa aacaggaagg caaaatgccg caaaaaaggg aataagggcg acacggaaat 6420
gttgaatact catactcttc ctttttcaat attattgaag catttatcag ggttattgtc 6480
tcatgagcgg atacatattt gaatgtattt agaaaaataa acaaataggg gttccgcgca 6540
catttccccg aaaagtgcca cctgacgtct aagaaaccat tattatcatg acattaacct 6600
ataaaaatag gcgtatcacg aggccctttc gtctcgcgcg tttcggtgat gacggtgaaa 6660
acctctgaca catgcagctc ccggagacgg tcacagcttg tctgtaagcg gatgccggga 6720
gcagacaagc ccgtcagggc gcgtcagcgg gtgttggcgg gtgtcggggc tggcttaact 6780
atgcggcatc agagcagatt gtactgagag tgcaccatat gcggtgtgaa ataccgcaca 6840
gatgcgtaag gagaaaatac cgcatcagga aattgtaaac gttaatattt tgttaaaatt 6900
cgcgttaaat ttttgttaaa tcagctcatt ttttaaccaa taggccgaaa tcggcaaaat 6960
cccttataaa tcaaaagaat agaccgagat agggttgagt gttgttccag tttggaacaa 7020
gagtccacta ttaaagaacg tggactccaa cgtcaaaggg cgaaaaaccg tctatcaggg 7080
cgatggccca ctacgtgaac catcacccta atcaagtttt ttggggtcga ggtgccgtaa 7140
agcactaaat cggaacccta aagggagccc ccgatttaga gcttgacggg gaaagccggc 7200
gaacgtggcg agaaaggaag ggaagaaagc gaaaggagcg ggcgctaggg cgctggcaag 7260
tgtagcggtc acgctgcgcg taaccaccac acccgccgcg cttaatgcgc cgctacaggg 7320
cgcgtcgcgc cattcgccat tcaggctacg caactgttgg gaagggcgat cggtgcgggc 7380
ctcttcgcta ttacgccagg ctgca                                       7405
```

FIG. 16C dE-A (Fragment 2 Circularized) (SEQ ID NO:3)

```
gggggggggg ggggggggtt ggccactccc tctctgcgcg ctcgctcgct cactgaggcc 60
gggcgaccaa aggtcgcccg acgcccgggc tttgcccggg cggcctcagt gagcgagcga 120
gcgcgcagag agggagtggc caactccatc actaggggtt cctagatctg aattcggtac 180
cttggagcta agccagcaat ggtagaggga agattctgca cgtcccttcc aggcggcctc 240
cccgtcacca cccccccaa cccgccccga ccggagctga gagtaattca tacaaaagga 300
ctcgcccctg ccttggggaa tcccagggac cgtcgttaaa ctcccactaa cgtagaaccc 360
agagatcgct gcgttcccgc cccctcaccc gcccgctctc gtcatcactg aggtggagaa 420
gagcatgcgt gaggctccgg tgcccgtcag tgggcagagc gcacatcgcc cacagtcccc 480
gagaagttgg ggggaggggt cggcaattga accggtgcct agagaaggtg gcgcggggta 540
aactgggaaa gtgatgtcgt gtactggctc cgcctttttc ccgagggtgg gggagaaccg 600
tatataagtg cagtagtcgc cgtgaacgtt ctttttcgca acgggtttgc cgccagaaca 660
caggtaagtg ccgtgtgtgg ttcccgcggg cggcgacggg gcccgtgcgt cccagcgcac 720
atgttcggcg aggcggggcc tgcgagcgcg gccaccgaga atcggacggg ggtagtctca 780
agctggccgg cctgctctgg tgcctggcct cgcgccgccg tgtatcgccc cgccctgggc 840
ggcaaggctg gcccggtcgg caccagttgc gtgagcggaa agatggccgc ttcccggccc 900
tgctgcaggg agctcaaaat ggaggacgcg gcgctcggga gagcgggcgg gtgagtcacc 960
cacacaaagg aaaagggcct ttccgtcctc agccgtcgct tcatgtgact ccacggagta 1020
ccgggcgccg tccaggcacc tcgattagtt ctcgagcttt tggagtacgt cgtctttagg 1080
ttggggggag gggttttatg cgatggagtt tccccacact gagtgggtgg agactgaagt 1140
taggccagct tggcacttga tgtaattctc cttggaattt gccctttttg agtttggatc 1200
ttggttcatt ctcaagcctc agacagtggt tcaaagtttt tttcttccat ttcaggtgtc 1260
gtgaaaatct agaactagtg gatcccccgg gctgcaggaa ttcgatatca agcttgggga 1320
ttttcaggca ccaccactga cctgggacag tgaatcgaca atgccgtctt ctgtctcgtg 1380
gggcatcctc ctgctggcag gcctgtgctg cctggtccct gtctccctgg ctgaggatcc 1440
ccagggagat gctgcccaga agacagatac atcccaccat gatcaggatc acccaacctt 1500
caacaagatc acccccaacc tggctgagtt cgccttcagc ctataccgcc agctggcaca 1560
ccagtccaac agcaccaata tcttcttctc cccagtgagc atcgctacag cctttgcaat 1620
gctctccctg gggaccaagg ctgacactca cgatgaaatc ctggagggcc tgaatttcaa 1680
cctcacggag attccggagg ctcagatcca tgaaggcttc caggaactcc tccgtaccct 1740
caaccagcca gacagccagc tccagctgac caccggcaat ggcctgttcc tcagcgaggg 1800
cctgaagcta gtggataagt tttggagga tgttaaaaag ttgtaccact cagaagcctt 1860
cactgtcaac ttcggggaca ccgaagaggc caagaaacag atcaacgatt acgtggagaa 1920
gggtactcaa gggaaaattg tggatttggt caaggagctt gacagagaca cagtttttgc 1980
tctggtgaat tacatcttct ttaaaggcaa atgggagaga ccctttgaag tcaaggacac 2040
cgaggaagag gacttccacg tggaccaggt gaccaccgtg aaggtgccta tgatgaagcg 2100
tttaggcatg tttaacatcc agcactgtaa gaagctgtcc agctgggtgc tgctgatgaa 2160
atacctgggc aatgccaccg ccatcttctt cctgcctgat gaggggaaac tacagcacct 2220
ggaaaatgaa ctcacccacg atatcatcac caagttcctg gaaaatgaag acagaaggtc 2280
tgccagctta catttaccca aactgtccat tactggaacc tatgatctga agagcgtcct 2340
gggtcaactg ggcatcacta aggtcttcag caatggggct gacctctccg gggtcacaga 2400
ggaggcaccc ctgaagctct ccaaggccgt gcataaggct gtgctgacca tcgacgagaa 2460
agggactgaa gctgctgggg ccatgttttt agaggccata cccatgtcta tcccccccga 2520
ggtcaagttc aacaaaccct ttgtcttctt aatgattgaa caaaatacca agtctcccct 2580
cttcatggga aaagtggtga atcccaccca aaaataactg cctctcgctc ctcaacccct 2640
```

FIG. 17A dE-A (Fragment 2 Circularized) (cont.)

```
cccctccatc cctggccccc tccctggatg acattaaaga agggttgagc tggtaacccc 2700
cccccccct gcaggggccc tcgagcagtg tggttttgca agaggaagca aaaagcctct 2760
ccacccaggc ctggaatgtt tccacccaag tcgaaggcag tgtggttttg caagaggaag 2820
caaaaagcct ctccacccag gcctggaatg tttccaccca atgtcgagca accccgccca 2880
gcgtcttgtc attggcgaat tcgaacacgc agatgcagtc ggggcggcgc ggtcccaggt 2940
ccacttcgca tattaaggtg acgcgtgtgg cctcgaacac cgagcgaccc tgcagccaat 3000
atgggatcgg ccattgaaca agatggattg cacgcaggtt ctccggccgc ttgggtggag 3060
aggctattcg gctatgactg ggcacaacag acaatcggct gctctgatgc cgccgtgttc 3120
cggctgtcag cgcaggggcg cccggttctt tttgtcaaga ccgacctgtc cggtgccctg 3180
aatgaactgc aggacgaggc agcgcggcta tcgtggctgg ccacgacggg cgttccttgc 3240
gcagctgtgc tcgacgttgt cactgaagcg ggaagggact ggctgctatt gggcgaagtg 3300
ccggggcagg atctcctgtc atctcacctt gctcctgccg agaaagtatc catcatggct 3360
gatgcaatgc ggcggctgca tacgcttgat ccggctacct gcccattcga ccaccaagcg 3420
aaacatcgca tcgagcgagc acgtactcgg atggaagccg gtcttgtcga tcaggatgat 3480
ctggacgaag agcatcaggg gctcgcgcca gccgaactgt tcgccaggct caaggcgcgc 3540
atgcccgacg gcgaggatct cgtcgtgacc catggcgatg cctgcttgcc gaatatcatg 3600
gtggaaaatg gccgcttttc tggattcatc gactgtggcc ggctgggtgt ggcggaccgc 3660
tatcaggaca tagcgttggc tacccgtgat attgctgaag agcttggcgg cgaatgggct 3720
gaccgcttcc tcgtgcttta cggtatcgcc gctcccgatt cgcagcgcat cgccttctat 3780
cgccttcttg acgagttctt ctgaggggat ccgtcgacta gagctcgctg atcagcctcg 3840
actgtgcctt ctagttgcca gccatctgtt gtttgcccct cccccgtgcc ttccttgacc 3900
ctggaaggtg ccactcccac tgtcctttcc taataaaatg aggaaattgc atcgcattgt 3960
ctgagtaggt gtcattctat tctggggggt ggggtggggc aggacagcaa gggggaggat 4020
tgggaagaca atagcaggca tgctggggag agatctagga acccctagtg atggagttgg 4080
ccactccctc tctgcgcgct cgctcgctca ctgaggccgc ccgggcaaag cccgggcgtc 4140
gggcgacctt tggtcgcccg gcctcagtga gcgagcgagc gcgcagagag ggagtggcca 4200
acccccccc ccccccccct gcagccctgc attaatgaat cggccaacgc gcggggagag 4260
gcggtttgcg tattgggcgc tcttccgctt cctcgctcac tgactcgctg cgctcggtcg 4320
ttcggctgcg gcgagcggta tcagctcact caaaggcggt aatacggtta tccacagaat 4380
caggggataa cgcaggaaag aacatgtgag caaaaggcca gcaaaaggcc aggaaccgta 4440
aaaaggccgc gttgctggcg tttttccata ggctccgccc ccctgacgag catcacaaaa 4500
atcgacgctc aagtcagagg tggcgaaacc cgacaggact ataaagatac caggcgtttc 4560
cccctggaag ctccctcgtg cgctctcctg ttccgaccct gccgcttacc ggatacctgt 4620
ccgcctttct cccttcggga agcgtggcgc tttctcaatg ctcacgctgt aggtatctca 4680
gttcggtgta ggtcgttcgc tccaagctgg gctgtgtgca cgaacccccc gttcagcccg 4740
accgctgcgc cttatccggt aactatcgtc ttgagtccaa cccggtaaga cacgacttat 4800
cgccactggc agcagccact ggtaacagga ttagcagagc gaggtatgta ggcggtgcta 4860
cagagttctt gaagtggtgg cctaactacg gctacactag aaggacagta tttggtatct 4920
gcgctctgct gaagccagtt accttcggaa aaagagttgg tagctcttga tccggcaaac 4980
aaaccaccgc tggtagcggt ggtttttttg tttgcaagca gcagattacg cgcagaaaaa 5040
aaggatctca agaagatcct ttgatctttt ctacggggtc tgacgctcag tggaacgaaa 5100
actcacgtta agggattttg gtcatgagat tatcaaaaag gatcttcacc tagatccttt 5160
taaattaaaa atgaagtttt aaatcaatct aaagtatata tgagtaaact tggtctgaca 5220
gttaccaatg cttaatcagt gaggcaccta tctcagcgat ctgtctattt cgttcatcca 5280
tagttgcctg actccccgtc gtgtagataa ctacgatacg ggagggctta ccatctggcc 5340
ccagtgctgc aatgataccg cgagacccac gctcaccggc tccagattta tcagcaataa 5400
```

FIG. 17B dE-A (Fragment 2 Circularized) (cont.)

```
accagccagc cggaagggcc gagcgcagaa gtggtcctgc aactttatcc gcctccatcc 5460
agtctattaa ttgttgccgg gaagctagag taagtagttc gccagttaat agtttgcgca 5520
acgttgttgc cattgctaca ggcatcgtgg tgtcacgctc gtcgtttggt atggcttcat 5580
tcagctccgg ttcccaacga tcaaggcgag ttacatgatc ccccatgttg tgcaaaaaag 5640
cggttagctc cttcggtcct ccgatcgttg tcagaagtaa gttggccgca gtgttatcac 5700
tcatggttat ggcagcactg cataattctc ttactgtcat gccatccgta agatgctttt 5760
ctgtgactgg tgagtactca accaagtcat tctgagaata gtgtatgcgg cgaccgagtt 5820
gctcttgccc ggcgtcaata cgggataata ccgcgccaca tagcagaact ttaaaagtgc 5880
tcatcattgg aaaacgttct tcggggcgaa aactctcaag gatcttaccg ctgttgagat 5940
ccagttcgat gtaacccact cgtgcaccca actgatcttc agcatctttt actttcacca 6000
gcgtttctgg gtgagcaaaa acaggaaggc aaaatgccgc aaaaaaggga ataagggcga 6060
cacggaaatg ttgaatactc atactcttcc tttttcaata ttattgaagc atttatcagg 6120
gttattgtct catgagcgga tacatatttg aatgtattta gaaaaataaa caaatagggg 6180
ttccgcgcac atttccccga aaagtgccac ctgacgtcta agaaaccatt attatcatga 6240
cattaaccta taaaaatagg cgtatcacga ggccctttcg tctcgcgcgt ttcggtgatg 6300
acggtgaaaa cctctgacac atgcagctcc cggagacggt cacagcttgt ctgtaagcgg 6360
atgccgggag cagacaagcc cgtcagggcg cgtcagcggg tgttggcggg tgtcggggct 6420
ggcttaacta tgcggcatca gagcagattg tactgagagt gcaccatatg cggtgtgaaa 6480
taccgcacag atgcgtaagg agaaaatacc gcatcaggaa attgtaaacg ttaatatttt 6540
gttaaaattc gcgttaaatt tttgttaaat cagctcattt tttaaccaat aggccgaaat 6600
cggcaaaatc ccttataaat caaaagaata gaccgagata gggttgagtg ttgttccagt 6660
ttggaacaag agtccactat taaagaacgt ggactccaac gtcaaagggc gaaaaaccgt 6720
ctatcagggc gatggcccac tacgtgaacc atcaccctaa tcaagttttt tggggtcgag 6780
gtgccgtaaa gcactaaatc ggaaccctaa agggagcccc cgatttagag cttgacgggg 6840
aaagccggcg aacgtggcga gaaaggaagg gaagaaagcg aaaggagcgg gcgctagggc 6900
gctggcaagt gtagcggtca cgctgcgcgt aaccaccaca cccgccgcgc ttaatgcgcc 6960
gctacagggc gcgtcgcgcc attcgccatt caggctacgc aactgttggg aagggcgatc 7020
ggtgcgggcc tcttcgctat tacgccaggc tgca                             7054
```

FIG. 17C p43C-AT (Ligation of TR and aat) (SEQ ID NO:4)

```
gggggggggg ggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatcttc aatattggcc 180
attagccata ttattcattg gttatatagc ataaatcaat attggctatt ggccattgca 240
tacgttgtat ctatatcata atatgtacat ttatattggc tcatgtccaa tatgaccgcc 300
atgttggcat tgattattga ctagttatta atagtaatca attacggggt cattagttca 360
tagcccatat atggagttcc gcgttacata acttacggta aatggcccgc ctggctgacc 420
gcccaacgac ccccgcccat tgacgtcaat aatgacgtat gttcccatag taacgccaat 480
agggactttc cattgacgtc aatgggtgga gtatttacgg taaactgccc acttggcagt 540
acatcaagtg tatcatatgc caagtccgcc ccctattgac gtcaatgacg gtaaatggcc 600
cgcctggcat tatgcccagt acatgacctt acgggacttt cctacttggc agtacatcta 660
cgtattagtc atcgctatta ccatggtgat gcggttttgg cagtacacca atgggcgtgg 720
atagcggttt gactcacggg gatttccaag tctccacccc attgacgtca atgggagttt 780
gttttggcac caaaatcaac gggactttcc aaaatgtcgt aataaccccg ccccgttgac 840
gcaaatgggc ggtaggcgtg tacggtggga ggtctatata agcagagctc gtttagtgaa 900
ccgtcagatc actagaagct ttattgcggt agtttatcac agttaaattg ctaacgcagt 960
cagtgcttct gacacaacag tctcgaactt aagctgcaga agttggtcgt gaggcactgg 1020
gcaggtaagt atcaaggtta caagacaggt ttaaggagac caatagaaac tgggcttgtc 1080
gagacagaga agactcttgc gtttctgata ggcacctatt ggtcttactg acatccactt 1140
tgcctttctc tccacaggtg tccactccca gttcaattac agctcttaag gctagagtac 1200
ttaatacgac tcactatagg ctagaactag tggatccccc gggctgcagg aattcgatat 1260
caagcttggg gattttcagg caccaccact gacctgggac agtgaatcga caatgccgtc 1320
ttctgtctcg tggggcatcc tcctgctggc aggcctgtgc tgcctggtcc ctgtctccct 1380
ggctgaggat ccccagggag atgctgccca gaagacagat acatcccacc atgatcagga 1440
tcacccaacc ttcaacaaga tcacccccaa cctggctgag ttcgccttca gcctataccg 1500
ccagctggca caccagtcca acagcaccaa tatcttcttc tccccagtga gcatcgctac 1560
agcctttgca atgctctccc tggggaccaa ggctgacact cacgatgaaa tcctggaggg 1620
cctgaatttc aacctcacgg agattccgga ggctcagatc catgaaggct tccaggaact 1680
cctccgtacc ctcaaccagc cagacagcca gctccagctg accaccggca atggcctgtt 1740
cctcagcgag ggcctgaagc tagtggataa gtttttggag gatgttaaaa agttgtacca 1800
ctcagaagcc ttcactgtca acttcgggga caccgaagag gccaagaaac agatcaacga 1860
ttacgtggag aagggtactc aagggaaaat tgtggatttg gtcaaggagc ttgacagaga 1920
cacagttttt gctctggtga attacatctt ctttaaaggc aaatgggaga gaccctttga 1980
agtcaaggac accgaggaag aggacttcca cgtggaccag gtgaccaccg tgaaggtgcc 2040
tatgatgaag cgtttaggca tgtttaacat ccagcactgt aagaagctgt ccagctgggt 2100
gctgctgatg aaatacctgg gcaatgccac cgccatcttc ttcctgcctg atgaggggaa 2160
actacagcac ctggaaaatg aactcaccca cgatatcatc accaagttcc tggaaaatga 2220
agacagaagg tctgccagct tacatttacc caaactgtcc attactggaa cctatgatct 2280
gaagagcgtc ctgggtcaac tgggcatcac taaggtcttc agcaatgggg ctgacctctc 2340
cggggtcaca gaggaggcac ccctgaagct ctccaaggcc gtgcataagg ctgtgctgac 2400
catcgacgag aaagggactg aagctgctgg ggccatgttt ttagaggcca tacccatgtc 2460
tatccccccc gaggtcaagt tcaacaaacc ctttgtcttc ttaatgattg aacaaaatac 2520
caagtctccc ctcttcatgg gaaaagtggt gaatcccacc caaaaataac tgcctctcgc 2580
tcctcaaccc ctcccctcca tccctggccc cctccctgga tgacattaaa gaagggttga 2640
```

FIG. 18A p43C-AT (Ligation of TR and aat) (cont.)

```
gctggtaacc cccccccccc ctgcaggggc cctcgacccg ggcggccgct tcgagcagac 2700
atgataagat acattgatga gtttggacaa accacaacta gaatgcagtg aaaaaaatgc 2760
tttatttgtg aaatttgtga tgctattgct ttatttgtaa ccattataag ctgcaataaa 2820
caagttaaca acaacaattg cattcatttt atgtttcagg ttcaggggga gatgtgggag 2880
gtttttaaa gcaagtaaaa cctctacaaa tgtggtaaaa tcgataagga tctaggaacc 2940
cctagtgatg gagttggcca ctccctctct gcgcgctcgc tcgctcactg aggccgcccg 3000
ggcaaagccc gggcgtcggg cgacctttgg tcgcccggcc tcagtgagcg agcgagcgcg 3060
cagagaggga gtggccaacc cccccccccc cccccctgca gcctggcgta atagcgaaga 3120
ggcccgcacc gatcgccctt cccaacagtt gcgtagcctg aatggcgaat ggcgcgacgc 3180
gccctgtagc ggcgcattaa gcgcggcggg tgtggtggtt acgcgcagcg tgaccgctac 3240
acttgccagc gccctagcgc ccgctccttt cgctttcttc ccttcctttc tcgccacgtt 3300
cgccggcttt ccccgtcaag ctctaaatcg ggggctccct ttagggttcc gatttagtgc 3360
tttacggcac ctcgacccca aaaaacttga ttagggtgat ggttcacgta gtgggccatc 3420
gccctgatag acggtttttc gccctttgac gttggagtcc acgttcttta atagtggact 3480
cttgttccaa actggaacaa cactcaaccc tatctcggtc tattcttttg atttataagg 3540
gattttgccg atttcggcct attggttaaa aaatgagctg atttaacaaa aatttaacgc 3600
gaattttaac aaaatattaa cgtttacaat ttcctgatgc ggtattttct ccttacgcat 3660
ctgtgcggta tttcacaccg catatggtgc actctcagta caatctgctc tgatgccgca 3720
tagttaagcc agccccgaca cccgccaaca cccgctgacg cgccctgacg ggcttgtctg 3780
ctcccggcat ccgcttacag acaagctgtg accgtctccg ggagctgcat gtgtcagagg 3840
ttttcaccgt catcaccgaa acgcgcgaga cgaaagggcc tcgtgatacg cctattttta 3900
taggttaatg tcatgataat aatggtttct tagacgtcag gtggcacttt tcggggaaat 3960
gtgcgcggaa cccctatttg tttatttttc taaatacatt caaatatgta tccgctcatg 4020
agacaataac cctgataaat gcttcaataa tattgaaaaa ggaagagtat gagtattcaa 4080
catttccgtg tcgcccttat tccctttttt gcggcatttt gccttcctgt ttttgctcac 4140
ccagaaacgc tggtgaaagt aaaagatgct gaagatcagt tgggtgcacg agtgggttac 4200
atcgaactgg atctcaacag cggtaagatc cttgagagtt ttcgccccga agaacgtttt 4260
ccaatgatga gcacttttaa agttctgcta tgtggcgcgg tattatcccg tattgacgcc 4320
gggcaagagc aactcggtcg ccgcatacac tattctcaga atgacttggt tgagtactca 4380
ccagtcacag aaaagcatct tacggatggc atgacagtaa gagaattatg cagtgctgcc 4440
ataaccatga gtgataacac tgcggccaac ttacttctga caacgatcgg aggaccgaag 4500
gagctaaccg cttttttgca caacatgggg gatcatgtaa ctcgccttga tcgttgggaa 4560
ccggagctga atgaagccat accaaacgac gagcgtgaca ccacgatgcc tgtagcaatg 4620
gcaacaacgt tgcgcaaact attaactggc gaactactta ctctagcttc ccggcaacaa 4680
ttaatagact ggatggaggc ggataaagtt gcaggaccac ttctgcgctc ggcccttccg 4740
gctggctggt ttattgctga taaatctgga gccggtgagc gtgggtctcg cggtatcatt 4800
gcagcactgg ggccagatgg taagccctcc cgtatcgtag ttatctacac gacggggagt 4860
caggcaacta tggatgaacg aaatagacag atcgctgaga taggtgcctc actgattaag 4920
cattggtaac tgtcagacca agtttactca tatatacttt agattgattt aaaacttcat 4980
ttttaattta aaaggatcta ggtgaagatc ctttttgata atctcatgac caaaatccct 5040
taacgtgagt tttcgttcca ctgagcgtca gaccccgtag aaaagatcaa aggatcttct 5100
```

FIG. 18B p43C-AT (Ligation of TR and aat) (cont.)

```
tgagatcctt tttttctgcg cgtaatctgc tgcttgcaaa caaaaaaacc accgctacca 5160
gcggtggttt gtttgccgga tcaagagcta ccaactcttt ttccgaaggt aactggcttc 5220
agcagagcgc agataccaaa tactgtcctt ctagtgtagc cgtagttagg ccaccacttc 5280
aagaactctg tagcaccgcc tacatacctc gctctgctaa tcctgttacc agtggctgct 5340
gccagtggcg ataagtcgtg tcttaccggg ttggactcaa gacgatagtt accggataag 5400
gcgcagcggt cgggctgaac ggggggttcg tgcacacagc ccagcttgga gcgaacgacc 5460
tacaccgaac tgagatacct acagcgtgag cattgagaaa gcgccacgct tcccgaaggg 5520
agaaaggcgg acaggtatcc ggtaagcggc agggtcggaa caggagagcg cacgagggag 5580
cttccagggg gaaacgcctg gtatctttat agtcctgtcg ggtttcgcca cctctgactt 5640
gagcgtcgat ttttgtgatg ctcgtcaggg gggcggagcc tatggaaaaa cgccagcaac 5700
gcggcctttt tacggttcct ggccttttgc tggccttttg ctcacatgtt ctttcctgcg 5760
ttatcccctg attctgtgga taaccgtatt accgcctttg agtgagctga taccgctcgc 5820
cgcagccgaa cgaccgagcg cagcgagtca gtgagcgagg aagcggaaga gcgcccaata 5880
cgcaaaccgc ctctccccgc gcgttggccg attcattaat gcagggctgc ag          5932
```

FIG. 18C p43C-AT-IN (Ligation of p43-C into IN) (SEQ ID NO:5)

```
aattccgcat tgcagagata attgtattta agtgcctagc tcgatacaat aaacgccatt 60
tgaccattca ccacattggt gtgcacctcc actagctgcc ttgactgcct ggcccccca 120
tctctgtctt gcaggacaat gccgtcttct gtctcgtggg gcatcctcct gctggcaggc 180
ctgtgctgcc tggtccctgt ctccctggct gaggatcccc agggagatgc tgcccagaag 240
acagatacat cccaccatga tcaggatcac ccaaccttca acaagatcac ccccaacctg 300
gctgagttcg ccttcagcct ataccgccag ctggcacacc agtccaacag caccaatatc 360
ttcttctccc cagtgagcat cgctacagcc tttgcaatgc tctccctggg gaccaaggct 420
gacactcacg atgaaatcct ggagggcctg aatttcaacc tcacggagat tccggaggct 480
cagatccatg aaggcttcca ggaactcctc cgtaccctca accagccaga cagccagctc 540
cagctgacca ccggcaatgg cctgttcctc agcgagggcc tgaagctagt ggataagttt 600
ttggaggatg ttaaaaagtt gtaccactca gaagccttca ctgtcaactt cggggacacc 660
gaagaggcca agaaacagat caacgattac gtggagaagg gtactcaagg gaaaattgtg 720
gatttggtca aggagcttga cagagacaca gtttttgctc tggtgaatta catcttcttt 780
aaaggtaagg ttgctcaacc agcctgagct gtttcccata gaaacaagca aaaatatttc 840
tcaaaccatc agttcttgaa ctctccttgg caatgcatta tgggccatag caatgctttt 900
cagcgtggat tcttcagttt tctacacaca aacactaaaa tgttttccat cattgagtaa 960
tttgaggaaa taatagatta aactgtcaaa actactgacg ctctgcagaa cttttcagag 1020
cctttaatgt ccttgtgtat actgtatatg tagaatatat aatgcttaga actatagaac 1080
aaattgtaat acactgcata aagggatagt ttcatggaac atactttaca cgactctagt 1140
gtcccagaat cagtatcagt tttgcaatct gaaagacctg ggttcaaatc ctgcctctaa 1200
cacaattagc ttttgacaaa aacaatgcat tctacctctt tgaggtgcta atttctcatc 1260
ttagcatgga caaaatacca ttcttgctgt caggtttttt taggattaaa caaatgacaa 1320
agactgtggg gatggtgtgt ggcatacagc aggtgatgga ctcttctgta tctcaggctg 1380
ccttcctgcc cctgaggggt taaaatgcca gggtcctggg ggccccaggg cattctaagc 1440
cagctcccac tgtcccagga aaacagcata ggggagggga ggtgggaggc aaggccaggg 1500
gctgcttcct ccactctgag gctcccttgc tcttgaggca aaggagggca gtggaggcaa 1560
gccaggctgc agtcagcaca gctaaagtcc tggctctgct gtggccttag tgggggccca 1620
ggtccctctc cagccccagt ctcctccttc tgtccaatga gaaagctggg atcaggggtc 1680
cctgaggccc ctgtccactc tgcatgcctc gatggtgaag ctctgttggt atggcagagg 1740
ggaggctgct caggcatctg catttcccct gccaatctag aggatgagga aagctctcag 1800
gaatagtaag cagaatgttt gccctggatg aataactgag ctgccaatta acaaggggca 1860
gggagcctta gacagaaggt accaaatatg cctgatgctc caacatttta tttgtaatat 1920
ccaagacacc ctcaaataaa catatgattc caataaaaat gcacagccac gatggcatct 1980
cttagcctga catcgccacg atgtagaaat tctgcatctt cctctagttt tgaattatcc 2040
ccacacaatc tttttcggca gcttggatgg tcagtttcag caccttttac agatgatgaa 2100
gctgagcctc gagggatgtg tgtcgtcaag gggctcagg gcttctcagg gaggggactc 2160
atggtttctt attctgctac actcttccaa accttcactc accccctggtg atgcccacct 2220
tcccctctct ccaggcaaat gggagagacc ctttgaagtc aaggacaccg aggaagagga 2280
cttccacgtg gaccaggtga ccaccgtgaa ggtgcctatg atgaagcgtt taggcatgtt 2340
taacatccag cactgtaaga agctgtccag ctgggtgctg ctgatgaaat acctgggcaa 2400
tgccaccgcc atcttcttcc tgcctgatga ggggaaacta cagcacctgg aaaatgaact 2460
cacccacgat atcatcacca agttcctgga aaatgaagac agaaggtctg ccagcttaca 2520
tttacccaaa ctgtccatta ctggaaccta tgatctgaag agcgtcctgg gtcaactggg 2580
catcactaag gtcttcagca atggggctga cctctccggg gtcacagagg aggcaccccct 2640
gaagctctcc aaggccgtgc ataaggctgt gctgaccatc gacgagaaag ggactgaagc 2700
```

FIG. 19A p43C-AT-IN (Ligation of p43-C into IN) (cont.)

```
tgctggggcc atgtttttag aggccatacc catgtctatc ccccccgagg tcaagttcaa 2760
caaacccttt gtcttcttaa tgattgaaca aaataccaag tctcccctct tcatgggaaa 2820
agtggtgaat cccacccaaa aataactgcc tctcgctcct caacccctcc cctccatccc 2880
tggcccccctc cctggatgac attaaagaag ggttgagctg gtaacccccc cccccctgc 2940
aggccctcga gacgcgtggc atgcaagctt ggtaccgagc tcggatccac tagtaacggc 3000
cgccagtgtg ctggaattca cgcgtggtac ctctagagtc gacccgggcg gccgcttcga 3060
gcagacatga taagatacat tgatgagttt ggacaaacca caactagaat gcagtgaaaa 3120
aaatgcttta tttgtgaaat ttgtgatgct attgctttat ttgtaaccat tataagctgc 3180
aataaacaag ttaacaacaa caattgcatt cattttatgt ttcaggttca gggggagatg 3240
tgggaggttt tttaaagcaa gtaaaacctc tacaaatgtg gtaaaatcga taaggatcta 3300
ggaaccccta gtgatggagt tggccactcc ctctctgcgc gctcgctcgc tcactgaggc 3360
cgcccgggca aagcccgggc gtcgggcgac ctttggtcgc ccggcctcag tgagcgagcg 3420
agcgcgcaga gagggagtgg ccaactgcag ctgcattaat gaatcggcca acgcgcgggg 3480
agaggcggtt tgcgtattgg gcgctcttcc gcttcctcgc tcactgactc gctgcgctcg 3540
gtcgttcggc tgcggcgagc ggtatcagct cactcaaagg cggtaatacg gttatccaca 3600
gaatcagggg ataacgcagg aaagaacatg tgagcaaaag gccagcaaaa ggccaggaac 3660
cgtaaaaagg ccgcgttgct ggcgtttttc cataggctcc gcccccctga cgagcatcac 3720
aaaaatcgac gctcaagtca gaggtggcga aacccgacag gactataaag ataccaggcg 3780
tttccccctg gaagctccct cgtgcgctct cctgttccga ccctgccgct taccggatac 3840
ctgtccgcct ttctcccttc gggaagcgtg gcgctttctc aatgctcacg ctgtaggtat 3900
ctcagttcgg tgtaggtcgt tcgctccaag ctgggctgtg tgcacgaacc ccccgttcag 3960
cccgaccgct gcgccttatc cggtaactat cgtcttgagt ccaacccggt aagacacgac 4020
ttatcgccac tggcagcagc cactggtaac aggattagca gagcgaggta tgtaggcggt 4080
gctacagagt tcttgaagtg gtggcctaac tacggctaca ctagaaggac agtatttggt 4140
atctgcgctc tgctgaagcc agttaccttc ggaaaaagag ttggtagctc ttgatccggc 4200
aaacaaacca ccgctggtag cggtggtttt tttgtttgca agcagcagat tacgcgcaga 4260
aaaaaaggat ctcaagaaga tcctttgatc ttttctacgg ggtctgacgc tcagtggaac 4320
gaaaactcac gttaagggat tttggtcatg agattatcaa aaaggatctt cacctagatc 4380
cttttaaatt aaaaatgaag ttttaaatca atctaaagta tatatgagta aacttggtct 4440
gacagttacc aatgcttaat cagtgaggca cctatctcag cgatctgtct atttcgttca 4500
tccatagttg cctgactccc cgtcgtgtag ataactacga tacgggaggg cttaccatct 4560
ggccccagtg ctgcaatgat accgcgagac ccacgctcac cggctccaga tttatcagca 4620
ataaaccagc cagccggaag ggccgagcgc agaagtggtc ctgcaacttt atccgcctcc 4680
atccagtcta ttaattgttg ccgggaagct agagtaagta gttcgccagt taatagtttg 4740
cgcaacgttg ttgccattgc tacaggcatc gtggtgtcac gctcgtcgtt tggtatggct 4800
tcattcagct ccggttccca acgatcaagg cgagttacat gatcccccat gttgtgcaaa 4860
aaagcggtta gctccttcgg tcctccgatc gttgtcagaa gtaagttggc cgcagtgtta 4920
tcactcatgg ttatggcagc actgcataat tctcttactg tcatgccatc cgtaagatgc 4980
ttttctgtga ctggtgagta ctcaaccaag tcattctgag aatagtgtat gcggcgaccg 5040
agttgctctt gcccggcgtc aatacgggat aataccgcgc cacatagcag aactttaaaa 5100
gtgctcatca ttggaaaacg ttcttcgggg cgaaaactct caaggatctt accgctgttg 5160
agatccagtt cgatgtaacc cactcgtgca cccaactgat cttcagcatc ttttactttc 5220
accagcgttt ctgggtgagc aaaaacagga aggcaaaatg ccgcaaaaaa gggaataagg 5280
gcgacacgga aatgttgaat actcatactc ttcctttttc aatattattg aagcatttat 5340
cagggttatt gtctcatgag cggatacata tttgaatgta tttagaaaaa taaacaaata 5400
```

FIG. 19B p43C-AT-IN (Ligation of p43-C into IN) (cont.)

```
ggggttccgc gcacatttcc ccgaaaagtg ccacctgacg tctaagaaac cattattatc 5460
atgacattaa cctataaaaa taggcgtatc acgaggccct ttcgtctcgc gcgtttcggt 5520
gatgacggtg aaaacctctg acacatgcag ctcccggaga cggtcacagc ttgtctgtaa 5580
gcggatgccg ggagcagaca agcccgtcag ggcgcgtcag cgggtgttgg cgggtgtcgg 5640
ggctggctta actatgcggc atcagagcag attgtactga gagtgcacca tatgcggtgt 5700
gaaataccgc acagatgcgt aaggagaaaa taccgcatca ggaaattgta aacgttaata 5760
ttttgttaaa attcgcgtta aatttttgtt aaatcagctc attttttaac caataggccg 5820
aaatcggcaa aatcccttat aaatcaaaag aatagaccga gatagggttg agtgttgttc 5880
cagtttggaa caagagtcca ctattaaaga acgtggactc caacgtcaaa gggcgaaaaa 5940
ccgtctatca gggcgatggc ccactacgtg aaccatcacc ctaatcaagt tttttggggt 6000
cgaggtgccg taaagcacta aatcggaacc ctaaagggag cccccgattt agagcttgac 6060
ggggaaagcc ggcgaacgtg gcgagaaagg aagggaagaa agcgaaagga gcgggcgcta 6120
gggcgctggc aagtgtagcg gtcacgctgc gcgtaaccac cacacccgcc gcgcttaatg 6180
cgccgctaca gggcgcgtcg cgccattcgc cattcaggct acgcaactgt tgggaagggc 6240
gatcggtgcg ggcctcttcg ctattacgcc agctgcagtt ggccactccc tctctgcgcg 6300
ctcgctcgct cactgaggcc gggcgaccaa aggtcgcccg acgcccgggc tttgcccggg 6360
cggcctcagt gagcgagcga gcgcgcagag agggagtggc caactccatc actaggggtt 6420
cctagatctt caatattggc cattagccat attattcatt ggttatatag cataaatcaa 6480
tattggctat tggccattgc atacgttgta tctatatcat aatatgtaca tttatattgg 6540
ctcatgtcca atatgaccgc catgttggca ttgattattg actagttatt aatagtaatc 6600
aattacgggg tcattagttc atagcccata tatggagttc cgcgttacat aacttacggt 6660
aaatggcccg cctggctgac cgcccaacga cccccgccca ttgacgtcaa taatgacgta 6720
tgttcccata gtaacgccaa tagggacttt ccattgacgt caatgggtgg agtatttacg 6780
gtaaactgcc cacttggcag tacatcaagt gtatcatatg ccaagtccgc cccctattga 6840
cgtcaatgac ggtaaatggc ccgcctggca ttatgcccag tacatgacct tacgggactt 6900
tcctacttgg cagtacatct acgtattagt catcgctatt accatggtga tgcggttttg 6960
gcagtacacc aatgggcgtg gatagcggtt tgactcacgg ggatttccaa gtctccaccc 7020
cattgacgtc aatgggagtt tgttttggca ccaaaatcaa cgggactttc caaaatgtcg 7080
taataacccc gccccgttga cgcaaatggg cggtaggcgt gtacggtggg aggtctatat 7140
aagcagagct cgtttagtga accgtcagat cactagaagc tttattgcgg tagtttatca 7200
cagttaaatt gctaacgcag tcagtgcttc tgacacaaca gtctcgaact taagctgcag 7260
aagttggtcg tgaggcactg ggcaggtaag tatcaaggtt acaagacagg tttaaggaga 7320
ccaatagaaa ctgggcttgt cgagacagag aagactcttg cgtttctgat aggcacctat 7380
tggtcttact gacatccact ttgcctttct ctccacaggt gtccactccc agttcaatta 7440
cagctcttaa ggctagagta cttaatacga ctcactatag gctagcctcg ag         7492
```

FIG. 19C p43CB-AT (Ligation of Fragment 2 into Fragment 2) (SEQ ID NO:6)

```
gggggggggg ggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatcttc aatattggcc 180
attagccata ttattcattg gttatatagc ataaatcaat attggctatt ggccattgca 240
tacgttgtat ctatatcata atatgtacat ttatattggc tcatgtccaa tatgaccgcc 300
atgttggcat tgattattga ctagttatta atagtaatca attacggggt cattagttca 360
tagcccatat atggagttcc gcgttacata acttacggta aatggcccgc ctggctgacc 420
gcccaacgac ccccgcccat tgacgtcaat aatgacgtat gttcccatag taacgccaat 480
agggactttc cattgacgtc aatgggtgga gtatttacgg taaactgccc acttggcagt 540
acatcaagtg tatcatatgc caagtccgcc ccctattgac gtcaatgacg gtaaatggcc 600
cgcctggcat tatgcccagt acatgacctt acgggacttt cctacttggc agtacatcta 660
cgtattagtc atcgctatta ccatggtcga ggtgagcccc acgttctgct tcactctccc 720
catctccccc ccctccccac ccccaatttt gtatttattt atttttaat tattttgtgc 780
agcgatgggg gcggggggg gggggggcg cgcgccaggc ggggcggggc ggggcgaggg 840
gcggggcggg gcgaggcgga gaggtgcggc ggcagccaat cagagcggcg cgctccgaaa 900
gtttcctttt atggcgaggc ggcggcggcg gcggccctat aaaaagcgaa gcgcgcggcg 960
ggcgggagtc gctgcgacgc tgccttcgcc ccgtgccccg ctccgccgcc gcctcgcgcc 1020
gcccgccccg gctctgactg accgcgttac tcccacaggt gagcgggcgg gacggccctt 1080
ctcctccggg ctgtaattag cgcttggttt aatgacggct tgtttctttt ctgtggctgc 1140
gtgaaagcct tgaggggctc cgggagggcc ctttgtgcgg ggggagcgg ctcgggggt 1200
gcgtgcgtgt gtgtgtgcgt ggggagcgcc gcgtgcggcc cgcgctgccc ggcggctgtg 1260
agcgctgcgg gcgcggcgcg gggctttgtg cgctccgcag tgtgcgcgag gggagcgcgg 1320
ccgggggcgg tgccccgcgg tgcgggggg gctgcgaggg gaacaaaggc tgcgtgcggg 1380
gtgtgtgcgt ggggggtga gcaggggtg tgggcgcggc ggtcggctg taacccccc 1440
ctgcaccccc ctccccgagt tgctgagcac ggcccggctt cgggtgcggg gctccgtacg 1500
gggcgtggcg cggggctcgc cgtgccgggc gggggtggc ggcaggtggg ggtgccgggc 1560
ggggcggggc cgcctcgggc cggggagggc tcgggggagg ggcgcggcgg ccccggagc 1620
gccggcggct gtcgaggcgc ggcgagccgc agccattgcc ttttatggta atcgtgcgag 1680
agggcgcagg gacttccttt gtcccaaatc tgtgcggagc cgaaatctgg gaggcgccgc 1740
cgcacccct ctagcgggcg cggggcgaag cggtgcggcg ccggcaggaa ggaaatgggc 1800
ggggagggcc ttcgtgcgtc gccgcgccgc cgtccccttc tccctctcca gcctcggggc 1860
tgtccgcggg gggacggctg ccttcggggg ggacggggca gggcggggtt cggcttctgg 1920
cgtgtgaccg gcggctctag agcctctgct aaccatgttc atgccttctt ctttttccta 1980
cagctcctgg gcaacgtgct ggttattgtg ctgtctcatc attttggcaa agaattcgat 2040
atcaagcttg ggattttca ggcaccacca ctgacctggg acagtgaatc gacaatgccg 2100
tcttctgtct cgtggggcat cctcctgctg gcaggcctgt gctgcctggt ccctgtctcc 2160
ctggctgagg atccccaggg agatgctgcc cagaagacag atacatccca ccatgatcag 2220
gatcacccaa ccttcaacaa gatcaccccc aacctggctg agttcgcctt cagcctatac 2280
cgccagctgg cacaccagtc caacagcacc aatatcttct tctccccagt gagcatcgct 2340
acagcctttg caatgctctc cctggggacc aaggctgaca ctcacgatga aatcctggag 2400
ggcctgaatt tcaacctcac ggagattccg gaggctcaga tccatgaagg cttccaggaa 2460
ctcctccgta ccctcaacca gccagacagc cagctccagc tgaccaccgg caatggcctg 2520
ttcctcagcg agggcctgaa gctagtggat aagtttttgg aggatgttaa aaagttgtac 2580
cactcagaag ccttcactgt caacttcggg gacaccgaag aggccaagaa acagatcaac 2640
gattacgtgg agaagggtac tcaagggaaa attgtggatt tggtcaagga gcttgacaga 2700
```

FIG. 20A p43CB-AT (Ligation of Fragment 2 into Fragment 2) (cont.)

```
gacacagttt ttgctctggt gaattacatc ttctttaaag gcaaatggga gagacccttt 2760
gaagtcaagg acaccgagga agaggacttc cacgtggacc aggtgaccac cgtgaaggtg 2820
cctatgatga agcgtttagg catgtttaac atccagcact gtaagaagct gtccagctgg 2880
gtgctgctga tgaaatacct gggcaatgcc accgccatct tcttcctgcc tgatgagggg 2940
aaactacagc acctggaaaa tgaactcacc cacgatatca tcaccaagtt cctggaaaat 3000
gaagacagaa ggtctgccag cttacattta cccaaactgt ccattactgg aacctatgat 3060
ctgaagagcg tcctgggtca actgggcatc actaaggtct tcagcaatgg ggctgacctc 3120
tccggggtca cagaggaggc acccctgaag ctctccaagg ccgtgcataa ggctgtgctg 3180
accatcgacg agaaagggac tgaagctgct ggggccatgt ttttagaggc catacccatg 3240
tctatccccc ccgaggtcaa gttcaacaaa ccctttgtct tcttaatgat tgaacaaaat 3300
accaagtctc ccctcttcat gggaaaagtg gtgaatccca cccaaaaata actgcctctc 3360
gctcctcaac ccctcccctc catccctggc cccctccctg gatgacatta aagaagggtt 3420
gagctggtaa cccccccccc ccctgcaggg gccctcgacc cgggcggccg cttcgagcag 3480
acatgataag atacattgat gagtttggac aaaccacaac tagaatgcag tgaaaaaaat 3540
gctttatttg tgaaatttgt gatgctattg ctttatttgt aaccattata agctgcaata 3600
aacaagttaa caacaacaat tgcattcatt ttatgtttca ggttcagggg gagatgtggg 3660
aggtttttta aagcaagtaa aacctctaca aatgtggtaa aatcgataag gatctaggaa 3720
cccctagtga tggagttggc cactccctct ctgcgcgctc gctcgctcac tgaggccgcc 3780
cgggcaaagc ccgggcgtcg ggcgaccttt ggtcgcccgg cctcagtgag cgagcgagcg 3840
cgcagagagg gagtggccaa cccccccccc cccccccctg cagcctggcg taatagcgaa 3900
gaggcccgca ccgatcgccc ttcccaacag ttgcgtagcc tgaatggcga atggcgcgac 3960
gcgccctgta gcggcgcatt aagcgcggcg ggtgtggtgg ttacgcgcag cgtgaccgct 4020
acacttgcca gcgccctagc gcccgctcct ttcgctttct tcccttcctt tctcgccacg 4080
ttcgccggct ttccccgtca agctctaaat cgggggctcc ctttagggtt ccgatttagt 4140
gctttacggc acctcgaccc caaaaaactt gattagggtg atggttcacg tagtgggcca 4200
tcgccctgat agacggtttt tcgccctttg acgttggagt ccacgttctt taatagtgga 4260
ctcttgttcc aaactggaac aacactcaac cctatctcgg tctattcttt tgatttataa 4320
gggattttgc cgatttcggc ctattggtta aaaaatgagc tgatttaaca aaaatttaac 4380
gcgaatttta acaaaatatt aacgtttaca atttcctgat gcggtatttt ctccttacgc 4440
atctgtgcgg tatttcacac cgcatatggt gcactctcag tacaatctgc tctgatgccg 4500
catagttaag ccagccccga cacccgccaa cacccgctga cgcgccctga cgggcttgtc 4560
tgctcccggc atccgcttac agacaagctg tgaccgtctc cgggagctgc atgtgtcaga 4620
ggttttcacc gtcatcaccg aaacgcgcga gacgaaaggg cctcgtgata cgcctatttt 4680
tataggttaa tgtcatgata ataatggttt cttagacgtc aggtggcact tttcggggaa 4740
atgtgcgcgg aacccctatt tgtttatttt tctaaataca ttcaaatatg tatccgctca 4800
tgagacaata accctgataa atgcttcaat aatattgaaa aaggaagagt atgagtattc 4860
aacatttccg tgtcgccctt attccctttt ttgcggcatt ttgccttcct gtttttgctc 4920
acccagaaac gctggtgaaa gtaaaagatg ctgaagatca gttgggtgca cgagtgggtt 4980
acatcgaact ggatctcaac agcggtaaga tccttgagag ttttcgcccc gaagaacgtt 5040
ttccaatgat gagcactttt aaagttctgc tatgtggcgc ggtattatcc cgtattgacg 5100
ccgggcaaga gcaactcggt cgccgcatac actattctca gaatgacttg gttgagtact 5160
caccagtcac agaaaagcat cttacggatg gcatgacagt aagagaatta tgcagtgctg 5220
ccataaccat gagtgataac actgcggcca acttacttct gacaacgatc ggaggaccga 5280
aggagctaac cgcttttttg cacaacatgg gggatcatgt aactcgcctt gatcgttggg 5340
aaccggagct gaatgaagcc ataccaaacg acgagcgtga caccacgatg cctgtagcaa 5400
tggcaacaac gttgcgcaaa ctattaactg gcgaactact tactctagct tcccggcaac 5460
```

FIG. 20B p43CB-AT (Ligation of Fragment 2 into Fragment 2) (cont.)

```
aattaataga ctggatggag gcggataaag ttgcaggacc acttctgcgc tcggcccttc 5520
cggctggctg gtttattgct gataaatctg gagccggtga gcgtgggtct cgcggtatca 5580
ttgcagcact ggggccagat ggtaagccct cccgtatcgt agttatctac acgacgggga 5640
gtcaggcaac tatggatgaa cgaaatagac agatcgctga gataggtgcc tcactgatta 5700
agcattggta actgtcagac caagtttact catatatact ttagattgat ttaaaacttc 5760
atttttaatt taaaaggatc taggtgaaga tcctttttga taatctcatg accaaaatcc 5820
cttaacgtga gttttcgttc cactgagcgt cagaccccgt agaaaagatc aaaggatctt 5880
cttgagatcc tttttttctg cgcgtaatct gctgcttgca aacaaaaaaa ccaccgctac 5940
cagcggtggt ttgtttgccg gatcaagagc taccaactct ttttccgaag gtaactggct 6000
tcagcagagc gcagatacca aatactgtcc ttctagtgta gccgtagtta ggccaccact 6060
tcaagaactc tgtagcaccg cctacatacc tcgctctgct aatcctgtta ccagtggctg 6120
ctgccagtgg cgataagtcg tgtcttaccg ggttggactc aagacgatag ttaccggata 6180
aggcgcagcg gtcgggctga acggggggtt cgtgcacaca gcccagcttg gagcgaacga 6240
cctacaccga actgagatac ctacagcgtg agcattgaga aagcgccacg cttcccgaag 6300
ggagaaaggc ggacaggtat ccggtaagcg gcagggtcgg aacaggagag cgcacgaggg 6360
agcttccagg gggaaacgcc tggtatcttt atagtcctgt cgggtttcgc cacctctgac 6420
ttgagcgtcg atttttgtga tgctcgtcag gggggcggag cctatggaaa aacgccagca 6480
acgcggcctt tttacggttc ctggcctttt gctggccttt tgctcacatg ttctttcctg 6540
cgttatcccc tgattctgtg gataaccgta ttaccgcctt tgagtgagct gataccgctc 6600
gccgcagccg aacgaccgag cgcagcgagt cagtgagcga ggaagcggaa gagcgcccaa 6660
tacgcaaacc gcctctcccc gcgcgttggc cgattcatta atgcagggct gcag       6714
```

FIG. 20C

C-AT2 (Ligation of Fragment 1 and Fragment 2) (SEQ ID NO:7)

```
ctagaactag tggatccccc gggctgcagg aattcgatat caagcttggg gattttcagg 60
caccaccact gacctgggac agtgaatcga caatgccgtc ttctgtctcg tggggcatcc 120
tcctgctggc aggcctgtgc tgcctggtcc ctgtctccct ggctgaggat ccccagggag 180
atgctgccca gaagacagat acatcccacc atgatcagga tcacccaacc ttcaacaaga 240
tcacccccaa cctggctgag ttcgccttca gcctataccg ccagctggca caccagtcca 300
acagcaccaa tatcttcttc tccccagtga gcatcgctac agcctttgca atgctctccc 360
tggggaccaa ggctgacact cacgatgaaa tcctggaggg cctgaatttc aacctcacgg 420
agattccgga ggctcagatc catgaaggct tccaggaact cctccgtacc ctcaaccagc 480
cagacagcca gctccagctg accaccggca atggcctgtt cctcagcgag ggcctgaagc 540
tagtggataa gtttttggag gatgttaaaa agttgtacca ctcagaagcc ttcactgtca 600
acttcgggga caccgaagag gccaagaaac agatcaacga ttacgtggag aagggtactc 660
aagggaaaat tgtggatttg gtcaaggagc ttgacagaga cacagttttt gctctggtga 720
attacatctt ctttaaaggc aaatgggaga gaccctttga agtcaaggac accgaggaag 780
aggacttcca cgtggaccag gtgaccaccg tgaaggtgcc tatgatgaag cgtttaggca 840
tgtttaacat ccagcactgt aagaagctgt ccagctgggt gctgctgatg aaatacctgg 900
gcaatgccac cgccatcttc ttcctgcctg atgaggggaa actacagcac ctggaaaatg 960
aactcaccca cgatatcatc accaagttcc tggaaaatga agacagaagg tctgccagct 1020
tacatttacc caaactgtcc attactggaa cctatgatct gaagagcgtc ctgggtcaac 1080
tgggcatcac taaggtcttc agcaatgggg ctgacctctc cggggtcaca gaggaggcac 1140
ccctgaagct ctccaaggcc gtgcataagg ctgtgctgac catcgacgag aaagggactg 1200
aagctgctgg ggccatgttt ttagaggcca tacccatgtc tatccccccc gaggtcaagt 1260
tcaacaaacc ctttgtcttc ttaatgattg aacaaaatac caagtctccc ctcttcatgg 1320
gaaaagtggt gaatcccacc caaaaataac tgcctctcgc tcctcaaccc ctcccctcca 1380
tccctggccc cctccctgga tgacattaaa gaagggttga gctggtaacc cccccccccc 1440
ctgcaggggc cctcgaggcc gcggggatcc agacatgata agatacattg atgagtttgg 1500
acaaaccaca actagaatgc agtgaaaaaa atgctttatt tgtgaaattt gtgatgctat 1560
tgctttattt gtaaccatta taagctgcaa taaacaagtt aacaacaaca attgcattca 1620
ttttatgttt caggttcagg gggaggtgtg ggaggttttt tagtcgacct cgagcagtgt 1680
ggttttgcaa gaggaagcaa aaagcctctc cacccaggcc tggaatgttt ccacccaagt 1740
cgaaggcagt gtggttttgc aagaggaagc aaaaagcctc tccacccagg cctggaatgt 1800
ttccacccaa tgtcgagcaa ccccgcccag cgtcttgtca ttggcgaatt cgaacacgca 1860
gatgcagtcg gggcggcgcg gtcccaggtc cacttcgcat attaaggtga cgcgtgtggc 1920
ctcgaacacc gagcgaccct gcagccaata tgggatcggc cattgaacaa gatggattgc 1980
acgcaggttc tccggccgct tgggtggaga ggctattcgg ctatgactgg gcacaacaga 2040
caatcggctg ctctgatgcc gccgtgttcc ggctgtcagc gcaggggcgc ccggttcttt 2100
ttgtcaagac cgacctgtcc ggtgccctga atgaactgca ggacgaggca gcgcggctat 2160
cgtggctggc cacgacgggc gttccttgcg cagctgtgct cgacgttgtc actgaagcgg 2220
gaagggactg gctgctattg ggcgaagtgc cggggcagga tctcctgtca tctcaccttg 2280
ctcctgccga gaaagtatcc atcatggctg atgcaatgcg gcggctgcat acgcttgatc 2340
cggctacctg cccattcgac caccaagcga aacatcgcat cgagcgagca cgtactcgga 2400
tggaagccgg tcttgtcgat caggatgatc tggacgaaga gcatcagggg ctcgcgccag 2460
ccgaactgtt cgccaggctc aaggcgcgca tgcccgacgg cgaggatctc gtcgtgaccc 2520
atggcgatgc ctgcttgccg aatatcatgg tggaaaatgg ccgcttttct ggattcatcg 2580
actgtggccg gctgggtgtg gcggaccgct atcaggacat agcgttggct acccgtgata 2640
ttgctgaaga gcttggcggc gaatgggctg accgcttcct cgtgctttac ggtatcgccg 2700
```

FIG. 21A

C-AT2 (Ligation of Fragment 1 and Fragment 2) (cont.)

```
ctcccgattc gcagcgcatc gccttctatc gccttcttga cgagttcttc tgaggggatc 2760
cgtcgactag agctcgctga tcagcctcga ctgtgccttc tagttgccag ccatctgttg 2820
tttgcccctc ccccgtgcct tccttgaccc tggaaggtgc cactcccact gtcctttcct 2880
aataaaatga ggaaattgca tcgcattgtc tgagtaggtg tcattctatt ctggggggtg 2940
gggtggggca ggacagcaag ggggaggatt gggaagacaa tagcaggcat gctggggaga 3000
gatctaggaa cccctagtga tggagttggc cactccctct ctgcgcgctc gctcgctcac 3060
tgaggccgcc cgggcaaagc ccgggcgtcg ggcgaccttt ggtcgcccgg cctcagtgag 3120
cgagcgagcg cgcagagagg gagtggccaa cccccccccc cccccccctg cagccctgca 3180
ttaatgaatc ggccaacgcg cggggagagg cggtttgcgt attgggcgct cttccgcttc 3240
ctcgctcact gactcgctgc gctcggtcgt tcggctgcgg cgagcggtat cagctcactc 3300
aaaggcggta atacggttat ccacagaatc aggggataac gcaggaaaga acatgtgagc 3360
aaaaggccag caaaaggcca ggaaccgtaa aaaggccgcg ttgctggcgt ttttccatag 3420
gctccgcccc cctgacgagc atcacaaaaa tcgacgctca agtcagaggt ggcgaaaccc 3480
gacaggacta taaagatacc aggcgtttcc ccctggaagc tccctcgtgc gctctcctgt 3540
tccgaccctg ccgcttaccg gatacctgtc cgcctttctc ccttcgggaa gcgtggcgct 3600
ttctcaatgc tcacgctgta ggtatctcag ttcggtgtag gtcgttcgct ccaagctggg 3660
ctgtgtgcac gaaccccccg ttcagcccga ccgctgcgcc ttatccggta actatcgtct 3720
tgagtccaac ccggtaagac acgacttatc gccactggca gcagccactg gtaacaggat 3780
tagcagagcg aggtatgtag gcggtgctac agagttcttg aagtggtggc ctaactacgg 3840
ctacactaga aggacagtat ttggtatctg cgctctgctg aagccagtta ccttcggaaa 3900
aagagttggt agctcttgat ccggcaaaca aaccaccgct ggtagcggtg gtttttttgt 3960
ttgcaagcag cagattacgc gcagaaaaaa aggatctcaa gaagatcctt tgatcttttc 4020
tacggggtct gacgctcagt ggaacgaaaa ctcacgttaa gggattttgg tcatgagatt 4080
atcaaaaagg atcttcacct agatcctttt aaattaaaaa tgaagtttta aatcaatcta 4140
aagtatatat gagtaaactt ggtctgacag ttaccaatgc ttaatcagtg aggcacctat 4200
ctcagcgatc tgtctatttc gttcatccat agttgcctga ctccccgtcg tgtagataac 4260
tacgatacgg gagggcttac catctggccc cagtgctgca atgataccgc gagacccacg 4320
ctcaccggct ccagatttat cagcaataaa ccagccagcc ggaagggccg agcgcagaag 4380
tggtcctgca actttatccg cctccatcca gtctattaat tgttgccggg aagctagagt 4440
aagtagttcg ccagttaata gtttgcgcaa cgttgttgcc attgctacag gcatcgtggt 4500
gtcacgctcg tcgtttggta tggcttcatt cagctccggt tcccaacgat caaggcgagt 4560
tacatgatcc cccatgttgt gcaaaaaagc ggttagctcc ttcggtcctc cgatcgttgt 4620
cagaagtaag ttggccgcag tgttatcact catggttatg gcagcactgc ataattctct 4680
tactgtcatg ccatccgtaa gatgcttttc tgtgactggt gagtactcaa ccaagtcatt 4740
ctgagaatag tgtatgcggc gaccgagttg ctcttgcccg gcgtcaatac gggataatac 4800
cgcgccacat agcagaactt taaaagtgct catcattgga aaacgttctt cggggcgaaa 4860
actctcaagg atcttaccgc tgttgagatc cagttcgatg taacccactc gtgcacccaa 4920
ctgatcttca gcatctttta ctttcaccag cgtttctggg tgagcaaaaa caggaaggca 4980
aaatgccgca aaaaagggaa taagggcgac acggaaatgt tgaatactca tactcttcct 5040
ttttcaatat tattgaagca tttatcaggg ttattgtctc atgagcggat acatatttga 5100
atgtatttag aaaaataaac aaataggggt tccgcgcaca tttccccgaa aagtgccacc 5160
tgacgtctaa gaaaccatta ttatcatgac attaacctat aaaaataggc gtatcacgag 5220
gccctttcgt ctcgcgcgtt tcggtgatga cggtgaaaac ctctgacaca tgcagctccc 5280
ggagacggtc acagcttgtc tgtaagcgga tgccgggagc agacaagccc gtcagggcgc 5340
gtcagcgggt gttggcgggt gtcggggctg gcttaactat gcggcatcag agcagattgt 5400
```

FIG. 21B

C-AT2 (Ligation of Fragment 1 and Fragment 2) (cont.)

```
actgagagtg caccatatgc ggtgtgaaat accgcacaga tgcgtaagga gaaaataccg 5460
catcaggaaa ttgtaaacgt taatattttg ttaaaattcg cgttaaattt ttgttaaatc 5520
agctcatttt ttaaccaata ggccgaaatc ggcaaaatcc cttataaatc aaaagaatag 5580
accgagatag ggttgagtgt tgttccagtt tggaacaaga gtccactatt aaagaacgtg 5640
gactccaacg tcaaagggcg aaaaaccgtc tatcagggcg atggcccact acgtgaacca 5700
tcaccctaat caagtttttt ggggtcgagg tgccgtaaag cactaaatcg gaaccctaaa 5760
gggagccccc gatttagagc ttgacgggga aagccggcga acgtggcgag aaaggaaggg 5820
aagaaagcga aaggagcggg cgctagggcg ctggcaagtg tagcggtcac gctgcgcgta 5880
accaccacac ccgccgcgct taatgcgccg ctacagggcg cgtcgcgcca ttcgccattc 5940
aggctacgca actgttggga agggcgatcg gtgcgggcct cttcgctatt acgccaggct 6000
gcaggggggg gggggggggg gttggccact ccctctctgc gcgctcgctc gctcactgag 6060
gccgggcgac caaaggtcgc ccgacgcccg ggctttgccc gggcggcctc agtgagcgag 6120
cgagcgcgca gagagggagt ggccaactcc atcactaggg gttcctagat ctgaattcgg 6180
tacccgttac ataacttacg gtaaatggcc cgcctggctg accgcccaac gacccccgcc 6240
cattgacgtc aataatgacg tatgttccca tagtaacgcc aatagggact ttccattgac 6300
gtcaatgggt ggagtattta cggtaaactg cccacttggc agtacatcaa gtgtatcata 6360
tgccaagtac gccccctatt gacgtcaatg acggtaaatg gcccgcctgg cattatgccc 6420
agtacatgac cttatgggac tttcctactt ggcagtacat ctacgtatta gtcatcgcta 6480
ttaccatggt gatgcggttt tggcagtaca tcaatgggcg tggatagcgg tttgactcac 6540
ggggatttcc aagtctccac cccattgacg tcaatgggag tttgttttgg caccaaaatc 6600
aacgggactt tccaaaatgt cgtaacaact ccgccccatt gacgcaaatg ggcggtaggc 6660
gtgtacggtg ggaggtctat ataagcagag ctcgtttagt gaaccgtcag atcgcctgga 6720
gacgccatcc acgctgtttt gacctccata gaagacaccg ggaccgatcc agcctccgga 6780
ctctagagga tccggtactc gaggaactga aaaaccagaa agttaactgg taagtttagt 6840
ctttttgtct tttatttcag gtcccggatc cggtggtggt gcaaatcaaa gaactgctcc 6900
tcagtggatg ttgcctttac ttctaggcct gtacggaagt gttacttctg ctctaaaagc 6960
tgcggaattg tacccgcggc c                                          6981
```

FIG. 21C

**p43msENC-AT (Ligation of Inverted msEnhancer into p43-AAT*) (SEQ ID NO: 8)**

```
gggggggggg ggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatctca ccattcctca 180
cgacacccaa atatggcgac gggtgaggaa tggtggggag ttatttttag agcggtgagg 240
aatggtgggc aggcagcagg tgttggcgct ctaaaaataa ctcccgggag ttatttttag 300
agcggtgagg aatggtggac acccaaatat ggcgacggca ccattcctca ccccaggcca 360
tatttgggtg tcagatcttc aatattggcc attagccata ttattcattg gttatatagc 420
ataaatcaat attggctatt ggccattgca tacgttgtat ctatatcata atatgtacat 480
ttatattggc tcatgtccaa tatgaccgcc atgttggcat tgattattga ctagttatta 540
atagtaatca attacggggt cattagttca tagcccatat atggagttcc gcgttacata 600
acttacggta aatggcccgc ctggctgacc gcccaacgac ccccgcccat tgacgtcaat 660
aatgacgtat gttcccatag taacgccaat agggactttc cattgacgtc aatgggtgga 720
gtatttacgg taaactgccc acttggcagt acatcaagtg tatcatatgc caagtccgcc 780
ccctattgac gtcaatgacg gtaaatggcc cgcctggcat tatgcccagt acatgacctt 840
acgggacttt cctacttggc agtacatcta cgtattagtc atcgctatta ccatggtgat 900
gcggttttgg cagtacacca atgggcgtgg atagcggttt gactcacggg gatttccaag 960
tctccacccc attgacgtca atgggagttt gttttggcac caaaatcaac gggactttcc 1020
aaaatgtcgt aataaccccg ccccgttgac gcaaatgggc ggtaggcgtg tacggtggga 1080
ggtctatata agcagagctc gtttagtgaa ccgtcagatc actagaagct ttattgcggt 1140
agtttatcac agttaaattg ctaacgcagt cagtgcttct gacacaacag tctcgaactt 1200
aagctgcaga agttggtcgt gaggcactgg gcaggtaagt atcaaggtta caagacaggt 1260
ttaaggagac caatagaaac tgggcttgtc gagacagaga agactcttgc gtttctgata 1320
ggcacctatt ggtcttactg acatccactt tgcctttctc tccacaggtg tccactccca 1380
gttcaattac agctcttaag gctagagtac ttaatacgac tcactatagg ctagaactag 1440
tggatccccc gggctgcagg aattcgatat caagcttggg gattttcagg caccaccact 1500
gacctgggac agtgaatcga caatgccgtc ttctgtctcg tggggcatcc tcctgctggc 1560
aggcctgtgc tgcctggtcc ctgtctccct ggctgaggat ccccagggag atgctgccca 1620
gaagacagat acatcccacc atgatcagga tcacccaacc ttcaacaaga tcacccccaa 1680
cctggctgag ttcgccttca gcctataccg ccagctggca caccagtcca acagcaccaa 1740
tatcttcttc tccccagtga gcatcgctac agcctttgca atgctctccc tggggaccaa 1800
ggctgacact cacgatgaaa tcctggaggg cctgaatttc aacctcacgg agattccgga 1860
ggctcagatc catgaaggct tccaggaact cctccgtacc ctcaaccagc cagacagcca 1920
gctccagctg accaccggca atggcctgtt cctcagcgag ggcctgaagc tagtggataa 1980
gtttttggag gatgttaaaa agttgtacca ctcagaagcc ttcactgtca acttcgggga 2040
caccgaagag gccaagaaac agatcaacga ttacgtggag aagggtactc aagggaaaat 2100
tgtggatttg gtcaaggagc ttgacagaga cacagttttt gctctggtga attacatctt 2160
ctttaaaggc aaatgggaga gaccctttga agtcaaggac accgaggaag aggacttcca 2220
cgtggaccag gtgaccaccg tgaaggtgcc tatgatgaag cgtttaggca tgtttaacat 2280
ccagcactgt aagaagctgt ccagctgggt gctgctgatg aaatacctgg gcaatgccac 2340
cgccatcttc ttcctgcctg atgaggggaa actacagcac ctggaaaatg aactcaccca 2400
```

FIG. 22A

**p43msENC-AT (Ligation of Inverted msEnhancer into p43-AAT*) (cont.)**

```
cgatatcatc accaagttcc tggaaaatga agacagaagg tctgccagct tacatttacc 2460
caaactgtcc attactggaa cctatgatct gaagagcgtc ctgggtcaac tgggcatcac 2520
taaggtcttc agcaatgggg ctgacctctc cggggtcaca gaggaggcac ccctgaagct 2580
ctccaaggcc gtgcataagg ctgtgctgac catcgacgag aaagggactg aagctgctgg 2640
ggccatgttt ttagaggcca tacccatgtc tatccccccc gaggtcaagt tcaacaaacc 2700
ctttgtcttc ttaatgattg aacaaaatac caagtctccc ctcttcatgg gaaaagtggt 2760
gaatcccacc caaaaataac tgcctctcgc tcctcaaccc ctcccctcca tccctggccc 2820
cctccctgga tgacattaaa gaagggttga gctggtaacc cccccccccc ctgcaggggc 2880
cctcgacccg ggcggccgct tcgagcagac atgataagat acattgatga gtttggacaa 2940
accacaacta gaatgcagtg aaaaaaatgc tttatttgtg aaatttgtga tgctattgct 3000
ttatttgtaa ccattataag ctgcaataaa caagttaaca acaacaattg cattcatttt 3060
atgtttcagg ttcaggggga gatgtgggag gtttttttaaa gcaagtaaaa cctctacaaa 3120
tgtggtaaaa tcgataagga tctaggaacc cctagtgatg gagttggcca ctccctctct 3180
gcgcgctcgc tcgctcactg aggccgcccg ggcaaagccc gggcgtcggg cgacctttgg 3240
tcgcccggcc tcagtgagcg agcgagcgcg cagagaggga gtggccaacc cccccccccc 3300
ccccctgca gcctggcgta atagcgaaga ggcccgcacc gatcgccctt cccaacagtt 3360
gcgtagcctg aatggcgaat ggcgcgacgc gccctgtagc ggcgcattaa gcgcggcggg 3420
tgtggtggtt acgcgcagcg tgaccgctac acttgccagc gccctagcgc ccgctccttt 3480
cgctttcttc ccttcctttc tcgccacgtt cgccggcttt ccccgtcaag ctctaaatcg 3540
ggggctccct ttagggttcc gatttagtgc tttacggcac ctcgacccca aaaaacttga 3600
ttagggtgat ggttcacgta gtgggccatc gccctgatag acggtttttc gccctttgac 3660
gttggagtcc acgttcttta atagtggact cttgttccaa actggaacaa cactcaaccc 3720
tatctcggtc tattcttttg atttataagg gattttgccg atttcggcct attggttaaa 3780
aaatgagctg atttaacaaa aatttaacgc gaattttaac aaaatattaa cgtttacaat 3840
ttcctgatgc ggtattttct ccttacgcat ctgtgcggta tttcacaccg catatggtgc 3900
actctcagta caatctgctc tgatgccgca tagttaagcc agccccgaca cccgccaaca 3960
cccgctgacg cgccctgacg ggcttgtctg ctcccggcat ccgcttacag acaagctgtg 4020
accgtctccg ggagctgcat gtgtcagagg ttttcaccgt catcaccgaa acgcgcgaga 4080
cgaaagggcc tcgtgatacg cctattttta taggttaatg tcatgataat aatggtttct 4140
tagacgtcag gtggcacttt tcggggaaat gtgcgcggaa cccctatttg tttatttttc 4200
taaatacatt caaatatgta tccgctcatg agacaataac cctgataaat gcttcaataa 4260
tattgaaaaa ggaagagtat gagtattcaa catttccgtg tcgcccttat tccctttttt 4320
gcggcatttt gccttcctgt ttttgctcac ccagaaacgc tggtgaaagt aaaagatgct 4380
gaagatcagt tgggtgcacg agtgggttac atcgaactgg atctcaacag cggtaagatc 4440
cttgagagtt ttcgccccga agaacgtttt ccaatgatga gcacttttaa agttctgcta 4500
tgtggcgcgg tattatcccg tattgacgcc gggcaagagc aactcggtcg ccgcatacac 4560
tattctcaga atgacttggt tgagtactca ccagtcacag aaaagcatct tacggatggc 4620
atgacagtaa gagaattatg cagtgctgcc ataaccatga gtgataacac tgcggccaac 4680
ttacttctga caacgatcgg aggaccgaag gagctaaccg cttttttgca caacatgggg 4740
gatcatgtaa ctcgccttga tcgttgggaa ccggagctga atgaagccat accaaacgac 4800
gagcgtgaca ccacgatgcc tgtagcaatg gcaacaacgt tgcgcaaact attaactggc 4860
gaactactta ctctagcttc ccggcaacaa ttaatagact ggatggaggc ggataaagtt 4920
gcaggaccac ttctgcgctc ggcccttccg gctggctggt ttattgctga taaatctgga 4980
gccggtgagc gtgggtctcg cggtatcatt gcagcactgg ggccagatgg taagccctcc 5040
cgtatcgtag ttatctacac gacggggagt caggcaacta tggatgaacg aaatagacag 5100
atcgctgaga taggtgcctc actgattaag cattggtaac tgtcagacca agtttactca 5160
```

FIG. 22B p43msENC-AT (Ligation of Inverted msEnhancer into p43-AAT*) (cont.)

```
tatatacttt agattgattt aaaacttcat ttttaattta aaaggatcta ggtgaagatc 5220
ctttttgata atctcatgac caaaatccct taacgtgagt tttcgttcca ctgagcgtca 5280
gaccccgtag aaaagatcaa aggatcttct tgagatcctt tttttctgcg cgtaatctgc 5340
tgcttgcaaa caaaaaaacc accgctacca gcggtggttt gtttgccgga tcaagagcta 5400
ccaactcttt ttccgaaggt aactggcttc agcagagcgc agataccaaa tactgtcctt 5460
ctagtgtagc cgtagttagg ccaccacttc aagaactctg tagcaccgcc tacatacctc 5520
gctctgctaa tcctgttacc agtggctgct gccagtggcg ataagtcgtg tcttaccggg 5580
ttggactcaa gacgatagtt accggataag gcgcagcggt cgggctgaac ggggggttcg 5640
tgcacacagc ccagcttgga gcgaacgacc tacaccgaac tgagatacct acagcgtgag 5700
cattgagaaa gcgccacgct tcccgaaggg agaaaggcgg acaggtatcc ggtaagcggc 5760
agggtcggaa caggagagcg cacgagggag cttccagggg gaaacgcctg gtatctttat 5820
agtcctgtcg ggtttcgcca cctctgactt gagcgtcgat ttttgtgatg ctcgtcaggg 5880
gggcggagcc tatggaaaaa cgccagcaac gcggcctttt tacggttcct ggccttttgc 5940
tggccttttg ctcacatgtt ctttcctgcg ttatcccctg attctgtgga taaccgtatt 6000
accgcctttg agtgagctga taccgctcgc cgcagccgaa cgaccgagcg cagcgagtca 6060
gtgagcgagg aagcggaaga gcgcccaata cgcaaaccgc ctctccccgc gcgttggccg 6120
attcattaat gcagggctgc ag                                          6142
```

FIG. 22C

**p43rmsENC-AT (Ligation of Inverted msEnhancer into p43-AAT*) (SEQ ID NO:9)**

```
gggggggggg ggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatctga cacccaaata 180
tggcctgggg tgaggaatgg tgccgtcgcc atatttgggt gtccaccatt cctcaccgct 240
ctaaaaataa ctcccgggag ttatttttag agcgccaaca cctgctgcct gcccaccatt 300
cctcaccgct ctaaaaataa ctccccacca ttcctcaccc gtcgccatat ttgggtgtcg 360
tgaggaatgg tgagatcttc aatattggcc attagccata ttattcattg gttatatagc 420
ataaatcaat attggctatt ggccattgca tacgttgtat ctatatcata atatgtacat 480
ttatattggc tcatgtccaa tatgaccgcc atgttggcat tgattattga ctagttatta 540
atagtaatca attacggggt cattagttca tagcccatat atggagttcc gcgttacata 600
acttacggta aatggcccgc ctggctgacc gcccaacgac ccccgcccat tgacgtcaat 660
aatgacgtat gttcccatag taacgccaat agggactttc cattgacgtc aatgggtgga 720
gtatttacgg taaactgccc acttggcagt acatcaagtg tatcatatgc caagtccgcc 780
ccctattgac gtcaatgacg gtaaatggcc cgcctggcat tatgcccagt acatgacctt 840
acgggacttt cctacttggc agtacatcta cgtattagtc atcgctatta ccatggtcga 900
ggtgagcccc acgttctgct tcactctccc catctccccc ccctccccac ccccaatttt 960
gtatttattt atttttaat tattttgtgc agcgatgggg gcgggggggg ggggggggcg 1020
cgcgccaggc ggggcggggc ggggcgaggg gcggggcggg gcgaggcgga gaggtgcggc 1080
ggcagccaat cagagcggcg cgctccgaaa gtttcctttt atggcgaggc ggcggcggcg 1140
gcggccctat aaaaagcgaa gcgcgcggcg ggcgggagtc gctgcgacgc tgccttcgcc 1200
ccgtgccccg ctccgccgcc gcctcgcgcc gcccgccccg gctctgactg accgcgttac 1260
tcccacaggt gagcgggcgg gacggccctt ctcctccggg ctgtaattag cgcttggttt 1320
aatgacggct tgtttctttt ctgtggctgc gtgaaagcct tgaggggctc cgggagggcc 1380
ctttgtgcgg ggggagcgg ctcgggggt gcgtgcgtgt gtgtgtgcgt ggggagcgcc 1440
gcgtgcggcc cgcgctgccc ggcggctgtg agcgctgcgg gcgcggcgcg gggctttgtg 1500
cgctccgcag tgtgcgcgag gggagcgcgg ccgggggcgg tgccccgcgg tgcggggggg 1560
gctgcgaggg gaacaaaggc tgcgtgcggg gtgtgtgcgt gggggggtga gcagggggtg 1620
tgggcgcggc ggtcgggctg taaccccccc ctgcaccccc ctccccgagt tgctgagcac 1680
ggcccggctt cgggtgcggg gctccgtacg gggcgtggcg cggggctcgc cgtgccgggc 1740
gggggtggc ggcaggtggg ggtgccgggc ggggcggggc cgcctcgggc cggggagggc 1800
tcgggggagg ggcgcggcgg cccccggagc gccggcggct gtcgaggcgc ggcgagccgc 1860
agccattgcc ttttatggta atcgtgcgag agggcgcagg gacttccttt gtcccaaatc 1920
tgtgcggagc cgaaatctgg gaggcgccgc cgcacccccct ctagcgggcg cggggcgaag 1980
cggtgcggcg ccggcaggaa ggaaatgggc ggggagggcc ttcgtgcgtc gccgcgccgc 2040
cgtccccttc tccctctcca gcctcggggc tgtccgcggg gggacggctg ccttcggggg 2100
ggacggggca gggcggggtt cggcttctgg cgtgtgaccg gcggctctag agcctctgct 2160
aaccatgttc atgccttctt ctttttccta cagctcctgg gcaacgtgct ggttattgtg 2220
ctgtctcatc attttggcaa agaattcgat atcaagcttg ggattttca ggcaccacca 2280
ctgacctggg acagtgaatc gacaatgccg tcttctgtct cgtggggcat cctcctgctg 2340
gcaggcctgt gctgcctggt ccctgtctcc ctggctgagg atccccaggg agatgctgcc 2400
cagaagacag atacatccca ccatgatcag gatcacccaa ccttcaacaa gatcaccccc 2460
aacctggctg agttcgcctt cagcctatac cgccagctgg cacaccagtc caacagcacc 2520
aatatcttct tctccccagt gagcatcgct acagcctttg caatgctctc cctggggacc 2580
aaggctgaca ctcacgatga aatcctggag ggcctgaatt tcaacctcac ggagattccg 2640
gaggctcaga tccatgaagg cttccaggaa ctcctccgta ccctcaacca gccagacagc 2700
```

FIG. 23A

**p43rmsENC-AT (Ligation of Inverted msEnhancer into p43-AAT*) (cont.)**

```
cagctccagc tgaccaccgg caatggcctg ttcctcagcg agggcctgaa gctagtggat 2760
aagtttttgg aggatgttaa aaagttgtac cactcagaag ccttcactgt caacttcggg 2820
gacaccgaag aggccaagaa acagatcaac gattacgtgg agaagggtac tcaagggaaa 2880
attgtggatt tggtcaagga gcttgacaga gacacagttt ttgctctggt gaattacatc 2940
ttctttaaag gcaaatggga gagacccttt gaagtcaagg acaccgagga agaggacttc 3000
cacgtggacc aggtgaccac cgtgaaggtg cctatgatga agcgtttagg catgtttaac 3060
atccagcact gtaagaagct gtccagctgg gtgctgctga tgaaatacct gggcaatgcc 3120
accgccatct tcttcctgcc tgatgagggg aaactacagc acctggaaaa tgaactcacc 3180
cacgatatca tcaccaagtt cctggaaaat gaagacagaa ggtctgccag cttacattta 3240
cccaaactgt ccattactgg aacctatgat ctgaagagcg tcctgggtca actgggcatc 3300
actaaggtct tcagcaatgg ggctgacctc tccggggtca cagaggaggc acccctgaag 3360
ctctccaagg ccgtgcataa ggctgtgctg accatcgacg agaaagggac tgaagctgct 3420
ggggccatgt ttttagaggc catacccatg tctatccccc ccgaggtcaa gttcaacaaa 3480
ccctttgtct tcttaatgat tgaacaaaat accaagtctc ccctcttcat gggaaaagtg 3540
gtgaatccca cccaaaaata actgcctctc gctcctcaac ccctcccctc catccctggc 3600
cccctccctg gatgacatta aagaagggtt gagctggtaa cccccccccc ccctgcaggg 3660
gccctcgacc cgggcggccg cttcgagcag acatgataag atacattgat gagtttggac 3720
aaaccacaac tagaatgcag tgaaaaaaat gctttatttg tgaaatttgt gatgctattg 3780
ctttatttgt aaccattata agctgcaata aacaagttaa caacaacaat tgcattcatt 3840
ttatgtttca ggttcagggg gagatgtggg aggtttttta aagcaagtaa aacctctaca 3900
aatgtggtaa aatcgataag gatctaggaa cccctagtga tggagttggc cactccctct 3960
ctgcgcgctc gctcgctcac tgaggccgcc cgggcaaagc ccgggcgtcg ggcgaccttt 4020
ggtcgcccgg cctcagtgag cgagcgagcg cgcagagagg gagtggccaa cccccccccc 4080
cccccccctg cagcctggcg taatagcgaa gaggcccgca ccgatcgccc ttcccaacag 4140
ttgcgtagcc tgaatggcga atggcgcgac gcgccctgta gcggcgcatt aagcgcggcg 4200
ggtgtggtgg ttacgcgcag cgtgaccgct acacttgcca gcgccctagc gcccgctcct 4260
ttcgctttct tcccttcctt tctcgccacg ttcgccggct ttccccgtca agctctaaat 4320
cgggggctcc ctttagggtt ccgatttagt gctttacggc acctcgaccc caaaaaactt 4380
gattagggtg atggttcacg tagtgggcca tcgccctgat agacggtttt tcgccctttg 4440
acgttggagt ccacgttctt taatagtgga ctcttgttcc aaactggaac aacactcaac 4500
cctatctcgg tctattcttt tgatttataa gggattttgc cgatttcggc ctattggtta 4560
aaaaatgagc tgatttaaca aaaatttaac gcgaatttta acaaaatatt aacgtttaca 4620
atttcctgat gcggtatttt ctccttacgc atctgtgcgg tatttcacac cgcatatggt 4680
gcactctcag tacaatctgc tctgatgccg catagttaag ccagccccga cacccgccaa 4740
cacccgctga cgcgccctga cgggcttgtc tgctcccggc atccgcttac agacaagctg 4800
tgaccgtctc cgggagctgc atgtgtcaga ggttttcacc gtcatcaccg aaacgcgcga 4860
gacgaaaggg cctcgtgata cgcctatttt tataggttaa tgtcatgata ataatggttt 4920
cttagacgtc aggtggcact tttcggggaa atgtgcgcgg aacccctatt tgtttatttt 4980
tctaaataca ttcaaatatg tatccgctca tgagacaata accctgataa atgcttcaat 5040
aatattgaaa aaggaagagt atgagtattc aacatttccg tgtcgccctt attccctttt 5100
ttgcggcatt ttgccttcct gtttttgctc acccagaaac gctggtgaaa gtaaaagatg 5160
ctgaagatca gttgggtgca cgagtgggtt acatcgaact ggatctcaac agcggtaaga 5220
tccttgagag ttttcgcccc gaagaacgtt ttccaatgat gagcactttt aaagttctgc 5280
tatgtggcgc ggtattatcc cgtattgacg ccgggcaaga gcaactcggt cgccgcatac 5340
actattctca gaatgacttg gttgagtact caccagtcac agaaaagcat cttacggatg 5400
```

FIG. 23B

**p43rmsENC-AT (Ligation of Inverted msEnhancer into p43-AAT*) (cont.)**

```
gcatgacagt aagagaatta tgcagtgctg ccataaccat gagtgataac actgcggcca 5460
acttacttct gacaacgatc ggaggaccga aggagctaac cgcttttttg cacaacatgg 5520
gggatcatgt aactcgcctt gatcgttggg aaccggagct gaatgaagcc ataccaaacg 5580
acgagcgtga caccacgatg cctgtagcaa tggcaacaac gttgcgcaaa ctattaactg 5640
gcgaactact tactctagct tcccggcaac aattaataga ctggatggag gcggataaag 5700
ttgcaggacc acttctgcgc tcggcccttc cggctggctg gtttattgct gataaatctg 5760
gagccggtga gcgtgggtct cgcggtatca ttgcagcact ggggccagat ggtaagccct 5820
cccgtatcgt agttatctac acgacgggga gtcaggcaac tatggatgaa cgaaatagac 5880
agatcgctga gataggtgcc tcactgatta agcattggta actgtcagac caagtttact 5940
catatatact ttagattgat ttaaaacttc atttttaatt taaaaggatc taggtgaaga 6000
tcctttttga taatctcatg accaaaatcc cttaacgtga gttttcgttc cactgagcgt 6060
cagaccccgt agaaaagatc aaaggatctt cttgagatcc tttttttctg cgcgtaatct 6120
gctgcttgca aacaaaaaaa ccaccgctac cagcggtggt ttgtttgccg gatcaagagc 6180
taccaactct ttttccgaag gtaactggct tcagcagagc gcagatacca aatactgtcc 6240
ttctagtgta gccgtagtta ggccaccact tcaagaactc tgtagcaccg cctacatacc 6300
tcgctctgct aatcctgtta ccagtggctg ctgccagtgg cgataagtcg tgtcttaccg 6360
ggttggactc aagacgatag ttaccggata aggcgcagcg gtcgggctga acggggggtt 6420
cgtgcacaca gcccagcttg gagcgaacga cctacaccga actgagatac ctacagcgtg 6480
agcattgaga aagcgccacg cttcccgaag ggagaaaggc ggacaggtat ccggtaagcg 6540
gcagggtcgg aacaggagag cgcacgaggg agcttccagg gggaaacgcc tggtatcttt 6600
atagtcctgt cgggtttcgc cacctctgac ttgagcgtcg atttttgtga tgctcgtcag 6660
gggggcggag cctatggaaa aacgccagca acgcggcctt tttacggttc ctggcctttt 6720
gctggccttt tgctcacatg ttctttcctg cgttatcccc tgattctgtg gataaccgta 6780
ttaccgcctt tgagtgagct gataccgctc gccgcagccg aacgaccgag cgcagcgagt 6840
cagtgagcga ggaagcggaa gagcgcccaa tacgcaaacc gcctctcccc gcgcgttggc 6900
cgattcatta atgcagggct gcag                                        6924
```

FIG. 23C

**p43msENCB-AT (Ligation of msEnhancer into p43CB-AT*) (SEQ ID NO:10)**

```
gggggggggg gggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatctca ccattcctca 180
cgacacccaa atatggcgac gggtgaggaa tggtggggag ttatttttag agcggtgagg 240
aatggtgggc aggcagcagg tgttggcgct ctaaaaataa ctcccgggag ttatttttag 300
agcggtgagg aatggtggac acccaaatat ggcgacggca ccattcctca ccccaggcca 360
tatttgggtg tcagatcttc aatattggcc attagccata ttattcattg gttatatagc 420
ataaatcaat attggctatt ggccattgca tacgttgtat ctatatcata atatgtacat 480
ttatattggc tcatgtccaa tatgaccgcc atgttggcat tgattattga ctagttatta 540
atagtaatca attacggggt cattagttca tagcccatat atggagttcc gcgttacata 600
acttacggta aatggcccgc ctggctgacc gcccaacgac ccccgcccat tgacgtcaat 660
aatgacgtat gttcccatag taacgccaat agggactttc cattgacgtc aatgggtgga 720
gtatttacgg taaactgccc acttggcagt acatcaagtg tatcatatgc caagtccgcc 780
ccctattgac gtcaatgacg gtaaatggcc cgcctggcat tatgcccagt acatgacctt 840
acgggacttt cctacttggc agtacatcta cgtattagtc atcgctatta ccatggtcga 900
ggtgagcccc acgttctgct tcactctccc catctccccc ccctccccac ccccaatttt 960
gtatttattt atttttaat tattttgtgc agcgatgggg gcgggggggg gggggggcg 1020
cgcgccaggc ggggcggggc ggggcgaggg gcggggcggg gcgaggcgga gaggtgcggc 1080
ggcagccaat cagagcggcg cgctccgaaa gtttcctttt atggcgaggc ggcggcggcg 1140
gcggccctat aaaaagcgaa gcgcgcggcg ggcgggagtc gctgcgacgc tgccttcgcc 1200
ccgtgccccg ctccgccgcc gcctcgcgcc gcccgccccg gctctgactg accgcgttac 1260
tcccacaggt gagcgggcgg gacggccctt ctcctccggg ctgtaattag cgcttggttt 1320
aatgacggct tgtttctttt ctgtggctgc gtgaaagcct tgaggggctc cgggagggcc 1380
ctttgtgcgg ggggagcgg ctcgggggt gcgtgcgtgt gtgtgtgcgt ggggagcgcc 1440
gcgtgcggcc cgcgctgccc ggcggctgtg agcgctgcgg gcgcggcgcg gggctttgtg 1500
cgctccgcag tgtgcgcgag gggagcgcgg ccgggggcgg tgccccgcgg tgcggggggg 1560
gctgcgaggg gaacaaaggc tgcgtgcggg gtgtgtgcgt gggggggtga gcagggggtg 1620
tgggcgcggc ggtcgggctg taacccccc ctgcaccccc ctccccgagt tgctgagcac 1680
ggcccggctt cgggtgcggg gctccgtacg gggcgtggcg cggggctcgc cgtgccgggc 1740
gggggtggc ggcaggtggg ggtgccgggc ggggcggggc cgcctcgggc cggggagggc 1800
tcgggggagg ggcgcggcgg cccccggagc gccggcggct gtcgaggcgc ggcgagccgc 1860
agccattgcc ttttatggta atcgtgcgag agggcgcagg gacttccttt gtcccaaatc 1920
tgtgcggagc cgaaatctgg gaggcgccgc cgcacccccct ctagcgggcg cggggcgaag 1980
cggtgcggcg ccggcaggaa ggaaatgggc ggggagggcc ttcgtgcgtc gccgcgccgc 2040
cgtccccttc tccctctcca gcctcggggc tgtccgcggg gggacggctg ccttcggggg 2100
ggacggggca gggcggggtt cggcttctgg cgtgtgaccg gcggctctag agcctctgct 2160
aaccatgttc atgccttctt ctttttccta cagctcctgg gcaacgtgct ggttattgtg 2220
ctgtctcatc attttggcaa agaattcgat atcaagcttg ggattttca ggcaccacca 2280
ctgacctggg acagtgaatc gacaatgccg tcttctgtct cgtggggcat cctcctgctg 2340
gcaggcctgt gctgcctggt ccctgtctcc ctggctgagg atccccaggg agatgctgcc 2400
cagaagacag atacatccca ccatgatcag gatcacccaa ccttcaacaa gatcaccccc 2460
aacctggctg agttcgcctt cagcctatac cgccagctgg cacaccagtc caacagcacc 2520
aatatcttct tctccccagt gagcatcgct acagcctttg caatgctctc cctggggacc 2580
aaggctgaca ctcacgatga aatcctggag ggcctgaatt tcaacctcac ggagattccg 2640
gaggctcaga tccatgaagg cttccaggaa ctcctccgta ccctcaacca gccagacagc 2700
```

FIG. 24A

**p43msENCB-AT (Ligation of msEnhancer into p43CB-AT*) (cont.)**

```
cagctccagc tgaccaccgg caatggcctg ttcctcagcg agggcctgaa gctagtggat 2760
aagtttttgg aggatgttaa aaagttgtac cactcagaag ccttcactgt caacttcggg 2820
gacaccgaag aggccaagaa acagatcaac gattacgtgg agaagggtac tcaagggaaa 2880
attgtggatt tggtcaagga gcttgacaga gacacagttt ttgctctggt gaattacatc 2940
ttctttaaag gcaaatggga gagacccttt gaagtcaagg acaccgagga agaggacttc 3000
cacgtggacc aggtgaccac cgtgaaggtg cctatgatga agcgtttagg catgtttaac 3060
atccagcact gtaagaagct gtccagctgg gtgctgctga tgaaatacct gggcaatgcc 3120
accgccatct tcttcctgcc tgatgagggg aaactacagc acctggaaaa tgaactcacc 3180
cacgatatca tcaccaagtt cctggaaaat gaagacagaa ggtctgccag cttacattta 3240
cccaaactgt ccattactgg aacctatgat ctgaagagcg tcctgggtca actgggcatc 3300
actaaggtct tcagcaatgg ggctgacctc tccggggtca cagaggaggc acccctgaag 3360
ctctccaagg ccgtgcataa ggctgtgctg accatcgacg agaaagggac tgaagctgct 3420
ggggccatgt ttttagaggc catacccatg tctatccccc ccgaggtcaa gttcaacaaa 3480
ccctttgtct tcttaatgat tgaacaaaat accaagtctc ccctcttcat gggaaaagtg 3540
gtgaatccca cccaaaaata actgcctctc gctcctcaac ccctcccctc catccctggc 3600
cccctccctg gatgacatta aagaagggtt gagctggtaa cccccccccc ccctgcaggg 3660
gccctcgacc cgggcggccg cttcgagcag acatgataag atacattgat gagtttggac 3720
aaaccacaac tagaatgcag tgaaaaaaat gctttatttg tgaaatttgt gatgctattg 3780
ctttatttgt aaccattata agctgcaata aacaagttaa caacaacaat tgcattcatt 3840
ttatgtttca ggttcagggg gagatgtggg aggtttttta aagcaagtaa aacctctaca 3900
aatgtggtaa aatcgataag gatctaggaa cccctagtga tggagttggc cactccctct 3960
ctgcgcgctc gctcgctcac tgaggccgcc cgggcaaagc ccgggcgtcg ggcgaccttt 4020
ggtcgcccgg cctcagtgag cgagcgagcg cgcagagagg gagtggccaa cccccccccc 4080
ccccccccctg cagcctggcg taatagcgaa gaggcccgca ccgatcgccc ttcccaacag 4140
ttgcgtagcc tgaatggcga atggcgcgac gcgccctgta gcggcgcatt aagcgcggcg 4200
ggtgtggtgg ttacgcgcag cgtgaccgct acacttgcca gcgccctagc gcccgctcct 4260
ttcgctttct tcccttcctt tctcgccacg ttcgccggct ttccccgtca agctctaaat 4320
cgggggctcc ctttagggtt ccgatttagt gctttacggc acctcgaccc caaaaaactt 4380
gattagggtg atggttcacg tagtgggcca tcgccctgat agacggtttt tcgccctttg 4440
acgttggagt ccacgttctt taatagtgga ctcttgttcc aaactggaac aacactcaac 4500
cctatctcgg tctattcttt tgatttataa gggattttgc cgatttcggc ctattggtta 4560
aaaaatgagc tgatttaaca aaaatttaac gcgaatttta acaaaatatt aacgtttaca 4620
atttcctgat gcggtatttt ctccttacgc atctgtgcgg tatttcacac cgcatatggt 4680
gcactctcag tacaatctgc tctgatgccg catagttaag ccagccccga cacccgccaa 4740
cacccgctga cgcgccctga cgggcttgtc tgctcccggc atccgcttac agacaagctg 4800
tgaccgtctc cgggagctgc atgtgtcaga ggttttcacc gtcatcaccg aaacgcgcga 4860
gacgaaaggg cctcgtgata cgcctatttt tataggttaa tgtcatgata ataatggttt 4920
cttagacgtc aggtggcact tttcggggaa atgtgcgcgg aacccctatt tgtttatttt 4980
tctaaataca ttcaaatatg tatccgctca tgagacaata accctgataa atgcttcaat 5040
aatattgaaa aaggaagagt atgagtattc aacatttccg tgtcgccctt attccctttt 5100
ttgcggcatt ttgccttcct gtttttgctc acccagaaac gctggtgaaa gtaaaagatg 5160
ctgaagatca gttgggtgca cgagtgggtt acatcgaact ggatctcaac agcggtaaga 5220
tccttgagag ttttcgcccc gaagaacgtt ttccaatgat gagcactttt aaagttctgc 5280
tatgtggcgc ggtattatcc cgtattgacg ccgggcaaga gcaactcggt cgccgcatac 5340
actattctca gaatgacttg gttgagtact caccagtcac agaaaagcat cttacggatg 5400
```

FIG. 24B

**p43msENCB-AT (Ligation of msEnhancer into p43CB-AT*) (cont.)**

```
gcatgacagt aagagaatta tgcagtgctg ccataaccat gagtgataac actgcggcca 5460
acttacttct gacaacgatc ggaggaccga aggagctaac cgcttttttg cacaacatgg 5520
gggatcatgt aactcgcctt gatcgttggg aaccggagct gaatgaagcc ataccaaacg 5580
acgagcgtga caccacgatg cctgtagcaa tggcaacaac gttgcgcaaa ctattaactg 5640
gcgaactact tactctagct tcccggcaac aattaataga ctggatggag gcggataaag 5700
ttgcaggacc acttctgcgc tcggcccttc cggctggctg gtttattgct gataaatctg 5760
gagccggtga gcgtgggtct cgcggtatca ttgcagcact ggggccagat ggtaagccct 5820
cccgtatcgt agttatctac acgacgggga gtcaggcaac tatggatgaa cgaaatagac 5880
agatcgctga gataggtgcc tcactgatta agcattggta actgtcagac caagtttact 5940
catatatact ttagattgat ttaaaacttc atttttaatt taaaaggatc taggtgaaga 6000
tcctttttga taatctcatg accaaaatcc cttaacgtga gttttcgttc cactgagcgt 6060
cagaccccgt agaaaagatc aaaggatctt cttgagatcc tttttttctg cgcgtaatct 6120
gctgcttgca aacaaaaaaa ccaccgctac cagcggtggt ttgtttgccg gatcaagagc 6180
taccaactct ttttccgaag gtaactggct tcagcagagc gcagatacca aatactgtcc 6240
ttctagtgta gccgtagtta ggccaccact tcaagaactc tgtagcaccg cctacatacc 6300
tcgctctgct aatcctgtta ccagtggctg ctgccagtgg cgataagtcg tgtcttaccg 6360
ggttggactc aagacgatag ttaccggata aggcgcagcg gtcgggctga acggggggtt 6420
cgtgcacaca gcccagcttg gagcgaacga cctacaccga actgagatac ctacagcgtg 6480
agcattgaga aagcgccacg cttcccgaag ggagaaaggc ggacaggtat ccggtaagcg 6540
gcagggtcgg aacaggagag cgcacgaggg agcttccagg gggaaacgcc tggtatcttt 6600
atagtcctgt cgggtttcgc cacctctgac ttgagcgtcg atttttgtga tgctcgtcag 6660
gggggcggag cctatggaaa aacgccagca acgcggcctt tttacggttc ctggcctttt 6720
gctggccttt tgctcacatg ttctttcctg cgttatcccc tgattctgtg gataaccgta 6780
ttaccgcctt tgagtgagct gataccgctc gccgcagccg aacgaccgag cgcagcgagt 6840
cagtgagcga ggaagcggaa gagcgcccaa tacgcaaacc gcctctcccc gcgcgttggc 6900
cgattcatta atgcagggct gcag                                        6924
```

FIG. 24C p43rmsENCB-AT (Ligation of Inverted msEnhancer into p43CB-AT*) (SEQ ID NO:11)

```
gggggggggg ggggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatctga cacccaaata 180
tggcctgggg tgaggaatgg tgccgtcgcc atatttgggt gtccaccatt cctcaccgct 240
ctaaaaataa ctcccgggag ttatttttag agcgccaaca cctgctgcct gcccaccatt 300
cctcaccgct ctaaaaataa ctccccacca ttcctcaccc gtcgccatat ttgggtgtcg 360
tgaggaatgg tgagatcttc aatattggcc attagccata ttattcattg gttatatagc 420
ataaatcaat attggctatt ggccattgca tacgttgtat ctatatcata atatgtacat 480
ttatattggc tcatgtccaa tatgaccgcc atgttggcat tgattattga ctagttatta 540
atagtaatca attacggggt cattagttca tagcccatat atggagttcc gcgttacata 600
acttacggta aatggcccgc ctggctgacc gcccaacgac ccccgcccat tgacgtcaat 660
aatgacgtat gttcccatag taacgccaat agggactttc cattgacgtc aatgggtgga 720
gtatttacgg taaactgccc acttggcagt acatcaagtg tatcatatgc caagtccgcc 780
ccctattgac gtcaatgacg gtaaatggcc cgcctggcat tatgcccagt acatgacctt 840
acgggacttt cctacttggc agtacatcta cgtattagtc atcgctatta ccatggtcga 900
ggtgagcccc acgttctgct tcactctccc catctccccc ccctccccac ccccaatttt 960
gtatttattt atttttttaat tattttgtgc agcgatgggg gcgggggggg gggggggcg 1020
cgcgccaggc ggggcggggc ggggcgaggg gcggggcggg gcgaggcgga gaggtgcggc 1080
ggcagccaat cagagcggcg cgctccgaaa gtttcctttt atggcgaggc ggcggcggcg 1140
gcggccctat aaaaagcgaa gcgcgcggcg ggcgggagtc gctgcgacgc tgccttcgcc 1200
ccgtgccccg ctccgccgcc gcctcgcgcc gcccgccccg gctctgactg accgcgttac 1260
tcccacaggt gagcgggcgg gacggccctt ctcctccggg ctgtaattag cgcttggttt 1320
aatgacggct tgtttctttt ctgtggctgc gtgaaagcct tgaggggctc cgggagggcc 1380
ctttgtgcgg ggggggagcgg ctcggggggt gcgtgcgtgt gtgtgtgcgt ggggagcgcc 1440
gcgtgcggcc cgcgctgccc ggcggctgtg agcgctgcgg gcgcggcgcg gggctttgtg 1500
cgctccgcag tgtgcgcgag gggagcgcgg ccgggggcgg tgccccgcgg tgcggggggg 1560
gctgcgaggg gaacaaaggc tgcgtgcggg gtgtgtgcgt gggggggtga gcagggggtg 1620
tgggcgcggc ggtcgggctg taaccccccc ctgcaccccc ctccccgagt tgctgagcac 1680
ggcccggctt cgggtgcggg gctccgtacg gggcgtggcg cggggctcgc cgtgccgggc 1740
gggggggtggc ggcaggtggg ggtgccgggc ggggcggggc cgcctcgggc cggggagggc 1800
tcgggggagg ggcgcggcgg cccccggagc gccggcggct gtcgaggcgc ggcgagccgc 1860
agccattgcc ttttatggta atcgtgcgag agggcgcagg gacttccttt gtcccaaatc 1920
tgtgcggagc cgaaatctgg gaggcgccgc cgcacccccct ctagcgggcg cggggcgaag 1980
cggtgcggcg ccggcaggaa ggaaatgggc ggggagggcc ttcgtgcgtc gccgcgccgc 2040
cgtccccttc tccctctcca gcctcggggc tgtccgcggg gggacggctg ccttcggggg 2100
ggacggggca gggcggggtt cggcttctgg cgtgtgaccg gcggctctag agcctctgct 2160
aaccatgttc atgccttctt ctttttccta cagctcctgg gcaacgtgct ggttattgtg 2220
ctgtctcatc attttggcaa agaattcgat atcaagcttg ggattttca ggcaccacca 2280
ctgacctggg acagtgaatc gacaatgccg tcttctgtct cgtggggcat cctcctgctg 2340
gcaggcctgt gctgcctggt ccctgtctcc ctggctgagg atccccaggg agatgctgcc 2400
```

FIG. 25A p43rmsENCB-AT (Ligation of Inverted msEnhancer into p43CB-AT*) (cont.)

```
cagaagacag atacatccca ccatgatcag gatcacccaa ccttcaacaa gatcaccccc 2460
aacctggctg agttcgcctt cagcctatac cgccagctgg cacaccagtc caacagcacc 2520
aatatcttct tctccccagt gagcatcgct acagcctttg caatgctctc cctggggacc 2580
aaggctgaca ctcacgatga aatcctggag ggcctgaatt tcaacctcac ggagattccg 2640
gaggctcaga tccatgaagg cttccaggaa ctcctccgta ccctcaacca gccagacagc 2700
cagctccagc tgaccaccgg caatggcctg ttcctcagcg agggcctgaa gctagtggat 2760
aagtttttgg aggatgttaa aaagttgtac cactcagaag ccttcactgt caacttcggg 2820
gacaccgaag aggccaagaa acagatcaac gattacgtgg agaagggtac tcaagggaaa 2880
attgtggatt tggtcaagga gcttgacaga gacacagttt ttgctctggt gaattacatc 2940
ttctttaaag gcaaatggga gagacccttt gaagtcaagg acaccgagga agaggacttc 3000
cacgtggacc aggtgaccac cgtgaaggtg cctatgatga agcgtttagg catgtttaac 3060
atccagcact gtaagaagct gtccagctgg gtgctgctga tgaaatacct gggcaatgcc 3120
accgccatct tcttcctgcc tgatgagggg aaactacagc acctggaaaa tgaactcacc 3180
cacgatatca tcaccaagtt cctggaaaat gaagacagaa ggtctgccag cttacattta 3240
cccaaactgt ccattactgg aacctatgat ctgaagagcg tcctgggtca actgggcatc 3300
actaaggtct tcagcaatgg ggctgacctc tccggggtca cagaggaggc accccctgaag 3360
ctctccaagg ccgtgcataa ggctgtgctg accatcgacg agaaagggac tgaagctgct 3420
ggggccatgt ttttagaggc catacccatg tctatccccc ccgaggtcaa gttcaacaaa 3480
ccctttgtct tcttaatgat tgaacaaaat accaagtctc ccctcttcat gggaaaagtg 3540
gtgaatccca cccaaaaata actgcctctc gctcctcaac ccctcccctc catccctggc 3600
cccctccctg gatgacatta aagaagggtt gagctggtaa cccccccccc ccctgcaggg 3660
gccctcgacc cgggcggccg cttcgagcag acatgataag atacattgat gagtttggac 3720
aaaccacaac tagaatgcag tgaaaaaaat gctttatttg tgaaatttgt gatgctattg 3780
ctttatttgt aaccattata agctgcaata aacaagttaa caacaacaat tgcattcatt 3840
ttatgtttca ggttcagggg gagatgtggg aggtttttta aagcaagtaa aacctctaca 3900
aatgtggtaa aatcgataag gatctaggaa cccctagtga tggagttggc cactccctct 3960
ctgcgcgctc gctcgctcac tgaggccgcc cgggcaaagc ccgggcgtcg ggcgaccttt 4020
ggtcgcccgg cctcagtgag cgagcgagcg cgcagagagg gagtggccaa cccccccccc 4080
cccccccctg cagcctggcg taatagcgaa gaggcccgca ccgatcgccc ttcccaacag 4140
ttgcgtagcc tgaatggcga atggcgcgac gcgccctgta gcggcgcatt aagcgcggcg 4200
ggtgtggtgg ttacgcgcag cgtgaccgct acacttgcca gcgccctagc gcccgctcct 4260
ttcgctttct tcccttcctt tctcgccacg ttcgccggct ttccccgtca agctctaaat 4320
cgggggctcc ctttagggtt ccgatttagt gctttacggc acctcgaccc caaaaaactt 4380
gattagggtg atggttcacg tagtgggcca tcgccctgat agacggtttt tcgccctttg 4440
acgttggagt ccacgttctt taatagtgga ctcttgttcc aaactggaac aacactcaac 4500
cctatctcgg tctattcttt tgatttataa gggattttgc cgatttcggc ctattggtta 4560
aaaaatgagc tgatttaaca aaaatttaac gcgaatttta acaaaatatt aacgtttaca 4620
atttcctgat gcggtatttt ctccttacgc atctgtgcgg tatttcacac cgcatatggt 4680
gcactctcag tacaatctgc tctgatgccg catagttaag ccagccccga cacccgccaa 4740
cacccgctga cgcgccctga cgggcttgtc tgctcccggc atccgcttac agacaagctg 4800
tgaccgtctc cgggagctgc atgtgtcaga ggttttcacc gtcatcaccg aaacgcgcga 4860
gacgaaaggg cctcgtgata cgcctatttt tataggttaa tgtcatgata ataatggttt 4920
cttagacgtc aggtggcact tttcggggaa atgtgcgcgg aacccctatt tgtttatttt 4980
tctaaataca ttcaaatatg tatccgctca tgagacaata accctgataa atgcttcaat 5040
aatattgaaa aaggaagagt atgagtattc aacatttccg tgtcgccctt attccctttt 5100
```

FIG. 25B

**p43rmsENCB-AT (Ligation of Inverted msEnhancer into p43CB-AT*) (cont.)**

```
ttgcggcatt ttgccttcct gtttttgctc acccagaaac gctggtgaaa gtaaaagatg 5160
ctgaagatca gttgggtgca cgagtgggtt acatcgaact ggatctcaac agcggtaaga 5220
tccttgagag ttttcgcccc gaagaacgtt ttccaatgat gagcactttt aaagttctgc 5280
tatgtggcgc ggtattatcc cgtattgacg ccgggcaaga gcaactcggt cgccgcatac 5340
actattctca gaatgacttg gttgagtact caccagtcac agaaaagcat cttacggatg 5400
gcatgacagt aagagaatta tgcagtgctg ccataaccat gagtgataac actgcggcca 5460
acttacttct gacaacgatc ggaggaccga aggagctaac cgcttttttg cacaacatgg 5520
gggatcatgt aactcgcctt gatcgttggg aaccggagct gaatgaagcc ataccaaacg 5580
acgagcgtga caccacgatg cctgtagcaa tggcaacaac gttgcgcaaa ctattaactg 5640
gcgaactact tactctagct tcccggcaac aattaataga ctggatggag gcggataaag 5700
ttgcaggacc acttctgcgc tcggcccttc cggctggctg gtttattgct gataaatctg 5760
gagccggtga gcgtgggtct cgcggtatca ttgcagcact ggggccagat ggtaagccct 5820
cccgtatcgt agttatctac acgacgggga gtcaggcaac tatggatgaa cgaaatagac 5880
agatcgctga gataggtgcc tcactgatta agcattggta actgtcagac caagtttact 5940
catatatact ttagattgat ttaaaacttc atttttaatt taaaaggatc taggtgaaga 6000
tcctttttga taatctcatg accaaaatcc cttaacgtga gttttcgttc cactgagcgt 6060
cagaccccgt agaaaagatc aaaggatctt cttgagatcc tttttttctg cgcgtaatct 6120
gctgcttgca aacaaaaaaa ccaccgctac cagcggtggt ttgtttgccg gatcaagagc 6180
taccaactct ttttccgaag gtaactggct tcagcagagc gcagatacca aatactgtcc 6240
ttctagtgta gccgtagtta ggccaccact tcaagaactc tgtagcaccg cctacatacc 6300
tcgctctgct aatcctgtta ccagtggctg ctgccagtgg cgataagtcg tgtcttaccg 6360
ggttggactc aagacgatag ttaccggata aggcgcagcg gtcgggctga acggggggtt 6420
cgtgcacaca gcccagcttg gagcgaacga cctacaccga actgagatac ctacagcgtg 6480
agcattgaga aagcgccacg cttcccgaag ggagaaaggc ggacaggtat ccggtaagcg 6540
gcagggtcgg aacaggagag cgcacgaggg agcttccagg gggaaacgcc tggtatcttt 6600
atagtcctgt cgggtttcgc cacctctgac ttgagcgtcg atttttgtga tgctcgtcag 6660
gggggcggag cctatggaaa aacgccagca acgcggcctt tttacggttc ctggcctttt 6720
gctggccttt tgctcacatg ttctttcctg cgttatcccc tgattctgtg gataaccgta 6780
ttaccgcctt tgagtgagct gataccgctc gccgcagccg aacgaccgag cgcagcgagt 6840
cagtgagcga ggaagcggaa gagcgcccaa tacgcaaacc gcctctcccc gcgcgttggc 6900
cgattcatta atgcagggct gcag                                        6924
```

FIG. 25C

SEQUENCE LISTING

```
<160> NUMBER OF SEQ ID NOS: 13

<210> SEQ ID NO 1
<211> LENGTH: 6565
<212> TYPE: DNA
<213> ORGANISM: Artificial Sequence
<220> FEATURE:
<223> OTHER INFORMATION: Description of Artificial Sequence:PLASMID C-AT

<400> SEQUENCE: 1
```

-continued

```
gggggggggg ggggggggtt ggccactccc tctctgcgcg ctcgctcgct cactgaggcc     60
gggcgaccaa aggtcgcccg acgcccgggc tttgcccggg cggcctcagt gagcgagcga    120
gcgcgcagag agggagtggc caactccatc actaggggtt cctagatctg aattcggtac    180
ccgttacata acttacggta aatggcccgc ctggctgacc gcccaacgac ccccgcccat    240
tgacgtcaat aatgacgtat gttcccatag taacgccaat agggactttc cattgacgtc    300
aatgggtgga gtatttacgg taaactgccc acttggcagt acatcaagtg tatcatatgc    360
caagtacgcc ccctattgac gtcaatgacg gtaaatggcc cgcctggcat tatgcccagt    420
acatgacctt atgggacttt cctacttggc agtacatcta cgtattagtc atcgctatta    480
ccatggtgat gcggttttgg cagtacatca atgggcgtgg atagcggttt gactcacggg    540
gatttccaag tctccacccc attgacgtca atgggagttt gttttggcac caaaatcaac    600
gggactttcc aaaatgtcgt aacaactccg ccccattgac gcaaatgggc ggtaggcgtg    660
tacggtggga ggtctatata agcagagctc gtttagtgaa ccgtcagatc gcctggagac    720
gccatccacg ctgttttgac ctccatagaa gacaccggga ccgatccagc ctccggactc    780
tagaactagt ggatcccccg ggctgcagga attcgatatc aagcttgggg attttcaggc    840
accaccactg acctgggaca gtgaatcgac aatgccgtct tctgtctcgt ggggcatcct    900
cctgctggca ggcctgtgct gcctggtccc tgtctccctg gctgaggatc cccagggaga    960
tgctgcccag aagacagata catcccacca tgatcaggat cacccaacct tcaacaagat   1020
cacccccaac ctggctgagt tcgccttcag cctataccgc cagctggcac accagtccaa   1080
cagcaccaat atcttcttct ccccagtgag catcgctaca gcctttgcaa tgctctccct   1140
ggggaccaag gctgacactc acgatgaaat cctggagggc ctgaatttca acctcacgga   1200
gattccggag gctcagatcc atgaaggctt ccaggaactc ctccgtaccc tcaaccagcc   1260
agacagccag ctccagctga ccaccggcaa tggcctgttc ctcagcgagg gcctgaagct   1320
agtggataag tttttggagg atgttaaaaa gttgtaccac tcagaagcct tcactgtcaa   1380
cttcggggac accgaagagg ccaagaaaca gatcaacgat tacgtggaga agggtactca   1440
agggaaaatt gtggatttgg tcaaggagct tgacagagac acagtttttg ctctggtgaa   1500
ttacatcttc tttaaaggca aatgggagag accctttgaa gtcaaggaca ccgaggaaga   1560
ggacttccac gtggaccagg tgaccaccgt gaaggtgcct atgatgaagc gtttaggcat   1620
gtttaacatc cagcactgta agaagctgtc cagctgggtg ctgctgatga aatacctggg   1680
caatgccacc gccatcttct tcctgcctga tgaggggaaa ctacagcacc tggaaaatga   1740
actcacccac gatatcatca ccaagttcct ggaaaatgaa gacagaaggt ctgccagctt   1800
acatttaccc aaactgtcca ttactggaac ctatgatctg aagagcgtcc tgggtcaact   1860
gggcatcact aaggtcttca gcaatggggc tgacctctcc ggggtcacag aggaggcacc   1920
cctgaagctc tccaaggccg tgcataaggc tgtgctgacc atcgacgaga aagggactga   1980
agctgctggg gccatgtttt tagaggccat acccatgtct atcccccccg aggtcaagtt   2040
caacaaaccc tttgtcttct taatgattga acaaaatacc aagtctcccc tcttcatggg   2100
aaaagtggtg aatcccaccc aaaaataact gcctctcgct cctcaacccc tcccctccat   2160
ccctggcccc ctccctggat gacattaaag aagggttgag ctggtaaccc cccccccccc   2220
tgcaggggcc ctcgagcagt gtggttttgc aagaggaagc aaaaagcctc tccacccagg   2280
cctggaatgt ttccacccaa gtcgaaggca gtgtggtttt gcaagaggaa gcaaaaagcc   2340
tctccaccca ggcctggaat gtttccaccc aatgtcgagc aaccccgccc agcgtcttgt   2400
```

-continued

```
cattggcgaa ttcgaacacg cagatgcagt cggggcggcg cggtcccagg tccacttcgc   2460

atattaaggt gacgcgtgtg gcctcgaaca ccgagcgacc ctgcagccaa tatgggatcg   2520

gccattgaac aagatggatt gcacgcaggt tctccggccg cttgggtgga gaggctattc   2580

ggctatgact gggcacaaca gacaatcggc tgctctgatg ccgccgtgtt ccggctgtca   2640

gcgcaggggc gcccggttct ttttgtcaag accgacctgt ccggtgccct gaatgaactg   2700

caggacgagg cagcgcggct atcgtggctg gccacgacgg gcgttccttg cgcagctgtg   2760

ctcgacgttg tcactgaagc gggaagggac tggctgctat tgggcgaagt gccggggcag   2820

gatctcctgt catctcacct tgctcctgcc gagaaagtat ccatcatggc tgatgcaatg   2880

cggcggctgc atacgcttga tccggctacc tgcccattcg accaccaagc gaaacatcgc   2940

atcgagcgag cacgtactcg gatggaagcc ggtcttgtcg atcaggatga tctggacgaa   3000

gagcatcagg ggctcgcgcc agccgaactg ttcgccaggc tcaaggcgcg catgcccgac   3060

ggcgaggatc tcgtcgtgac ccatggcgat gcctgcttgc cgaatatcat ggtggaaaat   3120

ggccgctttt ctggattcat cgactgtggc cggctgggtg tggcggaccg ctatcaggac   3180

atagcgttgg ctacccgtga tattgctgaa gagcttggcg gcgaatgggc tgaccgcttc   3240

ctcgtgcttt acggtatcgc cgctcccgat tcgcagcgca tcgccttcta tcgccttctt   3300

gacgagttct tctgagggga tccgtcgact agagctcgct gatcagcctc gactgtgcct   3360

tctagttgcc agccatctgt tgtttgcccc tcccccgtgc cttccttgac cctggaaggt   3420

gccactccca ctgtcctttc ctaataaaat gaggaaattg catcgcattg tctgagtagg   3480

tgtcattcta ttctgggggg tggggtgggg caggacagca agggggagga ttgggaagac   3540

aatagcaggc atgctgggga gagatctagg aaccccctagt gatggagttg gccactccct   3600

ctctgcgcgc tcgctcgctc actgaggccg cccgggcaaa gcccgggcgt cgggcgacct   3660

ttggtcgccc ggcctcagtg agcgagcgag cgcgcagaga gggagtggcc aacccccccc   3720

cccccccccc tgcagccctg cattaatgaa tcggccaacg cgcggggaga ggcggtttgc   3780

gtattgggcg ctcttccgct tcctcgctca ctgactcgct gcgctcggtc gttcggctgc   3840

ggcgagcggt atcagctcac tcaaaggcgg taatacggtt atccacagaa tcaggggata   3900

acgcaggaaa gaacatgtga gcaaaaggcc agcaaaaggc caggaaccgt aaaaaggccg   3960

cgttgctggc gtttttccat aggctccgcc cccctgacga gcatcacaaa aatcgacgct   4020

caagtcagag gtggcgaaac ccgacaggac tataaagata ccaggcgttt ccccctggaa   4080

gctccctcgt gcgctctcct gttccgaccc tgccgcttac cggatacctg tccgcctttc   4140

tcccttcggg aagcgtggcg ctttctcaat gctcacgctg taggtatctc agttcggtgt   4200

aggtcgttcg ctccaagctg ggctgtgtgc acgaaccccc cgttcagccc gaccgctgcg   4260

ccttatccgg taactatcgt cttgagtcca acccggtaag acacgactta tcgccactgg   4320

cagcagccac tggtaacagg attagcagag cgaggtatgt aggcggtgct acagagttct   4380

tgaagtggtg gcctaactac ggctacacta gaaggacagt atttggtatc tgcgctctgc   4440

tgaagccagt taccttcgga aaaagagttg gtagctcttg atccggcaaa caaaccaccg   4500

ctggtagcgg tggttttttt gtttgcaagc agcagattac gcgcagaaaa aaaggatctc   4560

aagaagatcc tttgatcttt tctacggggt ctgacgctca gtggaacgaa aactcacgtt   4620

aagggatttt ggtcatgaga ttatcaaaaa ggatcttcac ctagatcctt ttaaattaaa   4680

aatgaagttt taaatcaatc taaagtatat atgagtaaac ttggtctgac agttaccaat   4740
```

-continued

```
gcttaatcag tgaggcacct atctcagcga tctgtctatt tcgttcatcc atagttgcct   4800

gactccccgt cgtgtagata actacgatac gggagggctt accatctggc cccagtgctg   4860

caatgatacc gcgagaccca cgctcaccgg ctccagattt atcagcaata aaccagccag   4920

ccggaagggc cgagcgcaga agtggtcctg caactttatc cgcctccatc cagtctatta   4980

attgttgccg ggaagctaga gtaagtagtt cgccagttaa tagtttgcgc aacgttgttg   5040

ccattgctac aggcatcgtg gtgtcacgct cgtcgtttgg tatggcttca ttcagctccg   5100

gttcccaacg atcaaggcga gttacatgat cccccatgtt gtgcaaaaaa gcggttagct   5160

ccttcggtcc tccgatcgtt gtcagaagta agttggccgc agtgttatca ctcatggtta   5220

tggcagcact gcataattct cttactgtca tgccatccgt aagatgcttt tctgtgactg   5280

gtgagtactc aaccaagtca ttctgagaat agtgtatgcg gcgaccgagt tgctcttgcc   5340

cggcgtcaat acgggataat accgcgccac atagcagaac tttaaaagtg ctcatcattg   5400

gaaaacgttc ttcggggcga aaactctcaa ggatcttacc gctgttgaga tccagttcga   5460

tgtaacccac tcgtgcaccc aactgatctt cagcatcttt tactttcacc agcgtttctg   5520

ggtgagcaaa aacaggaagg caaaatgccg caaaaaaggg aataagggcg acacggaaat   5580

gttgaatact catactcttc ctttttcaat attattgaag catttatcag ggttattgtc   5640

tcatgagcgg atacatattt gaatgtattt agaaaaataa acaaataggg gttccgcgca   5700

catttccccg aaaagtgcca cctgacgtct aagaaaccat tattatcatg acattaacct   5760

ataaaaatag gcgtatcacg aggccctttc gtctcgcgcg tttcggtgat gacggtgaaa   5820

acctctgaca catgcagctc ccggagacgg tcacagcttg tctgtaagcg gatgccggga   5880

gcagacaagc ccgtcagggc gcgtcagcgg gtgttggcgg gtgtcggggc tggcttaact   5940

atgcggcatc agagcagatt gtactgagag tgcaccatat gcggtgtgaa ataccgcaca   6000

gatgcgtaag gagaaaatac cgcatcagga aattgtaaac gttaatattt tgttaaaatt   6060

cgcgttaaat ttttgttaaa tcagctcatt ttttaaccaa taggccgaaa tcggcaaaat   6120

cccttataaa tcaaaagaat agaccgagat agggttgagt gttgttccag tttggaacaa   6180

gagtccacta ttaaagaacg tggactccaa cgtcaaaggg cgaaaaaccg tctatcaggg   6240

cgatggccca ctacgtgaac catcacccta atcaagtttt ttggggtcga ggtgccgtaa   6300

agcactaaat cggaacccta aagggagccc ccgatttaga gcttgacggg gaaagccggc   6360

gaacgtggcg agaaaggaag ggaagaaagc gaaaggagcg ggcgctaggg cgctggcaag   6420

tgtagcggtc acgctgcgcg taaccaccac acccgccgcg cttaatgcgc cgctacaggg   6480

cgcgtcgcgc cattcgccat tcaggctacg caactgttgg gaagggcgat cggtgcgggc   6540

ctcttcgcta ttacgccagg ctgca                                         6565
```

<210> SEQ ID NO 2
<211> LENGTH: 7405
<212> TYPE: DNA
<213> ORGANISM: Artificial Sequence
<220> FEATURE:
<223> OTHER INFORMATION: Description of Artificial Sequence:PLASMID E-AT

<400> SEQUENCE: 2

```
gggggggggg ggggggggtt ggccactccc tctctgcgcg ctcgctcgct cactgaggcc     60

gggcgaccaa aggtcgcccg acgcccgggc tttgcccggg cggcctcagt gagcgagcga    120

gcgcgcagag agggagtggc caactccatc actaggggtt cctagatctg aattcggtac    180

cttggagcta agccagcaat ggtagaggga agattctgca cgtcccttcc aggcggcctc    240
```

-continued

```
cccgtcacca cccccccaa cccgccccga ccggagctga gagtaattca tacaaaagga    300
ctcgcccctg ccttggggaa tcccagggac cgtcgttaaa ctcccactaa cgtagaaccc    360
agagatcgct gcgttcccgc cccctcaccc gcccgctctc gtcatcactg aggtggagaa    420
gagcatgcgt gaggctccgg tgcccgtcag tgggcagagc gcacatcgcc cacagtcccc    480
gagaagttgg ggggaggggt cggcaattga accggtgcct agagaaggtg gcgcggggta    540
aactgggaaa gtgatgtcgt gtactggctc cgcctttttc ccgagggtgg gggagaaccg    600
tatataagtg cagtagtcgc cgtgaacgtt ctttttcgca acgggtttgc cgccagaaca    660
caggtaagtg ccgtgtgtgg ttcccgcggg cctggcctct ttacgggtta tggcccttgc    720
gtgccttgaa ttacttccac gcccctggct gcagtacgtg attcttgatc ccgagcttcg    780
ggttggaagt gggtgggaga gttcgaggcc ttgcgcttaa ggagcccctt cgcctcgtgc    840
ttgagttgag gcctggcctg ggcgctgggg ccgccgcgtg cgaatctggt ggcaccttcg    900
cgcctgtctc gctgctttcg ataagtctct agccatttaa aatttttgat gacctgctgc    960
gacgcttttt ttctggcaag atagtcttgt aaatgcgggc caagatctgc acactggtat   1020
ttcggttttt ggggccgcgg gcggcgacgg ggcccgtgcg tcccagcgca catgttcggc   1080
gaggcggggc ctgcgagcgc ggccaccgag aatcggacgg gggtagtctc aagctggccg   1140
gcctgctctg gtgcctggcc tcgcgccgcc gtgtatcgcc ccgccctggg cggcaaggct   1200
ggcccggtcg gcaccagttg cgtgagcgga aagatggccg cttcccggcc ctgctgcagg   1260
gagctcaaaa tggaggacgc ggcgctcggg agagcgggcg ggtgagtcac ccacacaaag   1320
gaaaagggcc tttccgtcct cagccgtcgc ttcatgtgac tccacggagt accgggcgcc   1380
gtccaggcac ctcgattagt tctcgagctt ttggagtacg tcgtctttag gttgggggga   1440
ggggttttat gcgatggagt ttccccacac tgagtgggtg gagactgaag ttaggccagc   1500
ttggcacttg atgtaattct ccttggaatt tgcccttttt gagtttggat cttggttcat   1560
tctcaagcct cagacagtgg ttcaaagttt ttttcttcca tttcaggtgt cgtgaaaatc   1620
tagaactagt ggatcccccg ggctgcagga attcgatatc aagcttgggg attttcaggc   1680
accaccactg acctgggaca gtgaatcgac aatgccgtct tctgtctcgt ggggcatcct   1740
cctgctggca ggcctgtgct gcctggtccc tgtctccctg gctgaggatc cccagggaga   1800
tgctgcccag aagacagata catcccacca tgatcaggat cacccaacct tcaacaagat   1860
cacccccaac ctggctgagt tcgccttcag cctataccgc cagctggcac accagtccaa   1920
cagcaccaat atcttcttct ccccagtgag catcgctaca gcctttgcaa tgctctccct   1980
ggggaccaag gctgacactc acgatgaaat cctggagggc ctgaatttca acctcacgga   2040
gattccggag gctcagatcc atgaaggctt ccaggaactc ctccgtaccc tcaaccagcc   2100
agacagccag ctccagctga ccaccggcaa tggcctgttc ctcagcgagg gcctgaagct   2160
agtggataag tttttggagg atgttaaaaa gttgtaccac tcagaagcct tcactgtcaa   2220
cttcggggac accgaagagg ccaagaaaca gatcaacgat tacgtggaga agggtactca   2280
agggaaaatt gtggatttgg tcaaggagct tgacagagac acagtttttg ctctggtgaa   2340
ttacatcttc tttaaaggca aatgggagag accctttgaa gtcaaggaca ccgaggaaga   2400
ggacttccac gtggaccagg tgaccaccgt gaaggtgcct atgatgaagc gtttaggcat   2460
gtttaacatc cagcactgta agaagctgtc cagctgggtg ctgctgatga aatacctggg   2520
caatgccacc gccatcttct tcctgcctga tgaggggaaa ctacagcacc tggaaaatga   2580
```

-continued

```
actcacccac gatatcatca ccaagttcct ggaaaatgaa gacagaaggt ctgccagctt   2640

acatttaccc aaactgtcca ttactggaac ctatgatctg aagagcgtcc tgggtcaact   2700

gggcatcact aaggtcttca gcaatggggc tgacctctcc ggggtcacag aggaggcacc   2760

cctgaagctc tccaaggccg tgcataaggc tgtgctgacc atcgacgaga aagggactga   2820

agctgctggg gccatgtttt tagaggccat acccatgtct atcccccccg aggtcaagtt   2880

caacaaaccc tttgtcttct taatgattga acaaaatacc aagtctcccc tcttcatggg   2940

aaaagtggtg aatcccaccc aaaaataact gcctctcgct cctcaacccc tcccctccat   3000

ccctggcccc ctccctggat gacattaaag aagggttgag ctggtaaccc cccccccccc   3060

tgcaggggcc ctcgagcagt gtggttttgc aagaggaagc aaaaagcctc tccacccagg   3120

cctggaatgt ttccacccaa gtcgaaggca gtgtggtttt gcaagaggaa gcaaaaagcc   3180

tctccaccca ggcctggaat gtttccaccc aatgtcgagc aaccccgccc agcgtcttgt   3240

cattggcgaa ttcgaacacg cagatgcagt cggggcggcg cggtcccagg tccacttcgc   3300

atattaaggt gacgcgtgtg gcctcgaaca ccgagcgacc ctgcagccaa tatgggatcg   3360

gccattgaac aagatggatt gcacgcaggt tctccggccg cttgggtgga gaggctattc   3420

ggctatgact gggcacaaca gacaatcggc tgctctgatg ccgccgtgtt ccggctgtca   3480

gcgcaggggc gcccggttct ttttgtcaag accgacctgt ccggtgccct gaatgaactg   3540

caggacgagg cagcgcggct atcgtggctg gccacgacgg gcgttccttg cgcagctgtg   3600

ctcgacgttg tcactgaagc gggaagggac tggctgctat tgggcgaagt gccggggcag   3660

gatctcctgt catctcacct tgctcctgcc gagaaagtat ccatcatggc tgatgcaatg   3720

cggcggctgc atacgcttga tccggctacc tgcccattcg accaccaagc gaaacatcgc   3780

atcgagcgag cacgtactcg gatggaagcc ggtcttgtcg atcaggatga tctggacgaa   3840

gagcatcagg ggctcgcgcc agccgaactg ttcgccaggc tcaaggcgcg catgcccgac   3900

ggcgaggatc tcgtcgtgac ccatggcgat gcctgcttgc cgaatatcat ggtggaaaat   3960

ggccgctttt ctggattcat cgactgtggc cggctgggtg tggcggaccg ctatcaggac   4020

atagcgttgg ctacccgtga tattgctgaa gagcttggcg gcgaatgggc tgaccgcttc   4080

ctcgtgcttt acggtatcgc cgctcccgat tcgcagcgca tcgccttcta tcgccttctt   4140

gacgagttct tctgagggga tccgtcgact agagctcgct gatcagcctc gactgtgcct   4200

tctagttgcc agccatctgt tgtttgcccc tcccccgtgc cttccttgac cctggaaggt   4260

gccactccca ctgtcctttc ctaataaaat gaggaaattg catcgcattg tctgagtagg   4320

tgtcattcta ttctgggggg tggggtgggg caggacagca agggggagga ttgggaagac   4380

aatagcaggc atgctgggga gagatctagg aacccctagt gatggagttg gccactccct   4440

ctctgcgcgc tcgctcgctc actgaggccg cccgggcaaa gcccgggcgt cgggcgacct   4500

ttggtcgccc ggcctcagtg agcgagcgag cgcgcagaga gggagtggcc aacccccccc   4560

cccccccccc tgcagccctg cattaatgaa tcggccaacg cgcggggaga ggcggtttgc   4620

gtattgggcg ctcttccgct tcctcgctca ctgactcgct gcgctcggtc gttcggctgc   4680

ggcgagcggt atcagctcac tcaaaggcgg taatacggtt atccacagaa tcaggggata   4740

acgcaggaaa gaacatgtga gcaaaaggcc agcaaaaggc caggaaccgt aaaaaggccg   4800

cgttgctggc gtttttccat aggctccgcc cccctgacga gcatcacaaa aatcgacgct   4860

caagtcagag gtggcgaaac ccgacaggac tataaagata ccaggcgttt ccccctggaa   4920

gctccctcgt gcgctctcct gttccgaccc tgccgcttac cggatacctg tccgcctttc   4980
```

-continued

```
tcccttcggg aagcgtggcg ctttctcaat gctcacgctg taggtatctc agttcggtgt   5040
aggtcgttcg ctccaagctg ggctgtgtgc acgaaccccc cgttcagccc gaccgctgcg   5100
ccttatccgg taactatcgt cttgagtcca acccggtaag acacgactta tcgccactgg   5160
cagcagccac tggtaacagg attagcagag cgaggtatgt aggcggtgct acagagttct   5220
tgaagtggtg gcctaactac ggctacacta gaaggacagt atttggtatc tgcgctctgc   5280
tgaagccagt taccttcgga aaaagagttg gtagctcttg atccggcaaa caaaccaccg   5340
ctggtagcgg tggttttttt gtttgcaagc agcagattac gcgcagaaaa aaaggatctc   5400
aagaagatcc tttgatcttt tctacggggt ctgacgctca gtggaacgaa aactcacgtt   5460
aagggatttt ggtcatgaga ttatcaaaaa ggatcttcac ctagatcctt ttaaattaaa   5520
aatgaagttt taaatcaatc taaagtatat atgagtaaac ttggtctgac agttaccaat   5580
gcttaatcag tgaggcacct atctcagcga tctgtctatt tcgttcatcc atagttgcct   5640
gactccccgt cgtgtagata actacgatac gggagggctt accatctggc cccagtgctg   5700
caatgatacc gcgagaccca cgctcaccgg ctccagattt atcagcaata aaccagccag   5760
ccggaagggc cgagcgcaga agtggtcctg caactttatc cgcctccatc cagtctatta   5820
attgttgccg ggaagctaga gtaagtagtt cgccagttaa tagtttgcgc aacgttgttg   5880
ccattgctac aggcatcgtg gtgtcacgct cgtcgtttgg tatggcttca ttcagctccg   5940
gttcccaacg atcaaggcga gttacatgat cccccatgtt gtgcaaaaaa gcggttagct   6000
ccttcggtcc tccgatcgtt gtcagaagta agttggccgc agtgttatca ctcatggtta   6060
tggcagcact gcataattct cttactgtca tgccatccgt aagatgcttt tctgtgactg   6120
gtgagtactc aaccaagtca ttctgagaat agtgtatgcg gcgaccgagt tgctcttgcc   6180
cggcgtcaat acgggataat accgcgccac atagcagaac tttaaaagtg ctcatcattg   6240
gaaaacgttc ttcggggcga aaactctcaa ggatcttacc gctgttgaga tccagttcga   6300
tgtaacccac tcgtgcaccc aactgatctt cagcatcttt tactttcacc agcgtttctg   6360
ggtgagcaaa aacaggaagg caaaatgccg caaaaaaggg aataagggcg acacggaaat   6420
gttgaatact catactcttc ctttttcaat attattgaag catttatcag ggttattgtc   6480
tcatgagcgg atacatattt gaatgtattt agaaaaataa acaaataggg gttccgcgca   6540
catttccccg aaaagtgcca cctgacgtct aagaaaccat tattatcatg acattaacct   6600
ataaaaatag gcgtatcacg aggccctttc gtctcgcgcg tttcggtgat gacggtgaaa   6660
acctctgaca catgcagctc ccggagacgg tcacagcttg tctgtaagcg gatgccggga   6720
gcagacaagc ccgtcagggc gcgtcagcgg gtgttggcgg gtgtcggggc tggcttaact   6780
atgcggcatc agagcagatt gtactgagag tgcaccatat gcggtgtgaa ataccgcaca   6840
gatgcgtaag gagaaaatac cgcatcagga aattgtaaac gttaatattt tgttaaaatt   6900
cgcgttaaat ttttgttaaa tcagctcatt ttttaaccaa taggccgaaa tcggcaaaat   6960
cccttataaa tcaaaagaat agaccgagat agggttgagt gttgttccag tttggaacaa   7020
gagtccacta ttaaagaacg tggactccaa cgtcaaaggg cgaaaaaccg tctatcaggg   7080
cgatggccca ctacgtgaac catcacccta atcaagtttt ttggggtcga ggtgccgtaa   7140
agcactaaat cggaacccta aagggagccc ccgatttaga gcttgacggg gaaagccggc   7200
gaacgtggcg agaaaggaag ggaagaaagc gaaaggagcg ggcgctaggg cgctggcaag   7260
tgtagcggtc acgctgcgcg taaccaccac acccgccgcg cttaatgcgc cgctacaggg   7320
```

-continued

```
cgcgtcgcgc cattcgccat tcaggctacg caactgttgg gaagggcgat cggtgcgggc   7380

ctcttcgcta ttacgccagg ctgca                                         7405


<210> SEQ ID NO 3
<211> LENGTH: 7054
<212> TYPE: DNA
<213> ORGANISM: Artificial Sequence
<220> FEATURE:
<223> OTHER INFORMATION: Description of Artificial Sequence:PLASMID
      dE-AT

<400> SEQUENCE: 3

gggggggggg ggggggggtt ggccactccc tctctgcgcg ctcgctcgct cactgaggcc     60

gggcgaccaa aggtcgcccg acgcccgggc tttgcccggg cggcctcagt gagcgagcga    120

gcgcgcagag agggagtggc caactccatc actaggggtt cctagatctg aattcggtac    180

cttggagcta agccagcaat ggtagaggga agattctgca cgtcccttcc aggcggcctc    240

cccgtcacca cccccccaa cccgccccga ccggagctga gagtaattca tacaaaagga     300

ctcgcccctg ccttggggaa tcccagggac cgtcgttaaa ctcccactaa cgtagaaccc    360

agagatcgct gcgttcccgc cccctcaccc gcccgctctc gtcatcactg aggtggagaa    420

gagcatgcgt gaggctccgg tgcccgtcag tgggcagagc gcacatcgcc cacagtcccc    480

gagaagttgg ggggaggggt cggcaattga accggtgcct agagaaggtg gcgcggggta    540

aactgggaaa gtgatgtcgt gtactggctc cgcctttttc ccgagggtgg gggagaaccg    600

tatataagtg cagtagtcgc cgtgaacgtt ctttttcgca acgggtttgc cgccagaaca    660

caggtaagtg ccgtgtgtgg ttcccgcggg cggcgacggg gcccgtgcgt cccagcgcac    720

atgttcggcg aggcggggcc tgcgagcgcg gccaccgaga atcggacggg ggtagtctca    780

agctggccgg cctgctctgg tgcctggcct cgcgccgccg tgtatcgccc cgccctgggc    840

ggcaaggctg gcccggtcgg caccagttgc gtgagcggaa agatggccgc ttcccggccc    900

tgctgcaggg agctcaaaat ggaggacgcg gcgctcggga gagcgggcgg gtgagtcacc    960

cacacaaagg aaaagggcct ttccgtcctc agccgtcgct tcatgtgact ccacggagta   1020

ccgggcgccg tccaggcacc tcgattagtt ctcgagcttt tggagtacgt cgtctttagg   1080

ttggggggag gggttttatg cgatggagtt tccccacact gagtgggtgg agactgaagt   1140

taggccagct tggcacttga tgtaattctc cttggaattt gccctttttg agtttggatc   1200

ttggttcatt ctcaagcctc agacagtggt tcaaagtttt tttcttccat ttcaggtgtc   1260

gtgaaaatct agaactagtg gatcccccgg gctgcaggaa ttcgatatca agcttgggga   1320

ttttcaggca ccaccactga cctgggacag tgaatcgaca atgccgtctt ctgtctcgtg   1380

gggcatcctc ctgctggcag gcctgtgctg cctggtccct gtctccctgg ctgaggatcc   1440

ccagggagat gctgcccaga agacagatac atcccaccat gatcaggatc acccaacctt   1500

caacaagatc acccccaacc tggctgagtt cgccttcagc ctataccgcc agctggcaca   1560

ccagtccaac agcaccaata tcttcttctc cccagtgagc atcgctacag cctttgcaat   1620

gctctccctg gggaccaagg ctgacactca cgatgaaatc ctggagggcc tgaatttcaa   1680

cctcacggag attccggagg ctcagatcca tgaaggcttc caggaactcc tccgtaccct   1740

caaccagcca gacagccagc tccagctgac caccggcaat ggcctgttcc tcagcgaggg   1800

cctgaagcta gtggataagt tttggaggga tgttaaaaag ttgtaccact cagaagcctt   1860

cactgtcaac ttcggggaca ccgaagaggc caagaaacag atcaacgatt acgtggagaa   1920
```

-continued

```
gggtactcaa gggaaaattg tggatttggt caaggagctt gacagagaca cagtttttgc   1980
tctggtgaat tacatcttct ttaaaggcaa atgggagaga ccctttgaag tcaaggacac   2040
cgaggaagag gacttccacg tggaccaggt gaccaccgtg aaggtgccta tgatgaagcg   2100
tttaggcatg tttaacatcc agcactgtaa gaagctgtcc agctgggtgc tgctgatgaa   2160
atacctgggc aatgccaccg ccatcttctt cctgcctgat gaggggaaac tacagcacct   2220
ggaaaatgaa ctcacccacg atatcatcac caagttcctg gaaaatgaag acagaaggtc   2280
tgccagctta catttaccca aactgtccat tactggaacc tatgatctga agagcgtcct   2340
gggtcaactg ggcatcacta aggtcttcag caatggggct gacctctccg gggtcacaga   2400
ggaggcaccc ctgaagctct ccaaggccgt gcataaggct gtgctgacca tcgacgagaa   2460
agggactgaa gctgctgggg ccatgttttt agaggccata cccatgtcta tcccccccga   2520
ggtcaagttc aacaaaccct ttgtcttctt aatgattgaa caaaatacca agtctcccct   2580
cttcatggga aaagtggtga atcccaccca aaaataactg cctctcgctc ctcaacccct   2640
cccctccatc cctggccccc tccctggatg acattaaaga agggttgagc tggtaacccc   2700
ccccccccct gcaggggccc tcgagcagtg tggttttgca agaggaagca aaaagcctct   2760
ccacccaggc ctggaatgtt tccacccaag tcgaaggcag tgtggttttg caagaggaag   2820
caaaaagcct ctccacccag gcctggaatg tttccaccca atgtcgagca accccgccca   2880
gcgtcttgtc attggcgaat tcgaacacgc agatgcagtc ggggcggcgc ggtcccaggt   2940
ccacttcgca tattaaggtg acgcgtgtgg cctcgaacac cgagcgaccc tgcagccaat   3000
atgggatcgg ccattgaaca agatggattg cacgcaggtt ctccggccgc ttgggtggag   3060
aggctattcg gctatgactg ggcacaacag acaatcggct gctctgatgc cgccgtgttc   3120
cggctgtcag cgcaggggcg cccggttctt tttgtcaaga ccgacctgtc cggtgccctg   3180
aatgaactgc aggacgaggc agcgcggcta tcgtggctgg ccacgacggg cgttccttgc   3240
gcagctgtgc tcgacgttgt cactgaagcg ggaagggact ggctgctatt gggcgaagtg   3300
ccggggcagg atctcctgtc atctcacctt gctcctgccg agaaagtatc catcatggct   3360
gatgcaatgc ggcggctgca tacgcttgat ccggctacct gcccattcga ccaccaagcg   3420
aaacatcgca tcgagcgagc acgtactcgg atggaagccg gtcttgtcga tcaggatgat   3480
ctggacgaag agcatcaggg gctcgcgcca gccgaactgt tcgccaggct caaggcgcgc   3540
atgcccgacg gcgaggatct cgtcgtgacc catggcgatg cctgcttgcc gaatatcatg   3600
gtggaaaatg gccgcttttc tggattcatc gactgtggcc ggctgggtgt ggcggaccgc   3660
tatcaggaca tagcgttggc tacccgtgat attgctgaag agcttggcgg cgaatgggct   3720
gaccgcttcc tcgtgcttta cggtatcgcc gctcccgatt cgcagcgcat cgccttctat   3780
cgccttcttg acgagttctt ctgaggggat ccgtcgacta gagctcgctg atcagcctcg   3840
actgtgcctt ctagttgcca gccatctgtt gtttgcccct cccccgtgcc ttccttgacc   3900
ctggaaggtg ccactcccac tgtcctttcc taataaaatg aggaaattgc atcgcattgt   3960
ctgagtaggt gtcattctat tctggggggt ggggtggggc aggacagcaa gggggaggat   4020
tgggaagaca atagcaggca tgctggggag agatctagga acccctagtg atggagttgg   4080
ccactccctc tctgcgcgct cgctcgctca ctgaggccgc ccgggcaaag cccgggcgtc   4140
gggcgacctt tggtcgcccg gcctcagtga gcgagcgagc gcgcagagag ggagtggcca   4200
acccccccccc cccccccct gcagccctgc attaatgaat cggccaacgc gcggggagag   4260
gcggtttgcg tattgggcgc tcttccgctt cctcgctcac tgactcgctg cgctcggtcg   4320
```

-continued

```
ttcggctgcg gcgagcggta tcagctcact caaaggcggt aatacggtta tccacagaat   4380
caggggataa cgcaggaaag aacatgtgag caaaaggcca gcaaaaggcc aggaaccgta   4440
aaaaggccgc gttgctggcg tttttccata ggctccgccc ccctgacgag catcacaaaa   4500
atcgacgctc aagtcagagg tggcgaaacc cgacaggact ataaagatac caggcgtttc   4560
cccctggaag ctccctcgtg cgctctcctg ttccgaccct gccgcttacc ggatacctgt   4620
ccgcctttct cccttcggga agcgtggcgc tttctcaatg ctcacgctgt aggtatctca   4680
gttcggtgta ggtcgttcgc tccaagctgg gctgtgtgca cgaacccccc gttcagcccg   4740
accgctgcgc cttatccggt aactatcgtc ttgagtccaa cccggtaaga cacgacttat   4800
cgccactggc agcagccact ggtaacagga ttagcagagc gaggtatgta ggcggtgcta   4860
cagagttctt gaagtggtgg cctaactacg gctacactag aaggacagta tttggtatct   4920
gcgctctgct gaagccagtt accttcggaa aaagagttgg tagctcttga tccggcaaac   4980
aaaccaccgc tggtagcggt ggtttttttg tttgcaagca gcagattacg cgcagaaaaa   5040
aaggatctca agaagatcct ttgatctttt ctacggggtc tgacgctcag tggaacgaaa   5100
actcacgtta agggattttg gtcatgagat tatcaaaaag gatcttcacc tagatccttt   5160
taaattaaaa atgaagtttt aaatcaatct aaagtatata tgagtaaact tggtctgaca   5220
gttaccaatg cttaatcagt gaggcaccta tctcagcgat ctgtctattt cgttcatcca   5280
tagttgcctg actccccgtc gtgtagataa ctacgatacg ggagggctta ccatctggcc   5340
ccagtgctgc aatgataccg cgagacccac gctcaccggc tccagattta tcagcaataa   5400
accagccagc cggaagggcc gagcgcagaa gtggtcctgc aactttatcc gcctccatcc   5460
agtctattaa ttgttgccgg gaagctagag taagtagttc gccagttaat agtttgcgca   5520
acgttgttgc cattgctaca ggcatcgtgg tgtcacgctc gtcgtttggt atggcttcat   5580
tcagctccgg ttcccaacga tcaaggcgag ttacatgatc ccccatgttg tgcaaaaaag   5640
cggttagctc cttcggtcct ccgatcgttg tcagaagtaa gttggccgca gtgttatcac   5700
tcatggttat ggcagcactg cataattctc ttactgtcat gccatccgta agatgctttt   5760
ctgtgactgg tgagtactca accaagtcat tctgagaata gtgtatgcgg cgaccgagtt   5820
gctcttgccc ggcgtcaata cgggataata ccgcgccaca tagcagaact ttaaaagtgc   5880
tcatcattgg aaaacgttct tcggggcgaa aactctcaag gatcttaccg ctgttgagat   5940
ccagttcgat gtaacccact cgtgcaccca actgatcttc agcatctttt actttcacca   6000
gcgtttctgg gtgagcaaaa acaggaaggc aaaatgccgc aaaaaaggga ataagggcga   6060
cacggaaatg ttgaatactc atactcttcc tttttcaata ttattgaagc atttatcagg   6120
gttattgtct catgagcgga tacatatttg aatgtattta gaaaaataaa caaatagggg   6180
ttccgcgcac atttccccga aaagtgccac ctgacgtcta agaaaccatt attatcatga   6240
cattaaccta taaaaatagg cgtatcacga ggccctttcg tctcgcgcgt ttcggtgatg   6300
acggtgaaaa cctctgacac atgcagctcc cggagacggt cacagcttgt ctgtaagcgg   6360
atgccgggag cagacaagcc cgtcagggcg cgtcagcggg tgttggcggg tgtcggggct   6420
ggcttaacta tgcggcatca gagcagattg tactgagagt gcaccatatg cggtgtgaaa   6480
taccgcacag atgcgtaagg agaaaatacc gcatcaggaa attgtaaacg ttaatatttt   6540
gttaaaattc gcgttaaatt tttgttaaat cagctcattt tttaaccaat aggccgaaat   6600
cggcaaaatc ccttataaat caaaagaata gaccgagata gggttgagtg ttgttccagt   6660
```

-continued

```
ttggaacaag agtccactat taaagaacgt ggactccaac gtcaaagggc gaaaaaccgt   6720

ctatcagggc gatggcccac tacgtgaacc atcaccctaa tcaagttttt tggggtcgag   6780

gtgccgtaaa gcactaaatc ggaaccctaa agggagcccc cgatttagag cttgacgggg   6840

aaagccggcg aacgtggcga gaaaggaagg gaagaaagcg aaaggagcgg gcgctagggc   6900

gctggcaagt gtagcggtca cgctgcgcgt aaccaccaca cccgccgcgc ttaatgcgcc   6960

gctacagggc gcgtcgcgcc attcgccatt caggctacgc aactgttggg aagggcgatc   7020

ggtgcgggcc tcttcgctat tacgccaggc tgca                              7054
```

<210> SEQ ID NO 4
<211> LENGTH: 5932
<212> TYPE: DNA
<213> ORGANISM: Artificial Sequence
<220> FEATURE:
<223> OTHER INFORMATION: Description of Artificial Sequence:p43C-AT

<400> SEQUENCE: 4

```
gggggggggg ggggggggttg gccactccct ctctgcgcgc tcgctcgctc actgaggccg     60

ggcgaccaaa ggtcgcccga cgcccgggct ttgcccgggc ggcctcagtg agcgagcgag    120

cgcgcagaga gggagtggcc aactccatca ctaggggttc ctagatcttc aatattggcc    180

attagccata ttattcattg gttatatagc ataaatcaat attggctatt ggccattgca    240

tacgttgtat ctatatcata atatgtacat ttatattggc tcatgtccaa tatgaccgcc    300

atgttggcat tgattattga ctagttatta atagtaatca attacggggt cattagttca    360

tagcccatat atggagttcc gcgttacata acttacggta aatggcccgc ctggctgacc    420

gcccaacgac ccccgcccat tgacgtcaat aatgacgtat gttcccatag taacgccaat    480

agggactttc cattgacgtc aatgggtgga gtatttacgg taaactgccc acttggcagt    540

acatcaagtg tatcatatgc caagtccgcc ccctattgac gtcaatgacg gtaaatggcc    600

cgcctggcat tatgcccagt acatgacctt acgggacttt cctacttggc agtacatcta    660

cgtattagtc atcgctatta ccatggtgat gcggttttgg cagtacacca atgggcgtgg    720

atagcggttt gactcacggg gatttccaag tctccacccc attgacgtca atgggagttt    780

gttttggcac caaaatcaac gggactttcc aaaatgtcgt aataaccccg ccccgttgac    840

gcaaatgggc ggtaggcgtg tacggtggga ggtctatata agcagagctc gtttagtgaa    900

ccgtcagatc actagaagct ttattgcggt agtttatcac agttaaattg ctaacgcagt    960

cagtgcttct gacacaacag tctcgaactt aagctgcaga agttggtcgt gaggcactgg   1020

gcaggtaagt atcaaggtta caagacaggt ttaaggagac caatagaaac tgggcttgtc   1080

gagacagaga agactcttgc gtttctgata ggcacctatt ggtcttactg acatccactt   1140

tgcctttctc tccacaggtg tccactccca gttcaattac agctcttaag gctagagtac   1200

ttaatacgac tcactatagg ctagaactag tggatccccc gggctgcagg aattcgatat   1260

caagcttggg gattttcagg caccaccact gacctgggac agtgaatcga caatgccgtc   1320

ttctgtctcg tggggcatcc tcctgctggc aggcctgtgc tgcctggtcc ctgtctccct   1380

ggctgaggat ccccagggag atgctgccca gaagacagat acatcccacc atgatcagga   1440

tcacccaacc ttcaacaaga tcacccccaa cctggctgag ttcgccttca gcctataccg   1500

ccagctggca caccagtcca acagcaccaa tatcttcttc tccccagtga gcatcgctac   1560

agcctttgca atgctctccc tggggaccaa ggctgacact cacgatgaaa tcctggaggg   1620

cctgaatttc aacctcacgg agattccgga ggctcagatc catgaaggct tccaggaact   1680
```

-continued

```
cctccgtacc ctcaaccagc cagacagcca gctccagctg accaccggca atggcctgtt   1740
cctcagcgag ggcctgaagc tagtggataa gtttttggag gatgttaaaa agttgtacca   1800
ctcagaagcc ttcactgtca acttcgggga caccgaagag gccaagaaac agatcaacga   1860
ttacgtggag aagggtactc aagggaaaat tgtggatttg gtcaaggagc ttgacagaga   1920
cacagttttt gctctggtga attacatctt ctttaaaggc aaatgggaga gaccctttga   1980
agtcaaggac accgaggaag aggacttcca cgtggaccag gtgaccaccg tgaaggtgcc   2040
tatgatgaag cgtttaggca tgtttaacat ccagcactgt aagaagctgt ccagctgggt   2100
gctgctgatg aaatacctgg gcaatgccac cgccatcttc ttcctgcctg atgaggggaa   2160
actacagcac ctggaaaatg aactcaccca cgatatcatc accaagttcc tggaaaatga   2220
agacagaagg tctgccagct tacatttacc caaactgtcc attactggaa cctatgatct   2280
gaagagcgtc ctgggtcaac tgggcatcac taaggtcttc agcaatgggg ctgacctctc   2340
cggggtcaca gaggaggcac ccctgaagct ctccaaggcc gtgcataagg ctgtgctgac   2400
catcgacgag aaagggactg aagctgctgg ggccatgttt ttagaggcca tacccatgtc   2460
tatccccccc gaggtcaagt tcaacaaacc ctttgtcttc ttaatgattg aacaaaatac   2520
caagtctccc ctcttcatgg gaaaagtggt gaatcccacc caaaaataac tgcctctcgc   2580
tcctcaaccc ctcccctcca tccctggccc cctccctgga tgacattaaa gaagggttga   2640
gctggtaacc cccccccccc ctgcaggggc cctcgacccg ggcggccgct tcgagcagac   2700
atgataagat acattgatga gtttggacaa accacaacta gaatgcagtg aaaaaaatgc   2760
tttatttgtg aaatttgtga tgctattgct ttatttgtaa ccattataag ctgcaataaa   2820
caagttaaca acaacaattg cattcatttt atgtttcagg ttcaggggga gatgtgggag   2880
gtttttttaaa gcaagtaaaa cctctacaaa tgtggtaaaa tcgataagga tctaggaacc   2940
cctagtgatg gagttggcca ctccctctct gcgcgctcgc tcgctcactg aggccgcccg   3000
ggcaaagccc gggcgtcggg cgacctttgg tcgcccggcc tcagtgagcg agcgagcgcg   3060
cagagaggga gtggccaacc cccccccccc cccccctgca gcctggcgta atagcgaaga   3120
ggcccgcacc gatcgccctt cccaacagtt gcgtagcctg aatggcgaat ggcgcgacgc   3180
gccctgtagc ggcgcattaa gcgcggcggg tgtggtggtt acgcgcagcg tgaccgctac   3240
acttgccagc gccctagcgc ccgctccttt cgctttcttc ccttcctttc tcgccacgtt   3300
cgccggcttt ccccgtcaag ctctaaatcg ggggctccct ttagggttcc gatttagtgc   3360
tttacggcac ctcgacccca aaaaacttga ttagggtgat ggttcacgta gtgggccatc   3420
gccctgatag acggtttttc gccctttgac gttggagtcc acgttcttta atagtggact   3480
cttgttccaa actggaacaa cactcaaccc tatctcggtc tattcttttg atttataagg   3540
gattttgccg atttcggcct attggttaaa aaatgagctg atttaacaaa aatttaacgc   3600
gaattttaac aaaatattaa cgtttacaat ttcctgatgc ggtattttct ccttacgcat   3660
ctgtgcggta tttcacaccg catatggtgc actctcagta caatctgctc tgatgccgca   3720
tagttaagcc agccccgaca cccgccaaca cccgctgacg cgccctgacg ggcttgtctg   3780
ctcccggcat ccgcttacag acaagctgtg accgtctccg ggagctgcat gtgtcagagg   3840
ttttcaccgt catcaccgaa acgcgcgaga cgaaagggcc tcgtgatacg cctattttta   3900
taggttaatg tcatgataat aatggtttct tagacgtcag gtggcacttt tcggggaaat   3960
gtgcgcggaa cccctatttg tttatttttc taaatacatt caaatatgta tccgctcatg   4020
```

-continued

```
agacaataac cctgataaat gcttcaataa tattgaaaaa ggaagagtat gagtattcaa   4080

catttccgtg tcgcccttat tccctttttt gcggcatttt gccttcctgt ttttgctcac   4140

ccagaaacgc tggtgaaagt aaaagatgct gaagatcagt tgggtgcacg agtgggttac   4200

atcgaactgg atctcaacag cggtaagatc cttgagagtt ttcgccccga agaacgtttt   4260

ccaatgatga gcacttttaa agttctgcta tgtggcgcgg tattatcccg tattgacgcc   4320

gggcaagagc aactcggtcg ccgcatacac tattctcaga atgacttggt tgagtactca   4380

ccagtcacag aaaagcatct tacggatggc atgacagtaa gagaattatg cagtgctgcc   4440

ataaccatga gtgataacac tgcggccaac ttacttctga caacgatcgg aggaccgaag   4500

gagctaaccg cttttttgca caacatgggg gatcatgtaa ctcgccttga tcgttgggaa   4560

ccggagctga atgaagccat accaaacgac gagcgtgaca ccacgatgcc tgtagcaatg   4620

gcaacaacgt tgcgcaaact attaactggc gaactactta ctctagcttc ccggcaacaa   4680

ttaatagact ggatggaggc ggataaagtt gcaggaccac ttctgcgctc ggcccttccg   4740

gctggctggt ttattgctga taaatctgga gccggtgagc gtgggtctcg cggtatcatt   4800

gcagcactgg ggccagatgg taagccctcc cgtatcgtag ttatctacac gacggggagt   4860

caggcaacta tggatgaacg aaatagacag atcgctgaga taggtgcctc actgattaag   4920

cattggtaac tgtcagacca agtttactca tatatacttt agattgattt aaaacttcat   4980

ttttaattta aaaggatcta ggtgaagatc ctttttgata atctcatgac caaaatccct   5040

taacgtgagt tttcgttcca ctgagcgtca gaccccgtag aaaagatcaa aggatcttct   5100

tgagatcctt tttttctgcg cgtaatctgc tgcttgcaaa caaaaaaacc accgctacca   5160

gcggtggttt gtttgccgga tcaagagcta ccaactcttt ttccgaaggt aactggcttc   5220

agcagagcgc agataccaaa tactgtcctt ctagtgtagc cgtagttagg ccaccacttc   5280

aagaactctg tagcaccgcc tacatacctc gctctgctaa tcctgttacc agtggctgct   5340

gccagtggcg ataagtcgtg tcttaccggg ttggactcaa gacgatagtt accggataag   5400

gcgcagcggt cgggctgaac ggggggttcg tgcacacagc ccagcttgga gcgaacgacc   5460

tacaccgaac tgagatacct acagcgtgag cattgagaaa gcgccacgct tcccgaaggg   5520

agaaaggcgg acaggtatcc ggtaagcggc agggtcggaa caggagagcg cacgagggag   5580

cttccagggg gaaacgcctg gtatctttat agtcctgtcg ggtttcgcca cctctgactt   5640

gagcgtcgat ttttgtgatg ctcgtcaggg gggcggagcc tatggaaaaa cgccagcaac   5700

gcggcctttt tacggttcct ggccttttgc tggccttttg ctcacatgtt ctttcctgcg   5760

ttatcccctg attctgtgga taaccgtatt accgcctttg agtgagctga taccgctcgc   5820

cgcagccgaa cgaccgagcg cagcgagtca gtgagcgagg aagcggaaga gcgcccaata   5880

cgcaaaccgc ctctccccgc gcgttggccg attcattaat gcagggctgc ag           5932
```

```
<210> SEQ ID NO 5
<211> LENGTH: 7492
<212> TYPE: DNA
<213> ORGANISM: Artificial Sequence
<220> FEATURE:
<223> OTHER INFORMATION: Description of Artificial Sequence:p43C-AT-IN

<400> SEQUENCE: 5

aattccgcat tgcagagata attgtattta agtgcctagc tcgatacaat aaacgccatt     60

tgaccattca ccacattggt gtgcacctcc actagctgcc ttgactgcct ggcccccca    120

tctctgtctt gcaggacaat gccgtcttct gtctcgtggg gcatcctcct gctggcaggc    180
```

-continued

```
ctgtgctgcc tggtccctgt ctccctggct gaggatcccc agggagatgc tgcccagaag    240
acagatacat cccaccatga tcaggatcac ccaaccttca acaagatcac ccccaacctg    300
gctgagttcg ccttcagcct ataccgccag ctggcacacc agtccaacag caccaatatc    360
ttcttctccc cagtgagcat cgctacagcc tttgcaatgc tctccctggg gaccaaggct    420
gacactcacg atgaaatcct ggagggcctg aatttcaacc tcacggagat tccggaggct    480
cagatccatg aaggcttcca ggaactcctc cgtaccctca accagccaga cagccagctc    540
cagctgacca ccggcaatgg cctgttcctc agcgagggcc tgaagctagt ggataagttt    600
ttggaggatg ttaaaaagtt gtaccactca gaagccttca ctgtcaactt cggggacacc    660
gaagaggcca agaaacagat caacgattac gtggagaagg gtactcaagg gaaaattgtg    720
gatttggtca aggagcttga cagagacaca gtttttgctc tggtgaatta catcttcttt    780
aaaggtaagg ttgctcaacc agcctgagct gtttcccata gaaacaagca aaaatatttc    840
tcaaaccatc agttcttgaa ctctccttgg caatgcatta tgggccatag caatgctttt    900
cagcgtggat tcttcagttt tctacacaca aacactaaaa tgttttccat cattgagtaa    960
tttgaggaaa taatagatta aactgtcaaa actactgacg ctctgcagaa cttttcagag   1020
cctttaatgt ccttgtgtat actgtatatg tagaatatat aatgcttaga actatagaac   1080
aaattgtaat acactgcata aagggatagt ttcatggaac atactttaca cgactctagt   1140
gtcccagaat cagtatcagt tttgcaatct gaaagacctg ggttcaaatc ctgcctctaa   1200
cacaattagc ttttgacaaa aacaatgcat tctacctctt tgaggtgcta atttctcatc   1260
ttagcatgga caaaatacca ttcttgctgt caggtttttt taggattaaa caaatgacaa   1320
agactgtggg gatggtgtgt ggcatacagc aggtgatgga ctcttctgta tctcaggctg   1380
ccttcctgcc cctgaggggt taaaatgcca gggtcctggg ggccccaggg cattctaagc   1440
cagctcccac tgtcccagga aaacagcata ggggaggga ggtgggaggc aaggccaggg   1500
gctgcttcct ccactctgag gctcccttgc tcttgaggca aaggagggca gtggaggcaa   1560
gccaggctgc agtcagcaca gctaaagtcc tggctctgct gtggccttag tgggggccca   1620
ggtccctctc cagccccagt ctcctccttc tgtccaatga gaaagctggg atcaggggtc   1680
cctgaggccc ctgtccactc tgcatgcctc gatggtgaag ctctgttggt atggcagagg   1740
ggaggctgct caggcatctg catttcccct gccaatctag aggatgagga aagctctcag   1800
gaatagtaag cagaatgttt gccctggatg aataactgag ctgccaatta acaaggggca   1860
gggagcctta gacagaaggt accaaatatg cctgatgctc caacatttta tttgtaatat   1920
ccaagacacc ctcaaataaa catatgattc caataaaaat gcacagccac gatggcatct   1980
cttagcctga catcgccacg atgtagaaat tctgcatctt cctctagttt tgaattatcc   2040
ccacacaatc tttttcggca gcttggatgg tcagtttcag caccttttac agatgatgaa   2100
gctgagcctc gagggatgtg tgtcgtcaag gggctcagg gcttctcagg gaggggactc   2160
atggtttctt attctgctac actcttccaa accttcactc acccctggtg atgcccacct   2220
tcccctctct ccaggcaaat gggagagacc ctttgaagtc aaggacaccg aggaagagga   2280
cttccacgtg gaccaggtga ccaccgtgaa ggtgcctatg atgaagcgtt taggcatgtt   2340
taacatccag cactgtaaga agctgtccag ctgggtgctg ctgatgaaat acctgggcaa   2400
tgccaccgcc atcttcttcc tgcctgatga ggggaaacta cagcacctgg aaaatgaact   2460
cacccacgat atcatcacca agttcctgga aaatgaagac agaaggtctg ccagcttaca   2520
```

-continued

```
tttacccaaa ctgtccatta ctggaaccta tgatctgaag agcgtcctgg gtcaactggg   2580
catcactaag gtcttcagca atggggctga cctctccggg gtcacagagg aggcacccct   2640
gaagctctcc aaggccgtgc ataaggctgt gctgaccatc gacgagaaag ggactgaagc   2700
tgctggggcc atgtttttag aggccatacc catgtctatc ccccccgagg tcaagttcaa   2760
caaacccttt gtcttcttaa tgattgaaca aaataccaag tctcccctct tcatgggaaa   2820
agtggtgaat cccacccaaa aataactgcc tctcgctcct caacccctcc cctccatccc   2880
tggccccctc cctggatgac attaaagaag ggttgagctg gtaacccccc ccccccctgc   2940
aggccctcga gacgcgtggc atgcaagctt ggtaccgagc tcggatccac tagtaacggc   3000
cgccagtgtg ctggaattca cgcgtggtac ctctagagtc gacccgggcg gccgcttcga   3060
gcagacatga taagatacat tgatgagttt ggacaaacca caactagaat gcagtgaaaa   3120
aaatgcttta tttgtgaaat ttgtgatgct attgctttat ttgtaaccat tataagctgc   3180
aataaacaag ttaacaacaa caattgcatt cattttatgt ttcaggttca gggggagatg   3240
tgggaggttt tttaaagcaa gtaaaacctc tacaaatgtg gtaaaatcga taaggatcta   3300
ggaaccccta gtgatggagt tggccactcc ctctctgcgc gctcgctcgc tcactgaggc   3360
cgcccgggca aagcccgggc gtcgggcgac ctttggtcgc ccggcctcag tgagcgagcg   3420
agcgcgcaga gagggagtgg ccaactgcag ctgcattaat gaatcggcca acgcgcgggg   3480
agaggcggtt tgcgtattgg gcgctcttcc gcttcctcgc tcactgactc gctgcgctcg   3540
gtcgttcggc tgcggcgagc ggtatcagct cactcaaagg cggtaatacg gttatccaca   3600
gaatcagggg ataacgcagg aaagaacatg tgagcaaaag gccagcaaaa ggccaggaac   3660
cgtaaaaagg ccgcgttgct ggcgtttttc cataggctcc gcccccctga cgagcatcac   3720
aaaaatcgac gctcaagtca gaggtggcga aacccgacag gactataaag ataccaggcg   3780
tttccccctg gaagctccct cgtgcgctct cctgttccga ccctgccgct taccggatac   3840
ctgtccgcct ttctcccttc gggaagcgtg gcgctttctc aatgctcacg ctgtaggtat   3900
ctcagttcgg tgtaggtcgt tcgctccaag ctgggctgtg tgcacgaacc ccccgttcag   3960
cccgaccgct gcgccttatc cggtaactat cgtcttgagt ccaacccggt aagacacgac   4020
ttatcgccac tggcagcagc cactggtaac aggattagca gagcgaggta tgtaggcggt   4080
gctacagagt tcttgaagtg gtggcctaac tacggctaca ctagaaggac agtatttggt   4140
atctgcgctc tgctgaagcc agttaccttc ggaaaaagag ttggtagctc ttgatccggc   4200
aaacaaacca ccgctggtag cggtggtttt tttgtttgca agcagcagat tacgcgcaga   4260
aaaaaaggat ctcaagaaga tcctttgatc ttttctacgg ggtctgacgc tcagtggaac   4320
gaaaactcac gttaagggat tttggtcatg agattatcaa aaaggatctt cacctagatc   4380
cttttaaatt aaaaatgaag ttttaaatca atctaaagta tatatgagta aacttggtct   4440
gacagttacc aatgcttaat cagtgaggca cctatctcag cgatctgtct atttcgttca   4500
tccatagttg cctgactccc cgtcgtgtag ataactacga tacgggaggg cttaccatct   4560
ggccccagtg ctgcaatgat accgcgagac ccacgctcac cggctccaga tttatcagca   4620
ataaaccagc cagccggaag ggccgagcgc agaagtggtc ctgcaacttt atccgcctcc   4680
atccagtcta ttaattgttg ccgggaagct agagtaagta gttcgccagt taatagtttg   4740
cgcaacgttg ttgccattgc tacaggcatc gtggtgtcac gctcgtcgtt tggtatggct   4800
tcattcagct ccggttccca acgatcaagg cgagttacat gatcccccat gttgtgcaaa   4860
aaagcggtta gctccttcgg tcctccgatc gttgtcagaa gtaagttggc cgcagtgtta   4920
```

-continued

```
tcactcatgg ttatggcagc actgcataat tctcttactg tcatgccatc cgtaagatgc   4980
ttttctgtga ctggtgagta ctcaaccaag tcattctgag aatagtgtat gcggcgaccg   5040
agttgctctt gcccggcgtc aatacgggat aataccgcgc cacatagcag aactttaaaa   5100
gtgctcatca ttggaaaacg ttcttcgggg cgaaaactct caaggatctt accgctgttg   5160
agatccagtt cgatgtaacc cactcgtgca cccaactgat cttcagcatc ttttactttc   5220
accagcgttt ctgggtgagc aaaaacagga aggcaaaatg ccgcaaaaaa gggaataagg   5280
gcgacacgga aatgttgaat actcatactc ttcctttttc aatattattg aagcatttat   5340
cagggttatt gtctcatgag cggatacata tttgaatgta tttagaaaaa taaacaaata   5400
ggggttccgc gcacatttcc ccgaaaagtg ccacctgacg tctaagaaac cattattatc   5460
atgacattaa cctataaaaa taggcgtatc acgaggccct ttcgtctcgc gcgtttcggt   5520
gatgacggtg aaaacctctg acacatgcag ctcccggaga cggtcacagc ttgtctgtaa   5580
gcggatgccg ggagcagaca agcccgtcag ggcgcgtcag cgggtgttgg cgggtgtcgg   5640
ggctggctta actatgcggc atcagagcag attgtactga gagtgcacca tatgcggtgt   5700
gaaataccgc acagatgcgt aaggagaaaa taccgcatca ggaaattgta aacgttaata   5760
ttttgttaaa attcgcgtta aatttttgtt aaatcagctc attttttaac caataggccg   5820
aaatcggcaa aatcccttat aaatcaaaag aatagaccga gatagggttg agtgttgttc   5880
cagtttggaa caagagtcca ctattaaaga acgtggactc caacgtcaaa gggcgaaaaa   5940
ccgtctatca gggcgatggc ccactacgtg aaccatcacc ctaatcaagt tttttggggt   6000
cgaggtgccg taaagcacta aatcggaacc ctaaagggag cccccgattt agagcttgac   6060
ggggaaagcc ggcgaacgtg gcgagaaagg aagggaagaa agcgaaagga gcgggcgcta   6120
gggcgctggc aagtgtagcg gtcacgctgc gcgtaaccac cacacccgcc gcgcttaatg   6180
cgccgctaca gggcgcgtcg cgccattcgc cattcaggct acgcaactgt tgggaagggc   6240
gatcggtgcg ggcctcttcg ctattacgcc agctgcagtt ggccactccc tctctgcgcg   6300
ctcgctcgct cactgaggcc gggcgaccaa aggtcgcccg acgcccgggc tttgcccggg   6360
cggcctcagt gagcgagcga gcgcgcagag agggagtggc caactccatc actaggggtt   6420
cctagatctt caatattggc cattagccat attattcatt ggttatatag cataaatcaa   6480
tattggctat tggccattgc atacgttgta tctatatcat aatatgtaca tttatattgg   6540
ctcatgtcca atatgaccgc catgttggca ttgattattg actagttatt aatagtaatc   6600
aattacgggg tcattagttc atagcccata tatggagttc cgcgttacat aacttacggt   6660
aaatggcccg cctggctgac cgcccaacga cccccgccca ttgacgtcaa taatgacgta   6720
tgttcccata gtaacgccaa tagggacttt ccattgacgt caatgggtgg agtatttacg   6780
gtaaactgcc cacttggcag tacatcaagt gtatcatatg ccaagtccgc cccctattga   6840
cgtcaatgac ggtaaatggc ccgcctggca ttatgcccag tacatgacct tacgggactt   6900
tcctacttgg cagtacatct acgtattagt catcgctatt accatggtga tgcggttttg   6960
gcagtacacc aatgggcgtg gatagcggtt tgactcacgg ggatttccaa gtctccaccc   7020
cattgacgtc aatgggagtt tgttttggca ccaaaatcaa cgggactttc caaaatgtcg   7080
taataacccc gccccgttga cgcaaatggg cggtaggcgt gtacggtggg aggtctatat   7140
aagcagagct cgtttagtga accgtcagat cactagaagc tttattgcgg tagtttatca   7200
cagttaaatt gctaacgcag tcagtgcttc tgacacaaca gtctcgaact taagctgcag   7260
```

-continued

```
aagttggtcg tgaggcactg ggcaggtaag tatcaaggtt acaagacagg tttaaggaga   7320

ccaatagaaa ctgggcttgt cgagacagag aagactcttg cgtttctgat aggcacctat   7380

tggtcttact gacatccact ttgcctttct ctccacaggt gtccactccc agttcaatta   7440

cagctcttaa ggctagagta cttaatacga ctcactatag gctagcctcg ag           7492


<210> SEQ ID NO 6
<211> LENGTH: 6714
<212> TYPE: DNA
<213> ORGANISM: Artificial Sequence
<220> FEATURE:
<223> OTHER INFORMATION: Description of Artificial Sequence:PLASMID
      p43CB-AT

<400> SEQUENCE: 6

gggggggggg ggggggttg gccactccct ctctgcgcgc tcgctcgctc actgaggccg     60

ggcgaccaaa ggtcgcccga cgcccgggct ttgcccgggc ggcctcagtg agcgagcgag    120

cgcgcagaga gggagtggcc aactccatca ctaggggttc ctagatcttc aatattggcc    180

attagccata ttattcattg gttatatagc ataaatcaat attggctatt ggccattgca    240

tacgttgtat ctatatcata atatgtacat ttatattggc tcatgtccaa tatgaccgcc    300

atgttggcat tgattattga ctagttatta atagtaatca attacggggt cattagttca    360

tagcccatat atggagttcc gcgttacata acttacggta aatggcccgc ctggctgacc    420

gcccaacgac ccccgcccat tgacgtcaat aatgacgtat gttcccatag taacgccaat    480

agggactttc cattgacgtc aatgggtgga gtatttacgg taaactgccc acttggcagt    540

acatcaagtg tatcatatgc caagtccgcc ccctattgac gtcaatgacg gtaaatggcc    600

cgcctggcat tatgcccagt acatgacctt acgggacttt cctacttggc agtacatcta    660

cgtattagtc atcgctatta ccatggtcga ggtgagcccc acgttctgct tcactctccc    720

catctccccc ccctccccac ccccaatttt gtatttattt atttttaat tattttgtgc     780

agcgatgggg gcgggggggg ggggggggcg cgcgccaggc ggggcggggc ggggcgaggg    840

gcggggcggg gcgaggcgga gaggtgcggc ggcagccaat cagagcggcg cgctccgaaa    900

gtttcctttt atggcgaggc ggcggcggcg gcggccctat aaaaagcgaa gcgcgcggcg    960

ggcgggagtc gctgcgacgc tgccttcgcc ccgtgccccg ctccgccgcc gcctcgcgcc   1020

gcccgccccg gctctgactg accgcgttac tcccacaggt gagcgggcgg gacggccctt   1080

ctcctccggg ctgtaattag cgcttggttt aatgacggct tgtttctttt ctgtggctgc   1140

gtgaaagcct tgaggggctc cgggagggcc ctttgtgcgg ggggagcgg ctcgggggt     1200

gcgtgcgtgt gtgtgtgcgt ggggagcgcc gcgtgcggcc cgcgctgccc ggcggctgtg   1260

agcgctgcgg gcgcggcgcg gggctttgtg cgctccgcag tgtgcgcgag gggagcgcgg   1320

ccgggggcgg tgccccgcgg tgcgggggg gctgcgaggg gaacaaaggc tgcgtgcggg    1380

gtgtgtgcgt gggggggtga gcagggggtg tgggcgcggc ggtcgggctg taacccccc    1440

ctgcaccccc ctccccgagt tgctgagcac ggcccggctt cgggtgcggg gctccgtacg   1500

gggcgtggcg cggggctcgc cgtgccgggc ggggggtggc ggcaggtggg ggtgccgggc   1560

ggggcggggc cgcctcgggc cggggagggc tcgggggagg ggcgcggcgg cccccggagc   1620

gccggcggct gtcgaggcgc ggcgagccgc agccattgcc ttttatggta atcgtgcgag   1680

agggcgcagg gacttccttt gtcccaaatc tgtgcggagc cgaaatctgg gaggcgccgc   1740

cgcacccct ctagcgggcg cggggcgaag cggtgcggcg ccggcaggaa ggaaatgggc    1800
```

-continued

```
ggggagggcc ttcgtgcgtc gccgcgccgc cgtccccttc tccctctcca gcctcggggc   1860
tgtccgcggg gggacggctg ccttcggggg ggacggggca gggcggggtt cggcttctgg   1920
cgtgtgaccg gcggctctag agcctctgct aaccatgttc atgccttctt ctttttccta   1980
cagctcctgg gcaacgtgct ggttattgtg ctgtctcatc attttggcaa agaattcgat   2040
atcaagcttg ggattttca ggcaccacca ctgacctggg acagtgaatc gacaatgccg   2100
tcttctgtct cgtggggcat cctcctgctg gcaggcctgt gctgcctggt ccctgtctcc   2160
ctggctgagg atccccaggg agatgctgcc cagaagacag atacatccca ccatgatcag   2220
gatcacccaa ccttcaacaa gatcaccccc aacctggctg agttcgcctt cagcctatac   2280
cgccagctgg cacaccagtc caacagcacc aatatcttct tctccccagt gagcatcgct   2340
acagcctttg caatgctctc cctggggacc aaggctgaca ctcacgatga aatcctggag   2400
ggcctgaatt tcaacctcac ggagattccg gaggctcaga tccatgaagg cttccaggaa   2460
ctcctccgta ccctcaacca gccagacagc cagctccagc tgaccaccgg caatggcctg   2520
ttcctcagcg agggcctgaa gctagtggat aagtttttgg aggatgttaa aaagttgtac   2580
cactcagaag ccttcactgt caacttcggg gacaccgaag aggccaagaa acagatcaac   2640
gattacgtgg agaagggtac tcaagggaaa attgtggatt tggtcaagga gcttgacaga   2700
gacacagttt ttgctctggt gaattacatc ttctttaaag gcaaatggga gagacccttt   2760
gaagtcaagg acaccgagga agaggacttc cacgtggacc aggtgaccac cgtgaaggtg   2820
cctatgatga agcgtttagg catgtttaac atccagcact gtaagaagct gtccagctgg   2880
gtgctgctga tgaaatacct gggcaatgcc accgccatct tcttcctgcc tgatgagggg   2940
aaactacagc acctggaaaa tgaactcacc cacgatatca tcaccaagtt cctggaaaat   3000
gaagacagaa ggtctgccag cttacattta cccaaactgt ccattactgg aacctatgat   3060
ctgaagagcg tcctgggtca actgggcatc actaaggtct tcagcaatgg ggctgacctc   3120
tccggggtca cagaggaggc acccctgaag ctctccaagg ccgtgcataa ggctgtgctg   3180
accatcgacg agaaagggac tgaagctgct ggggccatgt ttttagaggc catacccatg   3240
tctatccccc ccgaggtcaa gttcaacaaa ccctttgtct tcttaatgat tgaacaaaat   3300
accaagtctc ccctcttcat gggaaaagtg gtgaatccca cccaaaaata actgcctctc   3360
gctcctcaac ccctcccctc catccctggc cccctccctg gatgacatta aagaagggtt   3420
gagctggtaa ccccccccc ccctgcaggg gccctcgacc cgggcggccg cttcgagcag   3480
acatgataag atacattgat gagtttggac aaaccacaac tagaatgcag tgaaaaaaat   3540
gctttatttg tgaaatttgt gatgctattg ctttatttgt aaccattata agctgcaata   3600
aacaagttaa caacaacaat tgcattcatt ttatgtttca ggttcagggg gagatgtggg   3660
aggtttttta aagcaagtaa aacctctaca aatgtggtaa aatcgataag gatctaggaa   3720
cccctagtga tggagttggc cactccctct ctgcgcgctc gctcgctcac tgaggccgcc   3780
cgggcaaagc ccgggcgtcg ggcgaccttt ggtcgcccgg cctcagtgag cgagcgagcg   3840
cgcagagagg gagtggccaa cccccccccc ccccccctg cagcctggcg taatagcgaa   3900
gaggcccgca ccgatcgccc ttcccaacag ttgcgtagcc tgaatggcga atggcgcgac   3960
gcgccctgta gcggcgcatt aagcgcggcg ggtgtggtgg ttacgcgcag cgtgaccgct   4020
acacttgcca gcgccctagc gcccgctcct ttcgctttct tcccttcctt tctcgccacg   4080
ttcgccggct ttccccgtca agctctaaat cgggggctcc ctttagggtt ccgatttagt   4140
gctttacggc acctcgaccc caaaaaactt gattagggtg atggttcacg tagtgggcca   4200
```

-continued

```
tcgccctgat agacggtttt tcgccctttg acgttggagt ccacgttctt taatagtgga   4260
ctcttgttcc aaactggaac aacactcaac cctatctcgg tctattcttt tgatttataa   4320
gggattttgc cgatttcggc ctattggtta aaaaatgagc tgatttaaca aaaatttaac   4380
gcgaatttta acaaaatatt aacgtttaca atttcctgat gcggtatttt ctccttacgc   4440
atctgtgcgg tatttcacac cgcatatggt gcactctcag tacaatctgc tctgatgccg   4500
catagttaag ccagccccga cacccgccaa cacccgctga cgcgccctga cgggcttgtc   4560
tgctcccggc atccgcttac agacaagctg tgaccgtctc cgggagctgc atgtgtcaga   4620
ggttttcacc gtcatcaccg aaacgcgcga gacgaaaggg cctcgtgata cgcctatttt   4680
tataggttaa tgtcatgata ataatggttt cttagacgtc aggtggcact tttcggggaa   4740
atgtgcgcgg aacccctatt tgtttatttt tctaaataca ttcaaatatg tatccgctca   4800
tgagacaata accctgataa atgcttcaat aatattgaaa aaggaagagt atgagtattc   4860
aacatttccg tgtcgccctt attccctttt ttgcggcatt ttgccttcct gtttttgctc   4920
acccagaaac gctggtgaaa gtaaaagatg ctgaagatca gttgggtgca cgagtgggtt   4980
acatcgaact ggatctcaac agcggtaaga tccttgagag ttttcgcccc gaagaacgtt   5040
ttccaatgat gagcactttt aaagttctgc tatgtggcgc ggtattatcc cgtattgacg   5100
ccgggcaaga gcaactcggt cgccgcatac actattctca gaatgacttg gttgagtact   5160
caccagtcac agaaaagcat cttacggatg gcatgacagt aagagaatta tgcagtgctg   5220
ccataaccat gagtgataac actgcggcca acttacttct gacaacgatc ggaggaccga   5280
aggagctaac cgcttttttg cacaacatgg gggatcatgt aactcgcctt gatcgttggg   5340
aaccggagct gaatgaagcc ataccaaacg acgagcgtga caccacgatg cctgtagcaa   5400
tggcaacaac gttgcgcaaa ctattaactg gcgaactact tactctagct tcccggcaac   5460
aattaataga ctggatggag gcggataaag ttgcaggacc acttctgcgc tcggcccttc   5520
cggctggctg gtttattgct gataaatctg gagccggtga gcgtgggtct cgcggtatca   5580
ttgcagcact ggggccagat ggtaagccct cccgtatcgt agttatctac acgacgggga   5640
gtcaggcaac tatggatgaa cgaaatagac agatcgctga gataggtgcc tcactgatta   5700
agcattggta actgtcagac caagtttact catatatact ttagattgat ttaaaacttc   5760
atttttaatt taaaaggatc taggtgaaga tcctttttga taatctcatg accaaaatcc   5820
cttaacgtga gttttcgttc cactgagcgt cagaccccgt agaaaagatc aaaggatctt   5880
cttgagatcc tttttttctg cgcgtaatct gctgcttgca aacaaaaaaa ccaccgctac   5940
cagcggtggt ttgtttgccg gatcaagagc taccaactct ttttccgaag gtaactggct   6000
tcagcagagc gcagatacca aatactgtcc ttctagtgta gccgtagtta ggccaccact   6060
tcaagaactc tgtagcaccg cctacatacc tcgctctgct aatcctgtta ccagtggctg   6120
ctgccagtgg cgataagtcg tgtcttaccg ggttggactc aagacgatag ttaccggata   6180
aggcgcagcg gtcgggctga acggggggtt cgtgcacaca gcccagcttg gagcgaacga   6240
cctacaccga actgagatac ctacagcgtg agcattgaga aagcgccacg cttcccgaag   6300
ggagaaaggc ggacaggtat ccggtaagcg gcagggtcgg aacaggagag cgcacgaggg   6360
agcttccagg gggaaacgcc tggtatcttt atagtcctgt cgggtttcgc cacctctgac   6420
ttgagcgtcg atttttgtga tgctcgtcag gggggcggag cctatggaaa aacgccagca   6480
acgcggcctt tttacggttc ctggcctttt gctggccttt tgctcacatg ttctttcctg   6540
```

-continued

```
cgttatcccc tgattctgtg gataaccgta ttaccgcctt tgagtgagct gataccgctc   6600

gccgcagccg aacgaccgag cgcagcgagt cagtgagcga ggaagcggaa gagcgcccaa   6660

tacgcaaacc gcctctcccc gcgcgttggc cgattcatta atgcagggct gcag         6714


<210> SEQ ID NO 7
<211> LENGTH: 6981
<212> TYPE: DNA
<213> ORGANISM: Artificial Sequence
<220> FEATURE:
<223> OTHER INFORMATION: Description of Artificial Sequence:PLASMID
      C-AT2

<400> SEQUENCE: 7

ctagaactag tggatccccc gggctgcagg aattcgatat caagcttggg gattttcagg     60

caccaccact gacctgggac agtgaatcga caatgccgtc ttctgtctcg tggggcatcc    120

tcctgctggc aggcctgtgc tgcctggtcc ctgtctccct ggctgaggat ccccagggag    180

atgctgccca gaagacagat acatcccacc atgatcagga tcacccaacc ttcaacaaga    240

tcacccccaa cctggctgag ttcgccttca gcctataccg ccagctggca caccagtcca    300

acagcaccaa tatcttcttc tccccagtga gcatcgctac agcctttgca atgctctccc    360

tggggaccaa ggctgacact cacgatgaaa tcctggaggg cctgaatttc aacctcacgg    420

agattccgga ggctcagatc catgaaggct tccaggaact cctccgtacc ctcaaccagc    480

cagacagcca gctccagctg accaccggca atggcctgtt cctcagcgag ggcctgaagc    540

tagtggataa gtttttggag gatgttaaaa agttgtacca ctcagaagcc ttcactgtca    600

acttcgggga caccgaagag gccaagaaac agatcaacga ttacgtggag aagggtactc    660

aagggaaaat tgtggatttg gtcaaggagc ttgacagaga cacagttttt gctctggtga    720

attacatctt ctttaaaggc aaatgggaga gaccctttga agtcaaggac accgaggaag    780

aggacttcca cgtggaccag gtgaccaccg tgaaggtgcc tatgatgaag cgtttaggca    840

tgtttaacat ccagcactgt aagaagctgt ccagctgggt gctgctgatg aaatacctgg    900

gcaatgccac cgccatcttc ttcctgcctg atgaggggaa actacagcac ctggaaaatg    960

aactcaccca cgatatcatc accaagttcc tggaaaatga agacagaagg tctgccagct   1020

tacatttacc caaactgtcc attactggaa cctatgatct gaagagcgtc ctgggtcaac   1080

tgggcatcac taaggtcttc agcaatgggg ctgacctctc cggggtcaca gaggaggcac   1140

ccctgaagct ctccaaggcc gtgcataagg ctgtgctgac catcgacgag aaagggactg   1200

aagctgctgg ggccatgttt ttagaggcca tacccatgtc tatccccccc gaggtcaagt   1260

tcaacaaacc ctttgtcttc ttaatgattg aacaaaatac caagtctccc ctcttcatgg   1320

gaaaagtggt gaatcccacc caaaaataac tgcctctcgc tcctcaaccc ctcccctcca   1380

tccctggccc cctccctgga tgacattaaa gaagggttga gctggtaacc cccccccccc   1440

ctgcaggggc cctcgaggcc gcggggatcc agacatgata agatacattg atgagtttgg   1500

acaaaccaca actagaatgc agtgaaaaaa atgctttatt tgtgaaattt gtgatgctat   1560

tgctttattt gtaaccatta taagctgcaa taaacaagtt aacaacaaca attgcattca   1620

ttttatgttt caggttcagg gggaggtgtg ggaggttttt tagtcgacct cgagcagtgt   1680

ggttttgcaa gaggaagcaa aaagcctctc cacccaggcc tggaatgttt ccacccaagt   1740

cgaaggcagt gtggttttgc aagaggaagc aaaaagcctc tccacccagg cctggaatgt   1800

ttccacccaa tgtcgagcaa ccccgcccag cgtcttgtca ttggcgaatt cgaacacgca   1860
```

-continued

```
gatgcagtcg gggcggcgcg gtcccaggtc cacttcgcat attaaggtga cgcgtgtggc   1920
ctcgaacacc gagcgaccct gcagccaata tgggatcggc cattgaacaa gatggattgc   1980
acgcaggttc tccggccgct tgggtggaga ggctattcgg ctatgactgg gcacaacaga   2040
caatcggctg ctctgatgcc gccgtgttcc ggctgtcagc gcaggggcgc ccggttcttt   2100
ttgtcaagac cgacctgtcc ggtgccctga atgaactgca ggacgaggca gcgcggctat   2160
cgtggctggc cacgacgggc gttccttgcg cagctgtgct cgacgttgtc actgaagcgg   2220
gaagggactg gctgctattg ggcgaagtgc cggggcagga tctcctgtca tctcaccttg   2280
ctcctgccga gaaagtatcc atcatggctg atgcaatgcg gcggctgcat acgcttgatc   2340
cggctacctg cccattcgac caccaagcga aacatcgcat cgagcgagca cgtactcgga   2400
tggaagccgg tcttgtcgat caggatgatc tggacgaaga gcatcagggg ctcgcgccag   2460
ccgaactgtt cgccaggctc aaggcgcgca tgcccgacgg cgaggatctc gtcgtgaccc   2520
atggcgatgc ctgcttgccg aatatcatgg tggaaaatgg ccgcttttct ggattcatcg   2580
actgtggccg gctgggtgtg gcggaccgct atcaggacat agcgttggct acccgtgata   2640
ttgctgaaga gcttggcggc gaatgggctg accgcttcct cgtgctttac ggtatcgccg   2700
ctcccgattc gcagcgcatc gccttctatc gccttcttga cgagttcttc tgaggggatc   2760
cgtcgactag agctcgctga tcagcctcga ctgtgccttc tagttgccag ccatctgttg   2820
tttgcccctc ccccgtgcct tccttgaccc tggaaggtgc cactcccact gtcctttcct   2880
aataaaatga ggaaattgca tcgcattgtc tgagtaggtg tcattctatt ctggggggtg   2940
gggtggggca ggacagcaag ggggaggatt gggaagacaa tagcaggcat gctggggaga   3000
gatctaggaa cccctagtga tggagttggc cactccctct ctgcgcgctc gctcgctcac   3060
tgaggccgcc cgggcaaagc ccgggcgtcg ggcgaccttt ggtcgcccgg cctcagtgag   3120
cgagcgagcg cgcagagagg gagtggccaa cccccccccc cccccccctg cagccctgca   3180
ttaatgaatc ggccaacgcg cggggagagg cggtttgcgt attgggcgct cttccgcttc   3240
ctcgctcact gactcgctgc gctcggtcgt tcggctgcgg cgagcggtat cagctcactc   3300
aaaggcggta atacggttat ccacagaatc aggggataac gcaggaaaga acatgtgagc   3360
aaaaggccag caaaaggcca ggaaccgtaa aaaggccgcg ttgctggcgt ttttccatag   3420
gctccgcccc cctgacgagc atcacaaaaa tcgacgctca agtcagaggt ggcgaaaccc   3480
gacaggacta taaagatacc aggcgtttcc ccctggaagc tccctcgtgc gctctcctgt   3540
tccgaccctg ccgcttaccg gatacctgtc cgcctttctc ccttcgggaa gcgtggcgct   3600
ttctcaatgc tcacgctgta ggtatctcag ttcggtgtag gtcgttcgct ccaagctggg   3660
ctgtgtgcac gaaccccccg ttcagcccga ccgctgcgcc ttatccggta actatcgtct   3720
tgagtccaac ccggtaagac acgacttatc gccactggca gcagccactg gtaacaggat   3780
tagcagagcg aggtatgtag gcggtgctac agagttcttg aagtggtggc ctaactacgg   3840
ctacactaga aggacagtat ttggtatctg cgctctgctg aagccagtta ccttcggaaa   3900
aagagttggt agctcttgat ccggcaaaca aaccaccgct ggtagcggtg gtttttttgt   3960
ttgcaagcag cagattacgc gcagaaaaaa aggatctcaa gaagatcctt tgatcttttc   4020
tacggggtct gacgctcagt ggaacgaaaa ctcacgttaa gggattttgg tcatgagatt   4080
atcaaaaagg atcttcacct agatcctttt aaattaaaaa tgaagtttta aatcaatcta   4140
aagtatatat gagtaaactt ggtctgacag ttaccaatgc ttaatcagtg aggcacctat   4200
ctcagcgatc tgtctatttc gttcatccat agttgcctga ctccccgtcg tgtagataac   4260
```

-continued

```
tacgatacgg gagggcttac catctggccc cagtgctgca atgataccgc gagacccacg   4320
ctcaccggct ccagatttat cagcaataaa ccagccagcc ggaagggccg agcgcagaag   4380
tggtcctgca actttatccg cctccatcca gtctattaat tgttgccggg aagctagagt   4440
aagtagttcg ccagttaata gtttgcgcaa cgttgttgcc attgctacag gcatcgtggt   4500
gtcacgctcg tcgtttggta tggcttcatt cagctccggt tcccaacgat caaggcgagt   4560
tacatgatcc cccatgttgt gcaaaaaagc ggttagctcc ttcggtcctc cgatcgttgt   4620
cagaagtaag ttggccgcag tgttatcact catggttatg gcagcactgc ataattctct   4680
tactgtcatg ccatccgtaa gatgcttttc tgtgactggt gagtactcaa ccaagtcatt   4740
ctgagaatag tgtatgcggc gaccgagttg ctcttgcccg gcgtcaatac gggataatac   4800
cgcgccacat agcagaactt taaaagtgct catcattgga aaacgttctt cggggcgaaa   4860
actctcaagg atcttaccgc tgttgagatc cagttcgatg taacccactc gtgcacccaa   4920
ctgatcttca gcatctttta ctttcaccag cgtttctggg tgagcaaaaa caggaaggca   4980
aaatgccgca aaaaagggaa taagggcgac acggaaatgt tgaatactca tactcttcct   5040
ttttcaatat tattgaagca tttatcaggg ttattgtctc atgagcggat acatatttga   5100
atgtatttag aaaaataaac aaataggggt tccgcgcaca tttccccgaa aagtgccacc   5160
tgacgtctaa gaaaccatta ttatcatgac attaacctat aaaaataggc gtatcacgag   5220
gccctttcgt ctcgcgcgtt tcggtgatga cggtgaaaac ctctgacaca tgcagctccc   5280
ggagacggtc acagcttgtc tgtaagcgga tgccgggagc agacaagccc gtcagggcgc   5340
gtcagcgggt gttggcgggt gtcggggctg gcttaactat gcggcatcag agcagattgt   5400
actgagagtg caccatatgc ggtgtgaaat accgcacaga tgcgtaagga gaaaataccg   5460
catcaggaaa ttgtaaacgt taatattttg ttaaaattcg cgttaaattt ttgttaaatc   5520
agctcatttt ttaaccaata ggccgaaatc ggcaaaatcc cttataaatc aaaagaatag   5580
accgagatag ggttgagtgt tgttccagtt tggaacaaga gtccactatt aaagaacgtg   5640
gactccaacg tcaaagggcg aaaaaccgtc tatcagggcg atggcccact acgtgaacca   5700
tcaccctaat caagtttttt ggggtcgagg tgccgtaaag cactaaatcg gaaccctaaa   5760
gggagccccc gatttagagc ttgacgggga aagccggcga acgtggcgag aaaggaaggg   5820
aagaaagcga aaggagcggg cgctagggcg ctggcaagtg tagcggtcac gctgcgcgta   5880
accaccacac ccgccgcgct taatgcgccg ctacagggcg cgtcgcgcca ttcgccattc   5940
aggctacgca actgttggga agggcgatcg gtgcgggcct cttcgctatt acgccaggct   6000
gcaggggggg gggggggggg gttggccact ccctctctgc gcgctcgctc gctcactgag   6060
gccgggcgac caaaggtcgc ccgacgcccg ggctttgccc gggcggcctc agtgagcgag   6120
cgagcgcgca gagagggagt ggccaactcc atcactaggg gttcctagat ctgaattcgg   6180
tacccgttac ataacttacg gtaaatggcc cgcctggctg accgcccaac gacccccgcc   6240
cattgacgtc aataatgacg tatgttccca tagtaacgcc aatagggact ttccattgac   6300
gtcaatgggt ggagtattta cggtaaactg cccacttggc agtacatcaa gtgtatcata   6360
tgccaagtac gccccctatt gacgtcaatg acggtaaatg gcccgcctgg cattatgccc   6420
agtacatgac cttatgggac tttcctactt ggcagtacat ctacgtatta gtcatcgcta   6480
ttaccatggt gatgcggttt tggcagtaca tcaatgggcg tggatagcgg tttgactcac   6540
ggggatttcc aagtctccac cccattgacg tcaatgggag tttgttttgg caccaaaatc   6600
```

-continued

```
aacgggactt tccaaaatgt cgtaacaact ccgccccatt gacgcaaatg ggcggtaggc   6660

gtgtacggtg ggaggtctat ataagcagag ctcgtttagt gaaccgtcag atcgcctgga   6720

gacgccatcc acgctgtttt gacctccata gaagacaccg ggaccgatcc agcctccgga   6780

ctctagagga tccggtactc gaggaactga aaaaccagaa agttaactgg taagtttagt   6840

ctttttgtct tttatttcag gtcccggatc cggtggtggt gcaaatcaaa gaactgctcc   6900

tcagtggatg ttgcctttac ttctaggcct gtacggaagt gttacttctg ctctaaaagc   6960

tgcggaattg tacccgcggc c                                              6981
```

```
<210> SEQ ID NO 8
<211> LENGTH: 6142
<212> TYPE: DNA
<213> ORGANISM: Artificial Sequence
<220> FEATURE:
<223> OTHER INFORMATION: Description of Artificial Sequence:PLASMID
      p43msENC-AT

<400> SEQUENCE: 8

gggggggggg ggggggggttg gccactccct ctctgcgcgc tcgctcgctc actgaggccg     60

ggcgaccaaa ggtcgcccga cgcccgggct ttgcccgggc ggcctcagtg agcgagcgag    120

cgcgcagaga gggagtggcc aactccatca ctaggggttc ctagatctca ccattcctca    180

cgacacccaa atatggcgac gggtgaggaa tggtggggag ttatttttag agcggtgagg    240

aatggtgggc aggcagcagg tgttggcgct ctaaaaataa ctcccgggag ttatttttag    300

agcggtgagg aatggtggac acccaaatat ggcgacggca ccattcctca ccccaggcca    360

tatttgggtg tcagatcttc aatattggcc attagccata ttattcattg gttatatagc    420

ataaatcaat attggctatt ggccattgca tacgttgtat ctatatcata atatgtacat    480

ttatattggc tcatgtccaa tatgaccgcc atgttggcat tgattattga ctagttatta    540

atagtaatca attacggggt cattagttca tagcccatat atggagttcc gcgttacata    600

acttacggta aatggcccgc ctggctgacc gcccaacgac ccccgcccat tgacgtcaat    660

aatgacgtat gttcccatag taacgccaat agggactttc cattgacgtc aatgggtgga    720

gtatttacgg taaactgccc acttggcagt acatcaagtg tatcatatgc caagtccgcc    780

ccctattgac gtcaatgacg gtaaatggcc cgcctggcat tatgcccagt acatgacctt    840

acgggacttt cctacttggc agtacatcta cgtattagtc atcgctatta ccatggtgat    900

gcggttttgg cagtacacca atgggcgtgg atagcggttt gactcacggg gatttccaag    960

tctccacccc attgacgtca atgggagttt gttttggcac caaaatcaac gggactttcc   1020

aaaatgtcgt aataaccccg ccccgttgac gcaaatgggc ggtaggcgtg tacggtggga   1080

ggtctatata agcagagctc gtttagtgaa ccgtcagatc actagaagct ttattgcggt   1140

agtttatcac agttaaattg ctaacgcagt cagtgcttct gacacaacag tctcgaactt   1200

aagctgcaga agttggtcgt gaggcactgg gcaggtaagt atcaaggtta caagacaggt   1260

ttaaggagac caatagaaac tgggcttgtc gagacagaga agactcttgc gtttctgata   1320

ggcacctatt ggtcttactg acatccactt tgcctttctc tccacaggtg tccactccca   1380

gttcaattac agctcttaag gctagagtac ttaatacgac tcactatagg ctagaactag   1440

tggatccccc gggctgcagg aattcgatat caagcttggg gattttcagg caccaccact   1500

gacctgggac agtgaatcga caatgccgtc ttctgtctcg tggggcatcc tcctgctggc   1560

aggcctgtgc tgcctggtcc ctgtctccct ggctgaggat ccccagggag atgctgccca   1620
```

-continued

```
gaagacagat acatcccacc atgatcagga tcacccaacc ttcaacaaga tcacccccaa   1680
cctggctgag ttcgccttca gcctataccg ccagctggca caccagtcca acagcaccaa   1740
tatcttcttc tccccagtga gcatcgctac agcctttgca atgctctccc tggggaccaa   1800
ggctgacact cacgatgaaa tcctggaggg cctgaatttc aacctcacgg agattccgga   1860
ggctcagatc catgaaggct tccaggaact cctccgtacc ctcaaccagc cagacagcca   1920
gctccagctg accaccggca atggcctgtt cctcagcgag ggcctgaagc tagtggataa   1980
gtttttggag gatgttaaaa agttgtacca ctcagaagcc ttcactgtca acttcgggga   2040
caccgaagag gccaagaaac agatcaacga ttacgtggag aagggtactc aagggaaaat   2100
tgtggatttg gtcaaggagc ttgacagaga cacagttttt gctctggtga attacatctt   2160
ctttaaaggc aaatgggaga gaccctttga agtcaaggac accgaggaag aggacttcca   2220
cgtggaccag gtgaccaccg tgaaggtgcc tatgatgaag cgtttaggca tgtttaacat   2280
ccagcactgt aagaagctgt ccagctgggt gctgctgatg aaatacctgg gcaatgccac   2340
cgccatcttc ttcctgcctg atgaggggaa actacagcac ctggaaaatg aactcaccca   2400
cgatatcatc accaagttcc tggaaaatga agacagaagg tctgccagct tacatttacc   2460
caaactgtcc attactggaa cctatgatct gaagagcgtc ctgggtcaac tgggcatcac   2520
taaggtcttc agcaatgggg ctgacctctc cggggtcaca gaggaggcac ccctgaagct   2580
ctccaaggcc gtgcataagg ctgtgctgac catcgacgag aaagggactg aagctgctgg   2640
ggccatgttt ttagaggcca tacccatgtc tatccccccc gaggtcaagt tcaacaaacc   2700
ctttgtcttc ttaatgattg aacaaaatac caagtctccc ctcttcatgg gaaaagtggt   2760
gaatcccacc caaaaataac tgcctctcgc tcctcaaccc ctcccctcca tccctggccc   2820
cctccctgga tgacattaaa gaagggttga gctggtaacc cccccccccc ctgcaggggc   2880
cctcgacccg ggcggccgct tcgagcagac atgataagat acattgatga gtttggacaa   2940
accacaacta gaatgcagtg aaaaaaatgc tttatttgtg aaatttgtga tgctattgct   3000
ttatttgtaa ccattataag ctgcaataaa caagttaaca acaacaattg cattcatttt   3060
atgtttcagg ttcaggggga gatgtgggag gtttttaaa gcaagtaaaa cctctacaaa    3120
tgtggtaaaa tcgataagga tctaggaacc cctagtgatg gagttggcca ctccctctct   3180
gcgcgctcgc tcgctcactg aggccgcccg ggcaaagccc gggcgtcggg cgacctttgg   3240
tcgcccggcc tcagtgagcg agcgagcgcg cagagaggga gtggccaacc cccccccccc   3300
ccccctgca gcctggcgta atagcgaaga ggcccgcacc gatcgccctt cccaacagtt    3360
gcgtagcctg aatggcgaat ggcgcgacgc gccctgtagc ggcgcattaa gcgcggcggg   3420
tgtggtggtt acgcgcagcg tgaccgctac acttgccagc gccctagcgc ccgctccttt   3480
cgctttcttc ccttcctttc tcgccacgtt cgccggcttt ccccgtcaag ctctaaatcg   3540
ggggctccct ttagggttcc gatttagtgc tttacggcac ctcgacccca aaaaacttga   3600
ttagggtgat ggttcacgta gtgggccatc gccctgatag acggtttttc gccctttgac   3660
gttggagtcc acgttcttta atagtggact cttgttccaa actggaacaa cactcaaccc   3720
tatctcggtc tattcttttg atttataagg gattttgccg atttcggcct attggttaaa   3780
aaatgagctg atttaacaaa aatttaacgc gaattttaac aaaatattaa cgtttacaat   3840
ttcctgatgc ggtattttct ccttacgcat ctgtgcggta tttcacaccg catatggtgc   3900
actctcagta caatctgctc tgatgccgca tagttaagcc agccccgaca cccgccaaca   3960
cccgctgacg cgccctgacg ggcttgtctg ctcccggcat ccgcttacag acaagctgtg   4020
```

-continued

```
accgtctccg ggagctgcat gtgtcagagg ttttcaccgt catcaccgaa acgcgcgaga   4080
cgaaagggcc tcgtgatacg cctattttta taggttaatg tcatgataat aatggtttct   4140
tagacgtcag gtggcacttt tcggggaaat gtgcgcggaa cccctatttg tttatttttc   4200
taaatacatt caaatatgta tccgctcatg agacaataac cctgataaat gcttcaataa   4260
tattgaaaaa ggaagagtat gagtattcaa catttccgtg tcgcccttat tccctttttt   4320
gcggcatttt gccttcctgt ttttgctcac ccagaaacgc tggtgaaagt aaaagatgct   4380
gaagatcagt tgggtgcacg agtgggttac atcgaactgg atctcaacag cggtaagatc   4440
cttgagagtt ttcgccccga agaacgtttt ccaatgatga gcacttttaa agttctgcta   4500
tgtggcgcgg tattatcccg tattgacgcc gggcaagagc aactcggtcg ccgcatacac   4560
tattctcaga atgacttggt tgagtactca ccagtcacag aaaagcatct tacggatggc   4620
atgacagtaa gagaattatg cagtgctgcc ataaccatga gtgataacac tgcggccaac   4680
ttacttctga caacgatcgg aggaccgaag gagctaaccg cttttttgca caacatgggg   4740
gatcatgtaa ctcgccttga tcgttgggaa ccggagctga atgaagccat accaaacgac   4800
gagcgtgaca ccacgatgcc tgtagcaatg gcaacaacgt tgcgcaaact attaactggc   4860
gaactactta ctctagcttc ccggcaacaa ttaatagact ggatggaggc ggataaagtt   4920
gcaggaccac ttctgcgctc ggcccttccg gctggctggt ttattgctga taaatctgga   4980
gccggtgagc gtgggtctcg cggtatcatt gcagcactgg ggccagatgg taagccctcc   5040
cgtatcgtag ttatctacac gacggggagt caggcaacta tggatgaacg aaatagacag   5100
atcgctgaga taggtgcctc actgattaag cattggtaac tgtcagacca agtttactca   5160
tatatacttt agattgattt aaaacttcat ttttaattta aaaggatcta ggtgaagatc   5220
ctttttgata atctcatgac caaaatccct taacgtgagt tttcgttcca ctgagcgtca   5280
gaccccgtag aaaagatcaa aggatcttct tgagatcctt tttttctgcg cgtaatctgc   5340
tgcttgcaaa caaaaaaacc accgctacca gcggtggttt gtttgccgga tcaagagcta   5400
ccaactcttt ttccgaaggt aactggcttc agcagagcgc agataccaaa tactgtcctt   5460
ctagtgtagc cgtagttagg ccaccacttc aagaactctg tagcaccgcc tacatacctc   5520
gctctgctaa tcctgttacc agtggctgct gccagtggcg ataagtcgtg tcttaccggg   5580
ttggactcaa gacgatagtt accggataag gcgcagcggt cgggctgaac ggggggttcg   5640
tgcacacagc ccagcttgga gcgaacgacc tacaccgaac tgagatacct acagcgtgag   5700
cattgagaaa gcgccacgct tcccgaaggg agaaaggcgg acaggtatcc ggtaagcggc   5760
agggtcggaa caggagagcg cacgagggag cttccagggg gaaacgcctg gtatctttat   5820
agtcctgtcg ggtttcgcca cctctgactt gagcgtcgat ttttgtgatg ctcgtcaggg   5880
gggcggagcc tatggaaaaa cgccagcaac gcggcctttt tacggttcct ggccttttgc   5940
tggccttttg ctcacatgtt ctttcctgcg ttatcccctg attctgtgga taaccgtatt   6000
accgcctttg agtgagctga taccgctcgc cgcagccgaa cgaccgagcg cagcgagtca   6060
gtgagcgagg aagcggaaga gcgcccaata cgcaaaccgc ctctccccgc gcgttggccg   6120
attcattaat gcagggctgc ag                                             6142
```

<210> SEQ ID NO 9
<211> LENGTH: 6924
<212> TYPE: DNA
<213> ORGANISM: Artificial Sequence
<220> FEATURE:

-continued

<223> OTHER INFORMATION: Description of Artificial Sequence:PLASMID p43rmsENC-AT

<400> SEQUENCE: 9

```
gggggggggg gggggggttg gccactccct ctctgcgcgc tcgctcgctc actgaggccg     60
ggcgaccaaa ggtcgcccga cgcccgggct ttgcccgggc ggcctcagtg agcgagcgag    120
cgcgcagaga gggagtggcc aactccatca ctaggggttc ctagatctga cacccaaata    180
tggcctgggg tgaggaatgg tgccgtcgcc atatttgggt gtccaccatt cctcaccgct    240
ctaaaaataa ctcccgggag ttatttttag agcgccaaca cctgctgcct gcccaccatt    300
cctcaccgct ctaaaaataa ctccccacca ttcctcaccc gtcgccatat ttgggtgtcg    360
tgaggaatgg tgagatcttc aatattggcc attagccata ttattcattg gttatatagc    420
ataaatcaat attggctatt ggccattgca tacgttgtat ctatatcata atatgtacat    480
ttatattggc tcatgtccaa tatgaccgcc atgttggcat tgattattga ctagttatta    540
atagtaatca attacggggt cattagttca tagcccatat atggagttcc gcgttacata    600
acttacggta aatggcccgc ctggctgacc gcccaacgac ccccgcccat tgacgtcaat    660
aatgacgtat gttcccatag taacgccaat agggactttc cattgacgtc aatgggtgga    720
gtatttacgg taaactgccc acttggcagt acatcaagtg tatcatatgc caagtccgcc    780
ccctattgac gtcaatgacg gtaaatggcc cgcctggcat tatgcccagt acatgacctt    840
acgggacttt cctacttggc agtacatcta cgtattagtc atcgctatta ccatggtcga    900
ggtgagcccc acgttctgct tcactctccc catctccccc ccctccccac ccccaatttt    960
gtatttattt atttttaat tattttgtgc agcgatgggg gcgggggggg ggggggggcg   1020
cgcgccaggc ggggcggggc ggggcgaggg gcggggcggg gcgaggcgga gaggtgcggc   1080
ggcagccaat cagagcggcg cgctccgaaa gtttcctttt atggcgaggc ggcggcggcg   1140
gcggccctat aaaaagcgaa gcgcgcggcg ggcgggagtc gctgcgacgc tgccttcgcc   1200
ccgtgccccg ctccgccgcc gcctcgcgcc gcccgccccg gctctgactg accgcgttac   1260
tcccacaggt gagcgggcgg gacggccctt ctcctccggg ctgtaattag cgcttggttt   1320
aatgacggct tgtttctttt ctgtggctgc gtgaaagcct tgaggggctc cgggagggcc   1380
ctttgtgcgg ggggagcgg ctcgggggt gcgtgcgtgt gtgtgtgcgt ggggagcgcc   1440
gcgtgcggcc cgcgctgccc ggcggctgtg agcgctgcgg gcgcggcgcg gggctttgtg   1500
cgctccgcag tgtgcgcgag gggagcgcgg ccgggggcgg tgccccgcgg tgcggggggg   1560
gctgcgaggg gaacaaaggc tgcgtgcggg gtgtgtgcgt gggggggtga gcagggggtg   1620
tgggcgcggc ggtcgggctg taaccccccc ctgcaccccc ctccccgagt tgctgagcac   1680
ggcccggctt cgggtgcggg gctccgtacg gggcgtggcg cggggctcgc cgtgccgggc   1740
ggggggtggc ggcaggtggg ggtgccgggc ggggcggggc cgcctcgggc cggggagggc   1800
tcgggggagg ggcgcggcgg cccccggagc gccggcggct gtcgaggcgc ggcgagccgc   1860
agccattgcc ttttatggta atcgtgcgag agggcgcagg gacttccttt gtcccaaatc   1920
tgtgcggagc cgaaatctgg gaggcgccgc cgcaccccct ctagcgggcg cggggcgaag   1980
cggtgcggcg ccggcaggaa ggaaatgggc ggggagggcc ttcgtgcgtc gccgcgccgc   2040
cgtccccttc tccctctcca gcctcggggc tgtccgcggg gggacggctg ccttcggggg   2100
ggacggggca gggcggggtt cggcttctgg cgtgtgaccg gcggctctag agcctctgct   2160
aaccatgttc atgccttctt ctttttccta cagctcctgg gcaacgtgct ggttattgtg   2220
```

-continued

```
ctgtctcatc attttggcaa agaattcgat atcaagcttg gggattttca ggcaccacca   2280
ctgacctggg acagtgaatc gacaatgccg tcttctgtct cgtggggcat cctcctgctg   2340
gcaggcctgt gctgcctggt ccctgtctcc ctggctgagg atccccaggg agatgctgcc   2400
cagaagacag atacatccca ccatgatcag gatcacccaa ccttcaacaa gatcaccccc   2460
aacctggctg agttcgcctt cagcctatac cgccagctgg cacaccagtc caacagcacc   2520
aatatcttct tctccccagt gagcatcgct acagcctttg caatgctctc cctggggacc   2580
aaggctgaca ctcacgatga aatcctggag ggcctgaatt tcaacctcac ggagattccg   2640
gaggctcaga tccatgaagg cttccaggaa ctcctccgta ccctcaacca gccagacagc   2700
cagctccagc tgaccaccgg caatggcctg ttcctcagcg agggcctgaa gctagtggat   2760
aagtttttgg aggatgttaa aaagttgtac cactcagaag ccttcactgt caacttcggg   2820
gacaccgaag aggccaagaa acagatcaac gattacgtgg agaagggtac tcaagggaaa   2880
attgtggatt tggtcaagga gcttgacaga gacacagttt ttgctctggt gaattacatc   2940
ttctttaaag gcaaatggga gagacccttt gaagtcaagg acaccgagga agaggacttc   3000
cacgtggacc aggtgaccac cgtgaaggtg cctatgatga agcgtttagg catgtttaac   3060
atccagcact gtaagaagct gtccagctgg gtgctgctga tgaaatacct gggcaatgcc   3120
accgccatct tcttcctgcc tgatgagggg aaactacagc acctggaaaa tgaactcacc   3180
cacgatatca tcaccaagtt cctggaaaat gaagacagaa ggtctgccag cttacattta   3240
cccaaactgt ccattactgg aacctatgat ctgaagagcg tcctgggtca actgggcatc   3300
actaaggtct tcagcaatgg ggctgacctc tccggggtca cagaggaggc acccctgaag   3360
ctctccaagg ccgtgcataa ggctgtgctg accatcgacg agaaagggac tgaagctgct   3420
ggggccatgt ttttagaggc catacccatg tctatccccc ccgaggtcaa gttcaacaaa   3480
ccctttgtct tcttaatgat tgaacaaaat accaagtctc ccctcttcat gggaaaagtg   3540
gtgaatccca cccaaaaata actgcctctc gctcctcaac ccctcccctc catccctggc   3600
cccctccctg gatgacatta aagaagggtt gagctggtaa cccccccccc ccctgcaggg   3660
gccctcgacc cgggcggccg cttcgagcag acatgataag atacattgat gagtttggac   3720
aaaccacaac tagaatgcag tgaaaaaaat gctttatttg tgaaatttgt gatgctattg   3780
ctttatttgt aaccattata agctgcaata aacaagttaa caacaacaat tgcattcatt   3840
ttatgtttca ggttcagggg gagatgtggg aggtttttta aagcaagtaa aacctctaca   3900
aatgtggtaa aatcgataag gatctaggaa cccctagtga tggagttggc cactccctct   3960
ctgcgcgctc gctcgctcac tgaggccgcc cgggcaaagc ccgggcgtcg ggcgaccttt   4020
ggtcgcccgg cctcagtgag cgagcgagcg cgcagagagg gagtggccaa cccccccccc   4080
ccccccccctg cagcctggcg taatagcgaa gaggcccgca ccgatcgccc ttcccaacag   4140
ttgcgtagcc tgaatggcga atggcgcgac gcgccctgta gcggcgcatt aagcgcggcg   4200
ggtgtggtgg ttacgcgcag cgtgaccgct acacttgcca gcgccctagc gcccgctcct   4260
ttcgctttct tcccttcctt tctcgccacg ttcgccggct ttccccgtca agctctaaat   4320
cgggggctcc ctttagggtt ccgatttagt gctttacggc acctcgaccc caaaaaactt   4380
gattagggtg atggttcacg tagtgggcca tcgccctgat agacggtttt tcgccctttg   4440
acgttggagt ccacgttctt taatagtgga ctcttgttcc aaactggaac aacactcaac   4500
cctatctcgg tctattcttt tgatttataa gggattttgc cgatttcggc ctattggtta   4560
aaaaatgagc tgatttaaca aaaatttaac gcgaatttta acaaaatatt aacgtttaca   4620
```

-continued

```
atttcctgat gcggtatttt ctccttacgc atctgtgcgg tatttcacac cgcatatggt   4680
gcactctcag tacaatctgc tctgatgccg catagttaag ccagccccga cacccgccaa   4740
cacccgctga cgcgccctga cgggcttgtc tgctcccggc atccgcttac agacaagctg   4800
tgaccgtctc cgggagctgc atgtgtcaga ggttttcacc gtcatcaccg aaacgcgcga   4860
gacgaaaggg cctcgtgata cgcctatttt tataggttaa tgtcatgata ataatggttt   4920
cttagacgtc aggtggcact tttcggggaa atgtgcgcgg aacccctatt tgtttatttt   4980
tctaaataca ttcaaatatg tatccgctca tgagacaata accctgataa atgcttcaat   5040
aatattgaaa aaggaagagt atgagtattc aacatttccg tgtcgccctt attccctttt   5100
ttgcggcatt ttgccttcct gtttttgctc acccagaaac gctggtgaaa gtaaaagatg   5160
ctgaagatca gttgggtgca cgagtgggtt acatcgaact ggatctcaac agcggtaaga   5220
tccttgagag ttttcgcccc gaagaacgtt ttccaatgat gagcactttt aaagttctgc   5280
tatgtggcgc ggtattatcc cgtattgacg ccgggcaaga gcaactcggt cgccgcatac   5340
actattctca gaatgacttg gttgagtact caccagtcac agaaaagcat cttacggatg   5400
gcatgacagt aagagaatta tgcagtgctg ccataaccat gagtgataac actgcggcca   5460
acttacttct gacaacgatc ggaggaccga aggagctaac cgcttttttg cacaacatgg   5520
gggatcatgt aactcgcctt gatcgttggg aaccggagct gaatgaagcc ataccaaacg   5580
acgagcgtga caccacgatg cctgtagcaa tggcaacaac gttgcgcaaa ctattaactg   5640
gcgaactact tactctagct tcccggcaac aattaataga ctggatggag gcggataaag   5700
ttgcaggacc acttctgcgc tcggcccttc cggctggctg gtttattgct gataaatctg   5760
gagccggtga gcgtgggtct cgcggtatca ttgcagcact ggggccagat ggtaagccct   5820
cccgtatcgt agttatctac acgacgggga gtcaggcaac tatggatgaa cgaaatagac   5880
agatcgctga gataggtgcc tcactgatta agcattggta actgtcagac caagtttact   5940
catatatact ttagattgat ttaaaacttc atttttaatt taaaaggatc taggtgaaga   6000
tcctttttga taatctcatg accaaaatcc cttaacgtga gttttcgttc cactgagcgt   6060
cagaccccgt agaaaagatc aaaggatctt cttgagatcc tttttttctg cgcgtaatct   6120
gctgcttgca aacaaaaaaa ccaccgctac cagcggtggt ttgtttgccg gatcaagagc   6180
taccaactct ttttccgaag gtaactggct tcagcagagc gcagatacca aatactgtcc   6240
ttctagtgta gccgtagtta ggccaccact tcaagaactc tgtagcaccg cctacatacc   6300
tcgctctgct aatcctgtta ccagtggctg ctgccagtgg cgataagtcg tgtcttaccg   6360
ggttggactc aagacgatag ttaccggata aggcgcagcg gtcgggctga acggggggtt   6420
cgtgcacaca gcccagcttg gagcgaacga cctacaccga actgagatac ctacagcgtg   6480
agcattgaga aagcgccacg cttcccgaag ggagaaaggc ggacaggtat ccggtaagcg   6540
gcagggtcgg aacaggagag cgcacgaggg agcttccagg gggaaacgcc tggtatcttt   6600
atagtcctgt cgggtttcgc cacctctgac ttgagcgtcg atttttgtga tgctcgtcag   6660
gggggcggag cctatggaaa aacgccagca acgcggcctt tttacggttc ctggcctttt   6720
gctggccttt tgctcacatg ttctttcctg cgttatcccc tgattctgtg gataaccgta   6780
ttaccgcctt tgagtgagct gataccgctc gccgcagccg aacgaccgag cgcagcgagt   6840
cagtgagcga ggaagcggaa gagcgcccaa tacgcaaacc gcctctcccc gcgcgttggc   6900
cgattcatta atgcagggct gcag                                          6924
```

<210> SEQ ID NO 10
<211> LENGTH: 6924
<212> TYPE: DNA
<213> ORGANISM: Artificial Sequence
<220> FEATURE:
<223> OTHER INFORMATION: Description of Artificial Sequence:PLASMID p43msENCB-AT

<400> SEQUENCE: 10
gggggggggg ggggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatctca ccattcctca 180
cgacacccaa atatggcgac gggtgaggaa tggtggggag ttatttttag agcggtgagg 240
aatggtgggc aggcagcagg tgttggcgct ctaaaaataa ctcccgggag ttatttttag 300
agcggtgagg aatggtggac acccaaatat ggcgacggca ccattcctca ccccaggcca 360
tatttgggtg tcagatcttc aatattggcc attagccata ttattcattg gttatatagc 420
ataaatcaat attggctatt ggccattgca tacgttgtat ctatatcata atatgtacat 480
ttatattggc tcatgtccaa tatgaccgcc atgttggcat tgattattga ctagttatta 540
atagtaatca attacggggt cattagttca tagcccatat atggagttcc gcgttacata 600
acttacggta aatggcccgc ctggctgacc gcccaacgac ccccgcccat tgacgtcaat 660
aatgacgtat gttcccatag taacgccaat agggactttc cattgacgtc aatgggtgga 720
gtatttacgg taaactgccc acttggcagt acatcaagtg tatcatatgc caagtccgcc 780
ccctattgac gtcaatgacg gtaaatggcc cgcctggcat tatgcccagt acatgacctt 840
acgggacttt cctacttggc agtacatcta cgtattagtc atcgctatta ccatggtcga 900
ggtgagcccc acgttctgct tcactctccc catctccccc ccctccccac ccccaatttt 960
gtatttattt atttttaat tattttgtgc agcgatgggg gcgggggggg gggggggcg 1020 cgcgccaggc ggggcggggc ggggcgaggg gcggggcggg gcgaggcgga gaggtgcggc 1080
ggcagccaat cagagcggcg cgctccgaaa gtttcctttt atggcgaggc ggcggcggcg 1140
gcggccctat aaaaagcgaa gcgcgcggcg ggcgggagtc gctgcgacgc tgccttcgcc 1200
ccgtgccccg ctccgccgcc gcctcgcgcc gcccgccccg gctctgactg accgcgttac 1260
tcccacaggt gagcgggcgg gacggccctt ctcctccggg ctgtaattag cgcttggttt 1320
aatgacggct tgtttctttt ctgtggctgc gtgaaagcct tgaggggctc cgggagggcc 1380
ctttgtgcgg ggggggagcgg ctcgggggggt gcgtgcgtgt gtgtgtgcgt ggggagcgcc 1440
gcgtgcggcc cgcgctgccc ggcggctgtg agcgctgcgg gcgcggcgcg gggctttgtg 1500
cgctccgcag tgtgcgcgag gggagcgcgg ccgggggcgg tgccccgcgg tgcggggggg 1560
gctgcgaggg gaacaaaggc tgcgtgcggg gtgtgtgcgt gggggggtga gcagggggtg 1620
tgggcgcggc ggtcgggctg taaccccccc ctgcaccccc ctccccgagt tgctgagcac 1680
ggcccggctt cgggtgcggg gctccgtacg gggcgtggcg cggggctcgc cgtgccgggc 1740 gggggggtggc ggcaggtggg ggtgccgggc ggggcggggc cgcctcgggc cggggagggc 1800
tcgggggagg ggcgcggcgg cccccggagc gccggcggct gtcgaggcgc ggcgagccgc 1860
agccattgcc ttttatggta atcgtgcgag agggcgcagg gacttccttt gtcccaaatc 1920
tgtgcggagc cgaaatctgg gaggcgccgc cgcacccccct ctagcgggcg cggggcgaag 1980
cggtgcggcg ccggcaggaa ggaaatgggc ggggagggcc ttcgtgcgtc gccgcgccgc 2040

-continued

```
cgtccccttc tccctctcca gcctcggggc tgtccgcggg gggacggctg ccttcggggg   2100
ggacggggca gggcggggtt cggcttctgg cgtgtgaccg gcggctctag agcctctgct   2160
aaccatgttc atgccttctt ctttttccta cagctcctgg gcaacgtgct ggttattgtg   2220
ctgtctcatc attttggcaa agaattcgat atcaagcttg ggattttca ggcaccacca   2280
ctgacctggg acagtgaatc gacaatgccg tcttctgtct cgtggggcat cctcctgctg   2340
gcaggcctgt gctgcctggt ccctgtctcc ctggctgagg atccccaggg agatgctgcc   2400
cagaagacag atacatccca ccatgatcag gatcacccaa ccttcaacaa gatcaccccc   2460
aacctggctg agttcgcctt cagcctatac cgccagctgg cacaccagtc caacagcacc   2520
aatatcttct tctccccagt gagcatcgct acagcctttg caatgctctc cctggggacc   2580
aaggctgaca ctcacgatga aatcctggag ggcctgaatt tcaacctcac ggagattccg   2640
gaggctcaga tccatgaagg cttccaggaa ctcctccgta ccctcaacca gccagacagc   2700
cagctccagc tgaccaccgg caatggcctg ttcctcagcg agggcctgaa gctagtggat   2760
aagtttttgg aggatgttaa aaagttgtac cactcagaag ccttcactgt caacttcggg   2820
gacaccgaag aggccaagaa acagatcaac gattacgtgg agaagggtac tcaagggaaa   2880
attgtggatt tggtcaagga gcttgacaga gacacagttt ttgctctggt gaattacatc   2940
ttctttaaag gcaaatggga gagacccttt gaagtcaagg acaccgagga agaggacttc   3000
cacgtggacc aggtgaccac cgtgaaggtg cctatgatga agcgtttagg catgtttaac   3060
atccagcact gtaagaagct gtccagctgg gtgctgctga tgaaatacct gggcaatgcc   3120
accgccatct tcttcctgcc tgatgagggg aaactacagc acctggaaaa tgaactcacc   3180
cacgatatca tcaccaagtt cctggaaaat gaagacagaa ggtctgccag cttacattta   3240
cccaaactgt ccattactgg aacctatgat ctgaagagcg tcctgggtca actgggcatc   3300
actaaggtct tcagcaatgg ggctgacctc tccggggtca cagaggaggc acccctgaag   3360
ctctccaagg ccgtgcataa ggctgtgctg accatcgacg agaaagggac tgaagctgct   3420
ggggccatgt ttttagaggc catacccatg tctatccccc ccgaggtcaa gttcaacaaa   3480
ccctttgtct tcttaatgat tgaacaaaat accaagtctc ccctcttcat gggaaaagtg   3540
gtgaatccca cccaaaaata actgcctctc gctcctcaac cctcccctc catccctggc   3600
cccctccctg gatgacatta aagaagggtt gagctggtaa ccccccccc ccctgcaggg   3660
gccctcgacc cgggcggccg cttcgagcag acatgataag atacattgat gagtttggac   3720
aaaccacaac tagaatgcag tgaaaaaaat gctttatttg tgaaatttgt gatgctattg   3780
ctttatttgt aaccattata agctgcaata aacaagttaa caacaacaat tgcattcatt   3840
ttatgtttca ggttcagggg gagatgtggg aggtttttta aagcaagtaa aacctctaca   3900
aatgtggtaa aatcgataag gatctaggaa cccctagtga tggagttggc cactccctct   3960
ctgcgcgctc gctcgctcac tgaggccgcc cgggcaaagc ccgggcgtcg ggcgaccttt   4020
ggtcgcccgg cctcagtgag cgagcgagcg cgcagagagg gagtggccaa cccccccccc   4080
cccccccctg cagcctggcg taatagcgaa gaggcccgca ccgatcgccc ttcccaacag   4140
ttgcgtagcc tgaatggcga atggcgcgac gcgccctgta gcggcgcatt aagcgcggcg   4200
ggtgtggtgg ttacgcgcag cgtgaccgct acacttgcca gcgccctagc gcccgctcct   4260
ttcgctttct tcccttcctt tctcgccacg ttcgccggct ttccccgtca agctctaaat   4320
cgggggctcc ctttagggtt ccgatttagt gctttacggc acctcgaccc caaaaaactt   4380
gattagggtg atggttcacg tagtgggcca tcgccctgat agacggtttt tcgccctttg   4440
```

-continued

```
acgttggagt ccacgttctt taatagtgga ctcttgttcc aaactggaac aacactcaac   4500
cctatctcgg tctattcttt tgatttataa gggattttgc cgatttcggc ctattggtta   4560
aaaaatgagc tgatttaaca aaaatttaac gcgaatttta acaaaatatt aacgtttaca   4620
atttcctgat gcggtatttt ctccttacgc atctgtgcgg tatttcacac cgcatatggt   4680
gcactctcag tacaatctgc tctgatgccg catagttaag ccagccccga cacccgccaa   4740
cacccgctga cgcgccctga cgggcttgtc tgctcccggc atccgcttac agacaagctg   4800
tgaccgtctc cgggagctgc atgtgtcaga ggttttcacc gtcatcaccg aaacgcgcga   4860
gacgaaaggg cctcgtgata cgcctatttt tataggttaa tgtcatgata ataatggttt   4920
cttagacgtc aggtggcact tttcggggaa atgtgcgcgg aacccctatt tgtttatttt   4980
tctaaataca ttcaaatatg tatccgctca tgagacaata accctgataa atgcttcaat   5040
aatattgaaa aaggaagagt atgagtattc aacatttccg tgtcgccctt attccctttt   5100
ttgcggcatt ttgccttcct gtttttgctc acccagaaac gctggtgaaa gtaaaagatg   5160
ctgaagatca gttgggtgca cgagtgggtt acatcgaact ggatctcaac agcggtaaga   5220
tccttgagag ttttcgcccc gaagaacgtt ttccaatgat gagcactttt aaagttctgc   5280
tatgtggcgc ggtattatcc cgtattgacg ccgggcaaga gcaactcggt cgccgcatac   5340
actattctca gaatgacttg gttgagtact caccagtcac agaaaagcat cttacggatg   5400
gcatgacagt aagagaatta tgcagtgctg ccataaccat gagtgataac actgcggcca   5460
acttacttct gacaacgatc ggaggaccga aggagctaac cgcttttttg cacaacatgg   5520
gggatcatgt aactcgcctt gatcgttggg aaccggagct gaatgaagcc ataccaaacg   5580
acgagcgtga caccacgatg cctgtagcaa tggcaacaac gttgcgcaaa ctattaactg   5640
gcgaactact tactctagct tcccggcaac aattaataga ctggatggag gcggataaag   5700
ttgcaggacc acttctgcgc tcggcccttc cggctggctg gtttattgct gataaatctg   5760
gagccggtga gcgtgggtct cgcggtatca ttgcagcact ggggccagat ggtaagccct   5820
cccgtatcgt agttatctac acgacgggga gtcaggcaac tatggatgaa cgaaatagac   5880
agatcgctga gataggtgcc tcactgatta agcattggta actgtcagac caagtttact   5940
catatatact ttagattgat ttaaaacttc atttttaatt taaaaggatc taggtgaaga   6000
tcctttttga taatctcatg accaaaatcc cttaacgtga gttttcgttc cactgagcgt   6060
cagaccccgt agaaaagatc aaaggatctt cttgagatcc tttttttctg cgcgtaatct   6120
gctgcttgca aacaaaaaaa ccaccgctac cagcggtggt ttgtttgccg gatcaagagc   6180
taccaactct ttttccgaag gtaactggct tcagcagagc gcagatacca aatactgtcc   6240
ttctagtgta gccgtagtta ggccaccact tcaagaactc tgtagcaccg cctacatacc   6300
tcgctctgct aatcctgtta ccagtggctg ctgccagtgg cgataagtcg tgtcttaccg   6360
ggttggactc aagacgatag ttaccggata aggcgcagcg gtcgggctga acggggggtt   6420
cgtgcacaca gcccagcttg gagcgaacga cctacaccga actgagatac ctacagcgtg   6480
agcattgaga aagcgccacg cttcccgaag ggagaaaggc ggacaggtat ccggtaagcg   6540
gcagggtcgg aacaggagag cgcacgaggg agcttccagg gggaaacgcc tggtatcttt   6600
atagtcctgt cgggtttcgc cacctctgac ttgagcgtcg atttttgtga tgctcgtcag   6660
gggggcggag cctatggaaa aacgccagca acgcggcctt tttacggttc ctggcctttt   6720
gctggccttt tgctcacatg ttctttcctg cgttatcccc tgattctgtg gataaccgta   6780
```

-continued

```
ttaccgcctt tgagtgagct gataccgctc gccgcagccg aacgaccgag cgcagcgagt   6840

cagtgagcga ggaagcggaa gagcgcccaa tacgcaaacc gcctctcccc gcgcgttggc   6900

cgattcatta atgcagggct gcag                                          6924
```

<210> SEQ ID NO 11
<211> LENGTH: 6924
<212> TYPE: DNA
<213> ORGANISM: Artificial Sequence
<220> FEATURE:
<223> OTHER INFORMATION: Description of Artificial Sequence:PLASMID p43rmsENCB-AT

<400> SEQUENCE: 11

```
gggggggggg gggggggttg gccactccct ctctgcgcgc tcgctcgctc actgaggccg     60

ggcgaccaaa ggtcgcccga cgcccgggct ttgcccgggc ggcctcagtg agcgagcgag    120

cgcgcagaga gggagtggcc aactccatca ctaggggttc ctagatctga cacccaaata    180

tggcctgggg tgaggaatgg tgccgtcgcc atatttgggt gtccaccatt cctcaccgct    240

ctaaaaataa ctcccgggag ttatttttag agcgccaaca cctgctgcct gcccaccatt    300

cctcaccgct ctaaaaataa ctccccacca ttcctcaccc gtcgccatat ttgggtgtcg    360

tgaggaatgg tgagatcttc aatattggcc attagccata ttattcattg gttatatagc    420

ataaatcaat attggctatt ggccattgca tacgttgtat ctatatcata atatgtacat    480

ttatattggc tcatgtccaa tatgaccgcc atgttggcat tgattattga ctagttatta    540

atagtaatca attacggggt cattagttca tagcccatat atggagttcc gcgttacata    600

acttacggta aatggcccgc ctggctgacc gcccaacgac ccccgcccat tgacgtcaat    660

aatgacgtat gttcccatag taacgccaat agggactttc cattgacgtc aatgggtgga    720

gtatttacgg taaactgccc acttggcagt acatcaagtg tatcatatgc caagtccgcc    780

ccctattgac gtcaatgacg gtaaatggcc cgcctggcat tatgcccagt acatgacctt    840

acgggacttt cctacttggc agtacatcta cgtattagtc atcgctatta ccatggtcga    900

ggtgagcccc acgttctgct tcactctccc catctccccc ccctccccac ccccaatttt    960

gtatttattt atttttaat tattttgtgc agcgatgggg gcgggggggg ggggggggcg   1020

cgcgccaggc ggggcggggc ggggcgaggg gcggggcggg gcgaggcgga gaggtgcggc   1080

ggcagccaat cagagcggcg cgctccgaaa gtttcctttt atggcgaggc ggcggcggcg   1140

gcggccctat aaaaagcgaa gcgcgcggcg ggcgggagtc gctgcgacgc tgccttcgcc   1200

ccgtgccccg ctccgccgcc gcctcgcgcc gcccgccccg gctctgactg accgcgttac   1260

tcccacaggt gagcgggcgg gacggccctt ctcctccggg ctgtaattag cgcttggttt   1320

aatgacggct tgtttctttt ctgtggctgc gtgaaagcct tgaggggctc cgggagggcc   1380

ctttgtgcgg ggggagcggc ctcgggggt gcgtgcgtgt gtgtgtgcgt ggggagcgcc   1440

gcgtgcggcc cgcgctgccc ggcggctgtg agcgctgcgg gcgcggcgcg gggctttgtg   1500

cgctccgcag tgtgcgcgag gggagcgcgg ccgggggcgg tgccccgcgg tgcggggggg   1560

gctgcgaggg gaacaaaggc tgcgtgcggg gtgtgtgcgt gggggggtga gcagggggtg   1620

tgggcgcggc ggtcgggctg taaccccccc ctgcaccccc ctccccgagt tgctgagcac   1680

ggcccggctt cgggtgcggg gctccgtacg gggcgtggcg cggggctcgc cgtgccgggc   1740

ggggggtggc ggcaggtggg ggtgccgggc ggggcggggc cgcctcgggc cggggagggc   1800

tcgggggagg ggcgcggcgg cccccggagc gccggcggct gtcgaggcgc ggcgagccgc   1860
```

-continued

```
agccattgcc ttttatggta atcgtgcgag agggcgcagg gacttccttt gtcccaaatc   1920
tgtgcggagc cgaaatctgg gaggcgccgc cgcacccct ctagcgggcg cggggcgaag   1980
cggtgcggcg ccggcaggaa ggaaatgggc ggggagggcc ttcgtgcgtc gccgcgccgc   2040
cgtccccttc tccctctcca gcctcggggc tgtccgcggg gggacggctg ccttcggggg   2100
ggacggggca gggcggggtt cggcttctgg cgtgtgaccg gcggctctag agcctctgct   2160
aaccatgttc atgccttctt ctttttccta cagctcctgg gcaacgtgct ggttattgtg   2220
ctgtctcatc attttggcaa agaattcgat atcaagcttg ggatttttca ggcaccacca   2280
ctgacctggg acagtgaatc gacaatgccg tcttctgtct cgtggggcat cctcctgctg   2340
gcaggcctgt gctgcctggt ccctgtctcc ctggctgagg atccccaggg agatgctgcc   2400
cagaagacag atacatccca ccatgatcag gatcacccaa ccttcaacaa gatcaccccc   2460
aacctggctg agttcgcctt cagcctatac cgccagctgg cacaccagtc caacagcacc   2520
aatatcttct tctccccagt gagcatcgct acagcctttg caatgctctc cctggggacc   2580
aaggctgaca ctcacgatga aatcctggag ggcctgaatt tcaacctcac ggagattccg   2640
gaggctcaga tccatgaagg cttccaggaa ctcctccgta ccctcaacca gccagacagc   2700
cagctccagc tgaccaccgg caatggcctg ttcctcagcg agggcctgaa gctagtggat   2760
aagtttttgg aggatgttaa aaagttgtac cactcagaag ccttcactgt caacttcggg   2820
gacaccgaag aggccaagaa acagatcaac gattacgtgg agaagggtac tcaagggaaa   2880
attgtggatt tggtcaagga gcttgacaga gacacagttt ttgctctggt gaattacatc   2940
ttctttaaag gcaaatggga gagacccttt gaagtcaagg acaccgagga agaggacttc   3000
cacgtggacc aggtgaccac cgtgaaggtg cctatgatga agcgtttagg catgtttaac   3060
atccagcact gtaagaagct gtccagctgg gtgctgctga tgaaatacct gggcaatgcc   3120
accgccatct tcttcctgcc tgatgagggg aaactacagc acctggaaaa tgaactcacc   3180
cacgatatca tcaccaagtt cctggaaaat gaagacagaa ggtctgccag cttacattta   3240
cccaaactgt ccattactgg aacctatgat ctgaagagcg tcctgggtca actgggcatc   3300
actaaggtct tcagcaatgg ggctgacctc tccggggtca cagaggaggc acccctgaag   3360
ctctccaagg ccgtgcataa ggctgtgctg accatcgacg agaaagggac tgaagctgct   3420
ggggccatgt ttttagaggc catacccatg tctatccccc ccgaggtcaa gttcaacaaa   3480
ccctttgtct tcttaatgat tgaacaaaat accaagtctc ccctcttcat gggaaaagtg   3540
gtgaatccca cccaaaaata actgcctctc gctcctcaac ccctcccctc catccctggc   3600
cccctccctg gatgacatta aagaagggtt gagctggtaa cccccccccc ccctgcaggg   3660
gccctcgacc cgggcggccg cttcgagcag acatgataag atacattgat gagtttggac   3720
aaaccacaac tagaatgcag tgaaaaaaat gctttatttg tgaaatttgt gatgctattg   3780
ctttatttgt aaccattata agctgcaata aacaagttaa caacaacaat tgcattcatt   3840
ttatgtttca ggttcagggg gagatgtggg aggtttttta aagcaagtaa aacctctaca   3900
aatgtggtaa aatcgataag gatctaggaa cccctagtga tggagttggc cactccctct   3960
ctgcgcgctc gctcgctcac tgaggccgcc cgggcaaagc ccgggcgtcg ggcgaccttt   4020
ggtcgcccgg cctcagtgag cgagcgagcg cgcagagagg gagtggccaa cccccccccc   4080
ccccccctg cagcctggcg taatagcgaa gaggcccgca ccgatcgccc ttcccaacag   4140
ttgcgtagcc tgaatggcga atggcgcgac gcgccctgta gcggcgcatt aagcgcggcg   4200
ggtgtggtgg ttacgcgcag cgtgaccgct acacttgcca gcgccctagc gcccgctcct   4260
```

-continued

```
ttcgctttct tcccttcctt tctcgccacg ttcgccggct ttccccgtca agctctaaat   4320
cgggggctcc ctttagggtt ccgatttagt gctttacggc acctcgaccc caaaaaactt   4380
gattagggtg atggttcacg tagtgggcca tcgccctgat agacggtttt tcgccctttg   4440
acgttggagt ccacgttctt taatagtgga ctcttgttcc aaactggaac aacactcaac   4500
cctatctcgg tctattcttt tgatttataa gggattttgc cgatttcggc ctattggtta   4560
aaaaatgagc tgatttaaca aaaatttaac gcgaatttta acaaaatatt aacgtttaca   4620
atttcctgat gcggtatttt ctccttacgc atctgtgcgg tatttcacac cgcatatggt   4680
gcactctcag tacaatctgc tctgatgccg catagttaag ccagccccga cacccgccaa   4740
cacccgctga cgcgccctga cgggcttgtc tgctcccggc atccgcttac agacaagctg   4800
tgaccgtctc cgggagctgc atgtgtcaga ggttttcacc gtcatcaccg aaacgcgcga   4860
gacgaaaggg cctcgtgata cgcctatttt tataggttaa tgtcatgata ataatggttt   4920
cttagacgtc aggtggcact tttcggggaa atgtgcgcgg aacccctatt tgtttatttt   4980
tctaaataca ttcaaatatg tatccgctca tgagacaata accctgataa atgcttcaat   5040
aatattgaaa aaggaagagt atgagtattc aacatttccg tgtcgccctt attccctttt   5100
ttgcggcatt ttgccttcct gtttttgctc acccagaaac gctggtgaaa gtaaaagatg   5160
ctgaagatca gttgggtgca cgagtgggtt acatcgaact ggatctcaac agcggtaaga   5220
tccttgagag ttttcgcccc gaagaacgtt ttccaatgat gagcactttt aaagttctgc   5280
tatgtggcgc ggtattatcc cgtattgacg ccgggcaaga gcaactcggt cgccgcatac   5340
actattctca gaatgacttg gttgagtact caccagtcac agaaaagcat cttacggatg   5400
gcatgacagt aagagaatta tgcagtgctg ccataaccat gagtgataac actgcggcca   5460
acttacttct gacaacgatc ggaggaccga aggagctaac cgcttttttg cacaacatgg   5520
gggatcatgt aactcgcctt gatcgttggg aaccggagct gaatgaagcc ataccaaacg   5580
acgagcgtga caccacgatg cctgtagcaa tggcaacaac gttgcgcaaa ctattaactg   5640
gcgaactact tactctagct tcccggcaac aattaataga ctggatggag gcggataaag   5700
ttgcaggacc acttctgcgc tcggcccttc cggctggctg gtttattgct gataaatctg   5760
gagccggtga gcgtgggtct cgcggtatca ttgcagcact ggggccagat ggtaagccct   5820
cccgtatcgt agttatctac acgacgggga gtcaggcaac tatggatgaa cgaaatagac   5880
agatcgctga gataggtgcc tcactgatta agcattggta actgtcagac caagtttact   5940
catatatact ttagattgat ttaaaacttc atttttaatt taaaaggatc taggtgaaga   6000
tcctttttga taatctcatg accaaaatcc cttaacgtga gttttcgttc cactgagcgt   6060
cagaccccgt agaaaagatc aaaggatctt cttgagatcc tttttttctg cgcgtaatct   6120
gctgcttgca aacaaaaaaa ccaccgctac cagcggtggt ttgtttgccg gatcaagagc   6180
taccaactct ttttccgaag gtaactggct tcagcagagc gcagatacca aatactgtcc   6240
ttctagtgta gccgtagtta ggccaccact tcaagaactc tgtagcaccg cctacatacc   6300
tcgctctgct aatcctgtta ccagtggctg ctgccagtgg cgataagtcg tgtcttaccg   6360
ggttggactc aagacgatag ttaccggata aggcgcagcg gtcgggctga acggggggtt   6420
cgtgcacaca gcccagcttg gagcgaacga cctacaccga actgagatac ctacagcgtg   6480
agcattgaga aagcgccacg cttcccgaag ggagaaaggc ggacaggtat ccggtaagcg   6540
gcagggtcgg aacaggagag cgcacgaggg agcttccagg gggaaacgcc tggtatcttt   6600
```

-continued

```
atagtcctgt cgggtttcgc cacctctgac ttgagcgtcg atttttgtga tgctcgtcag   6660

gggggcggag cctatggaaa aacgccagca acgcggcctt tttacggttc ctggcctttt   6720

gctggccttt tgctcacatg ttctttcctg cgttatcccc tgattctgtg gataaccgta   6780

ttaccgcctt tgagtgagct gataccgctc gccgcagccg aacgaccgag cgcagcgagt   6840

cagtgagcga ggaagcggaa gagcgcccaa tacgcaaacc gcctctcccc gcgcgttggc   6900

cgattcatta atgcagggct gcag                                           6924


<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:SYNTHETIC
      PRIMER

<400> SEQUENCE: 12

tatgggatcg gccattgaac                                                  20


<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:SYNTHETIC
      PRIMER

<400> SEQUENCE: 13

cctgatgctc ttcgtccaga                                                  20
```

MATERIALS AND METHODS FOR GENE THERAPY

CROSS-REFERENCE TO A RELATED APPLICATION

This application claims priority from provisional application U.S. Ser. No. 60/083,025, filed Apr. 24, 1998.

The subject invention was made with government support under a research project supported by National Institute of Health NHLBI Grant No. HL 59412. The government has certain rights in this invention.

BACKGROUND OF THE INVENTION

Alpha-1-antitrypsin (AAT) deficiency is the second most common monogenic lung disease in man, accounting for approximately 3% of all early deaths due to obstructive pulmonary disease. AAT protein is normally produced in the liver, secreted into the serum and circulated to the lung where it protects the fine supporting network of elastin fibers from degradation by neutrophil elastase. Current therapy for AAT deficiency includes avoidance of cigarette smoke exposure and weekly intravenous infusions of recombinant human AAT (hAAT) protein. Attempts to devise gene therapy strategies to replace AAT either in the lung itself or within any of a number of other tissues which are capable of AAT secretion have been limited by the short duration of expression from some vectors and by the relatively high circulating levels of AAT which is required for therapeutic effect. Methods of gene therapy have been described in U.S. Pat. No. 5,399,346.

It has recently been demonstrated that adeno-associated virus (AAV) vectors are capable of stable in vivo expression and may be less immunogenic than other viral vectors (Flotte et al., 1996; Xiao et al., 1996; Kessler et al., 1996; Jooss et al., 1998). AAV is a non-pathogenic human parvovirus whose life cycle naturally includes a mechanism for long-term latency. In the case of wild-type AAV (wtAAV), this persistence is due to site-specific integration into a site on human chromosome 19 (the AAVSI site) in the majority of cells (Kotin et al., 1990), whereas with recombinant AAV (rAAV) vectors, persistence appears to be due to a combination of episomal persistence and integration into non-chromosome 19 locations (Afione et al., 1996; Kearns et al., 1996). Recombinant AAV latency also differs from that of wtAAV in that wtAAV is rapidly converted to double-stranded DNA in the absence of helper virus (e.g., adenovirus) infection, while with rAAV leading strand synthesis is delayed in the absence of helper virus (Fisher et al., 1996; Ferrari et al., 1996). U.S. Pat. No. 5,658,785 describes adeno-associated virus vectors and methods for gene transfer to cells.

Kessler et al. (1996) demonstrated that murine skeletal myofibers transduced by an rAAV vector were capable of sustained secretion of biologically active human erythropoietin (hEpo), apparently without eliciting a significant immune response against the secreted hEpo. See also U.S. Pat. No. 5,858,351 issued to Podsakoff et al. Likewise, Murphy et al. (1997) have observed the expression and secretion of sustained levels of leptin in ob/ob mice after AAV muscle transduction. Brantly et al. (U.S. Pat. No. 5,439,824) disclose methods for increasing expression of AAT using vectors comprising intron II of the human AAT gene. However, the level of leptin expression observed was only in the range of 2 to 5 ng/ml. Therapy for AAT deficiency requires serum levels of at least about 800 μg/ml. Thus, there remains a need in the art for a means of providing therapeutically beneficial levels of a protein to a person in need of such treatment.

BRIEF SUMMARY OF THE INVENTION

The subject invention concerns materials and methods for gene therapy. One aspect of the invention pertains to vectors which can be used to provide genetic therapy in animals or humans having a genetic disorder where relatively high levels of expression of a protein is required to treat the disorder. The vectors of the invention are based on adeno-associated virus (AAV). The vectors are designed to provide high levels of expression of heterologous DNA contained in the vector. In one embodiment, the vectors comprise AAV inverted terminal repeat sequences and constitutive or regulatable promoters for driving high levels of gene expression. The subject invention also pertains to methods for treating animals or humans in need of gene therapy, e.g., to correct a genetic deficiency disorder.

BRIEF DESCRIPTION OF THE DRAWINGS

FIG. 5A shows the mean total serum levels of hAAT observed in groups of either SCID (squares) or C57BL (circles) mice receiving either low dose ($5\times10^{11}$ particles) (open symbols) or high dose ($1.4\times10^{13}$ particles) (filled symbols) single injections into muscle of the C-AT vector measured at time points ranging from 1 to 16 wk after injection. For each strain, the high-dose curve is significantly different from the low-dose curve (P=0.009 for SCID, P=0.02 for C57BL), but the strains do not differ from each other. FIG. 5B shows analogous data with the E-AT vector. None of these differences were significant.

FIG. 7A shows serum hAAT levels and FIG. 7B shows serum anti-hAAT antibody levels as determined by ELISA performed on serum taken from mice injected with $1\times10^{11}$ particles of the C-AT vector. Each set of symbols represents an individual animal (□, no. 1; Δ, no. 2; ○, no. 3). Note the inverse correlation between the presence of antibody and the presence of circulating hAAT.

FIG. 9 shows serum hAAT in C57B1/6 mice transduced with C-AT and p43CB-AT. C57B1/6 mice were injected in muscle with C-AT ($3.5\times10^{10}$ IU/mouse, $1\times10^{12}$ particles/mouse) or p43CB-AT ($6\times10^{9}$ UI, $1\times10^{12}$ particles/mouse). The level of hAAT from p43CB-AT were projected based on an estimation of the equivalent dosage (infectious unit) of C-AT.

FIG. 15 and FIGS. 15A–15C shows a map and nucleotide sequence for the vector of the present invention designated as C-AT (SEQ ID NO:1).

FIG. 16 and FIGS. 16A–16C shows a map and nucleotide sequence for the vector of the present invention designated as E-AT (SEQ ID NO:2).

FIG. 17 and FIGS. 17A–17C shows a map and nucleotide sequence for the vector of the present invention designated as dE-AT (SEQ ID NO:3).

FIG. 18 and FIGS. 18A–18C shows a map and nucleotide sequence for the vector of the present invention designated as p43C-AT (SEQ ID NO:4).

FIG. 19 and FIGS. 19A–19C shows a map and nucleotide sequence for the vector of the present invention designated as p43C-AT-IN (SEQ ID NO:5). This vector includes intron II from human AAT gene to enhance transcription.

FIG. 20 and FIGS. 20A–20C shows a map and nucleotide sequence for the vector of the present invention designated as p43CB-AT (SEQ ID NO:6).

FIG. 21 and FIGS. 21A–20C shows a map and nucleotide sequence for the vector of the present invention designated as C-AT2 (SEQ ID NO:7).

FIG. 22 and FIGS. 22A–22C shows a map and nucleotide sequence for the vector of the present invention designated as p43msENC-AT (SEQ ID NO:8). This vector is similar to p43C-AT but also comprises an enhancer sequence upstream of the CMV promoter.

FIG. 23 and FIGS. 23A–23C shows a map and nucleotide sequence for the vector of the present invention designated as p43rmsENC-AT (SEQ ID NO:9). This vector is the same as the p43msENC-AT vector except that the enhancer sequence is in an opposite orientation.

FIG. 24 and FIGS. 24A–24C shows a map and nucleotide sequence for the vector of the present invention designated as p43msENCB-AT (SEQ ID NO:10). This vector is similar to p43CB-AT but also comprises an enhancer sequence upstream of the CMV promoter.

FIG. 25 and FIGS. 25A–25C shows a map and nucleotide sequence for the vector of the present invention designated as p43rmsENCB-AT (SEQ ID NO:11). This vector is the same as p43msENCB-AT except that the enhancer sequence is in an opposite orientation.

DETAILED DESCRIPTION OF THE INVENTION

Figure 1:
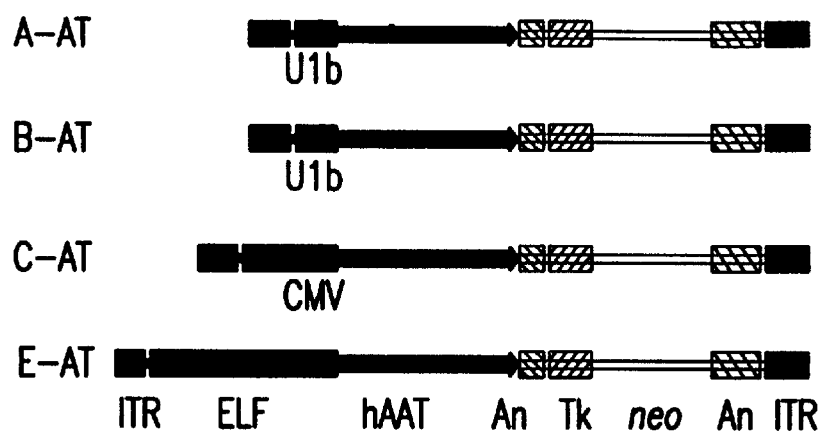
FIG. 1 shows rAAV-AAT vector cassettes used according to the subject invention. The A-AT and B-AT constructs contain the promoters from the small nuclear RNA genes, U1a and U1b, respectively. The C-AT construct contains the CMV promoter, whereas the E-AT vector uses the human elongation factor 1-α (ELF in the figure) promoter. ITR refers to AAV inverted terminal repeat; An refers to polyA signal; Tk refers to the HSV thymidine kinase promoter; neo refers to the Tn5 neomycin phosphotransferase gene.

The subject invention pertains to novel materials and methods for providing gene therapy to a mammal or human having a condition or disorder, such as genetic deficiency disorders, where high levels of expression of a protein are required to treat the disorder or condition. In one method of the subject invention, a viral vector is introduced into cells of an animal wherein a therapeutic protein is produced, thereby providing genetic therapy for the animal. In one embodiment, a method of the invention comprises introducing into an animal cell or tissue an effective amount of viral particles or vector comprising a recombinant genome which includes heterologous polynucleotide encoding a protein useful in genetic therapy and that can be expressed by the cell or tissue. Expression of the heterologous polynucleotide results in production of the protein. Preferably, the therapeutic protein encoded by the heterologous polynucleotide is a serum protein. In a preferred embodiment, vector material comprising the heterologous polynucleotide is integrated into a chromosome of the cell of the host animal.

In one embodiment, a recombinant polynucleotide vector of the present invention is derived from adeno-associated virus (AAV) and comprises a constitutive or regulatable promoter capable of driving sufficient levels of expression of the heterologous DNA in the viral vector. Preferably, a recombinant vector of the invention comprises inverted terminal repeat sequences of AAV, such as those described in WO 93/24641. In a preferred embodiment, a vector of the present invention comprises polynucleotide sequences of the pTR-UF5 plasmid. The pTR-UF5 plasmid is a modified version of the $pTR_{BS}$-UF/UF1/UF2/UFB series of plasmids (Zolotukhin et al., 1996; Klein et al., 1998). The pTR-UF5 plasmid contains modifications to the sequence encoding the green fluorescent protein (GFP).

Promoters useful with the subject invention include, for example, the cytomegalovirus immediate early promoter (CMV), the human elongation factor 1-alpha promoter (EF1), the small nuclear RNA promoters (U1a and U1b), α-myosin heavy chain promoter, Simian virus 40 promoter (SV40), Rous sarcoma virus promoter (RSV), adenovirus major late promoter, β-actin promoter and hybrid regulatory element comprising a CMV enhancer/β-actin promoter. These promoters have been shown to be active in a wide range of mammalian cells.

The promoters are operably linked with heterologous DNA encoding the protein of interest. By “operably linked,” it is intended that the promoter element is positioned relative to the coding sequence to be capable of effecting expression of the coding sequence.

Promoters particularly useful for expression of a protein in muscle cells include, for example, hybrid CMV enhancer/β-actin promoters, CMV promoters, synthetic promoters and EF1 promoter. Promoters particularly useful for expression of a protein in liver cells include, for example, hybrid CMV enhancer/β-actin promoters and EF1 promoters.

Also contemplated for use with the vectors of the present invention are inducible and cell type specific promoters. For example, Tet-inducible promoters (Clontech, Palo Alto, Calif.) and VP16-LexA promoters (Nettelbeck et al., 1998) can be used in the present invention.

The vectors can also include introns inserted into the polynucleotide sequence of the vector as a means for increasing expression of heterologous DNA encoding a protein of interest. For example, an intron can be inserted between a promoter sequence and the region coding for the protein of interest on the vector. Introns can also be inserted in the coding regions. Exemplified in the present invention is the use of intron II from the hAAT gene in a subject vector. Transcriptional enhancer elements which can function to increase levels of transcription from a given promoter can also be included in the vectors of the invention. Enhancers can generally be placed in either orientation, 3' or 5', with respect to promoter sequences. In addition to the natural enhancers, synthetic enhancers can be used in the present invention. For example, a synthetic enhancer randomly assembled from Spc5-12-derived elements including muscle-specific elements, serum response factor binding element (SRE), myocyte-specific enhancer factor-1 (MEF-1), myocyte-specific enhancer factor-2 (MEF-2), transcription enhancer factor-1 (TEF-1) and SP-1 (Li et al., 1999; Deshpande et al., 1997; Stewart et al., 1996; Mitchell et al., 1989; Briggs et al., 1986; Pitluk et al., 1991) can be used in vectors of the invention.

Heterologous polynucleotide in the recombinant vector can include, for example, polynucleotides encoding normal, functional proteins which provide therapeutic replacement for normal biological function in animals afflicted with genetic disorders which cause the animal to produce a defective protein, or abnormal or deficient levels of that protein. Proteins, and the polynucleotide sequences that encode them, which can be provided by gene therapy using the subject invention include, but are not limited to, anti-proteases, enzymes, structural proteins, coagulase factors, interleukins, cytokines, growth factors, interferons, and lymphokines. In an exemplified embodiment, heterologous DNA in a recombinant AAV vector encodes human alpha-1-antitrypsin protein.

As those of ordinary skill in the art will appreciate, any of a number of different nucleotide sequences can be used, based on the degeneracy of the genetic code, to produce a protein of interest for use in the present invention. Accordingly, any nucleotide sequence which encodes a protein of interest comes within the scope of this invention. Biologically active fragments and variants of a protein of interest can easily and routinely be produced by techniques well known in the art. For example, time-controlled Bal31 exonuclease digestion of the full-length DNA followed by expression of the resulting fragments and routine screening can be used to readily identify expression products having the desired activity (Wei et al., 1993).

As used herein, the terms “polynucleotide” and “polynucleotide sequence” refer to a deoxyribonucleotide or ribonucleotide polymer in either single- or double-stranded form, and unless otherwise limited, would encompass known analogs of natural nucleotides that can function in a similar manner as naturally-occurring nucleotides. Polynucleotide sequences can include both DNA strand sequences, such as that which is transcribed into RNA, and RNA sequences. The polynucleotide sequences include both full-length sequences as well as shorter sequences derived from the full-length sequences. It is understood that a particular polynucleotide sequence includes sequences, such as degenerate codons of the native sequence or sequences, which may be introduced to provide codon preference in a specific host cell. Polynucleotides of the invention encompass both the sense and antisense strands as either individual strands or in the duplex.

The polynucleotides of the subject invention also encompass equivalent and variant sequences containing mutations in the exemplified sequences. These mutations can include, for example, nucleotide substitutions, insertions, and deletions as long as the variant sequence functions in a manner similar to the exemplified sequences.

The gene therapy methods of the invention can be performed by ex vivo or in vivo treatment of the patient's cells or tissues. Cells and tissues contemplated within the scope of the invention include, for example, muscle, liver, lung, skin and other cells and tissues that are capable of producing and secreting serum proteins. The vectors of the invention can be introduced into suitable cells, cell lines or tissue using methods known in the art. The viral particles and vectors can be introduced into cells or tissue in vitro or in vivo. Methods contemplated include transfection, transduction, injection and inhalation. For example, vectors can be introduced into cells using liposomes containing the subject vectors, by direct transfection with vectors alone, electroporation or by particle bombardment. In an exemplified embodiment, muscle cells are infected in vivo by injection of viral particles comprising recombinant vector into muscle tissue of an animal. In another embodiment, liver cells are infected in vivo by injection of recombinant virus into either the portal vein or peripheral veins.

The methods and materials of the subject invention can be used to provide genetic therapy for any conditions or diseases treatable by protein or cytokine infusion such as, for example, alpha-1-antitrypsin deficiency, hemophilia, adenosine deaminase deficiency, and diabetes. The methods and materials of the subject invention can also be used to provide genetic therapy for treating conditions such as, for example, cancer, autoimmune diseases, neurological disorders, immunodeficiency diseases, and bacterial and viral infections. For example, the present invention can be used to provide genetic therapy to a patient wherein cells from the patient are transformed to express and produce interleukins such as interleukin-2.

Using the materials and methods of the subject invention, the skilled artisan can for the first time provide therapeutically effective levels of a serum protein through genetic therapy. In a preferred embodiment, the therapeutically effective level of serum protein that can be obtained using the subject materials and methods is at least about 1 μg/ml of protein in serum. Preferably, the level of serum protein that can be obtained using the present invention is at least about 100 μg/ml of protein in the serum. Most preferably, the level of serum protein that can be obtained by the present invention is at least about 500 μg/ml of protein in the serum.

Animals that can be treated with the materials and methods of the invention include mammals such as bovine, porcine, equine, ovine, feline and canine mammals. Preferably, the mammals are primates such as chimpanzees and humans.

The subject invention also concerns cells containing recombinant vectors of the present invention. The cells can be, for example, animal cells such as mammalian cells. Preferably, the cells are human cells. More preferably, the cells are human myofibers or myoblasts, hepatocytes or lung cells. In a preferred embodiment, a recombinant vector of the present invention is stably integrated into the host cell genome. Cell lines containing the recombinant vectors are also within the scope of the invention.

In an exemplified embodiment, recombinant AAV vectors comprising the human AAT gene (hAAT) using either the CMV promoter (AAV-C-AT) or the human elongation factor 1-alpha (EF1) promoter (AAV-E-AT) to drive expression were constructed and packaged using standard techniques. A murine myoblast cell line, C2C12, was transduced with each vector and expression of hAAT into the medium was measured by ELISA. In vitro, the EF1 promoter construct resulted in 10-fold higher hAAT expression than the CMV promoter construct. In vivo transduction was performed by injecting doses of up to $1.4\times10^{13}$ Dnase-resistant particles of each vector into skeletal muscles of a number of different strains of mice (including C57B1/6, Balb/c, and SCID). In vivo, the CMV promoter construct resulted in higher levels of expression, with sustained serum levels up to 800 μg/ml in SCID mice, approximately 10,000-fold higher than those previously observed with proteins secreted from AAV vectors in muscle. At lower doses in both C57B1/6 and SCID mice, expression was delayed for several weeks, but was sustained for over 10 weeks without declining. Thus, increasing dosage AAV vector via transduction of skeletal muscle provides a means for replacing AAT or other serum proteins.

Transduction of muscle using the vectors of the subject invention presents several advantages in that it is stable, non-toxic, and relatively nonimmunogenic. Furthermore, certain transcription promoters, such as the CMV promoter, which appear to be markedly down-regulated in other contexts have been found to remain active over time as used in the subject invention. Using the materials and methods of the subject invention, microgram/ml serum levels of a therapeutic protein can be achieved. In an exemplified embodiment, the levels of in vivo protein expression achieved represent a 10,000-fold or more increase over previously published results. In addition, a dose-effect relationship was demonstrable within the range of doses used, providing for further increases in expression levels as vector dose is increased.

In another embodiment of the invention, recombinant AAV vectors i.e., C-AT, p43C-AT, P43CB-AT, E-AT and dE-AT comprising the human AAT gene (hAAT) were constructed and packaged using standard techniques. A murine liver cell line, HO15, was transfected with each vector and expression of hAAT into the medium was measured by ELISA. In vitro, transduction with the p43CB-AT vector exhibited the highest level of hAAT expression. In vivo, the p43CB-AT vector also gave higher levels of expression. Portal vein administration appeared to be the more efficient route of administration as mice injected in this manner exhibited higher levels of expression than those receiving peripheral vein injections. Transduction of liver offers the same advantages as for muscle, but hepatocytes may be more efficient at secretion of protein.

The dosage of recombinant vector or the virus to be administered to an animal in need of such treatment can be determined by the ordinarily skilled clinician based on various parameters such as mode of administration, duration of treatment, the disease state or condition involved, and the like. Typically, recombinant virus of the invention is administered in doses between $10^5$ and $10^{14}$ infectious units. The recombinant vectors and virus of the present invention can be prepared in formulations using methods and materials known in the art. Numerous formulations can be found in Remington's Pharmaceutical Sciences, 15th Edition (1975).

All publications and patents cited herein are expressly incorporated by reference.

Materials and Methods

Construction of rAAV plasmids. The rAAV-AAT vector plasmids used for these experiments are depicted diagrammatically (FIG. 1). Briefly, the plasmid pN2FAT (Garver et al., 1987) was digested with XhoI to release 1.8-kb fragment containing the human AAT cDNA along with the SV40 promoter and a polyadenylation signal. This fragment was subcloned into a plasmid, pBlueScript (Stratagene) and, after the removal of the SV40 promoter by Hind III digestion and religation, the hAAT cDNA with its polyA signal was released by XbaI and XhoI digestion. This 1.4-kb XbaI-XhoI fragment was then cloned in to the pTR-UF5 (an AAV-inverted terminal repeat-containing vector) plasmid (Zolotukhin et al., 1996) between the XbaI site 3' to the CMV promoter and the XhoI site 5' to the polyoma virus enhancer/HSV thymidine kinase promoter cassette, which drives neo in that construct. This yielded the pAAV-CMV-AAT construct (C-AT). Analogous constructs using the promoter from the small nuclear RNA proteins, U1a and U1b, (to give the A-AT and B-AT constructs, respectively) and human elongation factor 1-alpha (EF1) promoter (to give the E-AT construct) were constructed by substituting each of these promoter cassettes in place of the CMV promoter, between the KpnI and XbaI sites.

The construct dE-AT was derived from E-AT by deletion of the silencer (52 bp) by SAC II-cut (Wakabayashi-Ito et al., 1994). C-AT2 is similar with C-AT except there are SV40 intron and poly (A) sequences flanking the cDNA of hAAT. The p43C-AT was constructed by insertion of hAAT cDNA to an AAV-vector plasmid (p43), which has CMV promoter, intron and poly (A) sequences. The p43CB-AT is derived by replacement of CMV promoter with CMV enhancer and chicken β-actin promoter sequences. The p43C-AT-IN is derived from p43C-AT by insertion of intron II sequences of hAAT gene to hAAT cDNA (Brantly et al., 1995).

Packaging of rAAV vectors. Vectors were packaged using a modification of the method described by Ferrari et al. (1997). Briefly, plasmids containing the AAV rep and cap genes (Li et al., 1997) and the Ad genes (E2a, E4 and VA-RNA) were co-transfected along with the appropriate AAV-AAT vector plasmid into 293 cells grown in Cell Factories (Nunc). Cells were harvested by trypsinization and disrupted by freeze-thaw lysis to release vector virions which were then purified by iodixanol gradient ultracentrifugation followed by heparin sepharose affinity column purification. Alternatively, recombinant virus can be prepared according to methods described in Zolotukhin et al. (1999).

Vector preparations had their physical titer assessed by quantitative competitive PCR and their biological titer assessed by infectious center assay. The presence of wild-type AAV was also assessed using these same assays with appropriate internal AAV probes. The high-dose C-AT stock had a particle-titer of $2.0\times10^{4}$ particles/ml and an infectious titer of $5.0\times10^{11}$ infectious units (i.u.)/ml (particle to i.u. ratio=400:1). The low-dose C-AT measured $8\times10^{12}$ particles/ml and $1.2\times10^{10}$ i.u./ml (particle to i.u.=667:1). For the E-AT experiments, the titers were $1\times10^{13}$ particles/ml and $2.5\times10^{10}$ i.u./ml (particle to i.u.=400:1). The low-dose C-AT stock had a wt-like AAV particle titer (i.e., positive AAV genome PCR) equal to 0.1 times the recombinant titer but no detectable infectious wtAAV. The other two preparations had wt-like AAV particle titers $<10^{-5}$ times the recombinant titer and no detectable infectious wtAAV.

In vitro transfection and transduction experiments. The C2C12 murine myoblast line was used for in vitro transfection and transduction experiments. Cells were grown in 35-mm wells with approximately $4\times10^{5}$ cells per well and transfected with 5 μg of each plasmid DNA using SUPERFECT (Qiagen Corp.). Secretion of hAAT into the medium was assessed at 2 days after transfection using an antigen-capture ELISA assay with standards (Brantly et al., 1991). An SV40 promoter luciferase-expression plasmid, pGL2 (Promega), was used as an internal control. For transduction experiments, cells were grown under similar conditions and were transduced with vector at multiplicities of infection ranging from $4\times10^{5}$ to $4\times10^{6}$ particles per cell. Cells were then passaged in the presence of geneticin sulfate (350 μg/ml) and geneticin-resistant clones were isolated for hAAT secretion studies.

In vivo injection of AAV-C-AT and AAV-E-AT vectors into murine muscle. Mice strains (C57B1/6, SCID, and Balb/c) were obtained from Jackson Laboratories (Bar Harbor, Me.) and were handled under specific pathogen-free conditions under a protocol approved by the University of Florida Institutional Animal Care and Use Committee. Animals were anesthetized by metaphane inhalation and aliquots of vector were injected percutaneously into the quadriceps femoris muscles of both hind limbs. The volume of vector ranged from 50 to 100 μl per injection site and the total amount of virus injected per animal ranged from $5\times10^{10}$ to $1.4\times10^{13}$ Dnase-resistant particles.

Antigen capture ELISA assay for hAAT expression. Microtiter plates (Immulon 4, Dynex Technologies, Chantilly, Va.) were coated with 100 μl of a 1:200 dilution of goat anti-human AAT (CAPPEL/ICN) in Vollers buffer (Na2CO3=2.76 g, NaHCO3=1.916 g, NaN3=0.2 g, d.H2O=1 liter, Adjust PH=9.6) overnight at 4° C. After washing, standards and unknown samples containing hAAT were incubated in the plates at 37° C. for 1 hour. After blocking in 3% BSA in PBS-Tween 20 at 37° C. for 1 hour, a second antibody (1:1000 dilution of rabbit anti-human AAT, Boehringer Mannheim) was reacted with the captured antigen at 37° C. for 1 hour. Detection was performned using a third antibody incubation (1:800 dilution of goat anti-rabbit IgG-peroxidase conjugate, 37° C.) followed by o-phenylenediamine (OPD, Sigma) detection and measurement of the absorbance at 490 nm.

ELISA assay for anti-hAAT and anti-AAV VP3 antibodies. Wells were coated with antigen (1 μg of hAAT or 100 ng of VP3) at 4° C. overnight, blocked with 3% BSA and then reacted with dilutions of either test serum or with positive control antibodies at 37° C. for 1 hour. After washing, a goat-anti-mouse IgG-peroxidase conjugate was used as a secondary antibody (1:1500 dilution) to detect bound anti-AAT antibody, using a standard OPD reaction, as described above. Antibody levels were quantitated by comparison with a standard curve generated by reacting dilutions of known positive monoclonal antibodies against VP3 and hAAT.

Lymphocyte proliferation assays to detect cell-mediated immune responses. Lymphocyte proliferation assays were performed in order to detect T cell responses to the hAAT and VP3 antigens. Freshly isolated splenocytes were grown in primary culture in 96 well plates coated with 0, 0.1, 1, and 10 μg of either hAAT or VP3 in RPMI-C+ medium. On day three, a pulse of $^{3}$H-thymidine was added, and the cells were harvested on day 4 for lysis and scintillation counting. Phytohemagglutinin (PHA) was used as a mitogen for positive control wells. A stimulation index was calculated for each antigen dosage level by dividing the counts per minute (cpm) of $^{3}$H-thymidine incorporated in the antigen-stimulated cells by the cpm in a control (unstimulated) well.

Following are examples which illustrate procedures for practicing the invention. These examples should not be construed as limiting. All percentages are by weight and all solvent mixture proportions are by volume unless otherwise noted.

EXAMPLE 1

In vitro Studies in Murine C2C12 Myoblasts

Figure 2:
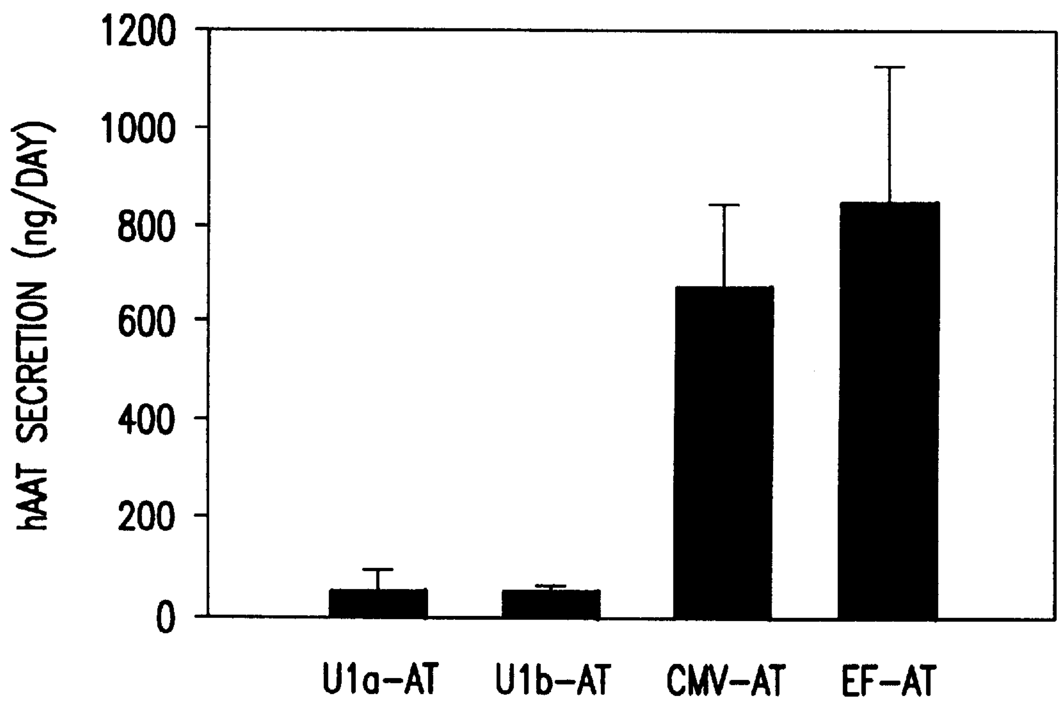
FIG. 2 shows hAAT secretion rates in vitro from transiently transfected murine C2C12 myoblast cell line using expression vectors according to the subject invention. C-AT does not differ significantly from E-AT, but both differ from A-AT and B-AT ($p<0.05$) AAT expression was detected using an ELISA assay specific for human AAT.

In order to determine the relative strength of a number of constitutively active promoters in the context of AAV-AAT vectors, packageable AAV-AAT expression vectors containing one of the CMV, EF1, U1a or U1b promoters (FIG. 1) were constructed. Each of these constructs were transfected in to the murine C2C12 myoblast cell line. Both the EF1 and the CMV promoter were active for AAT expression, with EF1 construct (AAV-E-AT) expressing 850 ng/$10^5$ cells/day and the CMV construct (AAV-C-AT) expressing approximately 670 ng/$10^5$ cells/day, as measured by a human-specific ELISA assay for AAT (FIG. 2). This difference was not statistically significant. The levels of expression from the U1a and U1b constructs were undetectable.

Figure 3:
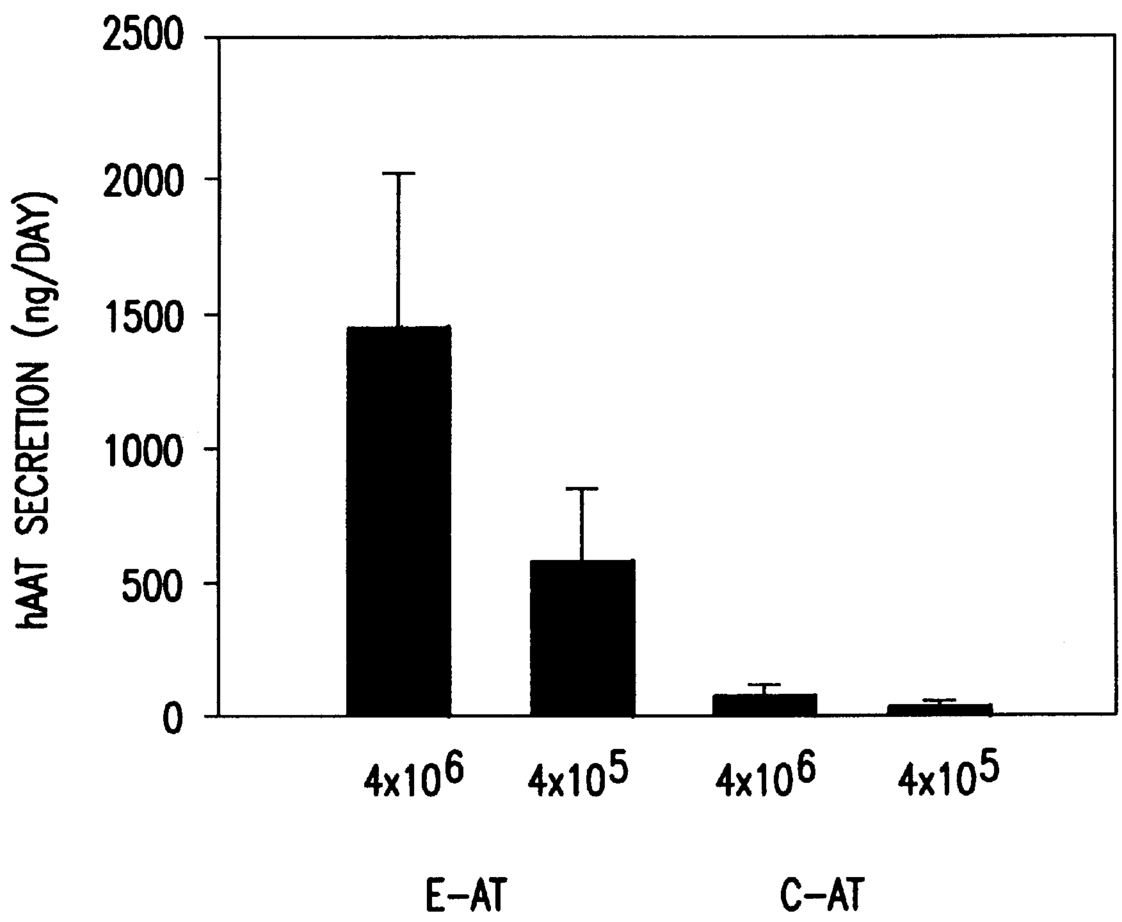
FIG. 3 shows hAAT secretion rates in vitro from stably transduced murine C2C12 myoblast cell line using viral particles comprising expression vectors according to the subject invention. The mean rates of secretion from G418-resistant cultures 1 mo after transduction with either packaged E-AT vector or packaged C-AT vector are shown. In each instance, a "low" multiplicity transduction ($4\times10^5$ particles/cell) and a high multiplicity transduction ($4\times10^6$ particles/cell) were performed. E-AT "low" and "high" are greater than "high" multiplicity C-AT ($P=0.02$) but are not significantly different from each other ($n=3$). AAT expression was detected using an ELISA assay specific for human AAT.
Figure 4:
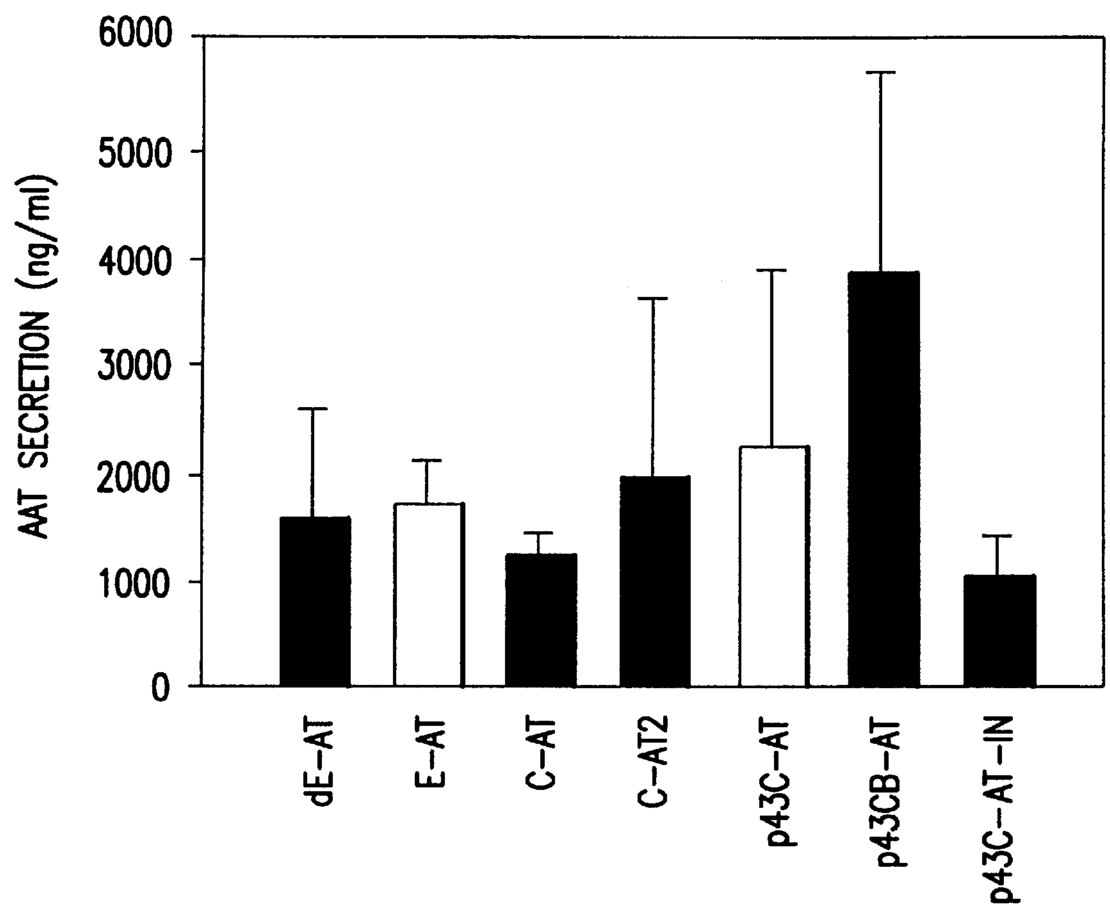
FIG. 4 shows additional constructs tested for hAAT expression. The murine myoblast C2C12 cells were grown in 35-mm Wells with approximately $4\times10^5$ cell per well and were transfected with 5 μg of the appropriate plasmid DNA using SUPERFECT transfection (Qiagen Inc., CA). Secretion of hAAT into the medium was assessed at 2 days after transfection using an antigen-capture ELISA. Each bar represents the mean of results from three experiments (triplicate in each experiment). Data from transfection experiments indicate that the expression from p43CB-AT was at least three times higher than that from C-AT in vitro.

In order to better characterize the level and duration of expression in the setting of vector transduction, cultures of C2C12 cells were transduced with either AAV-E-AT or AAV-C-AT at multiplicities of infection ranging from $4\times10^5$ to $4\times10^6$ Dnase-resistant particles per cell. Cells were then selected for expression of the neo gene (present in each of the AAV constructs) by growth in G418-containing medium. Several cell clones and pooled cell populations were independently analyzed for AAT expression at four weeks post-transduction (FIG. 3). There was a clear trend toward higher levels of expression at higher multiplicities of infection, and the E-AT construct expressed at least 10-fold greater quantities under all conditions in these long-term cultures. The most active E-AT clone expressed hAAT at a rate of over 1400 ng/$10^5$ cells/day.

EXAMPLE 2

In vivo Expression of hAAT from Murine Skeletal Muscle

Figure 5A:
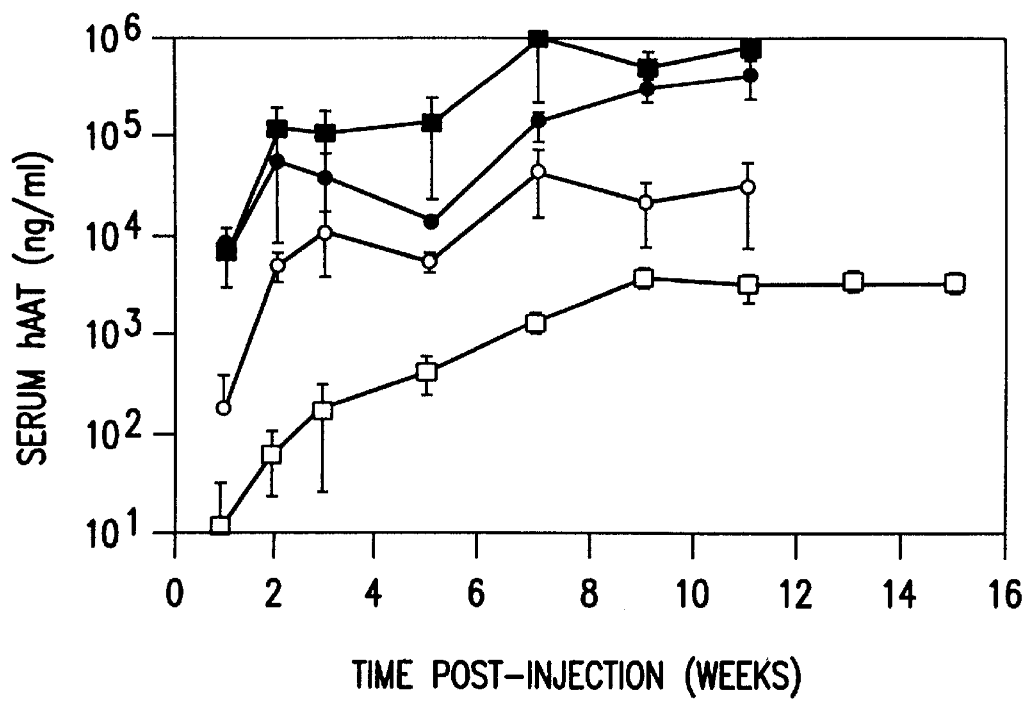
FIGS. 5A and 5B show sustained secretion of therapeutic levels of hAAT using either the C-AT vector or the E-AT vector in either SCID or C57BL mice.

In order to determine whether the AAV-AAT constructs would be active in vivo in skeletal muscle, doses of vector were injected into the quadriceps femoris muscle of mice. Circulating serum levels of hAAT were then measured for 11 to 15 weeks after the initial injection. Four saline-injected animals from each mouse strain served as controls. In the case of the C-AT vector (FIG. 5A), levels of expression were sufficient to achieve serum levels in excess of 800 μg/ml in SCID mice after a single injection of $1.4\times10^{13}$ particles. A dose-effect relationship was observed, with expression levels in SCID being at least 20-fold lower at the $5\times10^{11}$ particle dose. The levels of expression increased over the first several weeks after injection and were stable thereafter until the time of sacrifice. Since hAAT has a half-life of less than 1 week, this indicated continuous expression. Levels from C57B1/6 mice were comparable, and also achieved values close to the therapeutic range. In similar studies, two of three Balb/c mice injected with $1\times10^{11}$ particles of the C-AT vector did not express hAAT at detectable levels. Both of these were found to have developed high levels of anti-hAAT antibodies.

Figure 5B:
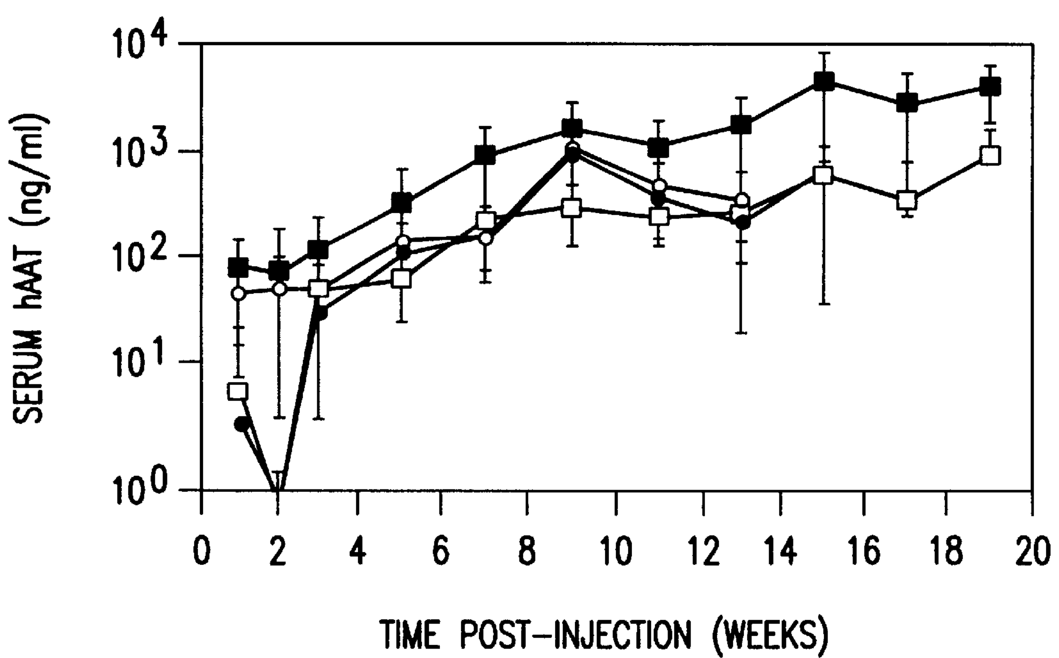
Figure 5C:
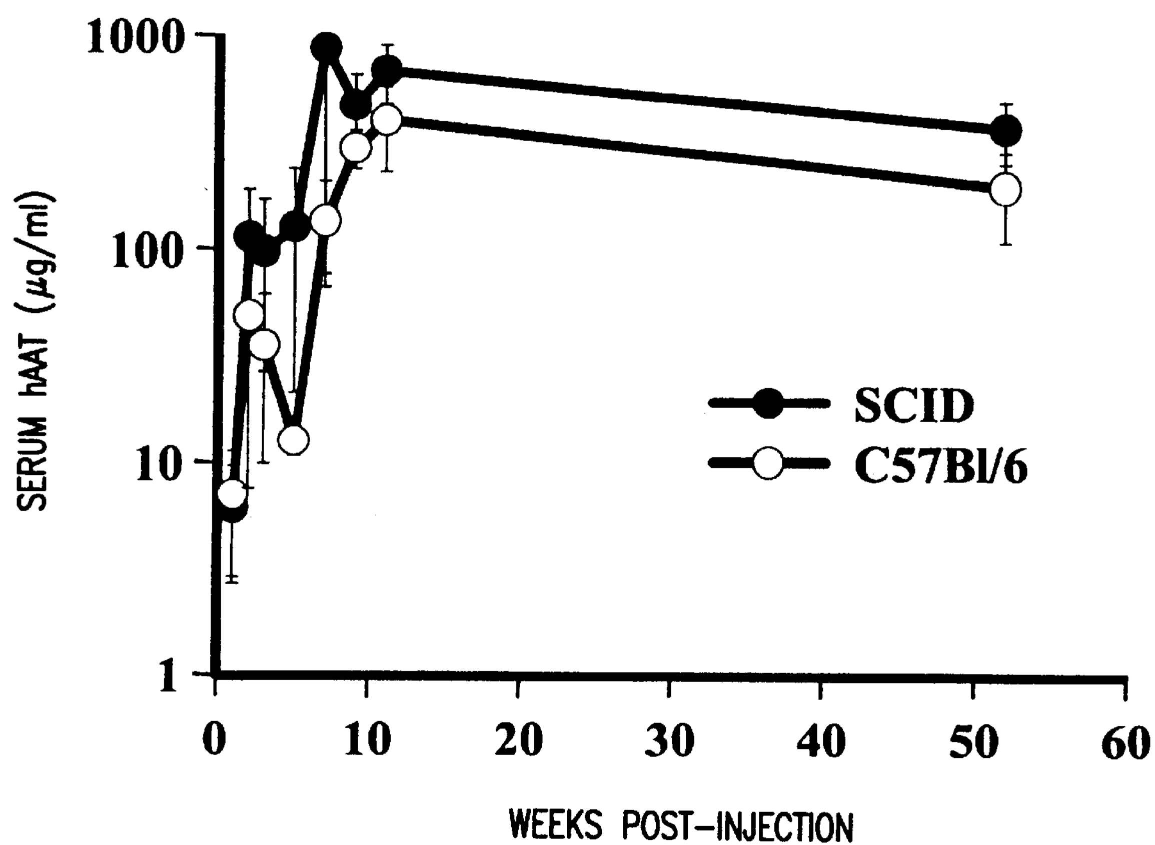
FIG. 5C shows long term secretion of hAAT from murine muscle transduced with C-AT. C57B1/6 or C57B1/6-SCID mice received $3.5\times10^{10}$ IU, $1.4\times10^{13}$ particles/mouse. One year after injection, serum hAAT levels were still 400 μg/ml in C57B1/6-SCID and 200 μg/ml in C57B1/6. This level are comparable with the peak levels observed (800 or 400 μg/ml, respectively).
Figure 6:
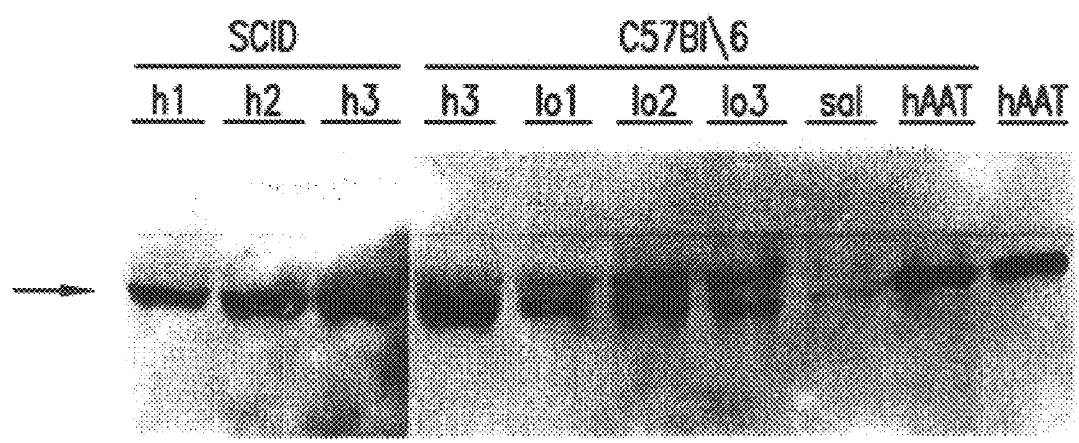
FIG. 6 shows an immunoblot of sera taken from several of the C-AT vector-treated mice at 11 weeks after vector administration. Ten microliters of a 1:100 dilution of serum was electrophoresed by 10% SDS/PAGE, blotted, and incubated with 1:1,500 dilution of goat anti-hAAT-horseradish peroxidase conjugate (Cappel/ICN). Samples from three high-dose SCID (h1–h3), one high-dose C57B1 (h3), and three low-dose C57B1 (lo1–lo3) were included, along with one negative control (saline-injected=sal) serum to indicate the level of reactivity with endogenous mAAT. As a standard, hAAT was added either to negative-control C57B1 serum (first hAAT lane) or to PBS (second hAAT) lane to final equivalent serum concentration of 100 μg/ml.
Figure 7A:
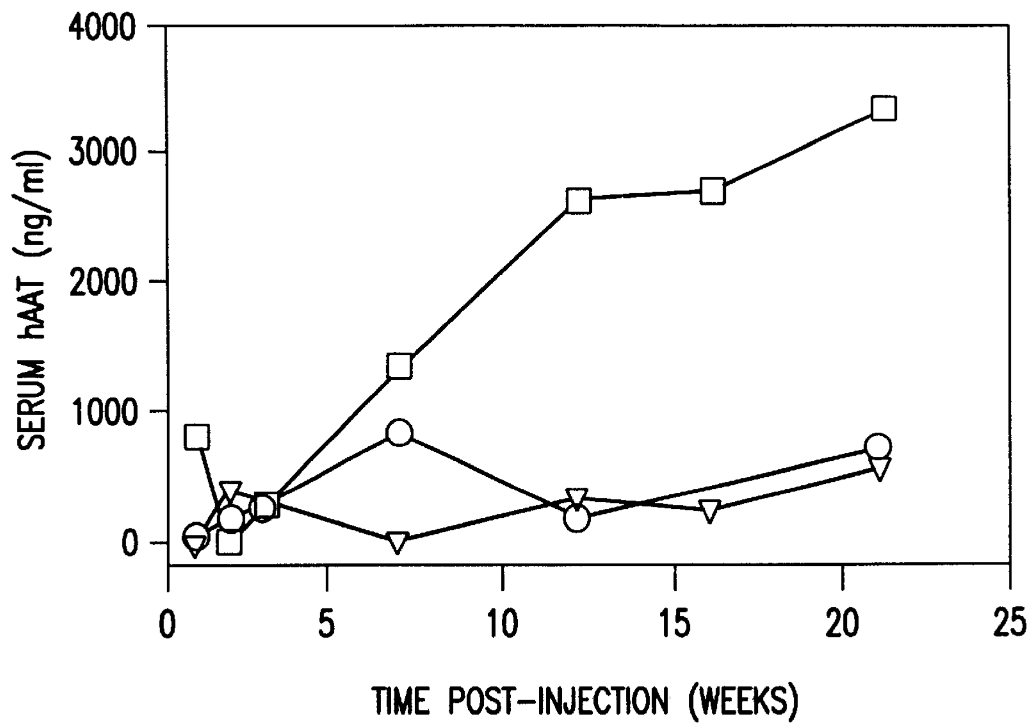
FIGS. 7A and 7B show that some BALB/c mice mount humoral immune responses to hAAT, which correlate with lower serum levels but no observable toxicity.
Figure 7B:
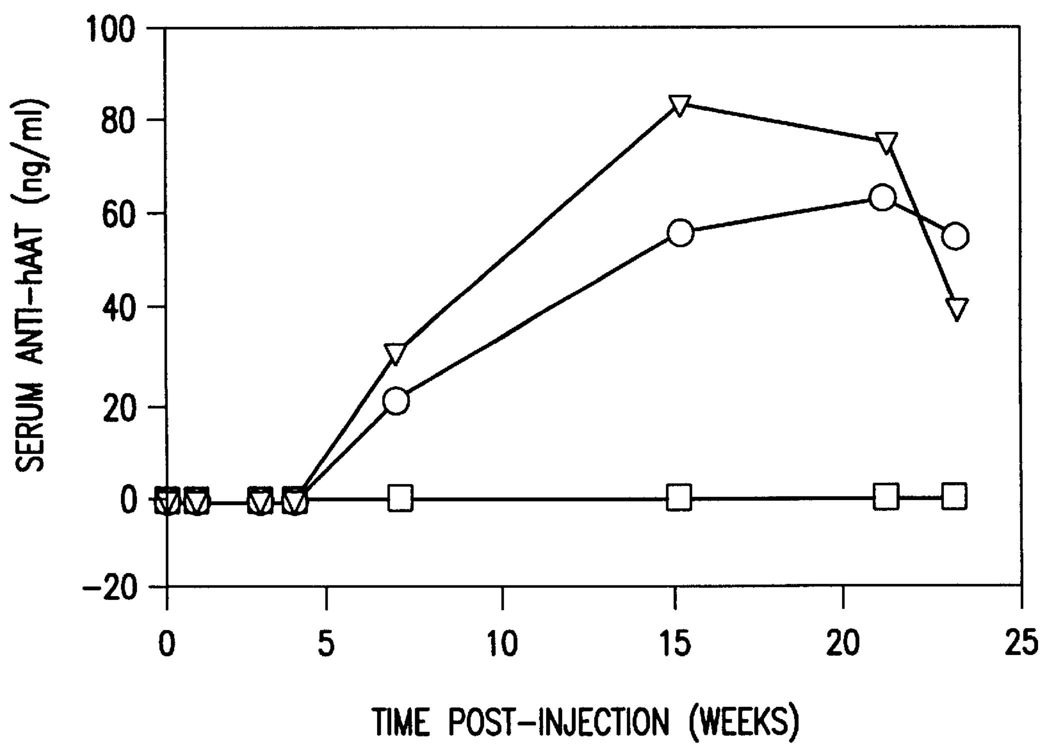

Surprisingly, expression levels from the AAV-E-AT vector after in vivo injection were modestly lower than those seen with the C-AT vector (FIG. 5B), with maximal levels of approximately 250 ng/ml at the $5\times10^{11}$ dose at and beyond 7 weeks in SCID mice. When the dose was further increased to $1\times10^{12}$ particles, levels of approximately 1200 ng/ml were observed. These levels were stable for one year post-injection (FIG. 5C). Levels observed in SCID and immune competent C57B1/6 mice were similar.

EXAMPLE 3

Immunologic Studies

In studies in Balb/c mice, antibody levels against hAAT were high in 2 of 3 animals injected. The one which did not have circulating anti-hAAT was the only animal with levels of hAAT expression similar to those in the C57B1/6 and SCID groups. The high-dose C57-C-AT injection group had detectable levels of antibody directed against VP3, but not hAAT.

In order to determine whether any cell-mediated immune responses were mounted, lymphocyte proliferation assays were performed using either hAAT or AAV-VP3 for antigenic stimulation of primary splenic lymphocytes harvested at the time of animal sacrifice, 16 weeks post-vector injection. Using this method, no immune responses were detectable in any of the mice.

EXAMPLE 4

Lack of Toxicity from Direct Vector Injection

In order to determine whether there was any direct toxicity, inflammation, or neoplastic change associated with vector injection, animals underwent complete necropsies. Histopathologic examination was performed on 5 μm sections taken from the site of vector injection and from a panel of other organs, including the brain, heart, lungs, trachea, pancreas, spleen, liver, kidney, and jejunum. No histologic abnormalities were observed in any of these sites, even among those mice which developed humoral immune responses against hAAT.

EXAMPLE 5

Molecular Evidence of AAV-AAT Vector Persistence

Figure 8:
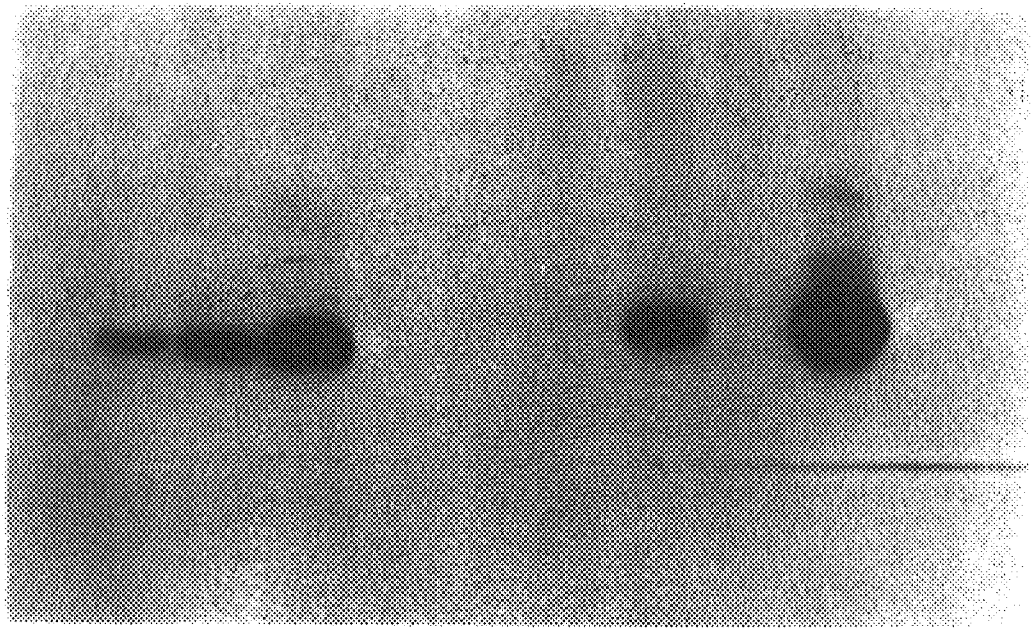
FIG. 8 shows the persistence of rAAV-AAT vector DNA in high molecular weight form. PCR products were amplified from DNA prepared by Hirt extraction from three SCID mice injected 16 wk earlier with $5\times10^{11}$ resistant-particles of C-AT and analyzed by Southern blot. The high molecular weight Hirt pellet (genomic DNA lanes) and the low molecular weight supernatant (episomal DNA lanes) were analyzed separately. Control lanes include a sample in which an hAAT cDNA plasmid was the template DNA (+) and a control in which water was the template (−). In this internal PCR reaction, a 500-bp product is expected regardless of whether or not the vector genome is integrated.
Figure 9:
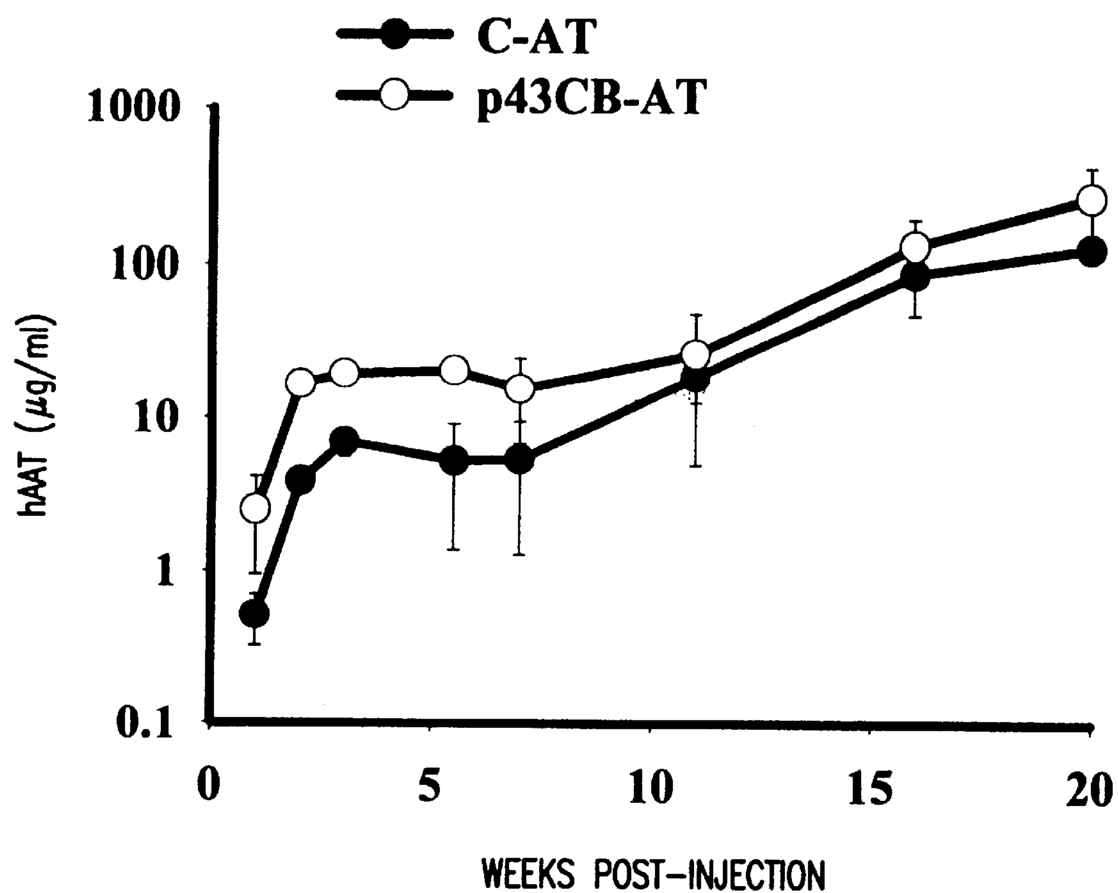
Figure 10:
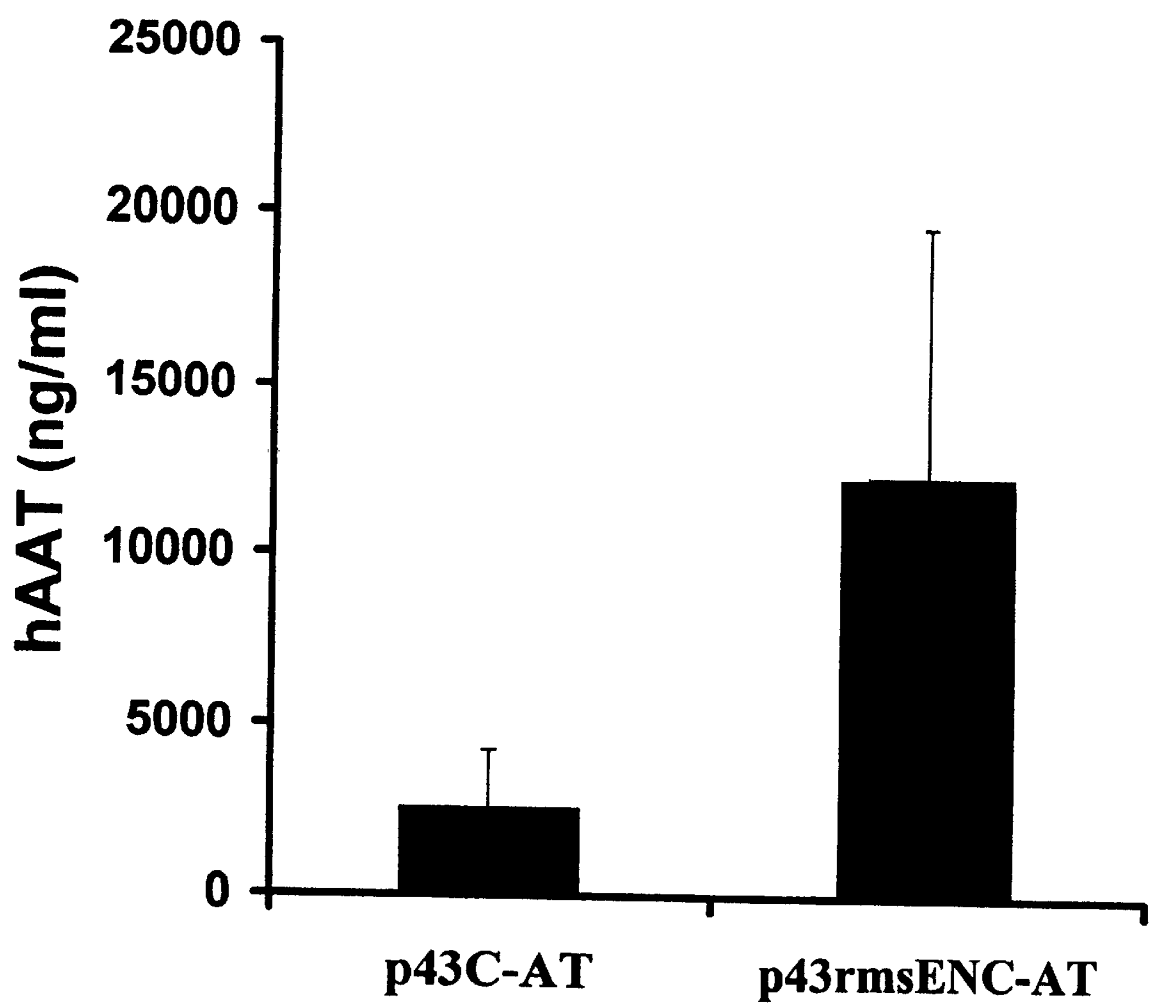
FIG. 10 shows enhancement of CMV promoter activity by a synthetic enhancer in C2C12 cells. The murine myoblast C2C12 cells were grown in 35-mm wells with approximately $4\times10^{5}$ cell per well and were transfected with 5 μg of p43rmsENC-AT vector DNA using SUPERFECT transfection (Qiagen Inc, CA). Secretion of hAAT into the medium was assessed at 2 days after transfection using an antigen-capture ELISA. Each bar represents the mean of results from one experiment (triplicate).
Figure 11:
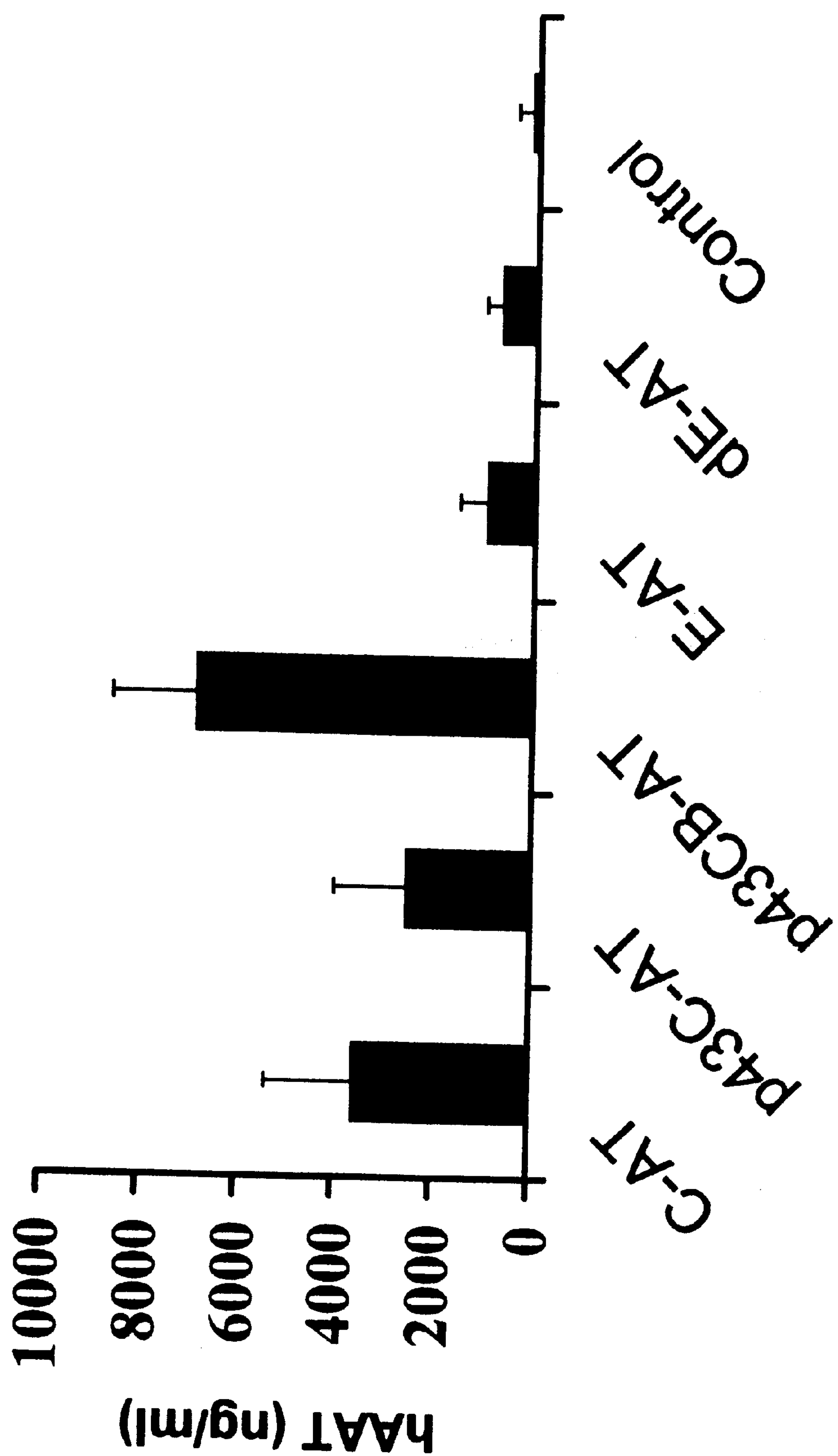
FIG. 11 shows secretion of hAAT from mouse liver cells (HO15) transfected with different constructs. The murine liver cells (HO15) were grown in 35-mm wells with approximately $4\times10^{5}$ cell per well and were transfected with 5 μg of the plasmid DNA using LIPOFECTAMINE reagents (Life Technologies Inc, MD). Secretion of hAAT into the medium was assessed at 2 days after transfection using an antigen-capture ELISA. Each bar represents the mean of results from two experiments (triplicate).
Figure 12:
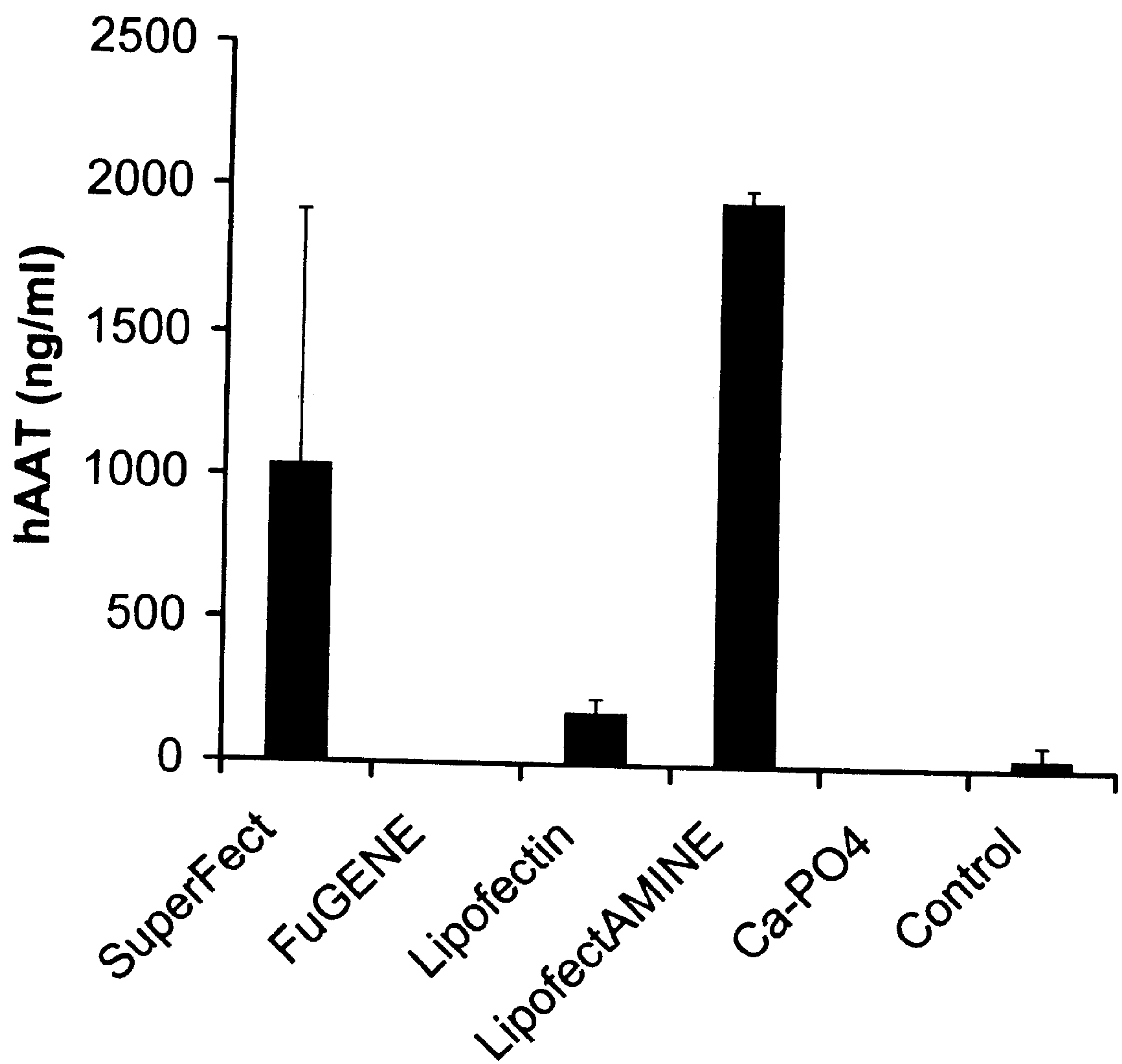
FIG. 12 shows secretion of HAAT from mouse liver cells (HO15) transfected using different methods. The murine liver cells (HO15) were grown in 35-mm wells with approximately $4\times10^{5}$ cell per well and were transfected with 5 μg of the p43CB-AT vector using SUPERFECT (Qiagen Inc., CA), FuGENE (Boehringer Mannhem Co, IN), Lipofectin, LIPOFECTAMINE (Life Technologies Inc, MD) reagents and Calcium phosphate (CA-PO4) transfection. Secretion of hAAT into the medium was assessed at 2 days after transfection using an antigen-capture ELISA. Each bar represents the mean of results from one experiment (triplicate).

To confirm the presence of vector DNA, a vector-specific PCR (neo primers 5'-TATGGGATCGGCCATTGAAC-3' (SEQ ID NO:12), and 5'-CCTGATGCTCTTC-GTCCAGA-3' (SEQ ID NO: 13), was performed on DNA extracted from 3 SCID mice 16 weeks after injection with the C-AT vector, and PCR products were analyzed by Southern blot analysis with a $^{32}P$-labeled vector-specific probe (FIG. 8). The state of vector DNA was analyzed using the Hirt procedure (Carter et al, 1983) to separate the low molecular weight episomal DNA from the high molecular weight fraction, which would contain integrated forms and large concatemers. In each case, vector DNA was present in the high molecular weight DNA fraction, whereas in only one of the animals was there a signal in the episomal fraction. This result indicates that by 16 weeks most of the vector DNA in our animals was either integrated or in large concatemers.

EXAMPLE 6

In vivo Expression of hAAT from Murine Liver

Portal vein or tail vein injections were performed on 18 female C57BL/6 mice 8–10 weeks of age. The injection volume was 100 μl per mouse.

Each group had the following parameters:

1. Group 1: 100 μl of PBS n=4.
2. Group 2: 100 μl of p43CB-AT ($3\times10^{10}$ IU/animal) n=3.
3. Group 3: 100 μl of p43CB-AT ($4\times10^9$ IU/animal) n=4.
4. Group 4: 100 μl of C-AT ($4\times10^9$ IU/animal) n=2.
5. Group 5: 100 μl of E-AT ($4\times10^9$ IU/animal) n=4.
6. Group 6: EATM TV=100 μl by tail vein injection of E-AT ($4\times10^9$ IU/animal) n=3.
7. Group 0: 100 μl of PBS by tail vein injection n=2. A total of 22 animals were used in this study.

All animals were anesthetized with 2-2-2 tribromoethanol (Avertin) using a working solution of 20 mg/ml at a dosage of 0.5 mg/g IP. A 2 cm ventral midline abdominal incision was made from the pubic symphysis extending cranially to the xyphoid process through skin and muscle layers. The portal vein was exposed by retracting the intestines and associated mesentery to the left side of the animal. Additionally, the quadrate and right medial lobes of the liver were retracted cranially. Intestines and peritoneal cavity were continuously lavaged with 0.9% NaCl.

Virus or PBS was delivered into the portal vein using a 30 g needle attached to a 100 ul capillary pipette using mouth delivery via rubber tubing and a Drummond self-locking double layer 0.8 um filter. A small piece of Gel-Foam (0.5×0.5 cm) was applied to the injection site before the needle was removed from the portal vein. The needle was retracted from beneath the Gel-Foam and the piece was held in place with forceps while the intestines were replaced into the peritoneal cavity.

The muscle and skin were closed in one layer using 2 simple interrupted 3-0 nylon sutures on an FS-1 cutting needle. Surgeries were performed on a thermoregulated operating board designed to maintain a temperature of 37 degrees. For recovery from anesthesia, the animals were placed under a heat lamp adjusted to maintain an ambient temperature of approximately 37 degrees and given subcutaneous fluid if there was a significant amount of blood loss during surgery.

Figure 13:
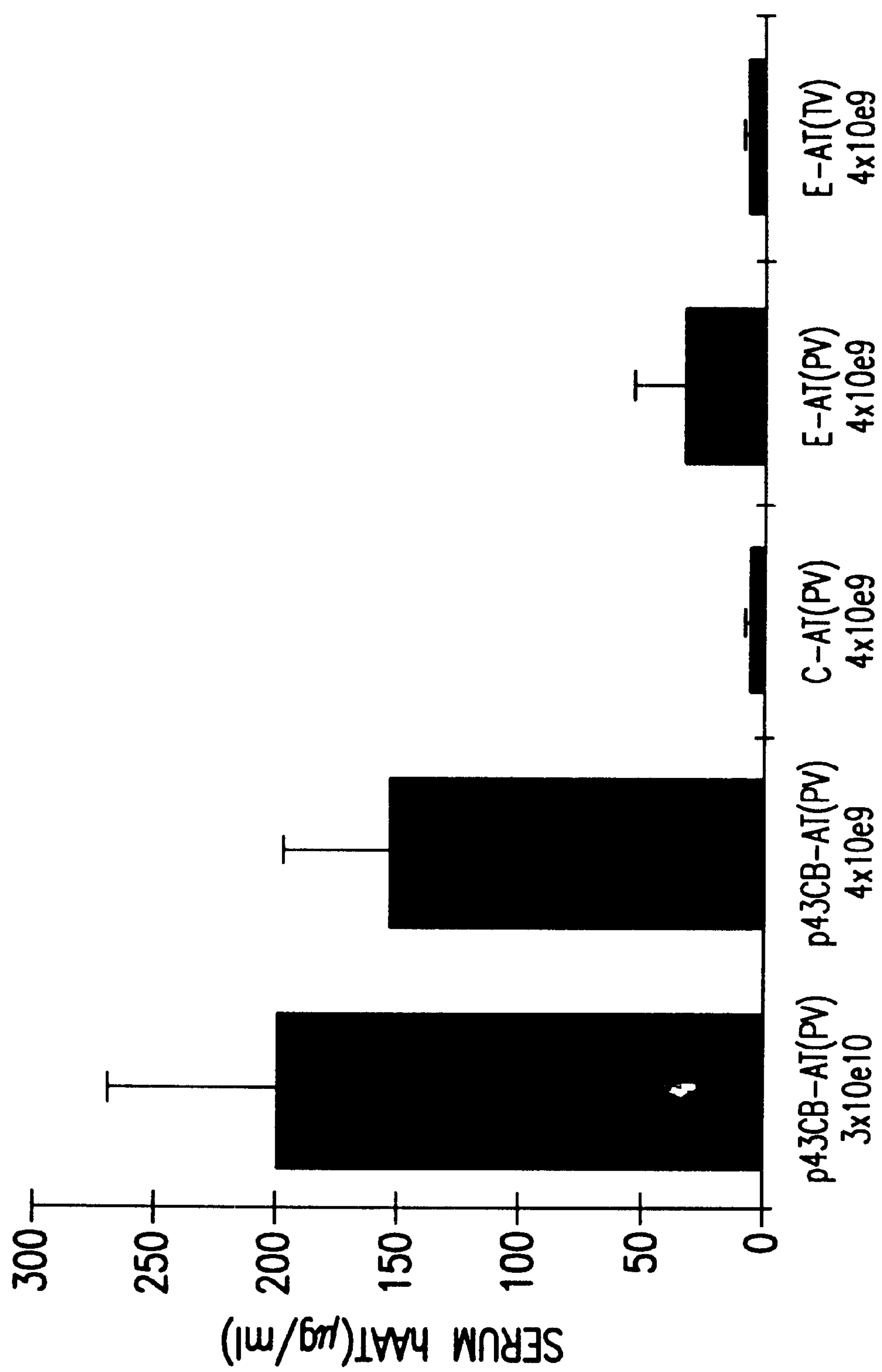
FIG. 13 shows HAAT secretion from mouse liver transduced with rAAV. C57B1/6 mice were injected with either p43CB-AT, C-AT or E-AT vector either by portal vein or tail vein injection. PV=portal vein injection. TV=tail vein injection.

Serum levels of hAAT in the mice were measured two weeks after injection. Serum levels of about 200–150 μg/ml hAAT were detected in mice receiving the p43CB-AT vector (FIG. 13). Studies using the E-AT vector show that injection of vector by portal vein led to greater levels of hAAT secretion as compared to E-AT administered by tail vein injection.

EXAMPLE 7

In vivo expression of hAAT from murine lung

Figure 14:
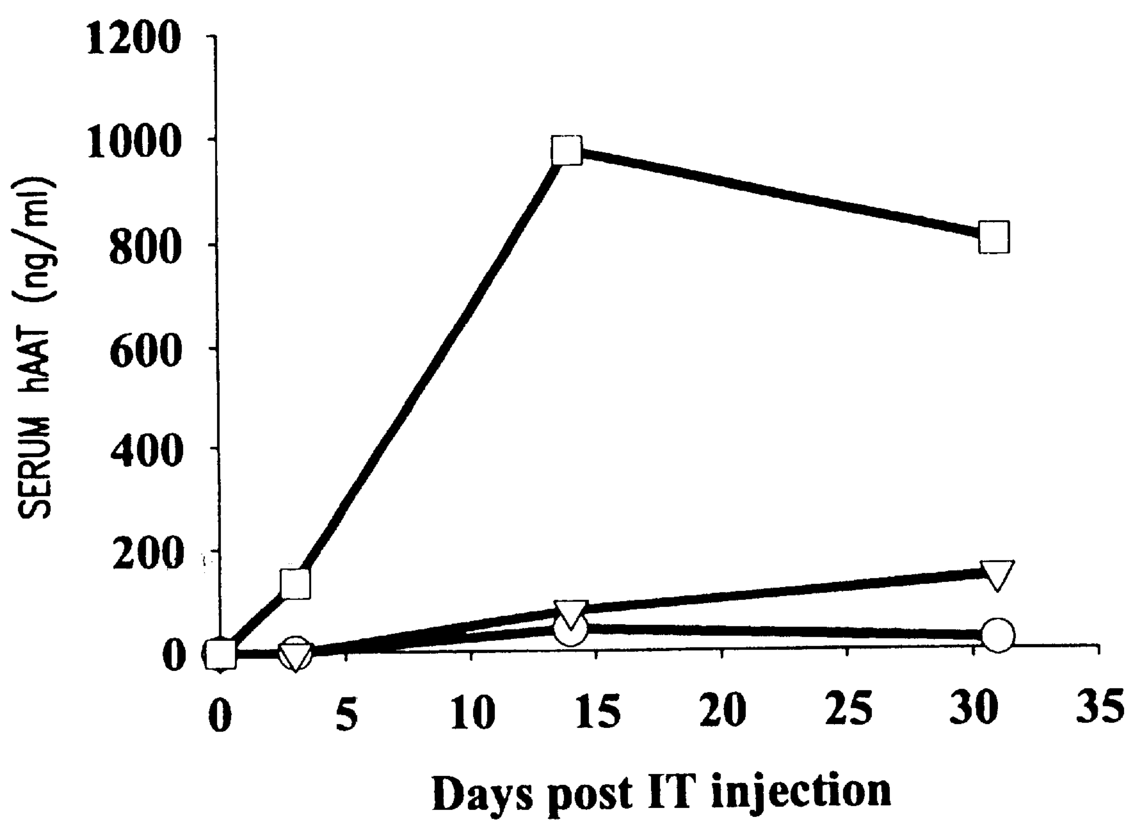
FIG. 14 shows serum hAAT levels in C57B1/6 mice after intratracheal (IT) injection of C-AT or p43CB-AT vector. Mice received either $10^{9}$ IU of C-AT (open circles), $10^{9}$ IU of p43CB-AT (open triangles) or $10^{10}$ IU of p43CB-AT (open squares).
Figure 15:
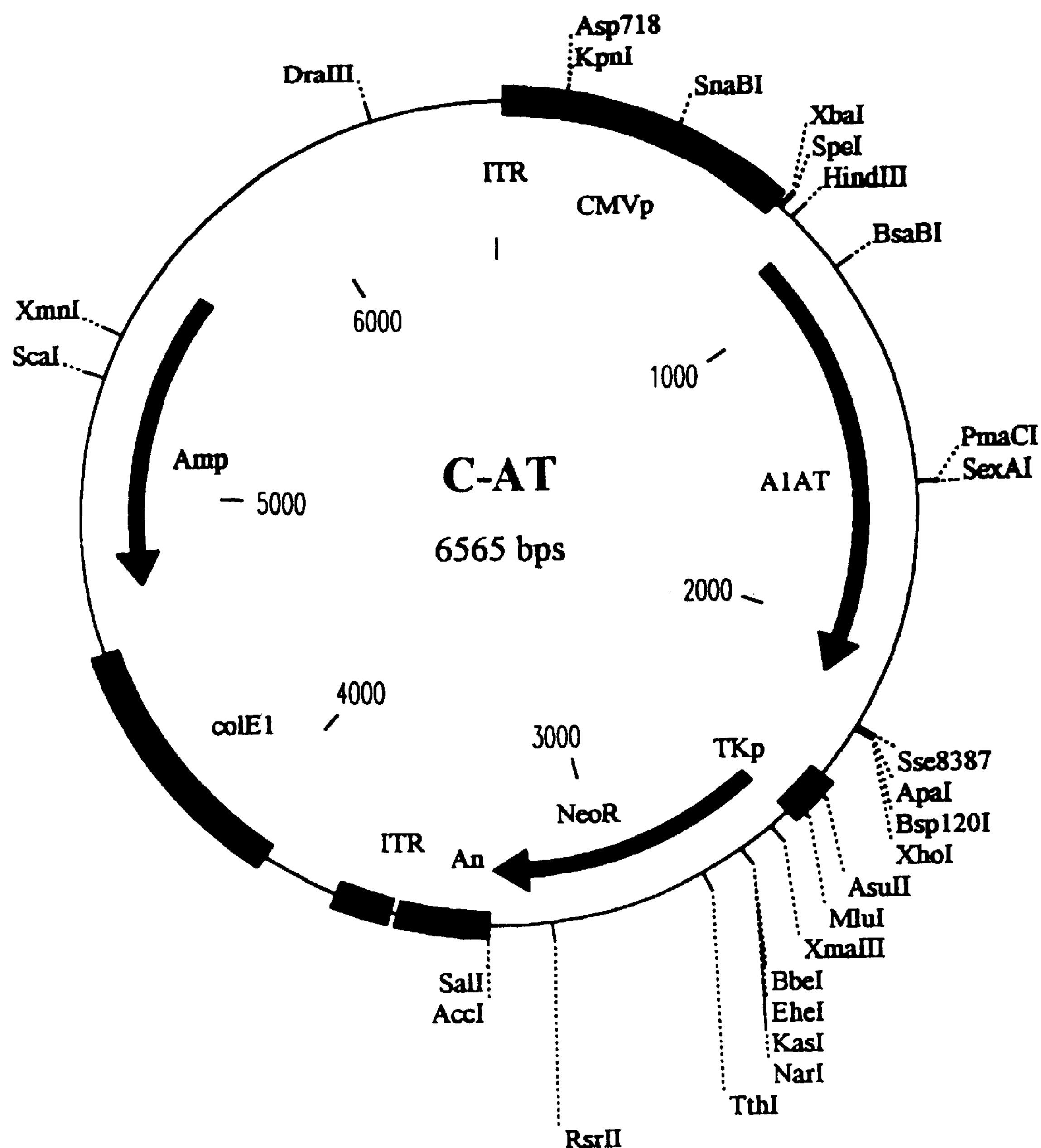
Figure 16:
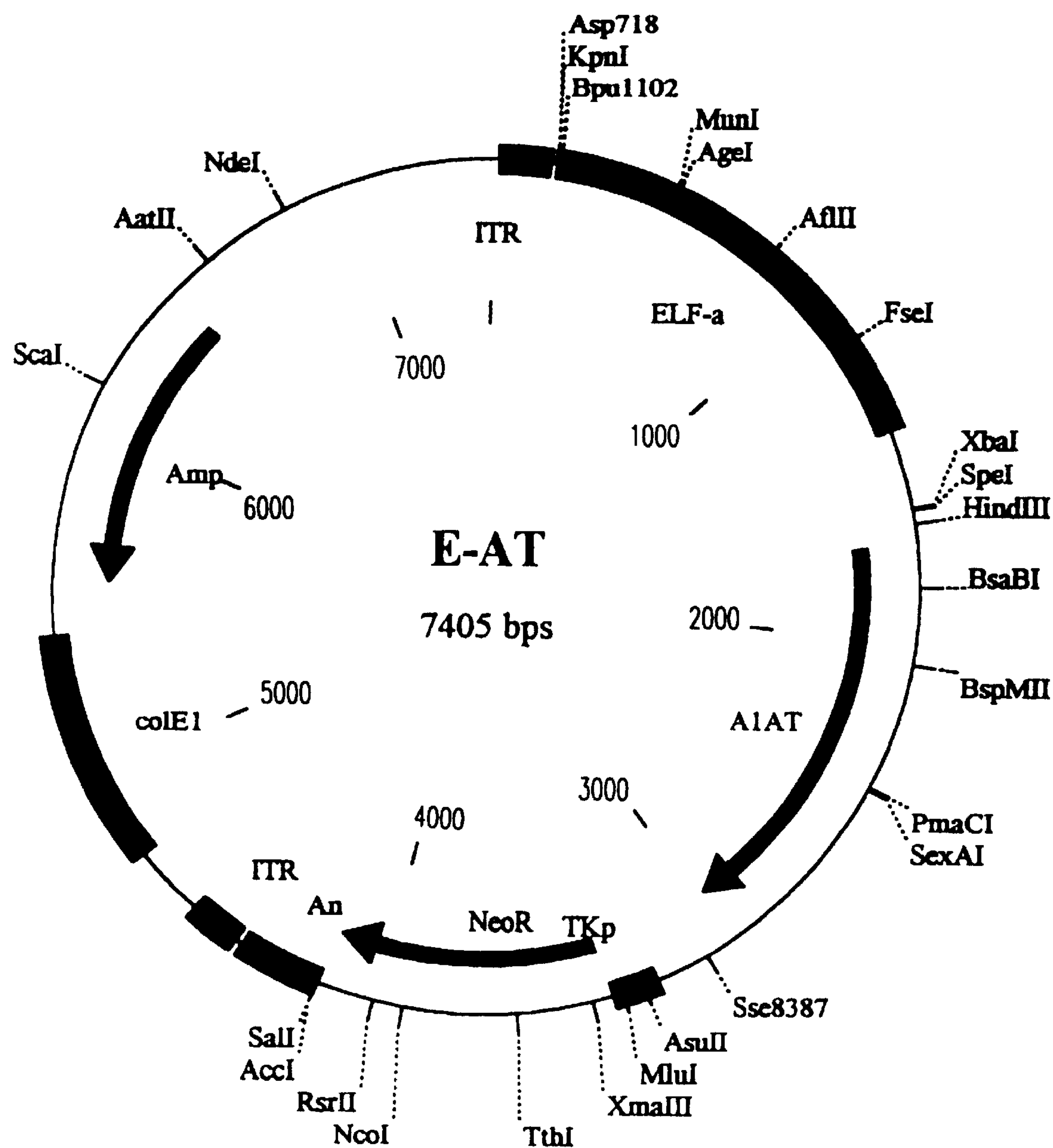
Figure 17:
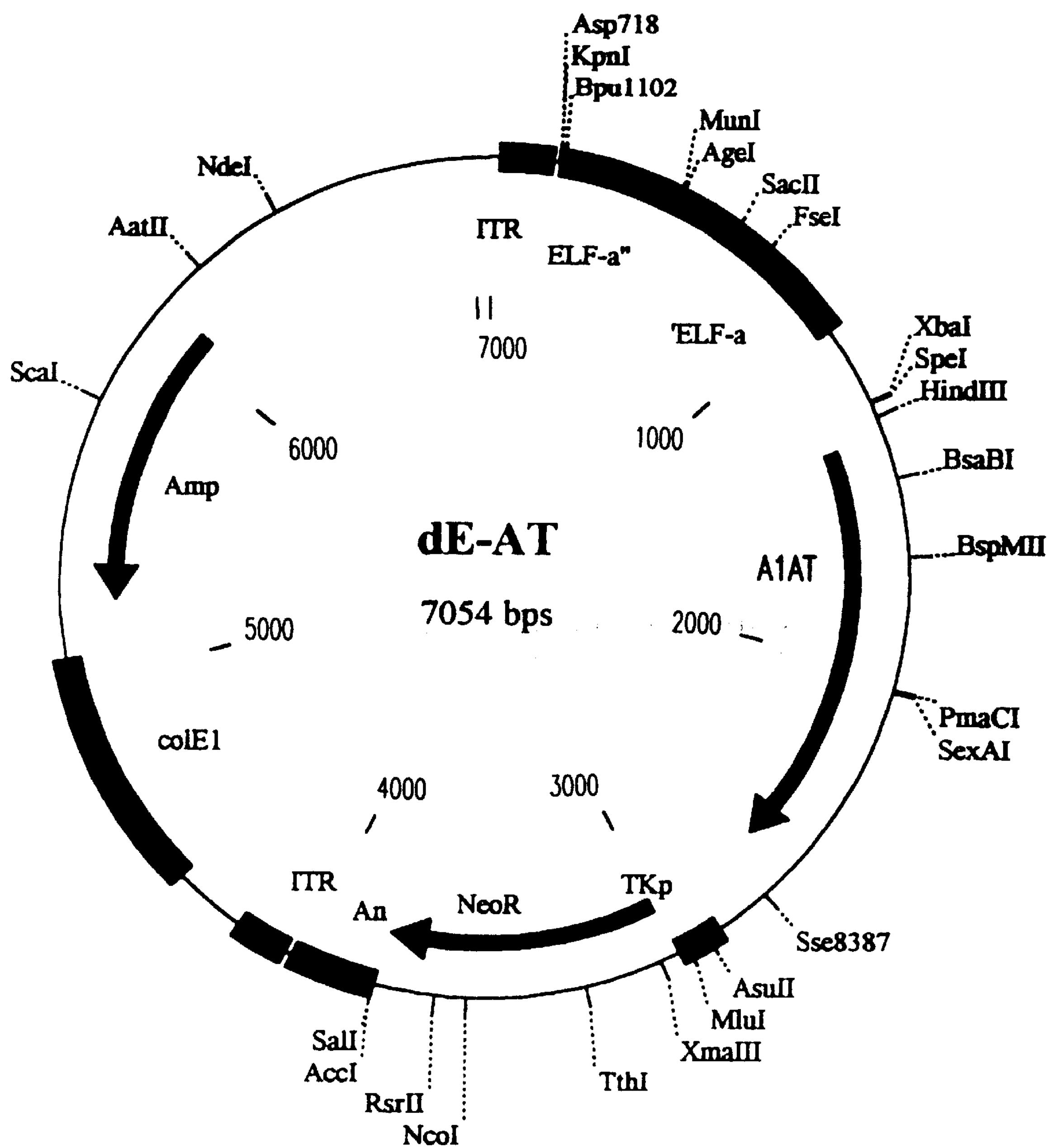
Figure 18:
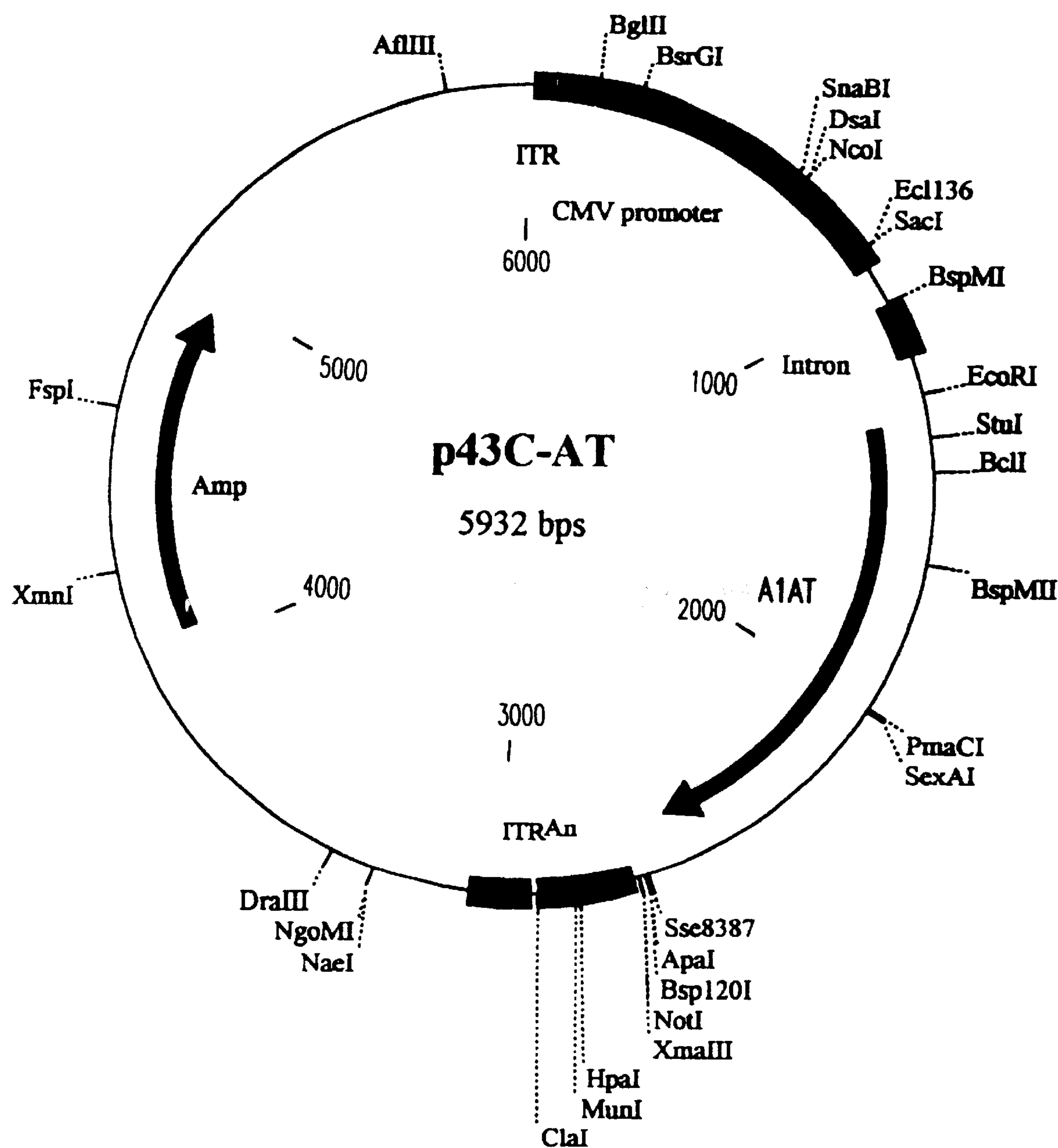
Figure 19:
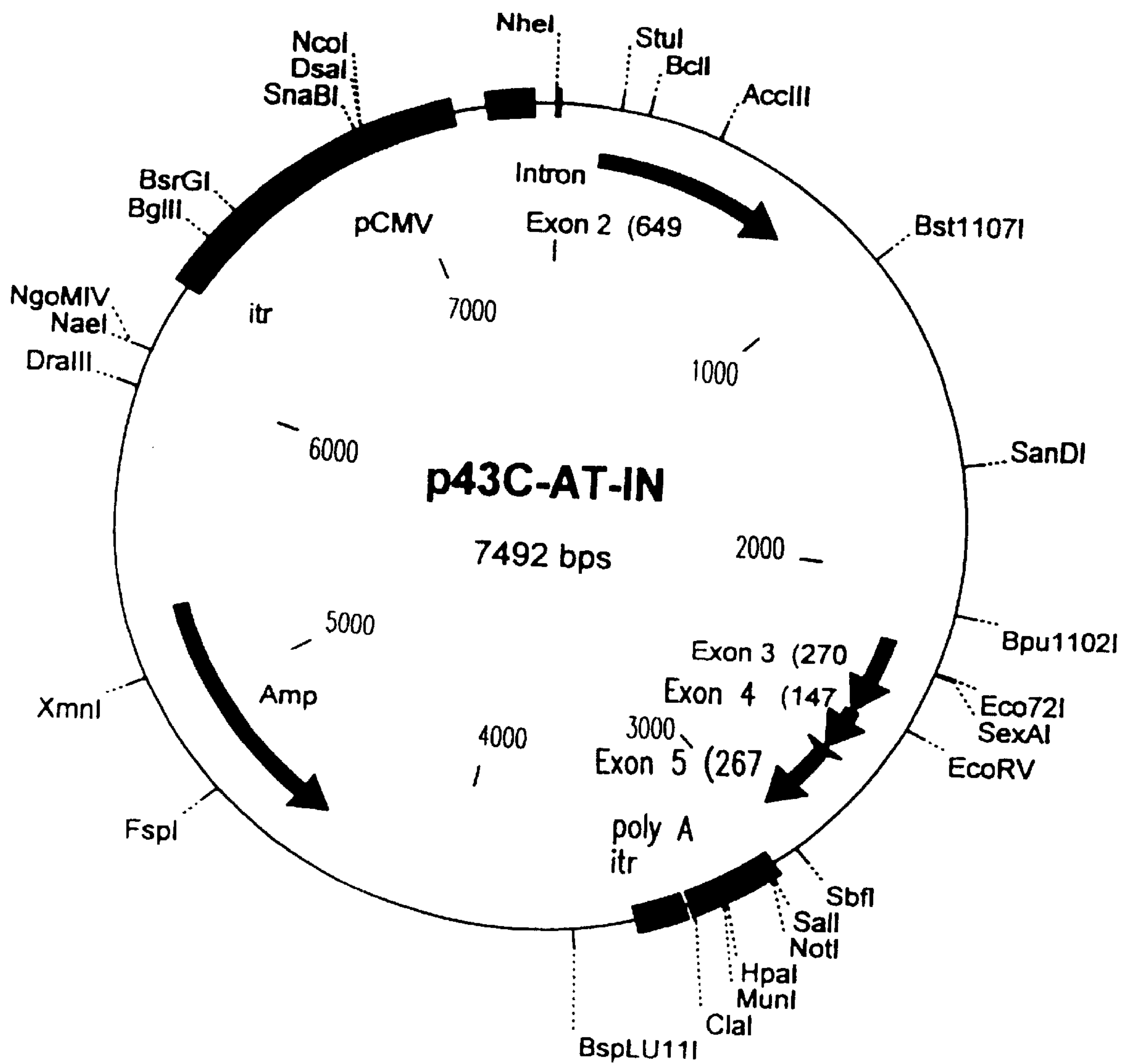
Figure 20:
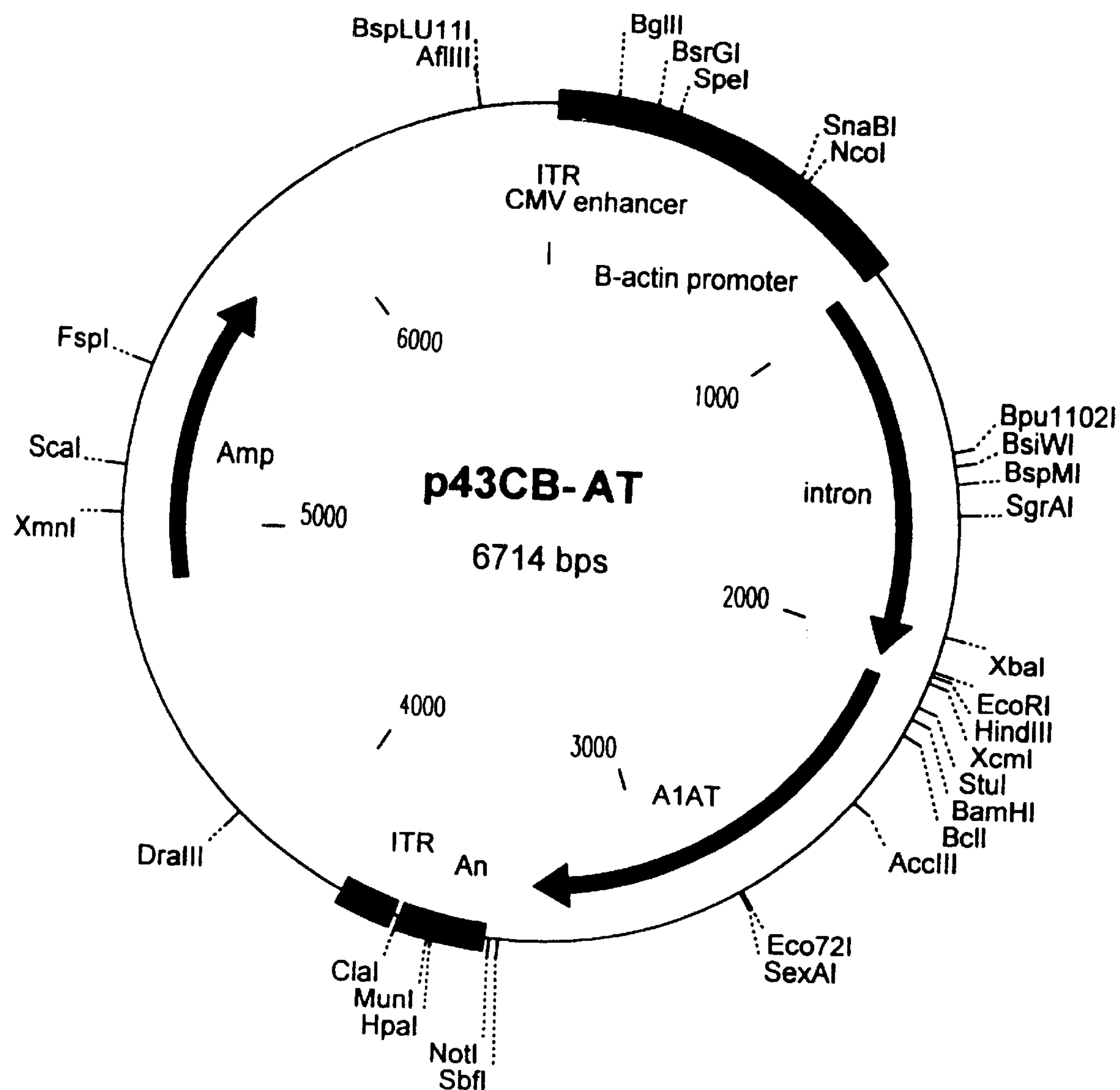
Figure 21:
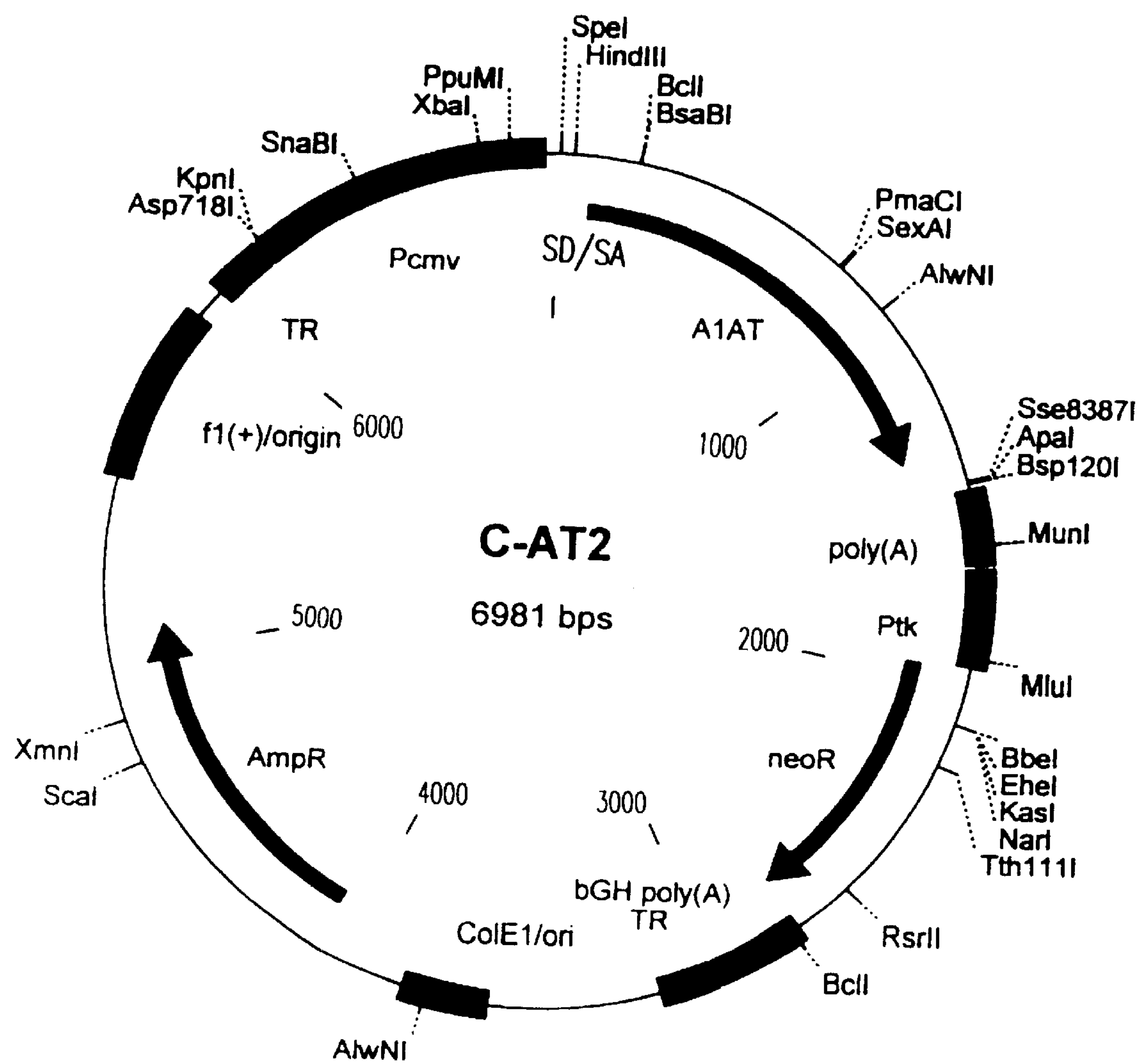
Figure 22:
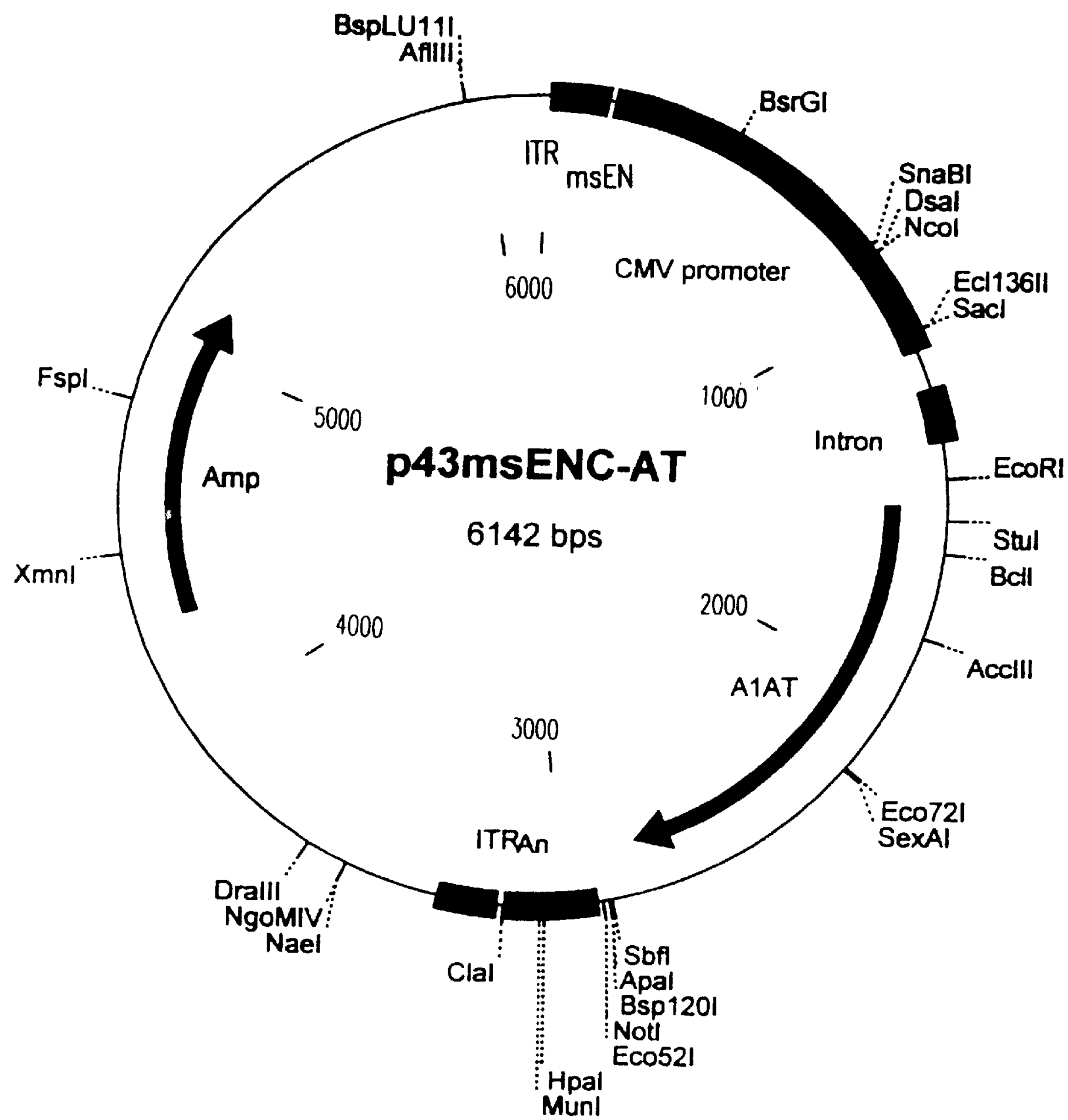
Figure 23:
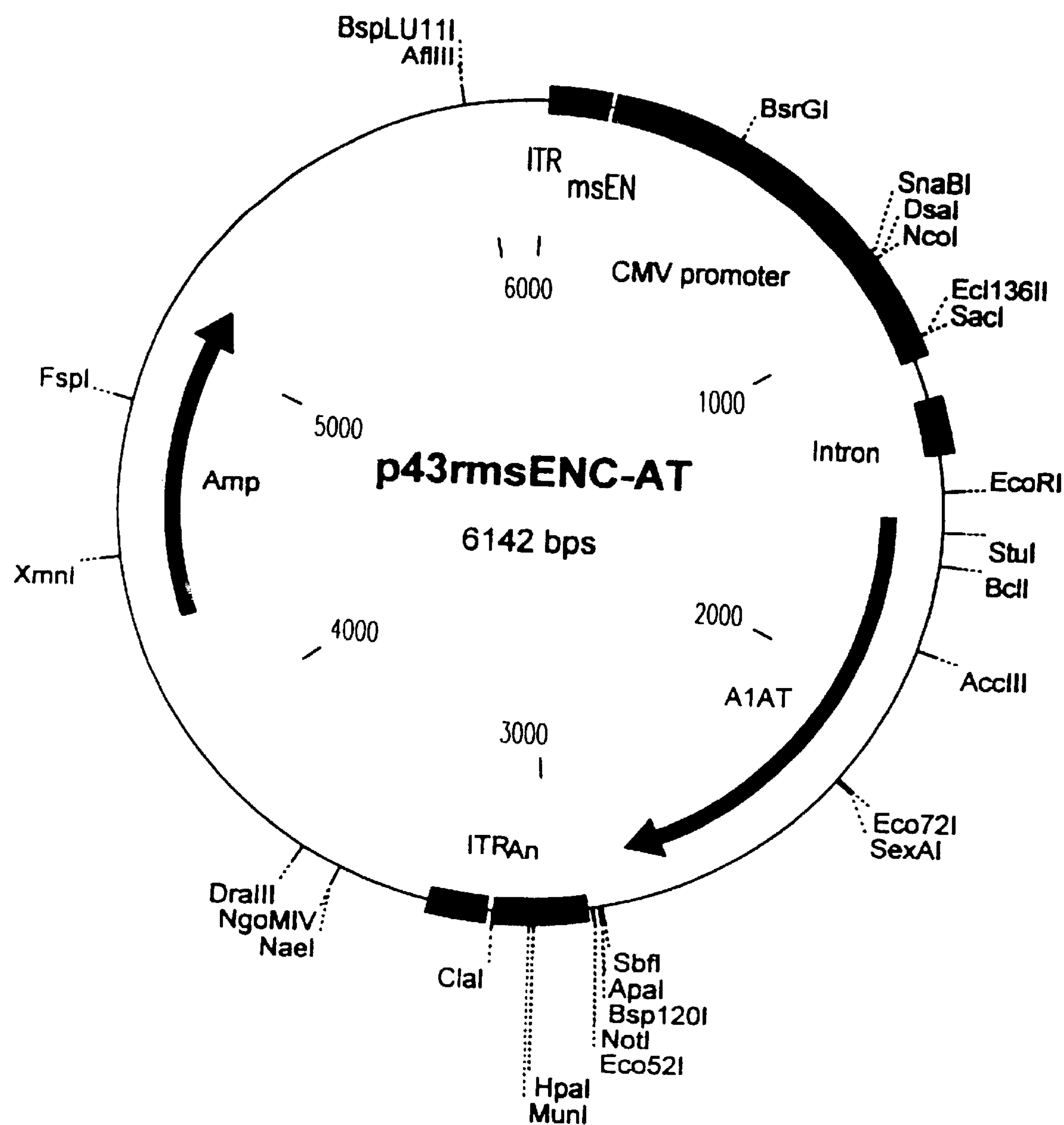
Figure 24:
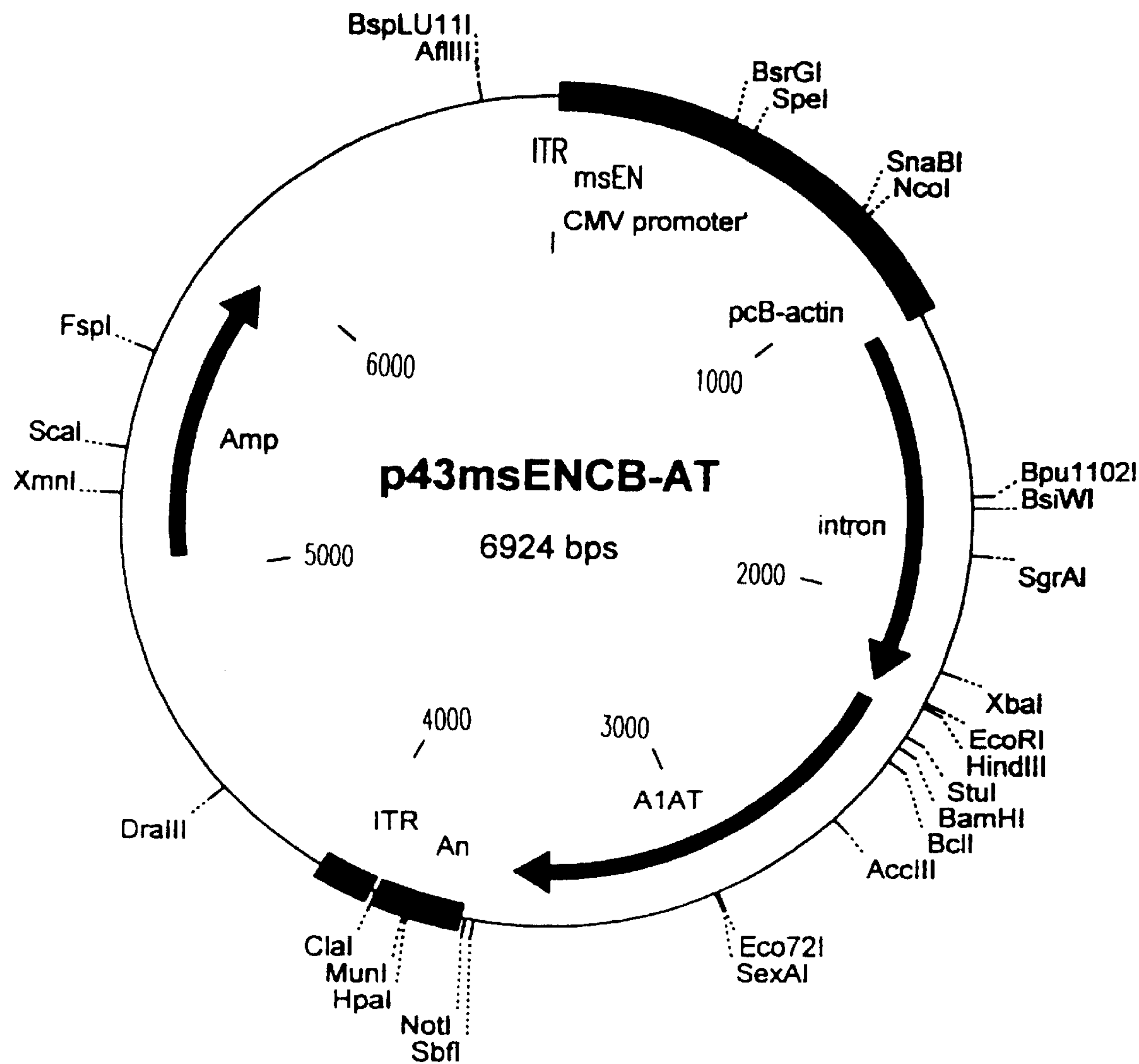
Figure 25:
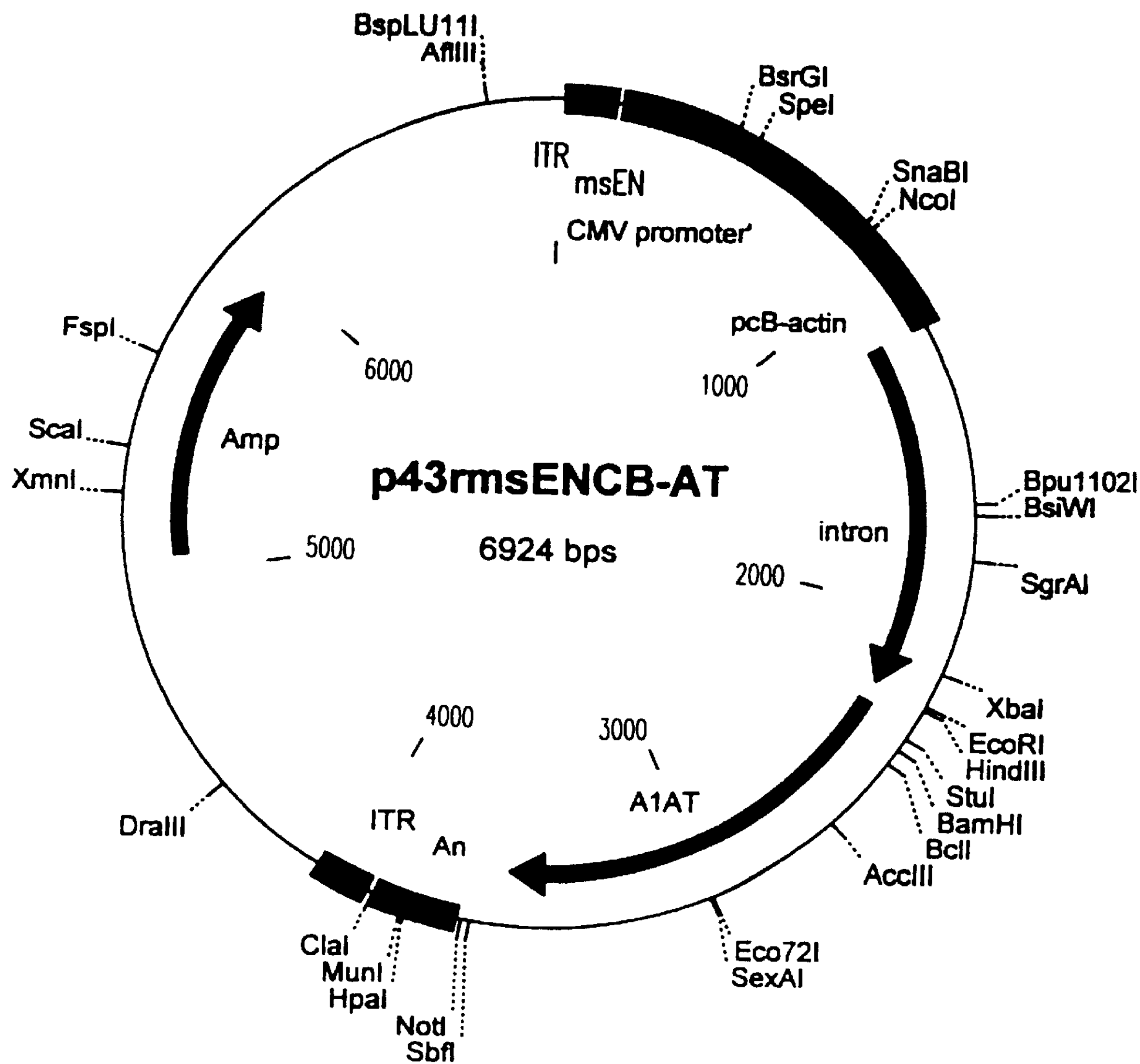

Mice were injected intratracheally with either C-AT or p43CB-AT vector. Serum levels of hAAT in the mice were measured at day 3, 14 and 31 after injection (FIG. 14). The p43CB-AT vector mediated high levels of expression of hAAT in lung.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 5,399,346
U.S. Pat. No. 5,439,824
U.S. Pat. No. 5,658,785
U.S. Pat. No. 5,858,351
Afione, S. A., Conrad, C. K., Kearns, W. G., Chunduru, S., Adams, R., Reynolds, T. C., Guggino, W. B., Cutting, G. R., Carter, B. J. and Flotte, T. R. (1996) *J. Virol.* 70:3235–3241.
Brantly, M. L., Wittes, J. T., Vogelmeier, C. F., Hubbard, R. C., Fells, G. A., Crystal, R. G. (1991) *Chest* 100:703–708.
Briggs, M. R., Kadonga, J. T., Bell, S. P., Tjian, R. (1986) *Science* 234:47–52.
Carter et al. (1983) *Virology* 126:505–515.
Deshpande, N., Chopra, A., Rangarajan, A., Shashidhara, L. S., Rodrigues, V., Krishna, S. (1997) *J. Biol. Chem* 272(16):10664–10668.
Garver, R. I., Jr., Chytil, A., Courtney, M., Crystal, R. G. (1987) *Science* 237:762–764.
Ferrari, F. K., Samulski, T., Shenk, T., Samulski, R. J. (1996) *J. Virol.* 70:3227–3234.
Ferrari, F. K., Xiao, X., McCarty, D. M., Samulski, R. J. (1997) *Nature Med* 3:1295–97.
Fisher, K. J., Gao, G. P., Weitzman, M. D., DeMatteo, R., Burda, J. F., Wilson, J. M. (1996) *J. Virol.* 70:520–532.
Flotte, T. R., Afione, S. A., Conrad, C., McGrath, S. A., Solow, R., Oka, H., Zeitlin, P. L., Guggino, W. B., Carter, B. J. (1993) *Proc. Natl. Acad. Sci. USA* 90:10613–10617.
Jooss, K., Yang, Y., Fisher, K. J., Wilson, J. M. (1998) *J. Virol.* 72:4212–4223.
Li, X, Eastman, E. M., Schwartz, R. J., Draghia-Akli, R. (1999) *Nat. Biotechnol* 17(3):241–245.
Li et al. (1997) *J. Virol.* 71:5236–43.
Kearns, W. G., Afione, S. A., Fulmer, S. B., Caruso, J., Flotte, T. R., Cutting, G. R. (1996) *Gene Ther.* 3:748–755.
Kessler, P. D., Podsakoff, G., Chen, X., McQuiston, S. A., Colosim, P. C., Matelis, L. A., Kurtzman, G. and Byrne, B. J. (1996) *Proc. Natl. Acad. Sci. USA* 93:14082–14087.
Klein, R. L. et al. (1998) *Exp. Neurol.* 150:183–194.
Kotin, R. M., Siniscalco, M., Samulski, R. J., Zhu, X. D., Hunter, L., Laughlin, C. A., McLaughlin, S., Muzyczka, N., Rocchi, M., Berns, K. I. (1990) *Proc. Natl. Acad. Sci. USA* 87:2211–2215.
Mitchell, P. J., Tjian, R. (1989) *Science* 245:371–378.
Murphy, J. E., Zhou, S., Giese, K., Williams, L. T., Escobedo, J. A., Dwarki, V. J. (1997) *Proc. Natl. Acad. Sci. USA* 94:13921–13926, 1997.
Nettelbeck, D. M., Jerome V., Muller R. (1998) *Gene Ther* 5(12)1656–1664.
Pitluk, Z. W., Ward, D. C. (1991) *J. Virol.* 65:6661–6670.
Stewart, A. F., Richard, III, C. W., Suzow, J., Stephan D., Weremowicz, S., Morton, C. C., Andra, C. N. (1996) *Genomics* 37(1):68–76.
Wei, C-F. et al (1993) *J. Biol Chem* 258(22):13506–13512.
Xiao, X., Li, J., Samulski, R. J. (1996) *J. Virol.* 70:8098–8108.
Zolotukhin, S., Potter, M., Hauswirth, W., Guy, J., Muzyczka, N. (1996) *J. Virol.* 70(7):4646–4654.
Zolotukhin, S. et al. (1999) *Gene Ther.* (6).

---

We claim:

1. A method for providing a mammal with a therapeutically effective amount of an alpha-1-antitrypsin protein, comprising introducing into suitable cells of said mammal an effective amount of an adeno-associated viral vector or an adeno-associated viral particle that comprises said vector; wherein said vector comprises a polynucleotide encoding an alpha-1-antitrypsin protein wherein said protein is expressed in said cell.

2. The method of claim 1, wherein said vector comprises a promoter operably linked to said polynucleotide.

3. The method of claim 2, wherein said promoter is selected from the group consisting of a CMV promoter, a hybrid CMV enhancer/β-actin promoter, an EF1 promoter, an U1a promoter and an U1b promoter.

4. The method of claim 2, wherein said promoter is an inducible promoter selected from the group consisting of a Tet-inducible promoter and a VP16-LexA promoter.

5. The method of claim 2, wherein said vector further comprises an enhancer sequence operably linked to said promoter.

6. The method of claim 5, wherein said enhancer is a CMV enhancer.

7. The method of claim 5, wherein said enhancer is a synthetic enhancer.

8. The method of claim 7, wherein said enhancer is a muscle-specific enhancer.

9. The method of claim 1, wherein said vector comprises an intron sequence.

10. The method of claim 9, wherein said intron sequence is intron II from a human alpha-1-antitrypsin gene.

11. The method of claim 1, wherein said vector comprises a polynucleotide encoding a human alpha-1-antitrypsin protein.

12. The method of claim 1, wherein said vector is selected from the group consisting of dE-AT (SEQ ID NO:3), E-AT (SEQ ID NO:2), C-AT (SEQ ID NO:1), C-AT2 (SEQ ID NO:7), p43C-AT (SEQ ID NO:4), p43CB-AT (SEQ ID NO:6), p43C-AT-IN (SEQ ID NO:5), p43msENC-AT (SEQ ID NO:8), p43rmsENC-AT (SEQ ID NO:9), p43msENCB-AT (SEQ ID NO:10) and p43rmsENCB-AT (SEQ ID NO:11).

13. The method of claim 1, wherein said mammal has a condition that results in a defective alpha-1-antitrypsin protein.

14. The method of claim 1, wherein said mammal has a condition that results in a deficiency of said alpha-1-antitrypsin protein.

15. The method of claim 1, wherein said mammal is a human.

16. The method of claim 1, wherein said adeno-associated viral vector or adeno-associated viral particle is introduced into myofibers, myoblasts, hepatocytes, or lung cells of said mammal.

17. The method of claim 1, wherein the adeno-associated viral particle is introduced into said cells by infection.

18. The method of claim 1, wherein the adeno-associated viral vector is introduced into said cells by transfection.

19. The method of claim 1, wherein said adeno-associated viral particle or adeno-associated viral vector is introduced into cells of said mammal in vitro and the transduced cells are then introduced into said mammal.

20. The method of claim 1, wherein said adeno-associated viral particle or adeno-associated viral vector is introduced into said cells in vivo.

21. The method of claim 20, wherein said adeno-associated viral particle or adeno-associated viral vector is injected into a muscle of said mammal.

22. The method of claim 20, wherein said adeno-associated viral particle or adeno-associated viral vector is injected into a portal or peripheral vein of said mammal.

23. The method of claim 20, wherein said adeno-associated viral particle or adeno-associated viral vector is injected intratracheally or inhaled into the lungs of said mammal.

24. A method for treating alpha-1-antitrypsin deficiency in a mammal, comprising introducing into suitable cells of said mammal an effective amount of an adeno-associated viral vector or an adeno-associated viral particle that comprises said vector; wherein said vector comprises a polynucleotide encoding an alpha-1-antitrypsin protein wherein said protein is expressed in said cell.

25. The method of claim 24, wherein said mammal is a human.

26. The method of claim 24, wherein said vector comprises a polynucleotide encoding a human alpha-1-antitrypsin protein.

27. The method of claim 24, wherein said alpha-1-antitrypsin deficiency is caused by a defective alpha-1-antitrypsin protein.

* * * * *

UNITED STATES PATENT AND TRADEMARK OFFICE
CERTIFICATE OF CORRECTION

PATENT NO. : 6,461,606 B1 
DATED : October 8, 2002
INVENTOR(S) : Terence R. Flotte, Sihong Song, Barry J. Byrne and Michael Morgan It is certified that error appears in the above-identified patent and that said Letters Patent is hereby corrected as shown below:

Column 81,
Line 41, after "protein" (first occurrence) insert -- , and --.

Column 84,
Line 1, after "protein" (first occurrence) insert -- , and --.

Signed and Sealed this

Thirty-first Day of December, 2002

JAMES E. ROGAN
*Director of the United States Patent and Trademark Office*